US010206926B2

(12) United States Patent
Baszczynski et al.

(10) Patent No.: US 10,206,926 B2
(45) Date of Patent: *Feb. 19, 2019

(54) QUINAZOLINE COMPOUNDS

(71) Applicants: Gilead Sciences, Inc., Foster City, CA (US); Institute of Organic Chemistry and Biochemistry of the AS CR, V.V.I., Prague (CZ)

(72) Inventors: Ondrej Baszczynski, Prague (CZ); Milan Dejmek, Prague (CZ); Yunfeng Eric Hu, San Mateo, CA (US); Petr Jansa, San Mateo, CA (US); Eric Lansdon, Belmont, CA (US); Richard L. Mackman, Milbrae, CA (US); Petr Simon, Prague (CZ)

(73) Assignees: Gilead Sciences, Inc., Foster City, CA (US); Institute of Organic Chemistry and Biochemistry of the AS CR, V.V.I. (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 15/634,527

(22) Filed: Jun. 27, 2017

(65) Prior Publication Data

US 2017/0354656 A1    Dec. 14, 2017

Related U.S. Application Data

(63) Continuation of application No. 14/998,042, filed on Dec. 23, 2015, now Pat. No. 9,730,936.

(60) Provisional application No. 62/096,748, filed on Dec. 24, 2014.

(51) Int. Cl.
| A61K 31/517 | (2006.01) |
| C07D 401/12 | (2006.01) |
| C07D 239/94 | (2006.01) |
| A61K 45/06 | (2006.01) |
| C07D 239/84 | (2006.01) |
| C07D 239/95 | (2006.01) |
| C07D 403/12 | (2006.01) |

(52) U.S. Cl.
CPC ............ *A61K 31/517* (2013.01); *A61K 45/06* (2013.01); *C07D 239/84* (2013.01); *C07D 239/94* (2013.01); *C07D 239/95* (2013.01); *C07D 401/12* (2013.01); *C07D 403/12* (2013.01)

(58) Field of Classification Search
CPC .......................... A61K 31/517; C07D 401/12
USPC ..................... 514/266.21; 544/284
See application file for complete search history.

(56) References Cited

U.S. PATENT DOCUMENTS

| 4,675,047 | A | 6/1987 | Serban et al. |
| 7,932,262 | B2 | 4/2011 | Ramurthy et al. |
| 9,701,677 | B2 | 7/2017 | Jansa et al. |
| 9,730,936 | B2 * | 8/2017 | Baszczynski ........ C07D 401/12 |
| 2002/0055516 | A1 | 5/2002 | Miyazaki et al. |
| 2007/0298104 | A1 | 12/2007 | Arend et al. |
| 2010/0143301 | A1 | 6/2010 | Desai et al. |
| 2011/0039845 | A1 | 2/2011 | Kashima et al. |
| 2013/0165489 | A1 | 6/2013 | Cocklin et al. |
| 2014/0221356 | A1 | 8/2014 | Jin et al. |
| 2014/0221378 | A1 | 8/2014 | Miyazaki et al. |
| 2014/0221380 | A1 | 8/2014 | Miyazaki et al. |
| 2014/0378443 | A1 | 12/2014 | Jorgenson et al. |
| 2016/0237062 | A1 | 8/2016 | Hu et al. |
| 2016/0250215 | A1 | 9/2016 | Basczcynski et al. |
| 2016/0251347 | A1 | 9/2016 | Jansa et al. |

FOREIGN PATENT DOCUMENTS

| JP | 2008-517978 | 5/2008 |
| WO | WO 01/21598 | 3/2001 |
| WO | WO 01/038315 | 5/2001 |
| WO | WO 01/55140 | 8/2001 |
| WO | WO 02/10136 | 2/2002 |
| WO | WO 02/24667 | 3/2002 |
| WO | WO 2004/030672 | 4/2004 |
| WO | WO 2004/096286 | 11/2004 |
| WO | WO 2004/108711 | 12/2004 |
| WO | WO 2005/035503 | 4/2005 |
| WO | WO 2006/015261 | 2/2006 |
| WO | WO 2006/039718 | 4/2006 |
| WO | WO 2006/045828 | 5/2006 |
| WO | WO 2006/071095 | 7/2006 |
| WO | WO 2006/099301 | 9/2006 |
| WO | WO 2006/110157 | 10/2006 |
| WO | WO 2006/118256 | 11/2006 |
| WO | WO 2007/000240 | 1/2007 |
| WO | WO 2007/012421 | 2/2007 |
| WO | WO 2007/076092 | 7/2007 |
| WO | WO 2007/125405 | 11/2007 |
| WO | WO 2008/011109 | 1/2008 |
| WO | WO 2008/030455 | 3/2008 |
| WO | WO 2008/050808 | 5/2008 |
| WO | WO 2008/077550 | 7/2008 |

(Continued)

OTHER PUBLICATIONS

Australian Office Action in Australian Patent Application No. 2015371198, dated Feb. 15, 2018, 3 pages.
Australian Office Action in Australian Patent Application No. 2015371255, dated Feb. 14, 2018, 3 pages.
International Preliminary Report on Patentability in International Application No. PCT/US2015/000460, dated Jun. 27, 2017, 6 pages.
International Preliminary Report on Patentability in International Application No. PCT/US2015/000310, dated Jun. 27, 2017, 7 pages.

(Continued)

*Primary Examiner* — Jeffrey H Murray
(74) *Attorney, Agent, or Firm* — Fish & Richardson, P.C.

(57) ABSTRACT

Described herein are compounds of Formula (I) and tautomers and pharmaceutical salts thereof, compositions and formulations containing such compounds, and methods of using and making such compounds.

4 Claims, 1 Drawing Sheet

(56) References Cited

FOREIGN PATENT DOCUMENTS

| | | |
|---|---|---|
| WO | WO 2008/077551 | 7/2008 |
| WO | WO 2008/077553 | 7/2008 |
| WO | WO 2008/086462 | 7/2008 |
| WO | WO 2008/122614 | 10/2008 |
| WO | WO 2008/157500 | 12/2008 |
| WO | WO 2009/062285 | 5/2009 |
| WO | WO 2009/155121 | 12/2009 |
| WO | WO 2010/076238 | 7/2010 |
| WO | WO 2010/007374 | 10/2010 |
| WO | WO 2010/118155 | 10/2010 |
| WO | WO 2010/130034 | 11/2010 |
| WO | WO 2011/035416 | 3/2011 |
| WO | WO 2011/156610 | 12/2011 |
| WO | WO 2011/161159 | 12/2011 |
| WO | WO 2011/163610 | 12/2011 |
| WO | WO 2012/003497 | 1/2012 |
| WO | WO 2012/003498 | 1/2012 |
| WO | WO 2012/050347 | 4/2012 |
| WO | WO 2012/044090 | 6/2012 |
| WO | WO 2012/080284 | 6/2012 |
| WO | WO 2012/116237 | 8/2012 |
| WO | WO 2012/145728 | 10/2012 |
| WO | WO 2013/006738 | 1/2013 |
| WO | WO 2013/006792 | 1/2013 |
| WO | WO 2013/091096 | 6/2013 |
| WO | WO 2013/159064 | 10/2013 |
| WO | WO 2014/100323 | 6/2014 |
| WO | WO 2014/128206 | 8/2014 |
| WO | WO 2014/128213 | 8/2014 |
| WO | WO 2016/105532 | 6/2016 |
| WO | WO 2016/105534 | 6/2016 |
| WO | WO 2016/105564 | 10/2016 |

OTHER PUBLICATIONS

International Preliminary Report on Patentability in International Application No. PCT/US2015/000308, dated. Jun. 27, 2017, 7 pages.
New Zealand Office Action in New Zealand Patent Application No. 733125, dated Nov. 28, 2017, 3 pages.
New Zealand Office Action in New Zealand Patent Application No. 733135, dated Dec. 1, 2017, 2 pages.
New Zealand Office Action in New Zealand Patent Application No. 733174, dated Dec. 1, 2017, 3 pages.
Berge, S.M., et al., (1977), "Pharmaceutical Salts" J. Pharma Sci., 66(1):1-19.
Das, K., et al., (2008), "High-resolution structures of HIV-1 reverse transcriptase/TMC278 complexes: Strategic flexibility explains potency against resistance mutations", Proc. Nat. Acad. Sci., 105(5):1466-1471.
Eigler and Hirsch, "Chemistry with Graphene and Graphene Oxide—Challenges for Synthetic Chemists" Angew. Chem. Int. Ed., (2014), vol. 53, pp. 2-21.
Foster, "Deuterium Isotope Effects in Studies of Drug Metabolism", Trends Pharmacol. Sci., (1984), vol. 5, No. 12, pp. 524-527.

International Search Report and Written Opinion in International Application No. PCT/US2015/000308, dated Mar. 31, 2016, 11 pages.
International Search Report and Written Opinion in International Application No. PCT/US2015/000310, dated Mar. 31, 2016, 11 pages.
International Search Report and Written Opinion in International Application No. PCT/US2015/000460, dated Mar. 17, 2016, 9 pages.
Janssen, P.A., et al., (2005), "In Search of a Novel Anti-HIV Drug: Multidisciplinary Coordination in the Discovery of 4-[[4-[[4-[(1 E)-2-Cyanoethenyl]-2,6-dimethylphenyl]amino]-2-pyrimidinvl]amino]benzonitrile (R278474, Rilpivirine)", J. Med. Chem, 48(6):1901-1909.
Johnson, B., et al., (Dec. 5, 2012) "A Comparison of the ability of rilpivirine (TMC278) and selected analogues to inhibit clinically relevant HIV-1 reverse transcriptase mutants", Retrovirology, BIOMED Central Ltd., London GB, 9(1):99.
Kuroda et al., (2013) "Snapshot of the equilibrium dynamics of a drug bound to HIV-1 reverse transcriptase", Nature Chemistry, pp. 1-8.
Non Final Office Action dated Aug. 5, 2016, for U.S. Appl. No. 14/998,042, filed Dec. 23, 2015, eight pages.
Non Final Office Action dated Oct. 20, 2016, for U.S. Appl. No. 14/998,074, filed Dec. 23, 2015, five pages.
Notice of Allowance dated Sep. 6, 2016, for U.S. Appl. No. 14/998,131, filed Dec. 23, 2015, eight pages.
Pakistan Office Action in Pakistan Application No. 828/2015, dated Dec. 27, 2016, 3 pages (English translation only).
Remington, "The Science and Practice of Pharmacy", R. Hendrickson, ed., 21st edition, Lippincott, Williams & Wilkins, Philadelphia, PA, (2005), at p. 732, Table 38-5.
Smith, M.B., et al., (2007), March's Advanced Organic Chemistry, "Reactions, Mechanisms, and Structure", Wiley-Interscience, sixth edition, pp. 1218-1223.
CA Office Action in Canadian Application No. 2,972,021, dated Apr. 26, 2018, 4 pages.
CA Office Action in Canadian Appln. No. 2,972,014, dated Jul. 13, 2018, 4 pages.
EA Office Action in Patent Application No. EA201791304, dated Feb. 13, 2018, 7 pages (with English translation).
EA Office Action in Eurasian Appln. No. 201791305, dated Mar. 20, 2018, 6 pages (with English translation).
EA Office Action in Eurasian Appln. No. 201791256, dated Jun. 7, 2018, 8 pages (with English translation).
IL Office Action in Israeli Appln. No. 36542/17, dated May 10, 2018, 5 pages (with English translation).
JP Office action in Japanese Application No. 2017-534253, dated Apr. 16, 2018, 5 pages (with English Translation).
KR Office Action in Korean Appln. No. 10-2017-7020464, dated Aug. 1, 2018, 10 pages (with English translation).
UA Office Action in Ukrainian Patent Application No. 2017 07115, dated Mar. 29, 2018, 7 pages (with English translation).
UA Notice of Allowance in Ukrainian Appln. No. 2017-07115, dated Jun. 1, 2018, 2 pages.

* cited by examiner

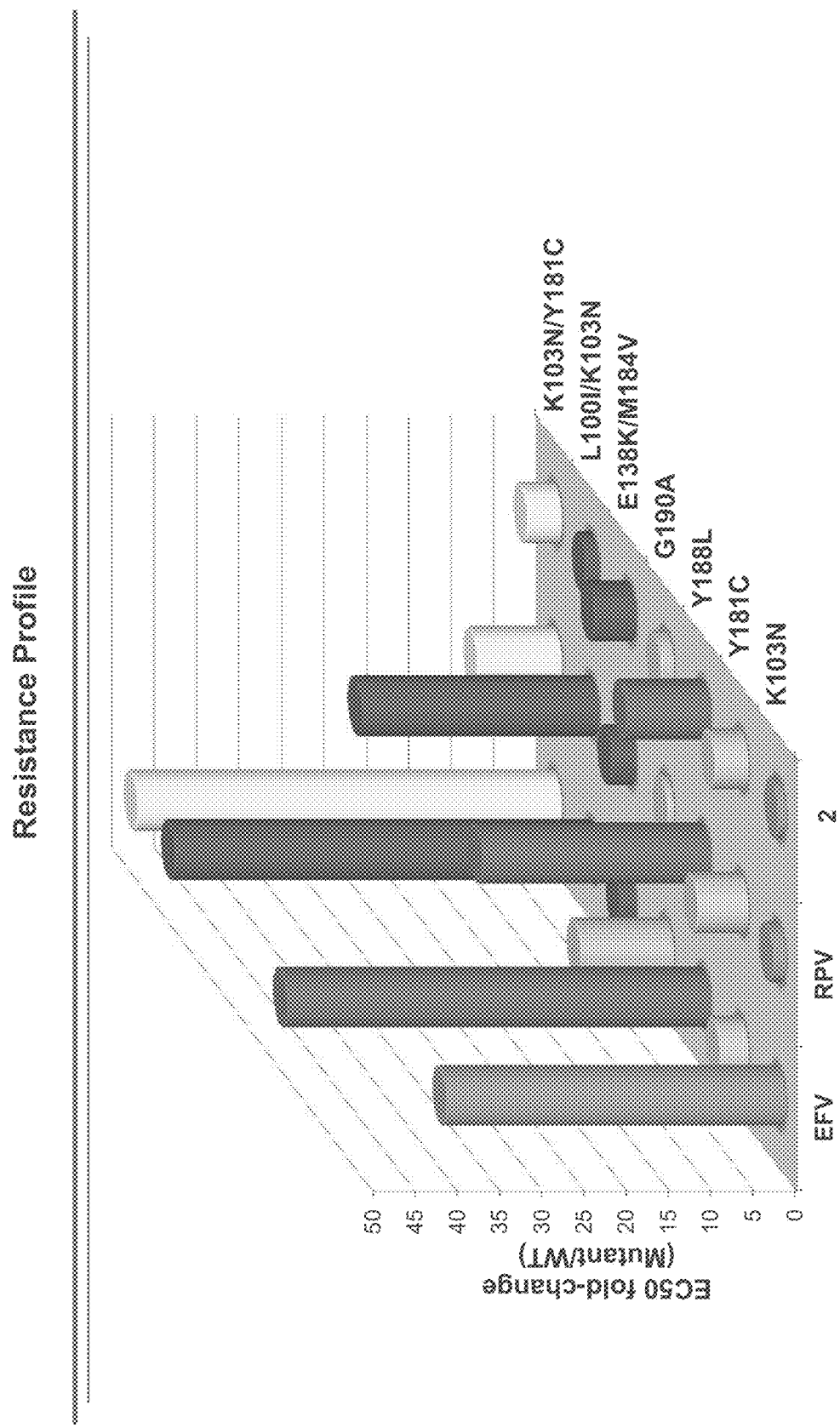

QUINAZOLINE COMPOUNDS

CROSS-REFERENCE TO RELATED APPLICATIONS

This application claims priority benefit to U.S. Application Ser. No. 62/096,748, filed Dec. 24, 2014, the disclosure of which is herein incorporated by reference in its entirety.

BACKGROUND

While progress has been made in treating HIV and AIDS, HIV infection remains a global health concern. As part of such treatments, non-nucleoside reverse transcriptase inhibitors (NNRTIs) have often been employed, particularly as part of highly active antiretroviral therapy (HAART) treatment regimens. Though potent, drawbacks exist for many of the known NNRTIs as their use has been associated with mutations in the HIV virus that may result in drug resistance. As such, there remains a need for further development of potent NNTRIs.

Described herein are compounds of Formula (I) and pharmaceutically acceptable salts thereof, compositions and formulations containing such compounds, or pharmaceutically acceptable salts thereof, and methods of using and making such compounds, or pharmaceutically acceptable salts thereof.

SUMMARY

In certain embodiments, the present disclosure relates to compounds of Formula (I) or a tautomer thereof,

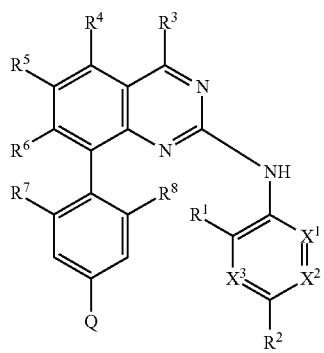

(I)

wherein
Q is

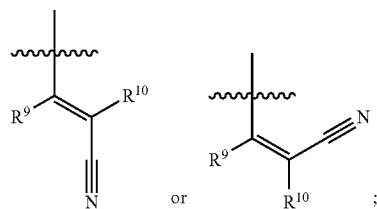

$X^1$, $X^2$, and $X^3$ are each independently N or $C(R^{11})$, provided that, at most 2 of $X^1$, $X^2$, and $X^3$ are N;

$R^1$ is —H, —CN, —$OR^a$, —C(O)$OR^a$, halogen, $C_{1-6}$alkyl, $C_{3-10}$cycloalkyl, or $C_{1-6}$heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^2$ is —H, —CN, —$OR^a$, —$NR^aR^b$, —C(O)$OR^a$, halogen, $C_{1-6}$alkyl, $C_{3-10}$cycloalkyl, or $C_{1-6}$heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^3$ is —H, —$OR^a$, —$SR^a$, —$NR^aR^b$, —NHC(O)$NR^aR^b$, $C_{1-6}$alkyl, $C_{3-10}$cycloalkyl, or $C_{1-6}$heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^4$ is —H, —$OR^a$, halogen, —$NO_2$, —CN, —$NR^aR^b$, —NHC(O)$NR^aR^b$, —OC(O)$NR^aR^b$, —$CH_2$C(O)$NR^aR^b$, $C_{1-6}$alkyl, $C_{3-10}$cycloalkyl, or $C_{1-6}$heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^5$ is —H, —$OR^a$, halogen, —$NO_2$, —CN, —$NR^aR^b$, —NHC(O)$NR^aR^b$, —OC(O)$NR^aR^b$, —$CH_2$C(O)$NR^aR^b$, $C_{1-6}$alkyl, $C_{3-10}$cycloalkyl, or $C_{1-6}$heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^6$ is —H, —$OR^a$, halogen, —$NO_2$, —CN, —$NR^aR^b$, —NHC(O)$NR^aR^b$, —OC(O)$NR^aR^b$, —$CH_2$C(O)$NR^aR^b$, $C_{1-6}$alkyl, $C_{3-10}$cycloalkyl, or $C_{1-6}$heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^7$ is $C_{1-6}$alkyl, $C_{3-10}$cycloalkyl, $C_{1-6}$heteroalkyl, halogen, —$OR^a$, —CN, or —$NO_2$, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^8$ is $C_{1-6}$alkyl, $C_{3-10}$cycloalkyl, $C_{1-6}$heteroalkyl, halogen, —$OR^a$, —CN, or —$NO_2$, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^9$ is —H, $C_{1-6}$alkyl, or $C_{3-10}$cycloalkyl, wherein each $C_{1-6}$alkyl and $C_{3-10}$cycloalkyl is optionally substituted with 1, 2, 3, 4, or 5 $R^{12}$ groups, which may be same or different;

$R^{10}$ is —H, $C_{1-6}$alkyl, or $C_{3-10}$cycloalkyl, wherein each $C_{1-6}$alkyl and $C_{3-10}$cycloalkyl is optionally substituted with 1, 2, 3, 4, or 5 $R^{12}$ groups, which may be same or different;

each $R^{11}$ is independently —H, —CN, —$OR^a$, —C(O)$OR^a$, halogen, $C_{1-6}$alkyl, $C_{3-10}$cycloalkyl, or $C_{1-6}$heteroalkyl, which may be same or different, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

each $R^{12}$ is independently $C_{1-6}$alkyl, $C_{3-10}$cycloalkyl, $C_{1-6}$heteroalkyl, 5-10 membered heterocyclyl, $C_{6-10}$aryl, 5-10 membered heteroaryl, halogen, —$OR^a$, —C(O)$R^a$, —C(O)$OR^a$, —C(O)$NR^aR^b$, —OC(O)$NR^aR^b$, —$NR^aC(O)OR^b$, —$SR^a$, —$S(O)_{1-2}R^a$, —$S(O)_2F$, —$S(O)_2NR^aR^b$, —$NR^aS(O)_2R^b$, —$N_3$, —CN, or —$NO_2$; wherein each $C_{1-6}$alkyl, $C_{3-10}$cycloalkyl, $C_{1-6}$heteroalkyl, and 5-10 membered heterocyclyl is optionally substituted with 1, 2, 3, 4, or 5 substituents selected from halogen, —$OR^a$, —C(O)$R^a$, —C(O)$OR^a$, —C(O)$NR^aR^b$, —OC(O)$NR^aR^b$, —$NR^aC(O)OR^b$, —$SR^a$, —$S(O)_{1-2}R^a$, —$S(O)_2F$, —$S(O)_2NR^aR^b$, —$NR^aS(O)_2R^b$, —$N_3$, —CN, and —$NO_2$, groups, which may be same or different;

each $R^a$ and $R^b$ is independently —H, —$NH_2$, $C_{1-6}$alkyl, $C_{3-10}$cycloalkyl, $C_{1-6}$heteroalkyl, 5-10 membered heterocyclyl, $C_{6-10}$aryl, or 5-10 membered heteroaryl, wherein each $C_{1-6}$alkyl, $C_{3-10}$cycloalkyl, $C_{1-6}$heteroalkyl, 5-10 membered heterocyclyl, $C_{6-10}$aryl, and 5-10 membered heteroaryl is optionally substituted with 1, 2, 3, 4, or 5 $R^{13}$ groups, which may be same or different; or $R^a$ and $R^b$ together with the atoms to which they are attached form a 5-10 membered heterocycle; and each $R^{13}$ is independently —CN, halogen, $C_{1-6}$alkyl, $C_{3-10}$cycloalkyl, $C_{1-6}$heteroalkyl, or 5-10 membered heterocyclyl;

or a pharmaceutically acceptable salt thereof.

In certain embodiments, the current disclosure relates to a pharmaceutical composition comprising a compound of Formula (I), or a pharmaceutically acceptable salt thereof, and a pharmaceutically acceptable carrier.

In certain embodiments, the current disclosure relates to an article of manufacture comprising a unit dosage of a compound of Formula (I), or a pharmaceutically acceptable salt thereof.

In certain embodiments, the current disclosure relates to a method of inhibiting reverse transcriptase in a subject in need thereof, comprising administering a compound of Formula (I), or a pharmaceutically acceptable salt thereof, to the subject.

In certain embodiments, the current disclosure relates to a method for treating or preventing an HIV infection in a subject in need thereof, comprising administering to the subject a compound of Formula (I), or a pharmaceutically acceptable salt thereof.

In certain embodiments, the current disclosure relates to a method for preventing an HIV infection in a subject, comprising administering to the subject a compound of Formula (I), or a pharmaceutically acceptable salt thereof. In certain embodiments, the subject is at risk of contracting the HIV virus, such as a subject who has one or more risk factors known to be associated with contracting the HIV virus.

In certain embodiments, the current disclosure relates to a method for treating or preventing an HIV infection in a subject in need thereof, comprising administering to the subject a compound of Formula (I), or a pharmaceutically acceptable salt thereof, in combination with a therapeutically effective amount of one or more additional therapeutic agents.

In certain embodiments, the current disclosure relates to a compound of Formula (I), or a pharmaceutically acceptable salt thereof, for use in medical therapy.

In certain embodiments, the current disclosure relates to a compound of Formula (I), or a pharmaceutically acceptable salt thereof, for use in treating or preventing an HIV virus infection in a subject.

In certain embodiments, the current disclosure relates to the use of a compound of Formula (I), or a pharmaceutically acceptable salt thereof, for the manufacture of a medicament for treating or preventing an HIV virus infection in a subject.

Additional embodiments of the present disclosure are disclosed herein.

BRIEF DESCRIPTION OF THE DRAWINGS

FIG. 1 shows results of resistance profile against HIV-1 RT (Reverse Transcriptase) mutants of certain compounds.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A wavy line drawn through a line in a chemical structure or a dashed line drawn through a line in a chemical structure indicates a point of attachment of a group. A dashed line within a chemical structure indicates an optional bond. A prefix such as "$C_{u-v}$" or ($C_u$-$C_v$) indicates that the following group has from u to v carbon atoms. For example, "$C_{1-6}$alkyl" indicates that the alkyl group has from 1 to 6 carbon atoms.

When trade names are used herein, it is intended to independently include the tradename product and the active pharmaceutical ingredient(s) of the tradename product.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

"Alkyl" as used herein is a linear or branched saturated monovalent hydrocarbon. For example, an alkyl group can have 1 to 20 carbon atoms (i.e., ($C_{1-20}$)alkyl) or an alkyl group can have 1 to 10 carbon atoms (i.e., ($C_{1-10}$)alkyl), or an alkyl group can have 1 to 8 carbon atoms (i.e., ($C_{1-8}$) alkyl), or 1 to 6 carbon atoms (i.e., ($C_{1-6}$ alkyl), or 1 to 4 carbon atoms (i.e., ($C_{1-4}$)alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

The term "aryl" as used herein refers to a single all carbon aromatic ring or a multiple condensed all carbon ring system wherein at least one of the rings is aromatic. For example, in certain embodiments, an aryl group has 6 to 20 annular carbon atoms, 6 to 14 annular carbon atoms, or 6 to 12 annular carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-12 membered aryl), the atom range is for the total ring (annular) atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" includes alkyl groups that are 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

"Boronic acid" refers to the group —B(OH)$_2$.

"Boronic acid ester" refers to an ester derivative of a boronic acid compound. Suitable boronic acid ester derivatives include those of the formula —B(OR)$_2$ where each R is independently alkyl, aryl, arylalkyl, heteroalkyl, or heteroaryl. Additionally, the two R groups of —B(OR)$_2$ may be taken together to form a cyclic ester, e.g. having the structure

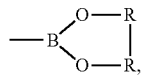

where each R may be the same or different. Examples of boronic acid ester include boronic acid pinacol ester and boronic acid catechol ester.

"Cycloalkyl" refers to a single saturated or partially unsaturated all carbon ring having 3 to 20 annular carbon atoms (i.e., $C_3$-$C_{20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g., tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl cyclohexyl, 1-cyclohex-1-enyl, 1-cyclohex-2-enyl and 1-cyclohex-3-enyl.

"Halo" or "halogen" refers to fluoro, chloro, bromo and iodo.

The term "heteroalkyl" as used herein refers to an alkyl as defined herein, wherein one or more of the carbon atoms of the alkyl are replaced by an O, S, or NR$^q$, (or if the carbon atom being replaced is a terminal carbon with an OH, SH or N(R$^q$)$_2$) wherein each R$^q$ is independently H or ($C_1$-$C_6$) alkyl. For example, ($C_1$-$C_8$)heteroalkyl intends a heteroalkyl wherein one or more carbon atoms of a $C_1$-$C_8$ alkyl is replaced by a heteroatom (e.g., O, S, NR$^q$, OH, SH or N(R$^q$)$_2$), which may the same or different. Examples of heteroalkyls include but are not limited to methoxymethyl, ethoxymethyl, methoxy, 2-hydroxyethyl and N,N'-dimethylpropylamine. A heteroatom of a heteroalkyl may optionally be oxidized or alkylated. A heteroatom may be placed at any interior position of the heteroalkyl group or at a position at which the group is attached to the remainder of the molecule. Examples include, but are not limited to, —CH$_2$OCH$_3$, —CH$_2$CH$_2$NHCH$_3$, —CH$_2$CH$_2$N(CH$_3$)—CH$_3$, —CH$_2$SCH$_2$CH$_3$, —S(O)CH$_3$, —CH$_2$CH$_2$S(O)$_2$CH$_3$, —CH$_2$CH$_2$OCH$_3$, —CHCHN(CH$_3$)CH$_3$, —CH$_2$NHOCH$_3$ and —CH$_2$OC(CH$_3$)$_3$.

The term "heteroaryl" as used herein refers to a single aromatic ring that has at least one atom other than carbon in the ring, wherein the atom is selected from the group consisting of oxygen, nitrogen and sulfur, the term also includes multiple condensed ring systems that have at least one such aromatic ring, which multiple condensed ring systems are further described below. Thus, the term includes single aromatic rings of from about 1 to 6 annular carbon atoms and about 1-4 annular heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycloalkyls, (to form for example a 1,2,3,4-tetrahydronaphthyridinyl such as 1,2,3,4-tetrahydro-1,8-naphthyridinyl), cycloalkyls (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 annular carbon atoms and about 1-6 annular heteroatoms. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

"Heterocycloalkyl" or "heterocyclyl" as used herein refers to a single saturated or partially unsaturated non-aromatic ring or a non-aromatic multiple ring system that has at least one heteroatom in the ring (at least one annular heteroatom selected from oxygen, nitrogen, and sulfur).

Unless otherwise specified, a heterocycloalkyl group has from 5 to about 20 annular atoms, for example from 5 to 14 annular atoms, for example from 5 to 10 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The term also includes single saturated or partially unsaturated rings (e.g., 5, 6, 7, 8, 9, or 10-membered rings) having from about 4 to 9 annular carbon atoms and from about 1 to 3 annular heteroatoms selected from the group consisting of oxygen, nitrogen and sulfur in the ring. The rings of the multiple condensed ring system can be connected to each other via fused, spiro and bridged bonds when allowed by valency requirements. Heterocycloalkyl groups include, but are not limited to, azetidine, aziridine, imidazolidine, imino-oxoimidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine. N-chloropiperidine, and the like.

"Hydroxy" or "hydroxyl" refers to the group —OH.

"Oxo" refers to a double-bonded oxygen (═O). In compounds where an oxo group is bound to an sp² nitrogen atom, an N-oxide is indicated.

It is understood that combinations of chemical groups may be used and will be recognized by persons of ordinary skill in the art. For instance, the group "hydroxyalkyl" would refer to a hydroxyl group attached to an alkyl group.

The terms "optional" or "optionally" mean that the subsequently described event or circumstance may but need not occur, and that the description includes instances where the event or circumstance occurs and instances in which it does not.

"Tautomers" as used herein refers to isomers of a compound that differ from each other in the position of a proton and/or in electronic distribution. Thus, both proton migration tautomers and valence tautomers are intended and described and it is understood that more than two tautomers may exist for a given compound. Examples of tautomers include, but are not limited to, enol-keto tautomers:

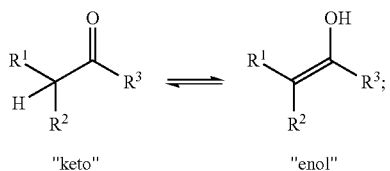

"keto"    "enol"

imine-enamine tautomers:

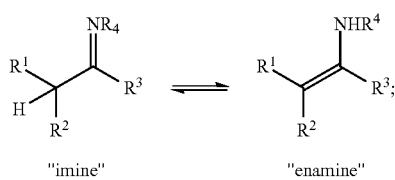

"imine"    "enamine"

lactam-lactim tautomers:

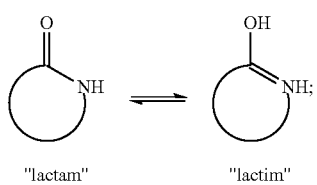

"lactam"    "lactim"

amide-imidic acid tautomers:

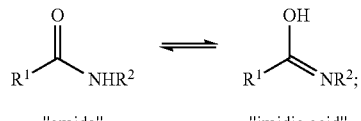

"amide"    "imidic acid"

amino-imine tautomers:

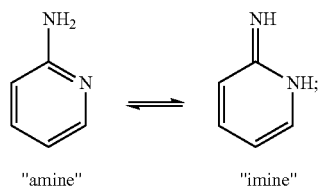

"amine"    "imine"

and tautomeric forms of heteroaryl groups containing a ring atom attached to both a ring —NH— moiety and a ring ═N— moiety such as present in pyrazoles, imidazoles, benzimidazoles, triazoles and tetrazoles (see, e.g., Smith, March's Advanced Organic Chemistry (5$^{th}$ ed.), pp. 1218-1223, Wiley-Interscience, 2001; Katritzky A, and Elguero J. et al., The Tautomerism of Heterocycles, Academic Press (1976)).

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion (e.g. a sodium or potassium), an alkaline earth ion (e.g. calcium or magnesium), or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott. Williams & Wilkins, Philadelphia, Pa., (2005), at p. 732, Table 38-5, both of which are hereby incorporated by reference herein.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming an individual's HIV$^+$ status and assessing the individual's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in individuals with functioning immune systems but does occur in AIDS patients). Development may also refer to disease progression that may be initially undetectable and includes occurrence, recurrence and onset.

As used herein. "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to an subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "effective amount" refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

Except as expressly defined otherwise, the present disclosure includes all tautomers of compounds detailed herein, even if only one tautomer is expressly represented (e.g., both tautomeric forms are intended and described by the presentation of one tautomeric form where a pair of two tautomers may exist). For example, if reference is made to a compound containing a lactam (e.g., by structure or chemical name), it is understood that the corresponding lactim tautomer is included by this disclosure and described the same as if the lactim were expressly recited either alone or together with the lactam. Where more than two tautomers may exist, the present disclosure includes all such tautuomers even if only a single tautomeric form is depicted by chemical name and/or structure.

Compositions detailed herein may comprise a compound of the present disclosure in a racemic or non-racemic mixture of stereoisomers or may comprise a compound of the present disclosure as a substantially pure isomer. Stereoisomers include enantiomers and diastereomers. The compounds may exist in stercoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

It is understood by one skilled in the art that this disclosure also includes any compound disclosed herein that may be enriched at any or all atoms above naturally occurring isotopic ratios with one or more isotopes such as, but not limited to, deuterium ($^2$H or D).

Disclosed are also compounds in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Compounds of a given formula described herein encompasses the compound disclosed and all pharmaceutically acceptable salts, esters, stereoisomers, tautomers, prodrugs, solvates, and deuterated forms thereof, unless otherwise specified.

Depending on the particular substituents, the compounds of Formula I may exist in tautomeric forms. It is understood that two or more tautomeric forms may exist for a given compound structure. For example, a compound of Formula I (where $R^3$ is —OH) may exist in at least the following tautomeric forms:

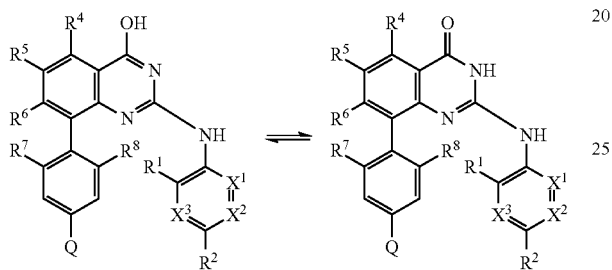

As is understood by those of skill in the art, various other tautomeric forms may exist and are intended to be encompassed by the compounds of Formula I. Some descriptions herein expressly refer to "tautomers thereof" but it is understood that, even in the absence of such language, tautomers are intended and described. Further, it is understood that the compounds of Formula I may shift between various tautomeric forms or exist in various ratios of each form based on the particular environment of the compound.

The compounds disclosed herein may contain chiral centers, which may be either of the (R) or (S) configuration, or which may comprise a mixture thereof. Accordingly, the present disclosure includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present disclosure.

The compounds of the present disclosure may be compounds according to Formula (I) with one or more chiral centers, which may be either of the (R) or (S) configuration, or which may comprise a mixture thereof.

The present disclosure includes both racemic mixtures of a compound of formula I and isolated isomers of Formula (I) or any variation thereof. Where more than one chiral center is present in a compound of the present disclosure, some, none, or all of the chiral centers may be enantiomerically enriched. Thus, mixtures of a compound of Formula (I) may be racemic with respect to one or more chiral centers and/or enantiomerically enriched with respect to one or more chiral centers.

The present disclosure relates to a compound of formula (I)

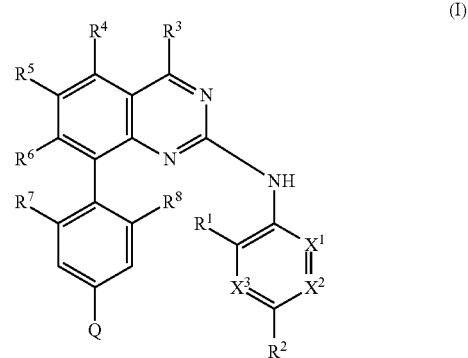

wherein

Q is

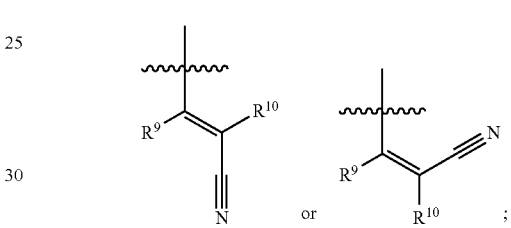

$X^1$, $X^2$, and $X^3$ are each independently N or $C(R^{11})$, provided that, at most 2 of $X^1$, $X^2$, and $X^3$ are N;

$R^1$ is —H, —CN, —OR$^a$, —C(O)OR$^a$, halogen, $C_{1-6}$alkyl, $C_{3-10}$cycloalkyl, or $C_{1-6}$heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^2$ is —H, —CN, —OR$^a$, —NR$^a$R$^b$, —C(O)OR$^a$, halogen, $C_{1-6}$alkyl, $C_{3-10}$cycloalkyl, or $C_{1-6}$ heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^3$ is —H, —OR$^a$, —SR$^a$, —NR$^a$R$^b$, —NHC(O)NR$^a$R$^b$, $C_{1-6}$alkyl, $C_{3-10}$cycloalkyl, or $C_{1-6}$ heteroalkyl, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^4$ is —H, —OR$^a$, halogen, —NO$_2$, —CN, —NR$^a$R$^b$, —NHC(O)NR$^a$R$^b$, —OC(O)NR$^a$R$^b$, —CH$_2$C(O)NR$^a$R$^b$, $C_{1-6}$alkyl, $C_{3-10}$cycloalkyl, or $C_{1-6}$ heteroalkyl, wherein each $C_{1-6}$alkyl, $C_{3-10}$ cycloalkyl, and $C_{1-6}$ heteroalkyl is optionally substituted with 1, 2, 3, 4, or 5 $R^{12}$ groups, which may be same or different;

$R^5$ is —H, —OR$^a$, halogen, —NO$_2$, —CN, —NR$^a$R$^b$, —NHC(O)NR$^a$R$^b$, —OC(O)NR$^a$R$^b$, —CH$_2$C(O)NR$^a$R$^b$, $C_{1-6}$alkyl, $C_{3-10}$cycloalkyl, or $C_{1-6}$ heteroalkyl, wherein each $C_{1-6}$alkyl, $C_{3-10}$ cycloalkyl, and $C_{1-6}$ heteroalkyl is optionally substituted with 1, 2, 3, 4, or 5 $R^{12}$ groups, which may be same or different;

$R^6$ is —H, —OR$^a$, halogen, —NO$_2$, —CN, —NR$^a$R$^b$, —NHC(O)NR$^a$R$^b$, —OC(O)NR$^a$R$^b$, —CH$_2$C(O)NR$^a$R$^b$, $C_{1-6}$alkyl, $C_{3-10}$cycloalkyl, or $C_{1-6}$ heteroalkyl, wherein each $C_{1-6}$alkyl, $C_{3-10}$ cycloalkyl, and $C_{1-6}$ heteroalkyl is optionally substituted with 1, 2, 3, 4, or 5 $R^{12}$ groups, which may be same or different;

$R^7$ is $C_{1-6}$alkyl, $C_{3-10}$cycloalkyl, $C_{1-6}$heteroalkyl, halogen, —$OR^a$, —CN, or —$NO_2$, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^8$ is $C_{1-6}$alkyl, $C_{3-10}$cycloalkyl, $C_{1-6}$heteroalkyl, halogen, —$OR^a$, —CN, or —$NO_2$, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

$R^9$ is —H, $C_{1-6}$alkyl, or $C_{3-10}$cycloalkyl, wherein each $C_{1-6}$alkyl and $C_{3-10}$cycloalkyl is optionally substituted with 1, 2, 3, 4, or 5 $R^{12}$ groups, which may be same or different;

$R^{10}$ is —H, $C_{1-6}$alkyl, or $C_{3-10}$cycloalkyl, wherein each $C_{1-6}$alkyl and $C_{3-10}$cycloalkyl is optionally substituted with 1, 2, 3, 4, or 5 $R^{12}$ groups, which may be same or different;

each $R^{11}$ is independently —H, —CN, —$OR^a$, —C(O)$OR^a$, halogen, $C_{1-6}$alkyl, $C_{3-10}$ cycloalkyl, or $C_{1-6}$heteroalkyl, which may be same or different, wherein each $C_{1-6}$alkyl, $C_{3-10}$cycloalkyl, and $C_{1-6}$heteroalkyl is optionally substituted with 1, 2, 3, 4, or 5 $R^{12}$ groups, which may be same or different;

each $R^{12}$ is independently $C_{1-6}$alkyl, $C_{3-10}$cycloalkyl, $C_{1-6}$heteroalkyl, 5-10 membered heterocyclyl, $C_{6-10}$aryl, 5-10 membered heteroaryl, halogen, —$OR^a$, —C(O)$R^a$, —C(O)$OR^a$, —C(O)$NR^aR^b$, —OC(O)$NR^aR^b$, —$NR^aC(O)OR^b$, —$SR^a$, —S(O)$_{1-2}R^a$, —S(O)$_2$F, —S(O)$_2NR^aR^b$, —$NR^aS(O)_2R^b$, —$N_3$, —CN, or —$NO_2$; wherein each $C_{1-6}$alkyl, $C_{3-10}$cycloalkyl, $C_{1-6}$heteroalkyl, and 5-10 membered heterocyclyl is optionally substituted with 1, 2, 3, 4, or 5 substituents selected from halogen, —$OR^a$, —C(O)$R^a$, —C(O)$OR^a$, —C(O)$NR^aR^b$, —OC(O)$NR^aR^b$, —$NR^aC(O)OR^b$, —$SR^a$, —S(O)$_{1-2}R^a$, —S(O)$_2$F, —S(O)$_2NR^aR^b$, —$NR^aS(O)_2R^b$, —$N_3$, —CN, and —$NO_2$, groups, which may be same or different;

each $R^a$ and $R^b$ is independently —H, —$NH_2$, $C_{1-6}$alkyl, $C_{3-10}$cycloalkyl, $C_{1-6}$heteroalkyl, 5-10 membered heterocyclyl, $C_{6-10}$aryl, or 5-10 membered heteroaryl, wherein each $C_{1-6}$alkyl, $C_{3-10}$cycloalkyl, $C_{1-6}$heteroalkyl, 5-10 membered heterocyclyl, $C_{6-10}$aryl, and 5-10 membered heteroaryl is optionally substituted with 1, 2, 3, 4, or 5 $R^{13}$ groups, which may be same or different; or $R^a$ and $R^b$ together with the atoms to which they are attached form a 5-10 membered heterocycle; and each $R^{13}$ is independently —CN, halogen, $C_{1-6}$alkyl, $C_{3-10}$cycloalkyl, $C_{1-6}$heteroalkyl, or 5-10 membered heterocyclyl;

or a tautomer or a pharmaceutically acceptable salt thereof.

In certain embodiments in formula (I), $R^2$ is —H, —CN, —$OR^a$, or $C_{1-6}$alkyl.

In certain embodiments in formula (I), $R^2$ is —CN.

In one variation, the present disclosure relates to compounds of formula (II), which are compounds of formula (I):

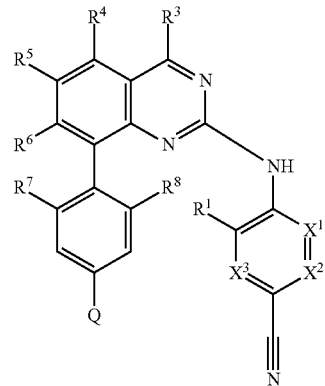

(II)

wherein
Q is

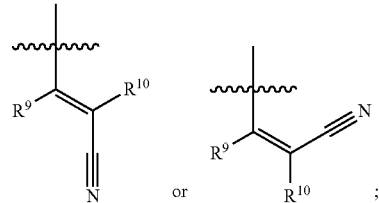

$X^1$, $X^2$, and $X^3$ are each independently N or C($R^{11}$), provided that, at most 2 of $X^1$, $X^2$, and $X^3$ are N;

$R^1$ is —H, —CN, —$OR^a$, —C(O)$OR^a$, halogen, or $C_{1-6}$alkyl, wherein $C_{1-6}$alkyl is optionally substituted with 1, 2, 3, 4, or 5 $R^{12}$ groups, which may be same or different;

$R^3$ is —H, —$OR^a$, —$NR^aR^b$, —NHC(O)$NR^aR^b$, $C_{1-6}$alkyl, or $C_{1-6}$heteroalkyl, wherein each $C_{1-6}$alkyl and $C_{1-6}$heteroalkyl is optionally substituted with 1, 2, 3, 4, or 5 $R^{12}$ groups, which may be same or different;

$R^4$ is —H, —$OR^a$, halogen, —$NO_2$, —CN, —$NR^aR^b$, $C_{1-6}$alkyl, or $C_{1-6}$ heteroalkyl, wherein each $C_{1-6}$alkyl and $C_{1-6}$ heteroalkyl is optionally substituted with 1, 2, 3, 4, or 5 $R^{12}$ groups, which may be same or different;

$R^5$ is —H, —$OR^a$, halogen, —$NO_2$, —CN, —$NR^aR^b$, $C_{1-6}$alkyl, or $C_{1-6}$ heteroalkyl, wherein each $C_{1-6}$alkyl and $C_{1-6}$ heteroalkyl is optionally substituted with 1, 2, 3, 4, or 5 $R^{12}$ groups, which may be same or different;

$R^6$ is —H, —$OR^a$, halogen, —$NO_2$, —CN, —$NR^aR^b$, $C_{1-6}$alkyl, or $C_{1-6}$ heteroalkyl, wherein each $C_{1-6}$alkyl and $C_{1-6}$ heteroalkyl is optionally substituted with 1, 2, 3, 4, or 5 $R^{12}$ groups, which may be same or different;

$R^7$ is $C_{1-6}$alkyl, $C_{1-6}$heteroalkyl, halogen, —$OR^a$, —CN, or —$NO_2$, wherein each $C_{1-6}$alkyl is optionally substituted with 1, 2, 3, 4, or 5 $R^{12}$ groups, which may be same or different;

$R^8$ is $C_{1-6}$alkyl, $C_{1-6}$heteroalkyl, halogen, —$OR^a$, —CN, or —$NO_2$, wherein each $C_{1-6}$ alkyl is optionally substituted with 1, 2, 3, 4, or 5 $R^{12}$ groups, which may be same or different;

$R^9$ is —H or $C_{1-6}$alkyl, wherein $C_{1-6}$alkyl is optionally substituted with 1, 2, 3, 4, or 5 $R^{12}$ groups, which may be same or different;

$R^{10}$ is —H or $C_{1-6}$alkyl wherein $C_{1-6}$alkyl is optionally substituted with 1, 2, 3, 4, or 5 $R^{12}$ groups, which may be same or different;

each $R^{11}$ is independently —H, —CN, —$OR^a$, —C(O)$OR^a$, halogen, or $C_{1-6}$alkyl, which may be same or different, wherein $C_{1-6}$alkyl is optionally substituted with 1, 2, 3, 4, or 5 $R^{12}$ groups, which may be same or different;

each $R^{12}$ is independently $C_{1-6}$alkyl, $C_{3-10}$cycloalkyl, $C_{1-6}$heteroalkyl, 5-10 membered heterocyclyl, $C_{6-10}$aryl, 5-10 membered heteroaryl, halogen, —$OR^a$, —C(O)$R^a$, —C(O)$OR^a$, —C(O)$NR^aR^b$, —OC(O)$NR^aR^b$, —$NR^aC(O)OR^b$, —$SR^a$, —$S(O)_{1-2}R^a$, —$S(O)_2F$, —$S(O)_2NR^aR^b$, —$NR^aS(O)_2R^b$, —$N_3$, —CN, or —$NO_2$; wherein each $C_{1-6}$alkyl, $C_{3-10}$cycloalkyl, $C_{1-6}$heteroalkyl, and 5-10 membered heterocyclyl is optionally substituted with 1, 2, 3, 4, or 5 substituents selected from halogen, —$OR^a$, —C(O)$R^a$, —C(O)$OR^a$, —C(O)$NR^aR^b$, —OC(O)$NR^aR^b$, —$NR^aC(O)OR^b$, —$SR^a$, —$S(O)_{1-2}R^a$, —$S(O)_2F$, —$S(O)_2NR^aR^b$, —$NR^aS(O)_2R^b$, —$N_3$, —CN, and —$NO_2$, groups, which may be same or different;

each $R^a$ and $R^b$ is independently —H, $C_{1-6}$alkyl, $C_{3-10}$cycloalkyl, $C_{1-6}$heteroalkyl, 5-10 membered heterocyclyl, $C_{6-10}$aryl, or 5-10 membered heteroaryl, wherein each $C_{1-6}$alkyl, $C_{3-10}$cycloalkyl, $C_{1-6}$heteroalkyl, 5-10 membered heterocyclyl, $C_{6-10}$aryl, and 5-10 membered heteroaryl is optionally substituted with 1, 2, 3, 4, or 5 $R^{13}$ groups, which may be same or different; or $R^a$ and $R^b$ together with the atoms to which they are attached form a 5-10 membered heterocycle; and each $R^{13}$ is independently —CN, halogen, $C_{1-6}$alkyl, $C_{3-10}$cycloalkyl, $C_{1-6}$heteroalkyl, or 5-10 membered heterocyclyl, or a tautomer or a pharmaceutically acceptable salt thereof.

In certain embodiments in formula (I) and (II), Q is

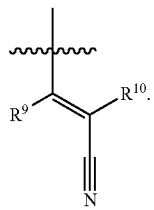

In certain embodiments in formula (I) and (II), Q is

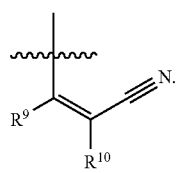

In certain embodiments in formula (I) and (II), $X^1$, $X^2$, and $X^3$ are each independently N or C($R^{11}$), wherein 2 of $X^1$, $X^2$, and $X^3$ are N. In certain embodiments, $X^1$, $X^2$, and $X^3$ are each independently N or C($R^{11}$), wherein one of $X^1$, $X^2$, and $X^3$ is N. In certain embodiments, $X^1$, $X^2$, and $X^3$ are each independently N or C($R^{11}$), wherein none of $X^1$, $X^2$, and $X^3$ is N.

In certain embodiments in formula (I) and (II), $X^1$, $X^2$, and $X^3$ are each C($R^{11}$). In certain embodiments in formula (I) and (II), $X^1$, $X^2$, and $X^3$ are each CH. In certain embodiments, $X^1$ is N; $X^2$ is C($R^{11}$); and $X^3$ is C($R^{11}$). In certain embodiments, $X^1$ is N; $X^2$ is CH; and $X^3$ is CH.

In certain embodiments in formula (I) and (II), $X^1$ is N; $X^2$ is N; and $X^3$ is C($R^{11}$). In certain embodiments, $X^1$ is N; $X^2$ is C($R^{11}$); and $X^3$ is N. In certain embodiments, $X^1$ is C($R^{11}$); $X^2$ is N; and $X^3$ is C($R^{11}$).

In certain embodiments in formula (I) and (II), $R^1$ is —H or $C_{1-6}$alkyl. In certain embodiments, $R^1$ is —H. In certain embodiments, $R^1$ is $C_{1-6}$alkyl. In certain embodiments, $R^1$ is methyl.

In certain embodiments in formula (I) and (II), $X^1$, $X^2$, and $X^3$ are C($R^{11}$); each $R^{11}$ are independently selected from —H, —CN, —$OR^a$, halogen, and $C_{1-6}$alkyl; and $R^1$ is selected from —H, —CN, —$OR^a$, halogen, and $C_{1-6}$alkyl. In certain embodiments, $X^1$, $X^2$, and $X^3$ are C($R^{11}$); each $R^{11}$ are —H; and $R^1$ is —H.

In certain embodiments in formula (I) and (II), $X^1$ is N; $X^2$ is C($R^{11}$); and $X^3$ is C($R^{11}$); each $R^{11}$ are independently selected from —H, —CN, —$OR^a$, halogen, and $C_{1-6}$alkyl; and $R^1$ is selected from —H, —CN, —$OR^a$, halogen, and $C_{1-6}$alkyl. In certain embodiments, $X^1$ is N; $X^2$ is C($R^{11}$); and $X^3$ is C($R^{11}$); each $R^{11}$ are —H; and $R^1$ is selected from —H and $C_{1-6}$alkyl. In certain embodiments, $X^1$ is N; $X^2$ is C($R^{11}$); and $X^3$ is C($R^{11}$); each $R^{11}$ are —H; and $R^1$ is —H.

In certain embodiments in formula (I) and (II),

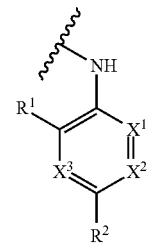

of formula (I) or (II) is selected from

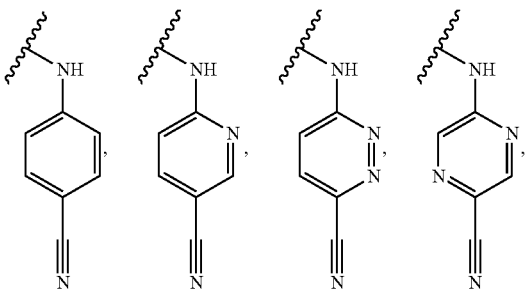

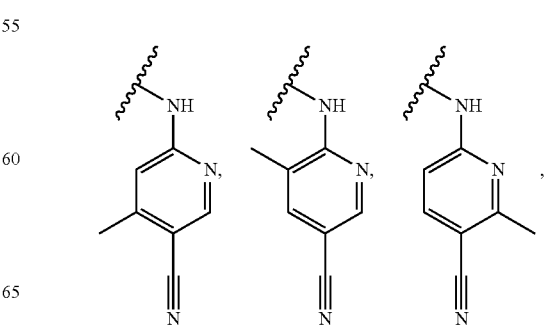

-continued

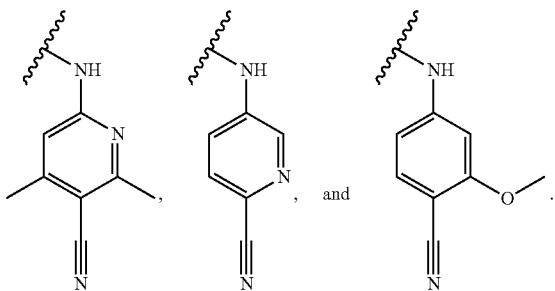

In certain embodiments in formula (I) and (II),

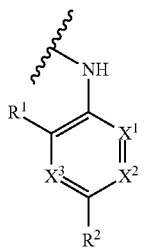

of formula (I) or (II) is

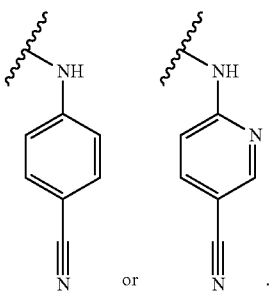 [SMILES: *Nc1ccc(C#N)cc1 ; *Nc1ccc(C#N)cn1]

In certain embodiments,

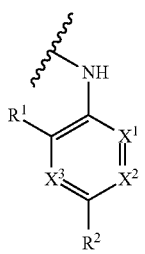

of formula (I) or (II) is

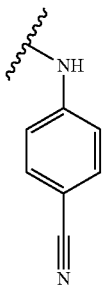

In certain embodiments,

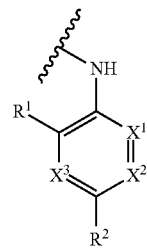

of formula (I) or (II) is

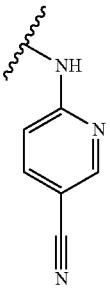

In certain embodiments in formula (I) and (II), $R^3$ is —H, —OR$^a$, —NR$^a$R$^b$, —NHC(O)NR$^a$R$^b$, $C_{1-6}$alkyl, or $C_{1-6}$ heteroalkyl. In certain embodiments, $R^3$ is —H, —OR$^a$, —NR$^a$R$^b$, or —NHC(O)NR$^a$R$^b$.

In certain embodiments in formula (I) and (II), $R^3$ is —NR$^a$R$^b$ or —OR$^a$. In certain embodiments, $R^3$ is —NH$_2$ or —OH.

In certain embodiments, $R^3$ is —NR$^a$R$^b$. In certain embodiments, $R^3$ is —NR$^a$R$^b$, wherein each $R^a$ and $R^b$ is independently —H or $C_{1-6}$alkyl, wherein the $C_{1-6}$alkyl is optionally substituted with 1, 2, 3, 4, or 5 $R^{13}$ groups. In certain embodiments, $R^3$ is —NR$^a$R$^b$, wherein each $R^a$ and $R^b$ is independently —H or $C_{1-6}$alkyl. In certain embodiments, $R^3$ is —NR$^a$R$^b$, wherein each $R^a$ and $R^b$ is independently —H, methyl, butyl, or cyclopropylmethyl. In certain embodiments, $R^3$ is —NH$_2$.

In certain embodiments in formula (I) and (II), $R^3$ is —OR$^a$. In certain embodiments, $R^3$ is —OH.

In certain embodiments in formula (I) and (II), $R^3$ is —H. In certain embodiments, $R^3$ is —NHC(O)NR$^a$R$^b$. In certain embodiments, $R^3$ is —NHC(O)NH$_2$.

In certain embodiments in formula (I) and (II), $R^4$ is —H, —OR$^a$, halogen, —NO$_2$, —CN, —NR$^a$R$^b$, —NHC(O)NR$^a$R$^b$, or $C_{1-6}$alkyl. In certain embodiments, $R^4$ is —H or —OR$^a$.

In certain embodiments in formula (I) and (II), R$^5$ is —H, —OR$^a$, halogen, —NO$_2$, —CN, —NR$^a$R$^b$, —NHC(O)NR$^a$R$^b$, or C$_{1-6}$alkyl. In certain embodiments, R$^5$ is —H, —OR$^a$, halogen, —NO$_2$, —CN, —NR$^a$R$^b$, or C$_{1-6}$alkyl.

In certain embodiments in formula (I) and (II), R$^6$ is —H, —OR$^a$, halogen, —NO$_2$, —CN, —NR$^a$R$^b$, —NHC(O)NR$^a$R$^b$, or C$_{1-6}$alkyl. In certain embodiments in formula (I) and (II), R$^6$ is —H.

In certain embodiments in formula (I) and (II), two of R$^4$, R$^5$, and R$^6$ are —H and one of R$^4$, R$^5$, and R$^6$ is —H, —OR$^a$, halogen, —NO$_2$, —CN, —NR$^a$R$^b$, —NHC(O)NR$^a$R$^b$, or C$_{1-6}$alkyl. In certain embodiments, two of R$^4$, R$^5$, and R$^6$ are —H and one of R$^4$, R$^5$, and R$^6$ is —H, —OR$^a$, halogen, —NO$_2$, —NR$^a$R$^b$, or C$_{1-6}$alkyl. In certain embodiments, two of R$^4$, R$^5$, and R$^6$ are —H and one of R$^4$, R$^5$, and R$^6$ is —H, —OCH$_3$, halogen, —NO$_2$, —NH$_2$, or methyl.

In certain embodiments in formula (I) and (II), R$^4$, R$^5$, and R$^6$ are —H.

In certain embodiments in formula (I) and (II), R$^7$ is C$_{1-6}$alkyl, C$_{1-6}$heteroalkyl, halogen, —OR$^a$, —CN, or —NO$_2$. In certain embodiments, R$^7$ is C$_{1-6}$alkyl, halogen, or —OR$^a$.

In certain embodiments in formula (I) and (II), R$^8$ is C$_{1-6}$alkyl, C$_{1-6}$heteroalkyl, halogen, —OR$^a$, —CN, or —NO$_2$. In certain embodiments, R$^8$ is C$_{1-6}$alkyl, halogen, or —OR$^a$.

In certain embodiments in formula (I) and (II), R$^7$ and R$^8$ are the same and are selected from C$_{1-6}$alkyl, C$_{1-6}$heteroalkyl, halogen, —OR$^a$, —CN, and —NO$_2$. In certain embodiments, R$^7$ and R$^8$ are the same and are selected from C$_{1-6}$alkyl, halogen, or —OR$^a$.

In certain embodiments in formula (I) and (II), R$^7$ and R$^8$ are C$_{1-6}$alkyl. In certain embodiments, R$^7$ and R$^8$ are methyl.

In certain embodiments in formula (I) and (II), R$^7$ and R$^8$ are —OR$^a$. In certain embodiments, R$^7$ and R$^8$ are —OCH$_3$.

In certain embodiments in formula (I) and (II), R$^7$ and R$^8$ are halogen. In certain embodiments, R$^7$ and R$^8$ are fluoro.

In certain embodiments in formula (I) and (II), R$^9$ is —H or C$_{1-6}$alkyl. In certain embodiments, R$^9$ is —H or methyl.

In certain embodiments in formula (I) and (II), R$^{10}$ is —H or C$_{1-6}$alkyl. In certain embodiments in formula (I) and (II), R$^{10}$ is —H or methyl.

In certain embodiments in formula (I) and (II), R$^9$ is —H or C$_{1-6}$alkyl; and R$^{10}$ is —H or C$_{1-6}$alkyl. In certain embodiments, R$^9$ is —H or methyl; and R$^{10}$ is —H or methyl. In certain embodiments in formula (I) and (II), R$^9$ and R$^{10}$ are —H.

In certain embodiments in formula (I) and (II), Q is selected from

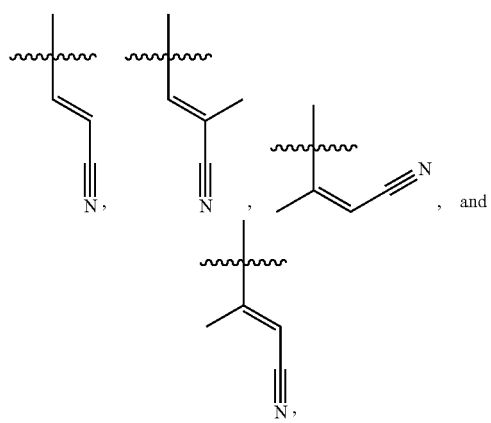

In certain embodiments in formula (I) and (II), Q is

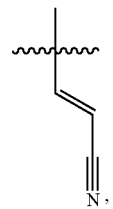

It is understood that any variable for Q of formula (I) and (II) may be combined with any variable of R$^3$ in formula (I) and (II), the same as if each and every combination were specifically and individually listed. For example, in one variation of formula (I) and (II), Q is

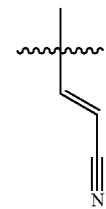 [SMILES: */C=C/C#N]

and R$^3$ is —NH$_2$. In another variation, Q is

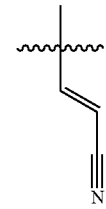 [SMILES: */C=C/C#N]

and R$^3$ is —OH.

It is understood that any variable for R$^7$ of formula (I) and (II) may be combined with any variable of R$^3$ in formula (I) and (II), the same as if each and every combination were specifically and individually listed. For example, in one variation of formula (I) and (II), R$^7$ is methyl and R$^3$ is —NH$_2$. In another variation, R$^7$ is methyl and R$^3$ is —OH.

It is understood that any variable for R$^8$ of formula (I) and (II) may be combined with any variable of R$^3$ in formula (I) and (II), the same as if each and every combination were specifically and individually listed. For example, in one variation of formula (I) and (II), R$^8$ is methyl and R$^3$ is —NH$_2$. In another variation, R$^8$ is methyl and R$^3$ is —OH.

It is understood that any variable for R$^4$, R$^5$, and R$^6$ of formula (I) and (II) may be combined with any variable of R$^3$ in formula (I) and (II), the same as if each and every combination were specifically and individually listed. For example, in one variation of formula (I) and (II), R$^4$, R$^5$, and R$^6$ are each —H; and R$^3$ is —NH$_2$. In another variation, R$^4$, R$^5$, and R$^6$ are each —H; and R$^3$ is —OH.

It is understood that any variable for X$^1$, X$^2$, and X$^3$ of formula (I) and (II) may be combined with any variable of R$^3$ in formula (I) and (II), the same as if each and every combination were specifically and individually listed. For example, in one variation of formula (I) and (II), X$^1$, X$^2$, and X$^3$ are each CH; and R$^3$ is —NH$_2$. In one variation of formula (I) and (II), $X^1$ is N; $X^2$ is CH; and $X^3$ is CH; and $R^3$ is —$NH_2$. In another variation, $X^1$ is N; $X^2$ is CH; and $X^3$ is CH; and $R^3$ is —OH. In another variation, $X^1$, $X^2$, and $X^3$ are each CH; and $R^3$ is —OH.

It is understood that any variable for $R^1$ of formula (I) and (II) may be combined with any variable of $R^3$ in formula (I) and (II), the same as if each and every combination were specifically and individually listed. For example, in one variation of formula (I) and (II), $R^1$ is hydrogen and $R^3$ is —$NH_2$. In another variation, $R^1$ is hydrogen and $R^3$ is —OH.

In certain embodiments of formula (I) and (II), where $R^3$ is —$NH_2$, the compounds may have any one or more of the following structural features:
a) $X^1$, $X^2$, and $X^3$ are each CH;
b) $R^7$ is methyl;
c) $R^8$ is methyl;
d) Q is

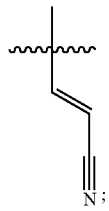

and
e) $R^4$, $R^5$, and $R^6$ are each —H.

In one variation, the compounds conform to at least one of features (a)-(e). In another variation, the compounds conform to two or more (and in certain variations, all) of features (a)-(e). In a particular variation, the compounds conform to feature (a). In another variation, the compounds conform to features (a), (b), and (c). In another variation, the compounds conform to features (a) and (d). In another variation, the compounds conform to features (a) and (e).

In certain embodiments of formula (I) and (II), where $R^3$ is —OH, the compounds may have any one or more of the following structural features:
a) $X^1$ is N; $X^2$ is CH; and $X^3$ is CH;
b) $R^7$ is methyl;
c) $R^8$ is methyl;
d) Q is

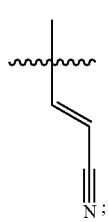

and
e) $R^4$, $R^5$, and $R^6$ are each —H.

In one variation, the compounds conform to at least one of features (a)-(e). In another variation, the compounds conform to two or more (and in certain variations, all) of features (a)-(e). In a particular variation, the compounds conform to feature (a). In another variation, the compounds conform to features (a), (b), and (c). In another variation, the compounds conform to features (a) and (d). In another variation, the compounds conform to features (a) and (e).

In certain embodiments of formula (I) and (II), where Q is

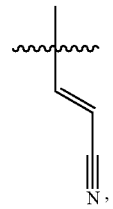 [SMILES: */C=C/C#N]

the compounds may have any one or more of the following structural features:
a) $X^1$, $X^2$, and $X^3$ are each CH or $X^1$ is N; $X^2$ is CH; and $X^3$ is CH;
b) $R^3$ is —$NH_2$ or —OH;
c) $R^7$ and $R^8$ are methyl;
d) $R^4$, $R^5$, and $R^6$ are each —H.

In one variation, the compounds conform to at least one of features (a)-(d). In another variation, the compounds conform to two or more (and in certain variations, all) of features (a)-(d). In a particular variation, the compounds conform to feature (a). In another variation, the compounds conform to features (a) and (b). In another variation, the compounds conform to features (a), (b), and (c). In another variation, the compounds conform to features (a), (b), and (d).

The present disclosure relates to the following compounds or a pharmaceutically acceptable salt thereof.

| Structure | Compound ID |
|---|---|
| 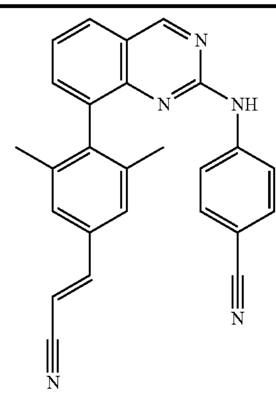 | 1 |
| 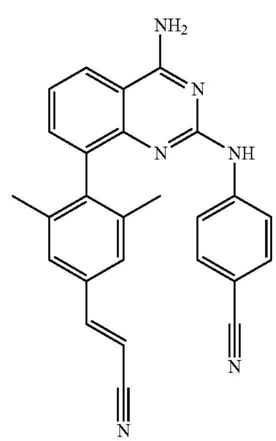 [SMILES: Cc1cc(/C=C/C#N)cc(C)c1-c1cccc2c(N)nc(Nc3ccc(C#N)cc3)nc12] | 2 |

-continued
| Structure | Compound ID |
|---|---|
| 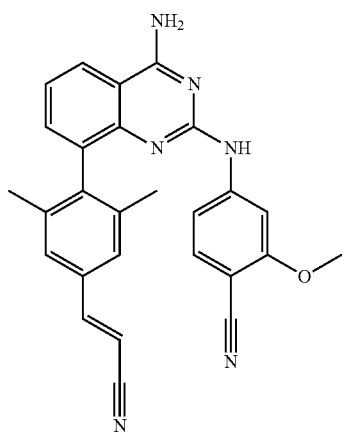 | 3 |
| 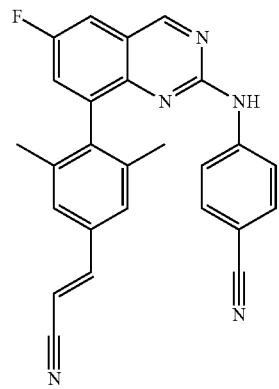 [SMILES: Cc1cc(/C=C/C#N)cc(C)c1-c1cc(F)cc2cnc(Nc3ccc(C#N)cc3)nc12] | 4 |
| 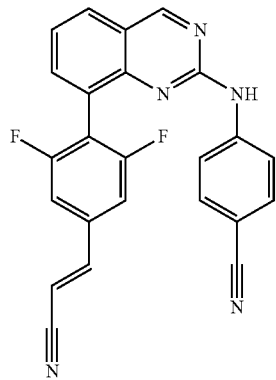 [SMILES: N#C/C=C/c1cc(F)c(-c2cccc3cnc(Nc4ccc(C#N)cc4)nc23)c(F)c1] | 5 |
-continued
| Structure | Compound ID |
|---|---|
| 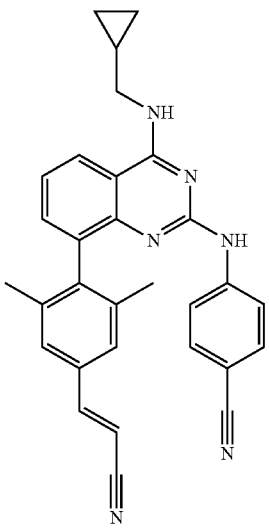 [SMILES: Cc1cc(/C=C/C#N)cc(C)c1-c1cccc2c(NCC3CC3)nc(Nc3ccc(C#N)cc3)nc12] | 6 |
| 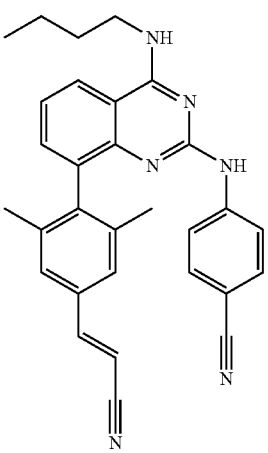 [SMILES: CCCCNc1nc(Nc2ccc(C#N)cc2)nc2c(-c3c(C)cc(/C=C/C#N)cc3C)cccc12] | 7 |
| 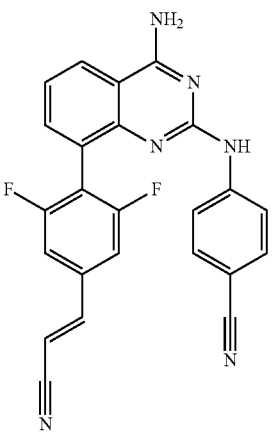 [SMILES: N#C/C=C/c1cc(F)c(-c2cccc3c(N)nc(Nc4ccc(C#N)cc4)nc23)c(F)c1] | 8 |

-continued
| Structure | Compound ID |
|---|---|
| 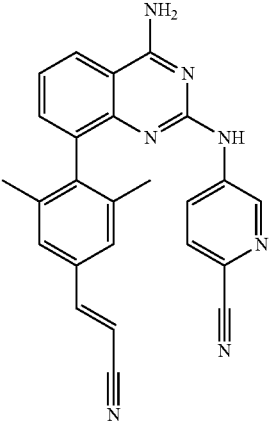 [SMILES: Cc1cc(/C=C/C#N)cc(C)c1-c1cccc2c(N)nc(Nc3ccc(C#N)nc3)nc12] | 9 |
| 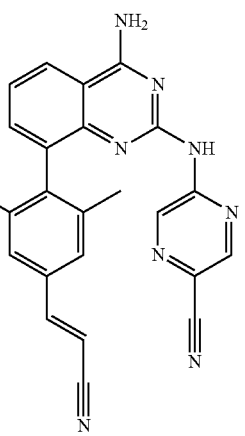 | 10 |
| 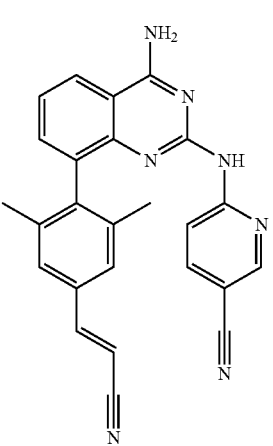 [SMILES: Cc1cc(/C=C/C#N)cc(C)c1-c1cccc2c(N)nc(Nc3ccc(C#N)cn3)nc12] | 11 |
-continued
| Structure | Compound ID |
|---|---|
| 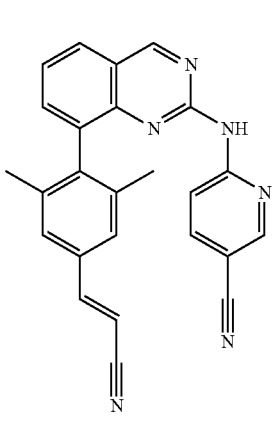 | 12 |
| 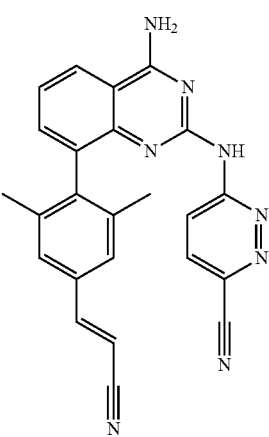 [SMILES: Cc1cc(/C=C/C#N)cc(C)c1-c1cccc2c(N)nc(Nc3ccc(C#N)nn3)nc12] | 13 |
| 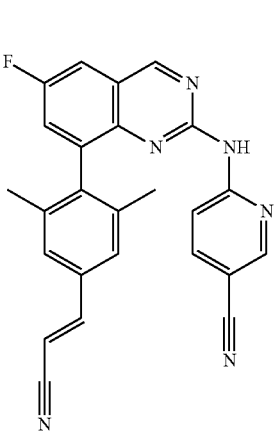 [SMILES: Cc1cc(/C=C/C#N)cc(C)c1-c1cc(F)cc2cnc(Nc3ccc(C#N)cn3)nc12] | 14 |

| Structure | Compound ID |
|---|---|
| 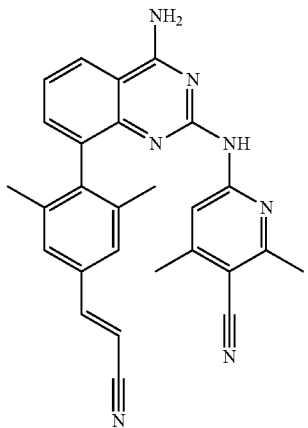 | 15 |
| 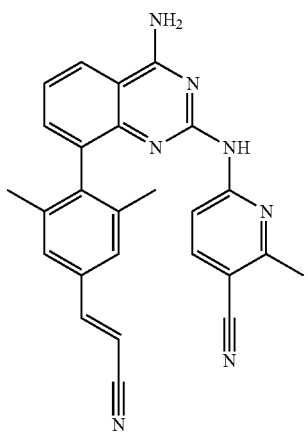 | 16 |
| 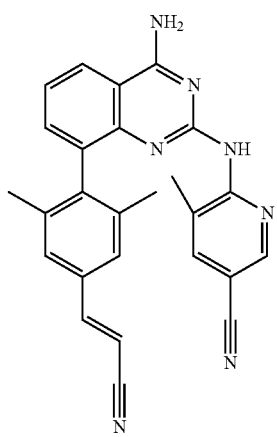 [SMILES: Cc1cc(C#N)cnc1Nc1nc(N)c2cccc(-c3c(C)cc(/C=C/C#N)cc3C)c2n1] | 17 |
| Structure | Compound ID |
|---|---|
| 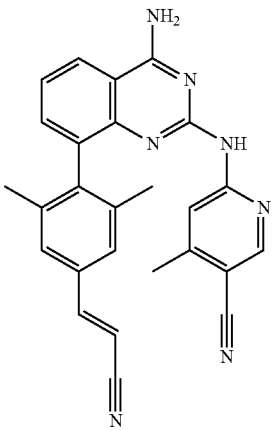 [SMILES: Cc1cc(Nc2nc(N)c3cccc(-c4c(C)cc(/C=C/C#N)cc4C)c3n2)ncc1C#N] | 18 |
| 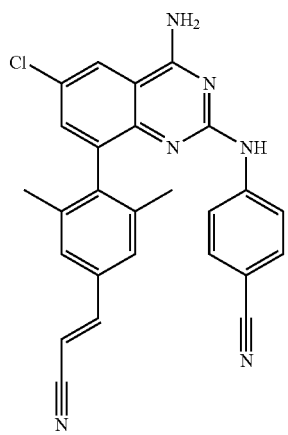 [SMILES: Cc1cc(/C=C/C#N)cc(C)c1-c1cc(Cl)cc2c(N)nc(Nc3ccc(C#N)cc3)nc12] | 19 |

-continued
| Structure | Compound ID |
|---|---|
| 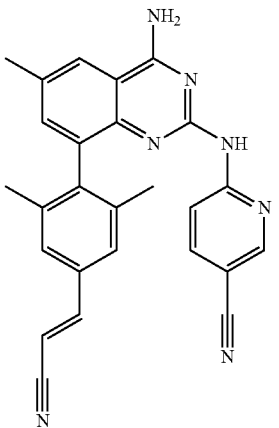 [SMILES: Cc1cc(-c2c(C)cc(/C=C/C#N)cc2C)c2nc(Nc3ccc(C#N)cn3)nc(N)c2c1] | 21 |
| 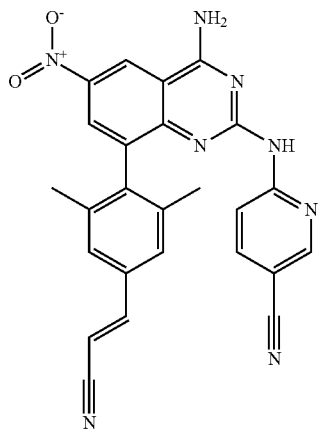 [SMILES: Cc1cc(/C=C/C#N)cc(C)c1-c1cc([N+](=O)[O-])cc2c(N)nc(Nc3ccc(C#N)cn3)nc12] | 22 |
| 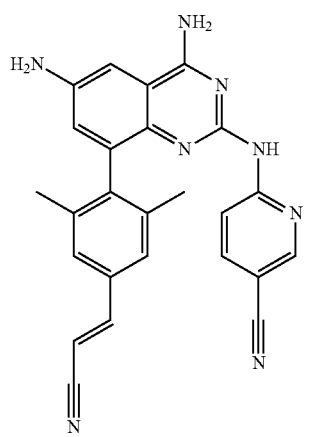 [SMILES: Cc1cc(/C=C/C#N)cc(C)c1-c1cc(N)cc2c(N)nc(Nc3ccc(C#N)cn3)nc12] | 23 |
-continued
| Structure | Compound ID |
|---|---|
| 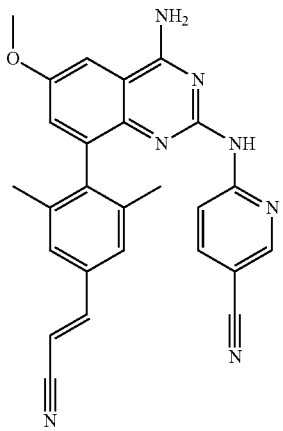 | 24 |
| 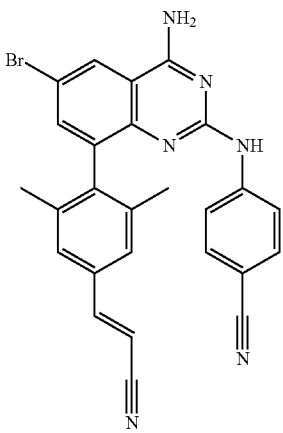 [SMILES: Cc1cc(/C=C/C#N)cc(C)c1-c1cc(Br)cc2c(N)nc(Nc3ccc(C#N)cc3)nc12] | 25 |
| 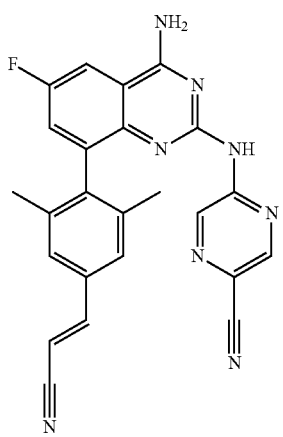 | 26 |

| Structure | Compound ID |
|---|---|
| 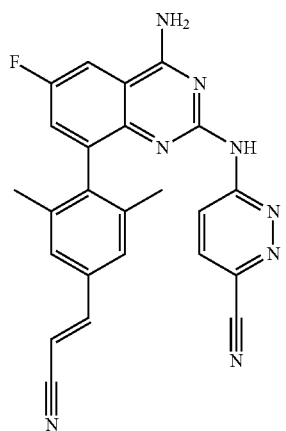 | 27 |
| 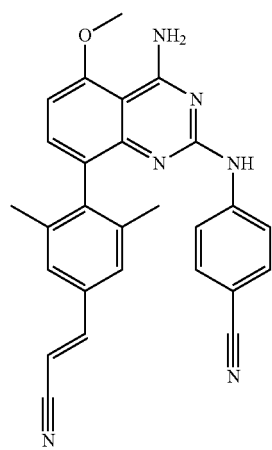 [SMILES: COc1ccc(-c2c(C)cc(/C=C/C#N)cc2C)c2nc(Nc3ccc(C#N)cc3)nc(N)c12] | 28 |
| 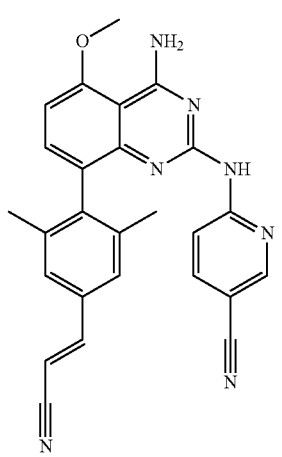 [SMILES: COc1ccc(-c2c(C)cc(/C=C/C#N)cc2C)c2nc(Nc3ccc(C#N)cn3)nc(N)c12] | 29 |
| Structure | Compound ID |
|---|---|
| 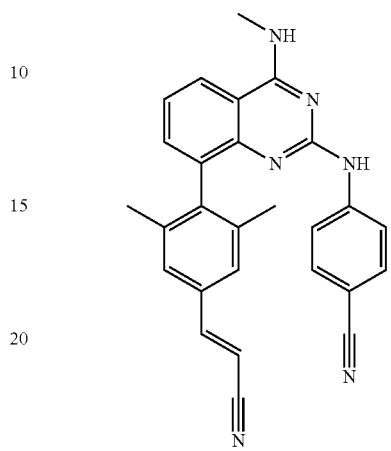 | 30 |
| 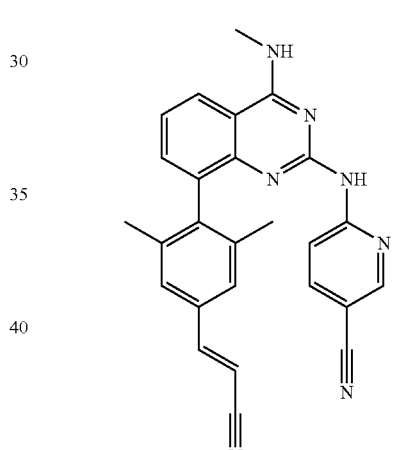 | 31 |
| 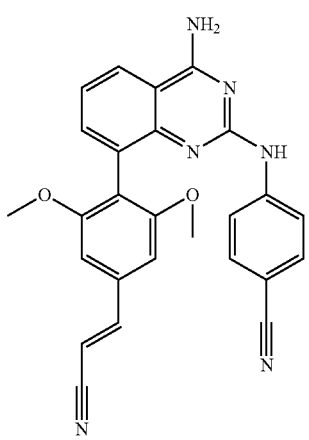 [SMILES: COc1cc(/C=C/C#N)cc(OC)c1-c1cccc2c(N)nc(Nc3ccc(C#N)cc3)nc12] | 32 |

| Structure | Compound ID |
|---|---|
| 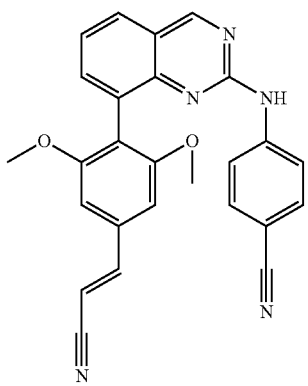 [SMILES: COc1cc(/C=C/C#N)cc(OC)c1-c1cccc2cnc(Nc3ccc(C#N)cc3)nc12] | 33 |
| 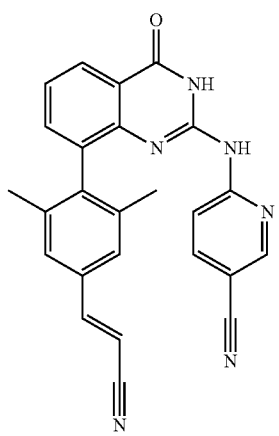 [SMILES: Cc1cc(/C=C/C#N)cc(C)c1-c1cccc2c(=O)[nH]c(Nc3ccc(C#N)cn3)nc12] | 34 |
| 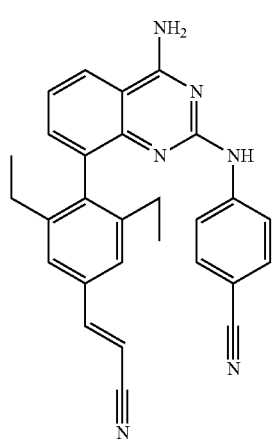 [SMILES: CCc1cc(/C=C/C#N)cc(CC)c1-c1cccc2c(N)nc(Nc3ccc(C#N)cc3)nc12] | 35 |
| Structure | Compound ID |
|---|---|
| 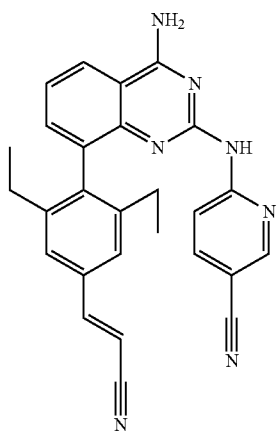 [SMILES: CCc1cc(/C=C/C#N)cc(CC)c1-c1cccc2c(N)nc(Nc3ccc(C#N)cn3)nc12] | 36 |
| 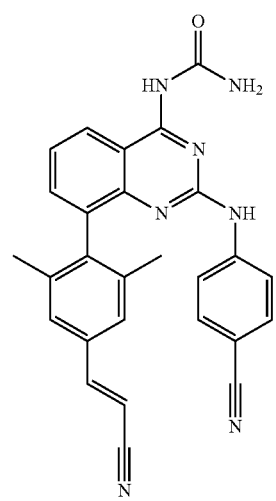 [SMILES: Cc1cc(/C=C/C#N)cc(C)c1-c1cccc2c(NC(N)=O)nc(Nc3ccc(C#N)cc3)nc12] | 37 |
| 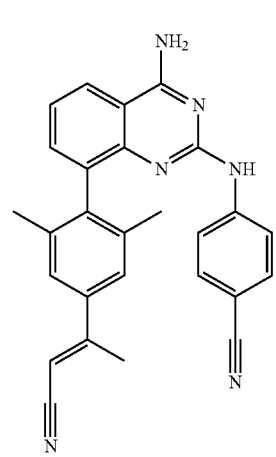 [SMILES: C/C(=C\C#N)c1cc(C)c(-c2cccc3c(N)nc(Nc4ccc(C#N)cc4)nc23)c(C)c1] | 38 |

| Structure | Compound ID |
|---|---|
| 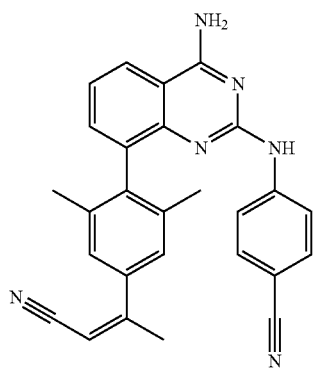 [SMILES: C/C(=C/C#N)c1cc(C)c(-c2cccc3c(N)nc(Nc4ccc(C#N)cc4)nc23)c(C)c1] | 39 |
| 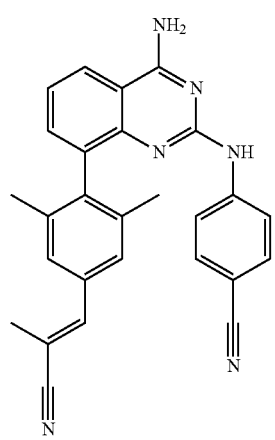 [SMILES: C/C(C#N)=C\c1cc(C)c(-c2cccc3c(N)nc(Nc4ccc(C#N)cc4)nc23)c(C)c1] | 40 |
| 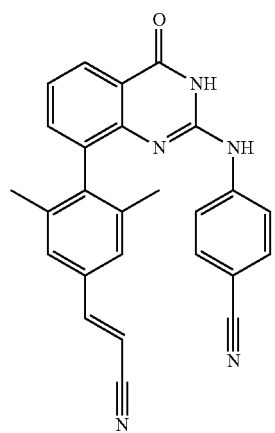 [SMILES: Cc1cc(/C=C/C#N)cc(C)c1-c1cccc2c(=O)[nH]c(Nc3ccc(C#N)cc3)nc12] | 41 |

The present disclosure relates to the following compound or a tautomer or a pharmaceutically acceptable salt thereof:

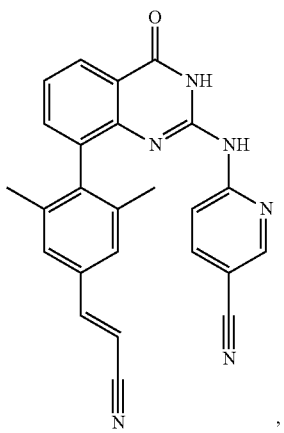 [SMILES: Cc1cc(/C=C/C#N)cc(C)c1-c1cccc2c(=O)[nH]c(Nc3ccc(C#N)cn3)nc12]

The present disclosure relates to the following compound or a pharmaceutically acceptable salt thereof:

and tautomers thereof such as

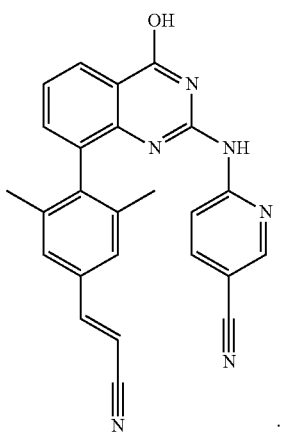 [SMILES: Cc1cc(/C=C/C#N)cc(C)c1-c1cccc2c(O)nc(Nc3ccc(C#N)cn3)nc12]

Pharmaceutical Compositions

Pharmaceutical compositions comprising the compounds disclosed herein, or pharmaceutically acceptable salts thereof, may be prepared with conventional carriers (e.g., inactive ingredient or excipient material) which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 5$^{th}$ edition. American Pharmacists Association, 1986. Excipients can include ascorbic acid and other antioxidants, chelating agents such as EDTA, carbohydrates such as dextrin, hydroxyalkylcellulose, hydroxyalkylmethylcellulose, stearic acid and the like. In certain embodiments, the composition relates to a solid dosage form, including a solid oral dosage form. The pH of a composition may range from about 3 to about 11, but is ordinarily about 7 to 10.

While it is possible for the active ingredients to be administered alone, it may be preferable to present them as pharmaceutical compositions. The compositions, both for veterinary and for human use, comprise at least one compound of formula (I), together with one or more acceptable carriers and optionally other therapeutic ingredients. In one embodiment, the pharmaceutical composition comprises a compound of formula (I), or a tautomer or a pharmaceutically acceptable salt thereof, a pharmaceutically acceptable carrier and one other therapeutic ingredient. The carrier(s) are "acceptable" in the sense of being compatible with the other ingredients of the composition and physiologically innocuous to the recipient thereof.

The compositions include those suitable for various administration routes, including oral administration. The compositions may conveniently be presented in unit dosage form and may be prepared by any of the methods well known in the art of pharmacy. Such methods include the step of bringing into association the active ingredient (e.g., a compound of formula (I) or a pharmaceutical salt thereof) with one or more inactive ingredients (e.g., a carrier, pharmaceutical excipient, etc.). The compositions may be prepared by uniformly and intimately bringing into association the active ingredient with liquid carriers or finely divided solid carriers or both, and then, if necessary, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient.

Pharmaceutical compositions disclosed herein comprise one or more compounds disclosed herein, or a pharmaceutically acceptable salt thereof, together with one or more pharmaceutically acceptable carriers or excipients and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight).

It should be understood that in addition to the ingredients particularly mentioned above the compositions of these embodiments may include other agents conventional in the art having regard to the type of composition in question, for example those suitable for oral administration may include flavoring agents.

In certain embodiments, a composition comprising an active ingredient disclosed herein (a compound of formula (I) or a pharmaceutically acceptable salt thereof) in one variation does not contain an agent that affects the rate at which the active ingredient is metabolized. Thus, it is understood that compositions comprising a compound of formula (I) in certain embodiments do not comprise an agent that would affect (e.g., slow, hinder or retard) the metabolism of a compound of formula (I) or any other active ingredient administered separately, sequentially or simultaneously with a compound of formula (I). It is also understood that any of the methods, kits, articles of manufacture and the like detailed herein in certain embodiments do not comprise an agent that would affect (e.g., slow, hinder or retard) the metabolism of a compound of formula (I) or any other active ingredient administered separately, sequentially or simultaneously with a compound of any one of formula (I).

Methods of Use

Disclosed herein is a method of inhibiting an HIV reverse transcriptase in an individual in need thereof, comprising administering a compound of Formula (I), or a pharmaceutically acceptable salt thereof, to the individual. In certain embodiments, the individual in need thereof is a human who has been infected with HIV. In certain embodiments, the individual in need thereof is a human who has been infected with HIV but who has not developed AIDS. In certain embodiments, the individual in need thereof is an individual at risk for developing AIDS. In certain embodiments, the individual in need thereof is a human who has been infected with HIV and who has developed AIDS. In certain embodiments of the methods disclosed herein, a compound of Formula (I), or a pharmaceutically acceptable salt thereof, is administered to the individual separately, sequentially or simultaneously with another active ingredient for treating HIV, such as HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

In certain embodiments, a method for treating or preventing an HIV viral infection in an individual (e.g., a human), comprising administering a compound of formula (I), or a pharmaceutically acceptable salt thereof, to the individual is disclosed.

In certain embodiments, a method for inhibiting the replication of the HIV virus, treating AIDS or delaying the onset of AIDS in an individual (e.g., a human), comprising administering a compound of any formula (I), or a pharmaceutically acceptable salt thereof, to the individual is disclosed.

In certain embodiments, a method for preventing an HIV infection in an individual (e.g., a human), comprising administering a compound of formula (I), or a pharmaceutically acceptable salt thereof, to the individual is disclosed. In certain embodiments, the individual is at risk of contracting the HIV virus, such as an individual who has one or more risk factors known to be associated with contracting the HIV virus.

In certain embodiments, a method for treating an HIV infection in an individual (e.g., a human), comprising administering a compound of formula (I), or a pharmaceutically acceptable salt thereof, to the individual is disclosed.

In certain embodiments, a method for treating an HIV infection in an individual (e.g., a human), comprising administering to the individual in need thereof a therapeutically effective amount of a compound of formula (I), or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof is disclosed.

In certain embodiments, a compound of formula (I), or a pharmaceutically acceptable salt thereof for use in medical therapy of an HIV viral infection (e.g. HIV-1 or the replication of the HIV virus (e.g. HIV-1) or AIDS or delaying the onset of AIDS in an individual (e.g., a human)) is disclosed.

In certain embodiments, a compound of any of formula (I), or a pharmaceutically acceptable salt thereof for use in the manufacture of a medicament for treating an HIV viral infection or the replication of the HIV virus or AIDS or delaying the onset of AIDS in an individual (e.g., a human) is disclosed. One embodiment relates to a compound of formula (I), or a pharmaceutically acceptable salt thereof, for use in the prophylactic or therapeutic treatment of an HIV infection or AIDS or for use in the therapeutic treatment or delaying the onset of AIDS is disclosed.

In certain embodiments, the use of a compound of formula (I), or a pharmaceutically acceptable salt thereof, for the manufacture of a medicament for an HIV virus infection in an individual (e.g., a human) is disclosed. In certain embodiments, a compound of any of formula (I), or a pharmaceutically acceptable salt thereof, for use in the prophylactic or therapeutic treatment of an HIV virus infection is disclosed.

In certain embodiments, in the methods of use, the administration is to an individual (e.g., a human) in need of the treatment. In certain embodiments, in the methods of use, the administration is to an individual (e.g., a human) who is at risk of developing AIDS.

Disclosed herein is a compound of formula (I), or a pharmaceutically acceptable salt thereof, for use in therapy. In one embodiment, the compound of formula (I), or a pharmaceutically acceptable salt thereof, is for use in a method of treating an HIV viral infection or the replication of the HIV virus or AIDS or delaying the onset of AIDS in an individual (e.g., a human).

Also disclosed herein is a compound of formula (I), or a pharmaceutically acceptable salt thereof, for use in a method of treating or preventing HIV in an individual in need thereof. In certain embodiments, the individual in need thereof is a human who has been infected with HIV. In certain embodiments, the individual in need thereof is a human who has been infected with HIV but who has not developed AIDS. In certain embodiments, the individual in need thereof is an individual at risk for developing AIDS. In certain embodiments, the individual in need thereof is a human who has been infected with HIV and who has developed AIDS.

Also disclosed herein is a compound of formula (I), or a pharmaceutically acceptable salt thereof, for use in the therapeutic treatment or delaying the onset of AIDS.

Also disclosed herein is a compound of formula (I), or a pharmaceutically acceptable salt thereof, for use in the prophylactic or therapeutic treatment of an HIV infection.

In certain embodiments, a compound of formula (I), or a pharmaceutically acceptable salt thereof can be used as a research tool (e.g. to study the inhibition of HIV reverse transcriptase in a subject or in vitro).

Routes of Administration

One or more compounds disclosed herein which are of the Formula (I) (also referred to herein as the active ingredients) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. In certain embodiments, the compounds disclosed are orally bioavailable and can be dosed orally.

Dosing Regimen

The compound, such as a compound of Formula (I), may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of Formula (I) may be adjusted over the course of the treatment, based on the judgment of the administering physician.

The compound may be administered to an individual (e.g., a human) in an effective amount. In certain embodiments, the compound is administered once daily.

A compound as disclosed herein (e.g., any compound of Formula (I)) may be administered in a dosage amount of the compound of Formula I that is effective. For example, the dosage amount can be from 10 mg to 1000 mg of compound, such as 75 mg to 100 mg of the compound.

Combinations

In certain embodiments, a method for treating or preventing an HIV infection in a human having or at risk of having the infection is disclosed, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is disclosed, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure relates to a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

Also disclosed herein is a compound of formula (I), or a pharmaceutically acceptable salt thereof, and another active ingredient for treating HIV, for use in a method of treating or preventing HIV. In one embodiment, the another active ingredient for treating HIV is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

Also disclosed herein is a compound of formula (I), or a pharmaceutically acceptable salt thereof, for use in a method of treating or preventing HIV, wherein the compound of formula (I) or a pharmaceutically acceptable salt thereof is administered simultaneously, separately or sequentially with another active ingredient for treating HIV. In one embodiment, the another active ingredient for treating HIV is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

A compound as disclosed herein (e.g., any compound of Formula (I)) may be combined with one or more additional therapeutic agents in any dosage amount of the compound of Formula I (e.g., from 10 mg to 1000 mg of compound or 75 mg to 100 mg of compound).

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent or excipient are disclosed.

In one embodiment, kits comprising a compound disclosed herein, or a pharmaceutically acceptable salt thereof, in combination with one or more (e.g., one, two, three, one or two, or one to three) additional therapeutic agents are disclosed.

In the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators. Pd-L modulators, toll like receptors modulators, IL-15 agonists), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators. Protein disulfide isomerase inhibitors, Complement C5a receptor antagonists, DNA methyltransferase inhibitor, HIV vif gene modulators, HIV-1 viral infectivity factor inhibitors, TAT protein inhibitors, HIV-1 Nef modulators, Hck tyrosine kinase modulators, mixed lineage kinase-3 (MLK-3) inhibitors. Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, reverse transcriptase priming complex inhibitors, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing. In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® (EVIPLERA®, rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, dolutegravir+abacavir sulfate+lamivudine, lamivudine+nevirapine+zidovudine, dolutegravir+rilpivirine, atazanavir sulfate+cobicistat, darunavir+cobicistat, efavirenz+lamivudine+tenofovir disoproxil fumarate, tenofovir alafenamide hemifumarate+emtricitabine+cobicistat+elvitegravir, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Livexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), tenofovir+lamivudine and lamivudine+tenofovir disoproxil fumarate;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddI), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir andcabotegravir;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), TBR-220 (TAK-220) and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;

(13) Pharmacokinetic enhancers selected from the group consisting of cobicistat and ritonavir;

(14) Immune-based therapies selected from the group consisting of dermaVir, interleukin-7, lexgenleucel-T (VRX-496), plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-2 XL, IL-12, polymer polyethyleneimine (PEI), Gepon, VGV-1, MOR-22, BMS-936559, toll-like receptors modulators (tlr1, tlr2, tlr3, tlr4, tlr5, tlr6, tlr7, tlr8, tlr9, tlr10, tlr11, tlr12 and tlr13), rintatolimod and IR-103;

(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), Remune, ITV-1, Contre Vir, Ad5-ENVA-48, DCVax-001 (CDX-2401), PEP-6409, Vacc-4x, Vacc-C5, VAC-3S, multiclade DNA recombinant adenovirus-5 (rAd5), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, Vichrepol, rAAV1-PG9DP, GOVX-B11, GOVX-B21, ThV-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, CombiHIVvac, ADVAX, MYM-V201, MVA-CMDR and DNA-Ad5 gag/pol/nef/nev (HVTN505);

(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C2F5, C2G12, C4E10, C2F5+C2G12+C4E10, 3-BNC-117, KD-247, PGT145, PGT121, MDX010 (ipilimumab), VRC01, A32, 7B2, 10E8 and VRC07;

(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;

(18) HIV nucleocapsid p7 (NCp7) inhibitors selected from the group consisting of azodicarbonamide;

(19) HIV maturation inhibitors selected from the group consisting of BMS-955176 and GSK-2838232;

(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and

(22) other drugs for treating HIV selected from the group consisting of TR-452, MK-8591, REP 9, CYT-107, alisporivir, NOV-205, IND-02, metenkefalin, PGN-007, Acemannan, Gamimune, SCY-635, Prolastin, 1,5-dicaffeoylquinic acid, BIT-225, RPI-MN, VSSP, Hlviral, IMO-3100, SB-728-T, RPI-MN, VIR-576, HGTV-43, MK-1376, rHIV7-shl-TAR-CCR5RZ, MazF gene therapy, BlockAide and PA-1050040 (PA-040).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from raltegravir, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicislat, Atripla® (efavirenz+tenofovir disoproxil fumarate+emtricitabine), atazanavir, atazanavir_sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, tenofovir alafenamide and tenofovir alafenamide hemifumarate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide and 200 mg emtricitabine. A compound as disclosed herein (e.g., a compound of formula (I)) may be combined with the agents disclosed herein in any dosage amount of the compound (e.g., from 10 mg to 1000 mg of compound, 10 mg to 500 mg, or 75 mg to 100 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil and 200 mg emtricitabine. A compound as disclosed herein (e.g., a compound of formula (I)) may be combined with the agents disclosed herein in any dosage amount of the compound (e.g., from 10 mg to 1000 mg of compound, 10 mg to 500 mg, or 75 mg to 100 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient.

When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In the above embodiments, the additional therapeutic agent may be an anti-HIV agent. For example, in some embodiments, the additional therapeutic agent is selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide, emtricitabine, and rilpivirine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, BIT-225, CYT-107, HGTV-43, HS-10234, IMO-3100, IND-02, MK-1376, MK-8507, MK-8591, NOV-205, PA-1050040 (PA-040), PGC-007, SCY-635, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500.

Examples of HIV nucleoside or nucleotide inhibitors of reverse transcriptase include adefovir, adefovir dipivoxil, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, fozivudine tidoxil, lamivudine, phosphazid, stavudine, zalcitabine, zidovudine, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, and cabotegravir.

Examples of HIV non-catalytic site, or allosteric, integrase inhibitors (NCINI) include CX-05045, CX-05168, T-169, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), TD-0680, and vMIP (Haimipu).

Examples of gp41 inhibitors include albuvirtide, enfuvirtide, and sifuvirtide.

Examples of CD4 attachment inhibitors include ibalizumab.

Examples of gp120 inhibitors include Radha-108 (receptol) and BMS-663068

Examples of CXCR4 inhibitors include plerixafor, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, and HIV p24 capsid protein inhibitors.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir, interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; rintatolimod; IL-12; WF-10; VGV-1; MOR-22; GS-9620; BMS-936559; and IR-103.

Phosphatidylinositol 3-kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

HIV Antibodies, Bispecific Antibodies, and "Antibody-like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, BMS-936559, TMB-360, and those targeting HIV gp120 or gp41.

Examples of those targeting HIV gp120 or gp41 include bavituximab, UB-421, C2F5, C2G12, C4E10, C2F5+ C2G12+C4E10, 3-BNC-117, PGT145, PGT121, MDX010 (ipilimumab), VRC01, A32, 7B2, 10E8, VRC-07-523, MGD-014 and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences); WO 2013/091096 (Boehringer Ingelheim); and U.S. 20100143301 (Gilead Sciences).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, VRC-HIV MAB060-00-AB, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+ FTC); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir, atazanavir sulfate and ritonavir, darunavir; lamivudine; prolastin; fosamprenavir; fosamprenavir calcium efavirenz; etravirine; nelfinavir, nelfinavir mesylate; interferon; didanosine; stavudine; indinavir, indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); Hlviral; lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein (e.g., any compound of Formula (I)) may be combined with one or more additional therapeutic agents in any dosage amount of the compound of Formula (I) (e.g., from 50 mg to 1000 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula (I)) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula (I)) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Kits and Articles of Manufacture

The present disclosure relates to a kit comprising a compound of formula (I), or a pharmaceutically acceptable salt thereof. The kit may further comprise instructions for use. e.g., for use in inhibiting an HIV reverse transcriptase, such as for use in treating an HIV infection or AIDS or as a research tool. The instructions for use are generally written instructions, although electronic storage media (e.g., magnetic diskette or optical disk) containing instructions are also acceptable.

The present disclosure also relates to a pharmaceutical kit comprising one or more containers comprising a compound of any of formula (I), or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also disclosed are articles of manufacture comprising a unit dosage of a compound of any of formula (I), or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

The present disclosure is also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions. Mechanisms, and Structure, 7$^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography. E. Stahl (ed.). Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to formula (I).

Representative syntheses of compounds of the present disclosure are described in schemes below, and the particular examples that follow.

The embodiments are also directed to processes and intermediates useful for preparing the subject compounds or pharmaceutically acceptable salts thereof.

Many general references providing commonly known chemical synthetic schemes and conditions useful for synthesizing the disclosed compounds are available (see. e.g., Smith, March's Advanced Organic Chemistry: Reactions. Mechanisms, and Structure, 7$^{th}$ edition, Wiley-Interscience, 2013.). Angew. Chem. Int. Ed. 2014, 53, 2-21, which is herein incorporated by reference in its entirety, provides a review of sulfur (VI) fluoride exchange, which can also be useful in the synthetic schemes.

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes may be run at a temperature from about 0° C. to the reflux temperature of the organic solvent used. Unless otherwise specified, the variables are as defined above in reference to formula (I).

Representative syntheses of compounds of the present disclosure are described in schemes below, and the particular examples that follow.

Scheme 1 shows a representative synthesis of the compounds of the embodiments. The methodology is compatible with a wide variety of functionalities.

the proper bonds and moieties in formula (I). Starting materials may be obtained from commercial sources or via well-established synthetic procedures. The synthesis of formula 1-D is discussed below in Schemes 4 and 5.

In Scheme 1, a nucleophilic substitution reaction between formula 1-A and 1-B occurs to produce a compound of formula 1-C. The amino group of formula 1-B reacts with formula 1-A to displace $Y^{1a}$, which is a leaving group, such as halogen, triflate, mesylate, and tosylate. In certain instances, $Y^{1a}$ is halogen, such as iodo, bromo, or chloro.

With continued reference to Scheme 1, a coupling reaction between formula 1-C and 1-D occurs to produce a compound of formula (I). In certain instances, a palladium-catalyzed reaction between an aryl halide and an organoboron compound (e.g., Suzuki coupling reaction) can be used. With a Suzuki coupling reaction. $Z^{1a}$ in formula 1-C can be a halide, such as iodo or bromo and $Z^{2a}$ in formula 1-D can be a boronic acid or boronic acid ester. In certain instances, $Z^{2a}$ is

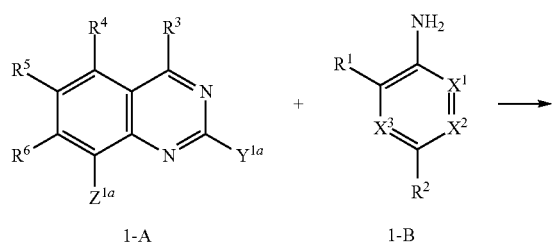

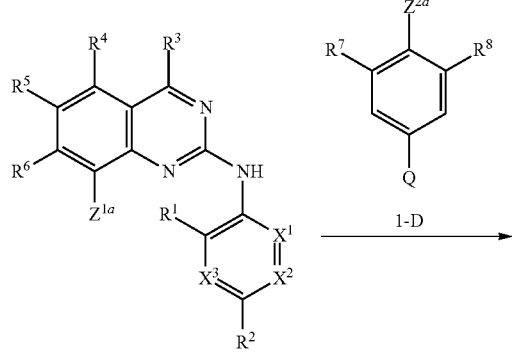

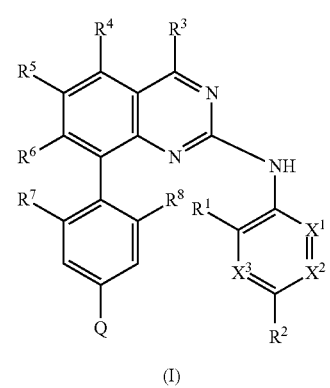

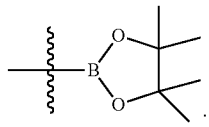 [SMILES: *B1OC(C)(C)C(C)(C)O1]

In certain instances, the coupling step includes a palladium catalyst, such as 1,1'-bis(di-tert-butylphosphino)ferrocene palladium dichloride or 1,1'-bis(diphenylphosphino)ferrocene palladium dichloride.

With continued reference to Scheme 1, as an alternative coupling reaction between formula 1-C and 1-D, a palladium-catalyzed reaction between an organotin compound and an aryl halide (e.g., Stille coupling reaction) can be used to produce a compound of formula (I). With the Stille reaction, $Z^{1a}$ in formula 1-C can be an organotin moiety (—SnR$_4$, where R is an alkyl group) and $Z^{2a}$ in formula 1-D can be a halide, such as iodo, or bromo. In certain instances, the coupling step includes a palladium catalyst, such as bis(tri-tert-butylphosphine)palladium(0).

Scheme 2 is another representative synthesis of the compounds of the embodiments. The methodology is compatible with a wide variety of functionalities.

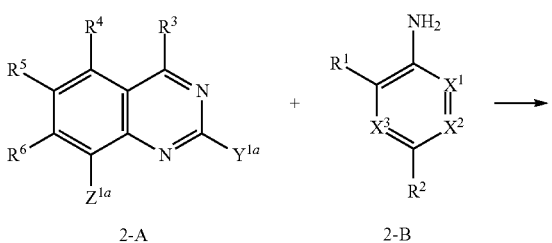

In Scheme 1, $R^1$, $R^2$, $R^3$, $R^4$, $R^5$, $R^6$, $R^7$, $R^8$, $X^1$, $X^2$, $X^3$, and Q are as defined herein. Also in Scheme 1, as discussed below, $Y^{1a}$, $Z^{1a}$, and $Z^{2a}$ are precursor moieties to forming

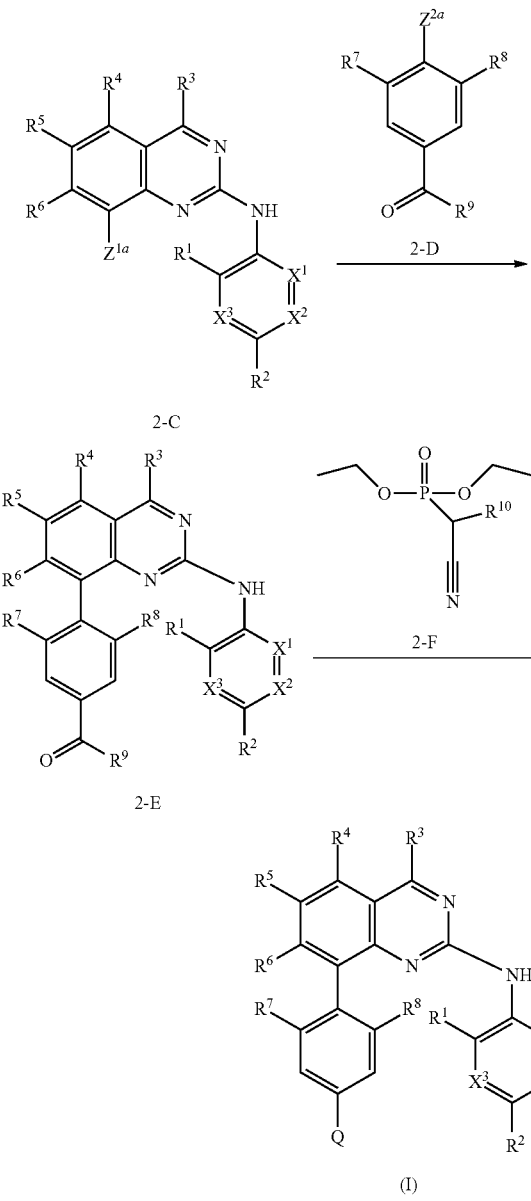

2-C

2-E (I)

In Scheme 2, $R^1$, $R^2$, $R^3$, $R^4$, $R^5$, $R^6$, $R^7$, $R^8$, $R^9$, $R^{10}$, $X^1$, $X^2$, $X^3$, and Q are as defined herein. Also in Scheme 2, as discussed below, $Y^{1a}$, $Z^{1a}$, and $Z^{2a}$ are precursor moieties to forming the proper bonds and moieties in formula (I). Starting materials may be obtained from commercial sources or via well-established synthetic procedures.

In Scheme 2, a nucleophilic substitution reaction between formula 2-A and 2-B occurs to produce a compound of formula 2-C. The amino group of formula 2-B reacts with formula 2-A to displace $Y^{1a}$, which is a leaving group, such as halogen, triflate, mesylate, and tosylate. In certain instances, $Y^{1a}$ is halogen, such as iodo, bromo, or chloro.

With continued reference to Scheme 2, a coupling reaction between formula 2-C and 2-D occurs to produce formula 2-E. In certain instances, a palladium-catalyzed reaction between an aryl halide and an organoboron compound (e.g., Suzuki coupling reaction) can be used. With a Suzuki coupling reaction, $Z^{1a}$ in formula 2-C can be a halide, such as iodo or bromo and $Z^{2a}$ in formula 2-D can be a boronic acid or boronic acid ester. In certain instances, $Z^{2a}$ is

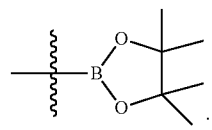 [SMILES: *B1OC(C)(C)C(C)(C)O1]

In certain instances, the coupling step includes a palladium catalyst, such as 1,1'-bis(di-tert-butylphosphino)ferrocene palladium dichloride or 1,1'-bis(diphenylphosphino)ferrocene palladium dichloride.

With continued reference to Scheme 2, as an alternative coupling reaction between formula 2-C and 2-D, a palladium-catalyzed reaction between an organotin compound and an aryl halide (e.g., Stille coupling reaction) can be used to produce a compound of formula (I). With the Stille reaction, $Z^{1a}$ in formula 2-C can be an organotin moiety (—$SnR_4$, where R is an alkyl group) and $Z^{2a}$ in formula 2-D can be a halide, such as iodo or bromo. In certain instances, the coupling step includes a palladium catalyst, such as bis(tri-tert-butylphosphine)palladium(0).

With continued reference to Scheme 2, a coupling reaction between formula 2-D and 2-E occurs to produce a compound of formula (I). In certain instances, a coupling reaction between a stabilized phosphonate carbanion and an aldehyde (e.g., Horner-Wadsworth-Emmons reaction) can be used.

Scheme 3 is another representative synthesis of the compounds of the embodiments. The methodology is compatible with a wide variety of functionalities.

Scheme 3

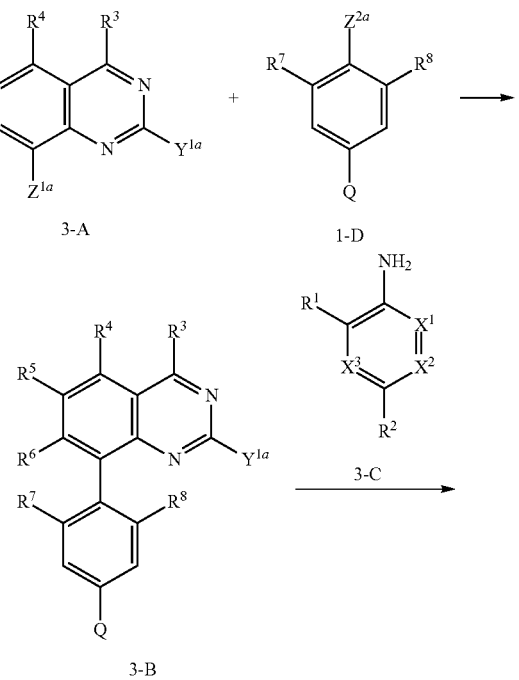

3-A

1-D

3-B

3-C

-continued

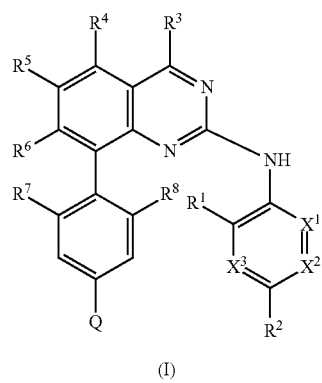

(I)

In Scheme 3, $R^1$, $R^2$, $R^3$, $R^4$, $R^5$, $R^6$, $R^7$, $R^8$, $X^1$, $X^2$, $X^3$, and Q are as defined herein. Also in Scheme 3, as discussed below, $Y^{1a}$, $Z^{1a}$, and $Z^{2a}$ are precursor moieties to forming the proper bonds and moieties in formula (I). Starting materials may be obtained from commercial sources or via well-established synthetic procedures. The synthesis of formula 1-D is discussed below in Schemes 4 and 5.

With reference to Scheme 3, a coupling reaction between formula 3-A and 1-D occurs to produce formula 3-B. In certain instances, a palladium-catalyzed reaction between an aryl halide and an organoboron compound (e.g., Suzuki coupling reaction) can be used. With a Suzuki coupling reaction. $Z^{1a}$ in formula 3-A can be a halide, such as iodo or bromo and $Z^{2a}$ in formula 1-D can be a boronic acid or boronic acid ester. In certain instances, $Z^{2a}$ is

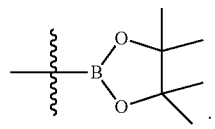

In certain instances, the coupling step includes a palladium catalyst, such as 1,1'-bis(di-tert-butylphosphino)ferrocene palladium dichloride or 1,1'-bis(diphenylphosphino)ferrocene palladium dichloride.

With continued reference to Scheme 3, as an alternative coupling reaction between formula 3-A and 1-D, a palladium-catalyzed reaction between an organotin compound and an aryl halide (e.g., Stille coupling reaction) can be used to produce a compound of formula (I). With the Stille reaction, $Z^{1a}$ in formula 1-C can be an organotin moiety (—$SnR_4$, where R is an alkyl group) and $Z^{2a}$ in formula 1-D can be a halide, such as iodo, or bromo. In certain instances, the coupling step includes a palladium catalyst, such as bis(tri-tert-butylphosphine)palladium(0).

With continued reference to Scheme 3, a nucleophilic substitution reaction between formula 3-B and 3-C occurs to produce a compound of formula (I). The amino group of formula 3-C reacts with formula 3-B to displace $Y^{1a}$, which is a leaving group, such as halogen, triflate, mesylate, and tosylate. In certain instances, $Y^{1a}$ is halogen, such as iodo, bromo, or chloro.

Scheme 4 shows a representative synthesis of formula 1-D. The methodology is compatible with a wide variety of functionalities.

Scheme 4

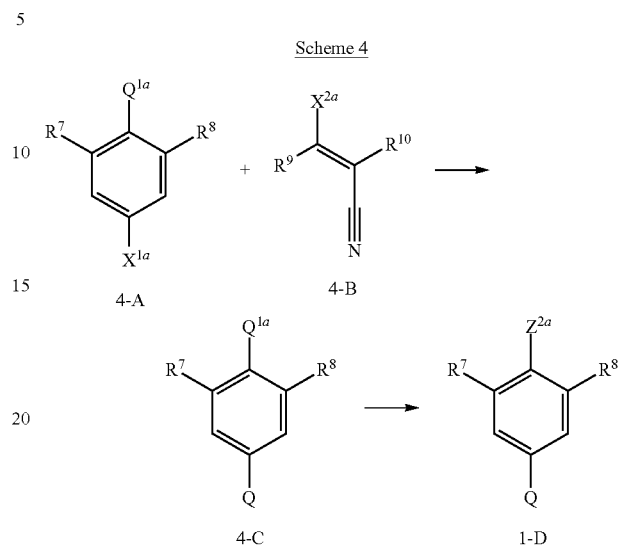

In Scheme 4, $R^7$, $R^8$, $R^9$, $R^{10}$, and Q are as defined herein. Also in Scheme 4, as discussed below, $Q^{1a}$, $X^{1a}$, and $X^{2a}$ are precursor moieties to forming the proper bonds and moieties in formula 1-D. Starting materials may be obtained from commercial sources or via well-established synthetic procedures.

In Scheme 4, a coupling reaction between formula 4-A and 4-B occurs to produce formula 4-C. In certain instances, a palladium-catalyzed reaction between an aryl halide and an alkene compound (e.g., Heck coupling reaction) can be used. With a Heck coupling reaction, $X^{1a}$ in formula 4-A can be a halide, such as iodo, or bromo and $X^{2a}$ in formula 4-B can be hydrogen. The Heck coupling reaction can be carried out in the presence of a palladium catalyst, such as palladium(II) acetate in a combination with tri(o-tolyl)phosphine.

With continued reference to Scheme 4, $Q^{1a}$ in formula 4-A and 4-C is a precursor moiety to a boronic acid or boronic acid ester in formula 1-D, wherein $Z^{2a}$ is a boronic acid or boronic acid ester. A borylation reaction of formula 4-C occurs to produce a compound of formula 1-D. In certain instances, a cross-coupling reaction of 4,4,4',4',5,5,5',5'-octamethyl-2,2'-bi(1,3,2-dioxaborolane) with an aryl halide (e.g., Miyaura borylation reaction) can be used. With a Miyaura borylation reaction, $Q^{1a}$ in formula 4-C can be a halide, such as iodo, or bromo. In certain instances, Formula 4-C can react with 4,4,4',4',5,5,5',5'-octamethyl-2,2'-bi(1,3,2-dioxaborolane) to provide for formula 1-D, in which $Z^{2a}$ is

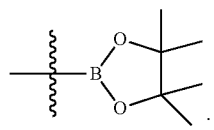

In certain instances, the borylation step includes a palladium catalyst, such as palladium(II) acetate in a combination with dicyclohexyl(2',6'-dimethoxy-[1,1'-biphenyl]-2-yl)phosphine. Other borylation reactions can be used.

Scheme 5 shows another representative synthesis of formula 1-D. The methodology is compatible with a wide variety of functionalities.

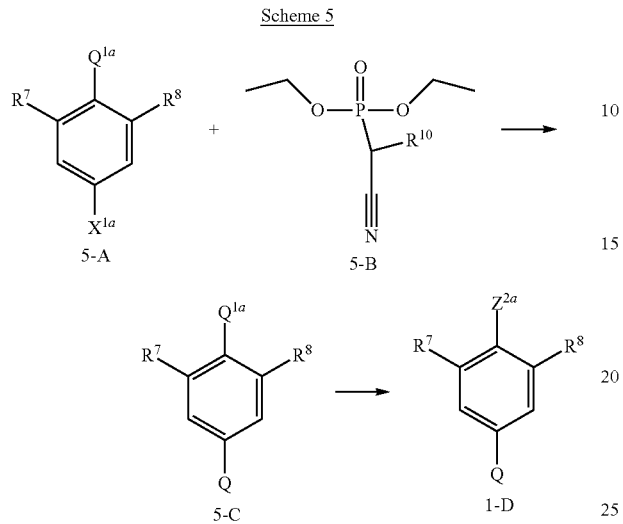

In Scheme 5, $R^7$, $R^8$, $R^9$, $R^{10}$, and Q are as defined herein. Also in Scheme 5, as discussed below, $Q^{1a}$ and $X^{1a}$ are precursor moieties to forming the proper bonds and moieties in formula 1-D. Starting materials may be obtained from commercial sources or via well-established synthetic procedures.

In Scheme 5, a coupling reaction between formula 5-A and 5-B occurs to produce formula 5-C. In certain instances, a coupling reaction between a stabilized phosphonate carbanion and an aldehyde (e.g., Horner-Wadsworth-Emmons reaction) can be used. With a Horner-Wadsworth-Emmons reaction, $X^{1a}$ in formula 4-A can be an aldehyde or ketone (e.g., $X^{1a}$ is —CHO or —C(O)$R^9$).

With continued reference to Scheme 5, $Q^{1a}$ in formula 5-A and 5-C is a precursor moiety to a boronic acid in formula 1-D, wherein $Z^{1a}$ is a boronic acid. A borylation reaction of formula 5-C occurs to produce a compound of formula 1-D. In certain instances, a cross-coupling reaction of 4,4,4',4',5,5,5',5'-octamethyl-2,2'-bi(1,3,2-dioxaborolane) with an aryl halide (e.g., Miyaura Borylation reaction) can be used. With a Miyaura Borylation reaction, $Q^{1a}$ in formula 5-C can be a halide, such as iodo, or bromo In certain instances, Formula 5-C can react with 4,4,4',4',5,5,5',5'-octamethyl-2,2'-bi(1,3,2-dioxaborolane) to provide for formula 1-D, in which $Z^{2a}$ is

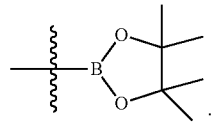 [SMILES: *B1OC(C)(C)C(C)(C)O1]

In certain instances, the borylation step includes a palladium catalyst, such as palladium(II) acetate in a combination with dicyclohexyl(2',6'-dimethoxy-[1,1'-biphenyl]-2-yl)phosphine. Other borylation reactions can be used.

Accordingly, and as described in more detail herein, the present disclosure relates to a process of preparing a compound of the present disclosure, the process involving:

reacting a compound of formula:

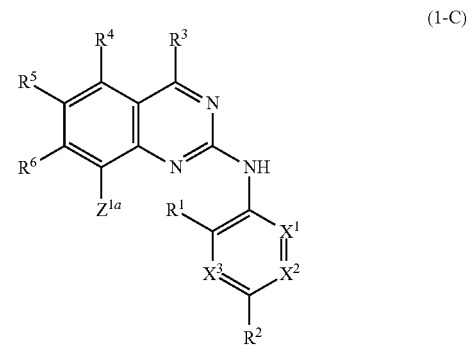

(1-C)

with a compound of formula:

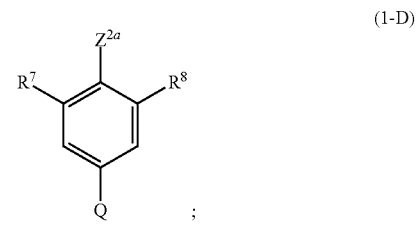

(1-D)

thereby producing a compound of formula

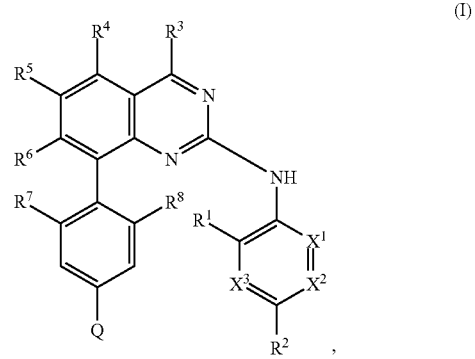

(I)

wherein $R^1$, $R^2$, $R^3$, $R^4$, $R^5$, $R^6$, $R^7$, $R^8$, $X^1$, $X^2$, $X^3$, $Z^{1a}$, $Z^{2a}$, and Q are as defined herein.

Accordingly, and as described in more detail herein, the present disclosure relates to a process of preparing a compound of the present disclosure, the process involving:

reacting a compound of formula:

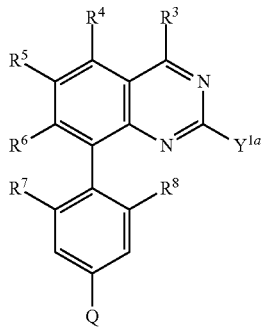

(3-B)

with a compound of formula:

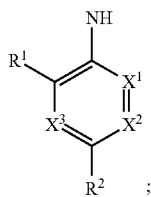

(3-C)

thereby producing a compound of formula

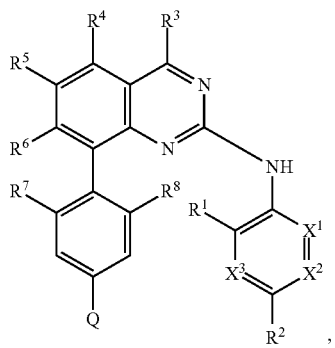

(I)

wherein $R^1$, $R^2$, $R^3$, $R^4$, $R^5$, $R^6$, $R^7$, $R^8$, $X^1$, $X^2$, $X^3$, $Y^{1a}$, and Q are as defined herein.

In certain instances, the above processes further involve the step of forming a salt of a compound of the present disclosure. Embodiments are directed to the other processes described herein; and to the product prepared by any of the processes described herein.

Except as otherwise noted, the methods and techniques of the present embodiments are generally performed according to conventional methods well known in the art and as described in various general and more specific references that are cited and discussed throughout the present specification. See. e.g., Loudon, Organic Chemistry, 5$^{th}$ edition, New York: Oxford University Press, 2009; Smith, March's Advanced Organic Chemistry: Reactions. Mechanisms, and Structure, 7$^{th}$ edition. Wiley-Interscience, 2013.

LIST OF ABBREVIATIONS AND ACRONYMS

Abbreviation—Meaning
Ac—Acetyl
$B_2pin_2$—4,4,4',4',5,5,5',5'-Octamethyl-2,2'-bi(1,3,2-dioxaborolane)
bs—Broad singlet
° C.—Degree Celsius
d—Doublet
DCM—Dichloromethane
dd—Doublet of doublet
DIPEA—N,N-Diisopropylethylamine
DMF—N,N-Dimethylformamide
DMSO—Dimethylsulfoxide
dppf—1,1'-Bis(diphenylphosphino)ferrocene
dtbpf—1,1'-Bis(di-tert-butylphosphino)ferrocene
$EC_{50}$—Half maximal effective concentration
Equiv/eq—Equivalents
Et—Ethyl
EtOH—Ethanol
g—Grams
HPLC—High-performance liquid chromatography
hrs/h—Hours
Hz—Hertz
J—Coupling constant
LCMS—Liquid chromatography-mass spectrometry
M—Molar
m—Multiplet
m/z—mass-to-charge ratio
M+—Mass peak
Me—Methyl
mg—Milligram
MHz—Megahertz
min—Minute
mL—Milliliter
mM—Millimolar
mm—Millimeter
mmol—Millimole
mol—Mole
MS—mass spectrometry
MW—Microwave
nM—Nanomolar
NMP—N-Methyl-2-pyrrolidone
NMR—Nuclear magnetic resonance
$P(oTol)_3$—Tri(o-tolyl)phosphine
$P(t-Bu)_3$—Tri-tert-butylphosphine
$Pd_2(dba)_3$—Tris(dibenzylideneacetone)palladium(0)
q—Quartet
quant—Quantitative
Rf—Retention factor
RT/rt/r.t.—Room temperature
s—Singlet
sat.—Saturated
SPhos—Dicyclohexyl(2',6'-dimethoxy-[1,1'-biphenyl]-2-yl)phosphine
t—Triplet
TFA—Trifluoroacetic acid
TMS—Trimethylsilyl
Tr/tr—Retention time
UV—Ultraviolet
wt.—Weight
Xantphos—(9,9-Dimethyl-9H-xanthene-4,5-diyl)bis(diphenylphosphine)
δ—Chemical shift
μL—Microliter
μM—Micromolar
μmol—Micromole The following examples are merely illustrative, and do not limit this disclosure in any way. Unless otherwise stated, preparative HPLC was performed on a Gilson HPLC system, using a 21.2×250 mm 10 micron C18 Phenomenex Gemini semi-preparative column and gradient 0-100% acetonitrile in water mobile phase with 0.1% trifluoroacetic acid at a flow rate of 20 mL/min.

Chemical names for all prepared compounds were generated using ChemBioDraw 12.0 software.

While the structures in the examples below are drawn as certain geometric isomers, a certain geometric isomer (e.g., E or Z isomer) or a ratio of the E and Z isomers may be indicated in the title and/or description of the example to represent the results of the example.

The following methods were used for the purification and characterization of certain compounds described in the following Examples.

LCMS method 1—Phenomenex Gemini-NX 3u C18 110 Å, 100×2 mm 3 micron column, Acetonitrile with 0.1% formic acid, Water with 0.1% formic acid; 0 min-7.0 min 0-100% ACN, flow rate 0.5 mL/min.

LCMS method 2—Gemini 5u C18 110 Å, 50×4.60 mm 5 micron column; Acetonitrile with 0.1% acetic acid, Water with 0.1% acetic acid; Gradient: 0 min-3.5 min 5-100% ACN; flow rate 2 mL/min.

LCMS method 3—Kinetex 2.6μ C18 100A, 50×3.00 mm column; Acetonitrile with 0.1% formic acid, Water with 0.1% formic acid; Gradient: 0 min-1.4 min 2-100% ACN, 1.4 min-1.8 min 100% ACN, 1.8 min-1.85 min 100%-2% ACN, 1.85 min-2 min 2% ACN; flow rate 1.8 mL/min.

Example 1

(E)-4-((8-(4-(2-Cyanovinyl)-2,6-dimethylphenyl)quinazolin-2-yl)amino)benzonitrile-Compound 1

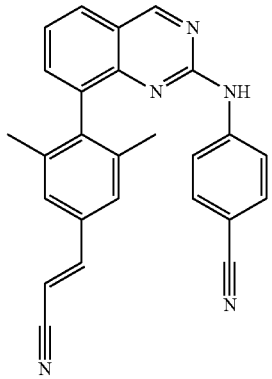 [SMILES: Cc1cc(/C=C/C#N)cc(C)c1-c1cccc2cnc(Nc3ccc(C#N)cc3)nc12]

Step 1: Synthesis of 4-((8-bromoquinazolin-2-yl)amino)benzonitrile (Compound 1a)

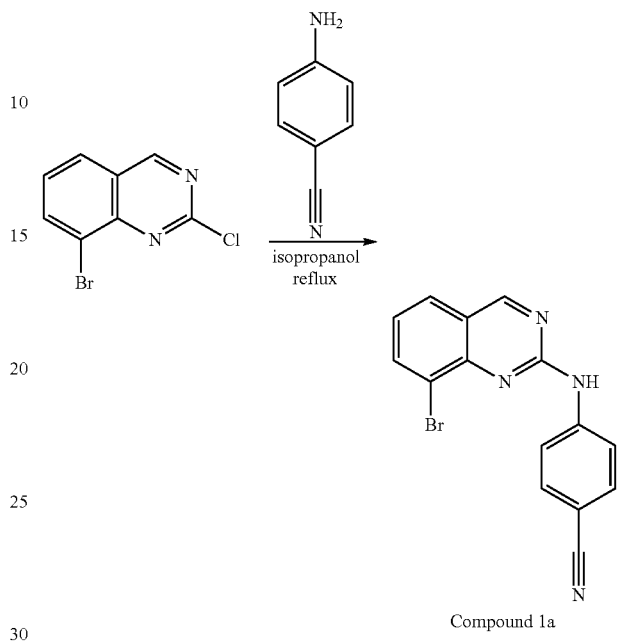

A mixture of 8-bromo-2-chloroquinazoline (1.0 g, 4.10 mmol, Ark Pharm Inc, AK-27609) and 4-cyanoaniline (533 mg, 4.52 mmol, Sigma-Aldrich) in isopropanol (15 mL) was heated under reflux for 15 hours. The solid product was filtered off and washed twice with cold isopropanol (2×10 mL). The product was dried on air to afford the title compound 1a. $^1$H NMR (400 MHz, DMSO-$d_6$) δ 10.76 (s, 1H), 9.47 (s, 1H), 8.41 (d, J=8.8 Hz, 2H), 8.28 (dd, J=7.8, 1.2 Hz, 1H), 8.06 (dd, J=7.8, 1.2 Hz, 1H), 7.85 (d, J=8.8 Hz, 2H), 7.44 (t, J=7.8 Hz, 1H). HRMS: (ESI+) calculated for $C_{15}H_{10}N_4Br$ [M+H] 325.00834, found 325.00821. LCMS (m/z) 325.0 [M+H], Tr=4.69 min (LCMS method 1).

Step 2: synthesis of (E)-3-(4-bromo-3,5-dimethylphenyl)acrylonitrile (compound 1b)

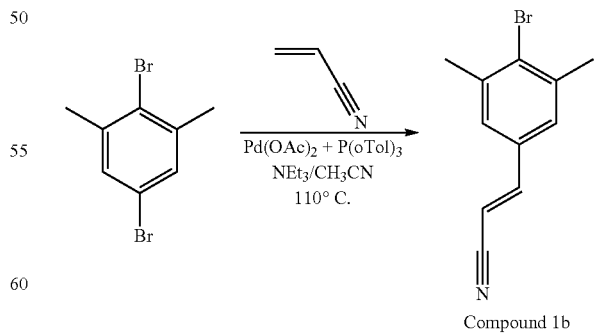

To a solution of 2,5-dibromo-1,3-dimethylbenzene (2640 mg, 10 mmol, Oakwood Products, Inc.—018507) in anhydrous acetonitrile (25 mL) was added palladium(II) acetate (112 mg, 0.5 mmol), acrylonitrile (531 mg, 10 mmol), tri(o-tolyl)phosphine (131 mg, 0.5 mmol) and triethylamine (4 mL, 30 mmol) then the mixture was purged with argon and heated at 110° C. for 2 hours. The reaction mixture was filtered through Celite and the filter pad was washed with tetrahydrofuran (0.10 mL). The filtrate was evaporated then re-dissolved with ethyl acetate (50 mL). The solution was washed with water (50 mL). The water layer was back extracted with ethyl acetate (50 mL). The combined organics were washed with brine (30 mL), dried over sodium sulfate, filtered and concentrated under reduced pressure to give a crude residue. This was subjected to silica gel chromatography (gradient from 0-20% ethyl acetate in iso-hexanes) to afford the crude product which was treated in sonic bath with hexane (10 mL) for 10 minutes. The product precipitated out of solution and was collected by filtration. The solids were washed with cold hexane to afford compound 1b. $^1$H NMR (400 MHz, CDCl$_3$) δ 7.25 (d, J=16.6 Hz, 1H), 7.12 (s, 2H), 5.84 (d, J=16.6 Hz, 1H), 2.42 (s, 6H). LCMS (m/z) no MS signal, Tr=2.78 min (LCMS method 2).

Step 3: synthesis of (E)-3-(3,5-dimethyl-4-(4,4,5,5-tetramethyl-1,3,2-dioxaborolan-2-yl)phenyl)acrylonitrile (compound 1c)

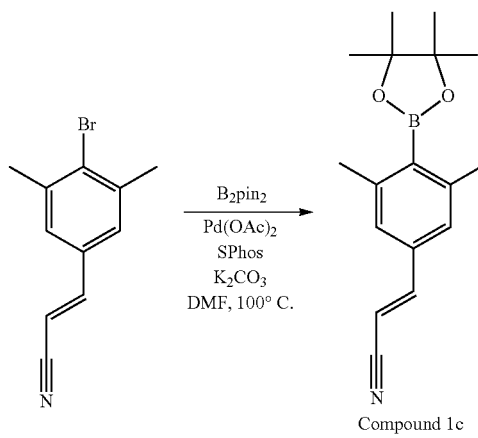

Compound 1c

A mixture of compound 1b (391 mg, 1.66 mmol), 4,4,4',4',5,5,5',5'-octamethyl-2,2'-bi(1,3,2-dioxaborolane) (630 mg, 2.48 mmol), potassium carbonate (687 mg, 5 mmol), palladium(II) acetate (19 mg, 0.08 mmol) and dicyclohexyl (2',6'-dimethoxy-[1,1'-biphenyl]-2-yl)phosphine (SPhos, 85 mg, 0.21 mmol) in dry N,N-dimethylformamide (20 mL) was purged with argon and heated at 100° C. for 1 hour. The reaction mixture was filtered through Celite and the filter pad was washed with tetrahydrofuran (10 mL). The filtrate was evaporated then re-dissolved with ethyl acetate (50 mL). The solution was washed with water (50 mL). The water layer was back extracted with ethyl acetate (50 mL). The combined organics were washed with brine (30 mL), dried over sodium sulfate, filtered and concentrated under reduced pressure to give a crude residue which was purified by silica gel chromatography (gradient from 0-20% ethyl acetate in iso-hexanes) to afford compound 1c. $^1$H NMR (400 MHz, CDCl$_3$) δ 7.28 (d, J=16.6 Hz, 1H), 7.00 (s, 2H), 5.84 (d, J=16.6 Hz, 1H), 2.39 (s, 6H), 1.37 (s, 12H). LCMS (m/z) 284.3 [M+H], Tr=2.85 min (LCMS method 2).

Step 4: synthesis of (E)-4-((8-(4-(2-cyanovinyl)-2,6-dimethylphenyl)quinazolin-2-yl)amino)benzonitrile (compound 1)

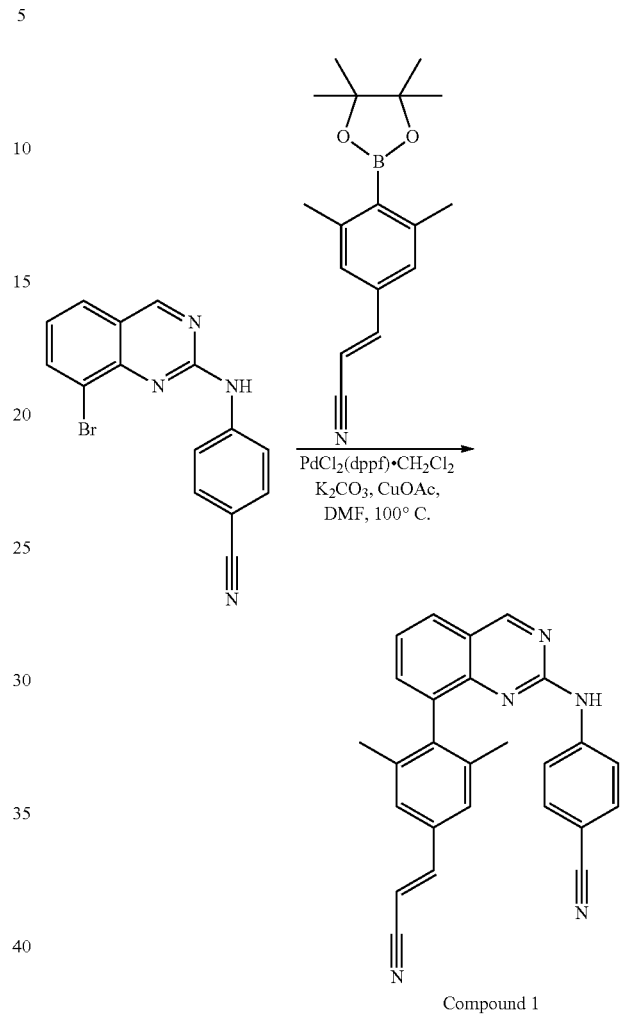

Compound 1

A mixture of compound 1a (50 mg, 0.15 mmol), compound 1c (129 mg, 0.45 mmol), [1,1'-bis(diphenylphosphino)ferrocene] dichloropalladium(II), complex with dichloromethane (100 mg, 0.12 mmol), potassium carbonate (64 mg, 0.45 mmol), and copper (I) acetate (19 mg, 0.15 mmol) in dry N,N-dimethylformamide (5 mL) was purged with argon and heated at 100° C. for 15 hours. Solvent was removed under reduced pressure and crude mixture was subjected to silica gel chromatography (gradient from 0-30% ethyl acetate in iso-hexanes). The crude product was then re-purified on HPLC (preparative column Phenomenex Gemini 10 micron C18, 250×21.2 mm, 10 mL/min, gradient from 10-100% acetonitrile in water) to afford the title compound 1. $^1$H NMR (400 MHz, DMSO-d$_6$) δ 10.48 (s, 1H), 9.50 (s, 1H), 8.09 (d, J=7.8 Hz, 1H), 7.70-7.87 (m, 4H), 7.63 (t, J=7.8 Hz, 1H), 7.61 (s, 2H), 7.40 (d, J=8.8 Hz, 2H), 6.62 (d, J=16.7 Hz, 1H), 1.94 (s, 6H). HRMS: (ESI+) calculated for C$_{26}$H$_{20}$N$_5$ [M+H] 402.17132. found 402.17126. LCMS (m/z) 402.2 [M+H], Tr=4.91 min (LCMS method 1).

Example 2

(E)-4-((4-Amino-8-(4-(2-cyanovinyl)-2,6-dimethylphenyl)quinazolin-2-yl)amino)benzonitrile—Compound 2

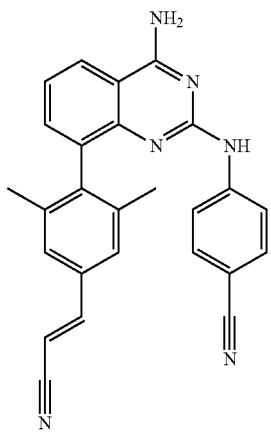 [SMILES: Cc1cc(/C=C/C#N)cc(C)c1-c1cccc2c(N)nc(Nc3ccc(C#N)cc3)nc12]

Step 1: Synthesis of (E)-3-(4-(4-amino-2-chloroquinazolin-8-yl)-3,5-dimethylphenyl)acrylonitrile (Compound 2a)

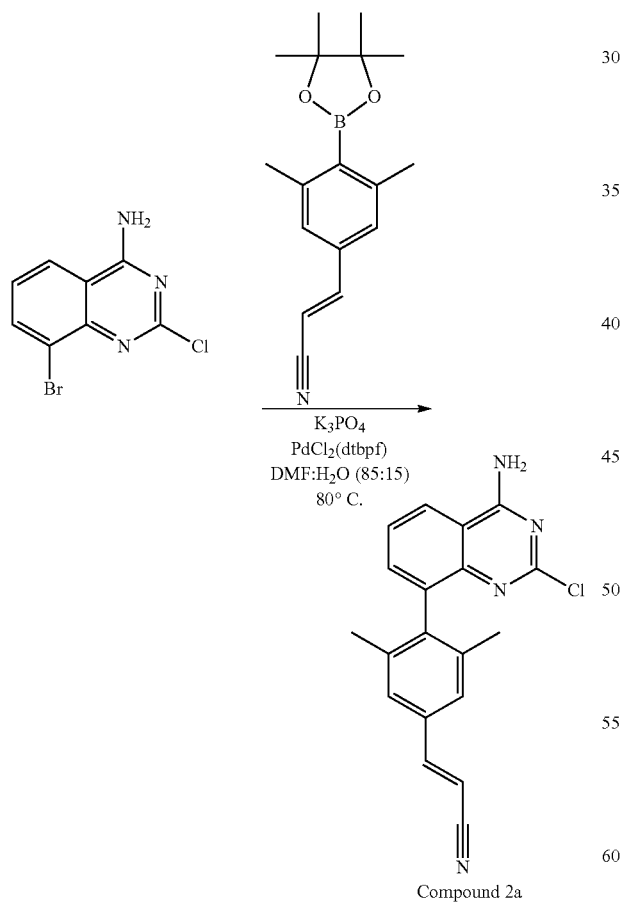

A mixture of 8-bromo-2-chloroquinazolin-4-amine (129 mg, 0.5 mmol, Ark Pharm Inc, AK-28702), compound 1c (184 mg, 0.65 mmol), potassium phosphate tribasic (159 mg, 0.75 mmol) and 1,1'-bis(di-tert-butylphosphino)ferrocene palladium dichloride (65 mg, 0.10 mmol) was dissolved in N,N-dimethylformamide:water mixture (85:15, 40 mL) under argon. The reaction was heated to 80° C. for 30 minutes. The reaction mixture was cooled down to room temperature and diluted with water and ethyl acetate. The organic layer was separated and washed twice with brine, dried over magnesium sulfate, 0.5 volume equivalent of hexane added and this mixture was filtered through a 2 cm layer of silica gel which was washed with additional ethyl acetate. Combined organics were concentrated down under reduced pressure and the residue was treated with diethyl ether in a sonic bath. The solid product was filtered off and washed twice with diethyl ether and once with hexane to afford the title compound 2a. $^1$H NMR (400 MHz, DMSO-$d_6$) δ 8.38 (bs, 2H), 8.28 (dd, J=8.1, 1.6 Hz, 1H), 7.66-7.52 (m, 3H), 7.43 (s, 2H), 6.46 (d, J=16.7 Hz, 1H), 1.86 (s, 6H). LCMS (m/z) 335.2 [M+H], Tr=2.48 min (LCMS method 2).

Step 2: synthesis of (E)-4-((4-amino-8-(4-(2-cyanovinyl)-2,6-dimethylphenyl)quinazolin-2-yl)amino)benzonitrile (compound 2)

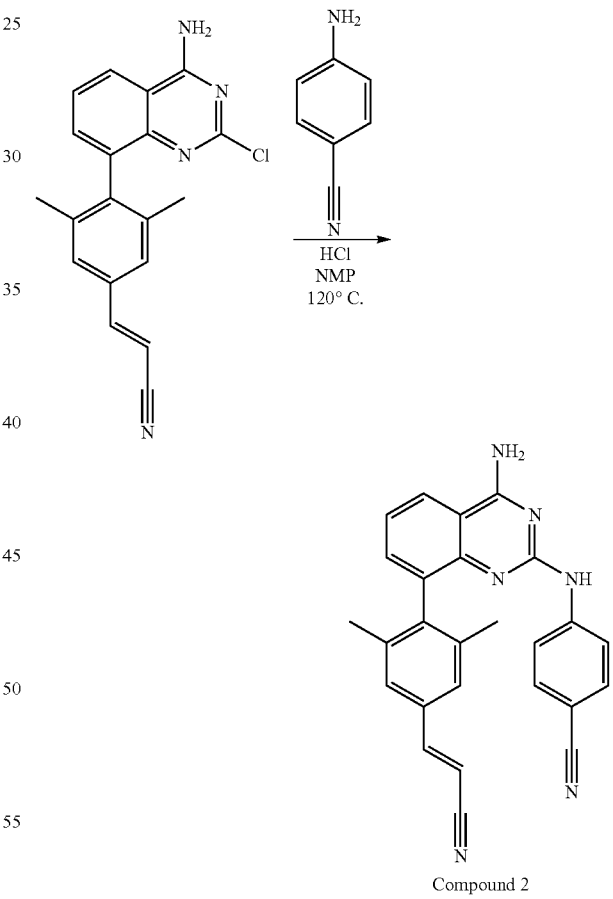

Compound 2

A mixture of compound 2a (100 mg, 0.30 mmol), 4-cyanoaniline (46 mg, 0.388 mmol, Sigma-Aldrich) and hydrogen chloride solution in 1,4-dioxane (4M, 7 μL, 0.03 mmol) in dry N-methyl-2-pyrrolidone (2 mL) was heated at 120° C. for 2 hours. The reaction mixture was cooled down to room temperature and triethylamine (0.1 mL, 0.72 mmol) was added. After 15 minutes, water (5 mL) was added and the solid product was filtered off and washed with water. The crude residue was taken up in a mixture of dichloromethane and diethyl ether (1:1, 5 mL) and then treated in a sonic bath for 3 minutes. The solid compound was filtered off and washed with diethyl ether (5 mL) to afford the title compound 2. $^1$H NMR (400 MHz, DMSO-$d_6$) δ 9.44 (s, 1H), 8.18 (dd, J=8.2, 1.5 Hz, 1H), 7.74 (d, J=16.7 Hz, 1H), 7.70 (d, J=8.9 Hz, 2H), 7.51 (s, 2H), 7.48 (dd, J=7.1, 1.3 Hz, 1H), 7.34 (dd, J=8.2, 7.1 Hz, 1H), 7.26 (d, J=8.9 Hz, 2H), 6.54 (d, J=16.7 Hz, 1H), 1.91 (s, 6H). HRMS: (ESI+) calculated for $C_{26}H_{21}N_6$ [M+H] 417.1822, found 417.1820. LCMS (m/z) 417.2 [M+H], Tr=4.68 min (LCMS method 1).

Example 3

(E)-4-((4-Amino-8-(4-(2-cyanovinyl)-2,6-dimethylphenyl)quinazolin-2-yl)amino)-2-methoxybenzonitrile—Compound 3

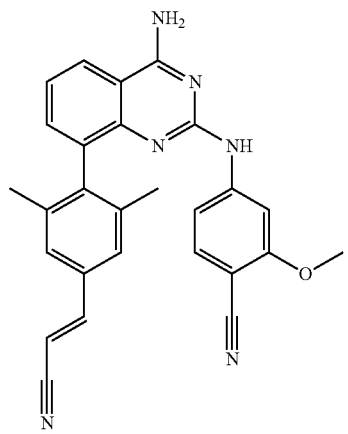

Step 1: Synthesis of 4-((4-amino-8-bromoquinazolin-2-yl)amino)-2-methoxybenzonitrile hydrochloride (Compound 3a)

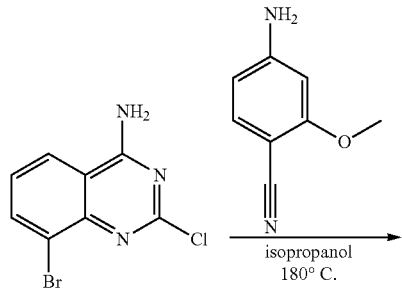

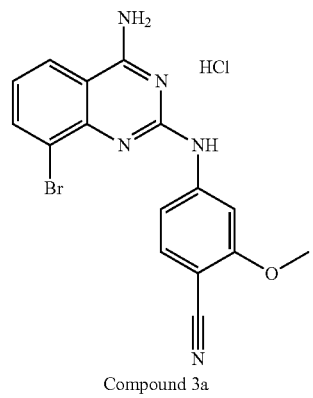

Compound 3a

A mixture of 8-bromo-2-chloroquinazolin-4-amine (259 mg, 1 mmol, Ark Pharm Inc, AK-28702) and 4-amino-2-methoxybenzonitrile (222 mg, 1.5 mmol, Ark Pharm Inc, AK-77827) in isopropanol (7 mL) was heated in microwave at 180° C. for 8 hours. The reaction mixture was cooled down to room temperature and the solid product was filtered off and washed with cold isopropanol and then with diethyl ether and hexane to afford the compound 3a as the HCl salt. $^1$H NMR (400 MHz, DMSO-$d_6$) δ 8.24 (d, J=8.1 Hz, 1H), 8.07 (d, J=7.6 Hz, 1H), 7.59 (d, J=8.5 Hz, 1H), 7.42 (dd, J=8.6, 1.9 Hz, 1H), 7.37-7.04 (m, 5H), 3.99 (s, 3H). LCMS (m/z) 370.3 [M+H], Tr=2.43 min (LCMS method 2).

Step 2: synthesis of (E)-4-((4-amino-8-(4-(2-cyanovinyl)-2,6-dimethylphenyl)quinazolin-2-yl)amino)-2-methoxybenzonitrile (compound 3)

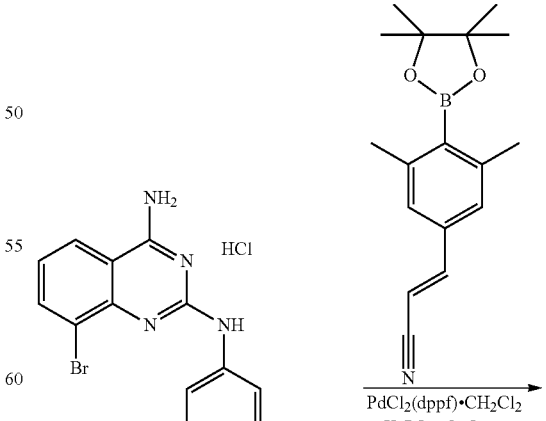

75
-continued

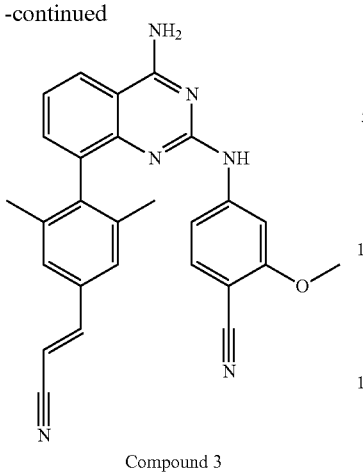

Compound 3

A mixture of compound 3a (50 mg, 0.14 mmol), compound 1c (76 mg, 0.27 mmol), [1,1'-bis(diphenylphosphino)ferrocene] dichloropalladium(II), complex with dichloromethane (33 mg, 0.04 mmol), potassium phosphate tribasic (86 mg, 0.41 mmol), and copper (I) acetate (2 mg, 0.01 mmol) in dry N,N-dimethylformamide (5 mL) was purged with argon and heated at 120° C. for 3 hours. The reaction mixture was cooled down to room temperature and diluted with water and ethyl acetate. The organic layer was separated and washed twice with brine, dried over magnesium sulfate, 1 volume equivalent of hexane added and this mixture was filtered through a 3 cm layer of silica gel which was washed with additional ethyl acetate. Combined organics were concentrated down under reduced pressure and the crude mixture was subjected to silica gel chromatography (gradient from 5-50% ethyl acetate in iso-hexanes). Product was then re-purified by reverse phase chromatography (5-100% acetonitrile in water with 0.1% trifluoroacetic acid) to afford the TFA salt of compound 3. $^1$H NMR (400 MHz, DMSO-$d_6$) δ 8.25 (bs, 1H), 7.74-7.65 (m, 2H), 7.62-7.42 (m, 5H), 7.30 (d, J=9.0 Hz, 2H), 7.26-6.95 (m, 1H), 6.53 (d, J=17.0 Hz, 1H), 3.41 (s, 3H), 1.93 (s, 6H). LCMS (m/z) 447.4 [M+H], Tr=2.39 min (LCMS method 2).

Example 4

(E)-4-((8-(4-(2-Cyanovinyl)-2,6-dimethylphenyl)-6-fluoroquinazolin-2-yl)amino)benzonitrile—Compound 4

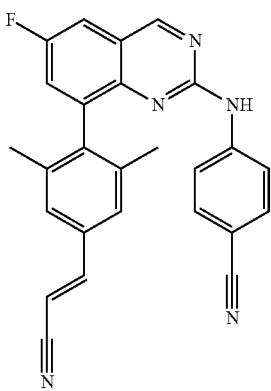 [SMILES: Cc1cc(/C=C/C#N)cc(C)c1-c1cc(F)cc2cnc(Nc3ccc(C#N)cc3)nc12]

76

Step 1: Synthesis of 4-((8-bromo-6-fluoroquinazolin-2-yl)amino)benzonitrile (Compound 4a)

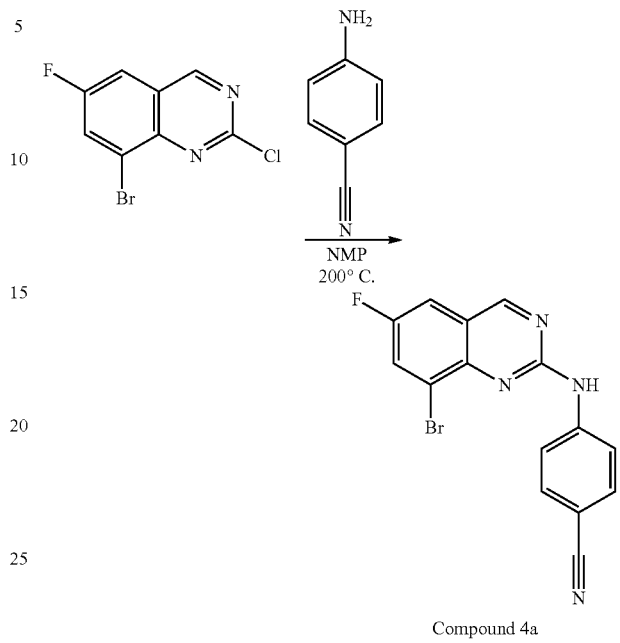

Compound 4a

A mixture of 8-bromo-2-chloro-6-fluoroquinazoline (500 mg, 1.91 mmol, Ark Pharm Inc, AK-93358) and 4-aminobenzonitrile (250 mg, 2.12 mmol, Sigma-Aldrich) in dry N-methylpyrrolidone was heated in microwave at 200° C. for 5 hours. The reaction mixture was cooled down to room temperature and subjected to silica gel chromatography (gradient from 5-50% ethyl acetate in iso-hexanes), to afford the title compound 4a. $^1$H NMR (400 MHz, DMSO-$d_6$) δ 10.69 (s, 1H), 9.37 (s, 1H), 8.32 (d, J=8.7 Hz, 2H), 8.26 (dd, J=8.5, 2.7 Hz, 1H), 7.86 (dd, J=8.5, 2.7 Hz, 1H), 7.78 (d, J=8.7 Hz, 2H). LCMS (m/z) 343.0 [M+H], Tr=4.72 min (LCMS method 1).

Step 2: synthesis of (E)-4-((8-(4-(2-cyanovinyl)-2,6-dimethylphenyl)-6-fluoroquinazolin-2-yl)amino)benzonitrile (compound 4)

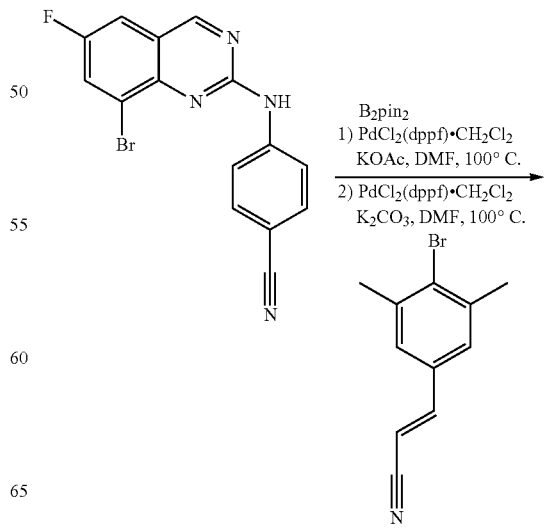

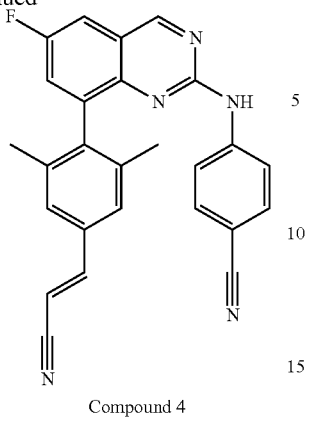

Compound 4

A mixture of compound 4a (50 mg, 0.14 mmol), 4,4,4',4',5,5,5',5'-octamethyl-2,2'-bi(1,3,2-dioxaborolane) (40 mg, 0.16 mmol), potassium acetate (60 mg, 0.61 mmol) and [1,1'-bis(diphenylphosphino)ferrocene] dichloropalladium (II), complex with dichloromethane (50 mg, 0.061 mmol) in dry N,N-dimethylformamide (5 mL) was purged with argon and heated at 100° C. for 1 hour. A mixture of compound 1b (33 mg, 0.14 mmol), [1,1'-bis(diphenylphosphino)ferrocene] dichloropalladium(II), complex with dichloromethane (50 mg, 0.061 mmol) and potassium carbonate (90 mg, 0.65 mmol) was added to the reaction mixture. The reaction mixture was heated to 100° C. for 5 hours, cooled down to room temperature, concentrated down under reduced pressure and subjected to silica gel chromatography (gradient from 5-50% ethyl acetate in iso-hexanes). The crude product was then re-purified on HPLC (preparative column Phenomenex Gemini 10 micron C18, 250×21.2 mm, 10 mL/min, gradient from 10-100% acetonitrile in water) to afford the title compound 4. $^1$H NMR (400 MHz, DMSO-$d_6$) δ 9.45 (s, 1H), 7.92-7.86 (m, 1H), 7.82-7.76 (m, 2H), 7.72 (s, 1H), 7.68 (d, J=8.9 Hz, 2H), 7.58 (s, 2H), 7.36 (d, J=8.9 Hz, 2H), 6.60 (d, J=16.7 Hz, 1H), 1.92 (s, 6H). LCMS (m/z) 420.1 [M+H], Tr=4.85 min (LCMS method 1).

Example 5

(E)-4-((8-(4-(2-Cyanovinyl)-2,6-difluorophenyl)quinazolin-2-yl)amino)benzonitrile-Compound 5 (mixture E/Z=4/1)

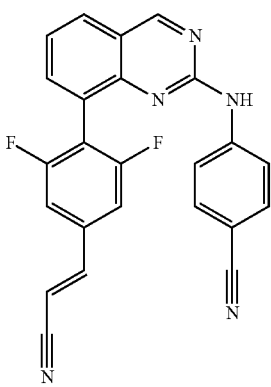 [SMILES: N#C/C=C/c1cc(F)c(-c2cccc3cnc(Nc4ccc(C#N)cc4)nc23)c(F)c1]

Step 1: Synthesis of 4-((8-(2,6-difluoro-4-formylphenyl)quinazolin-2-yl)amino)benzonitrile (Compound 5a)

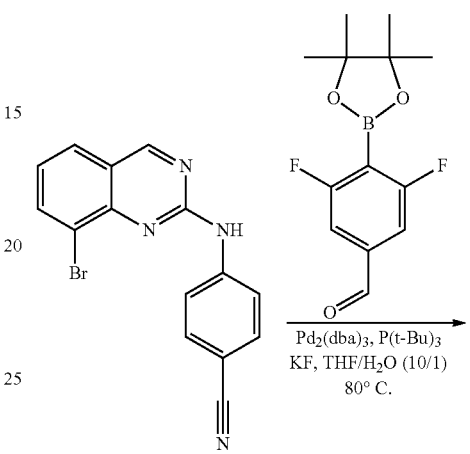

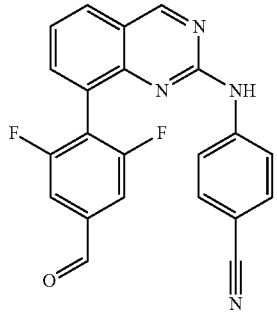

Compound 5a

A mixture of compound 1a (40 mg, 0.12 mmol), 3,5-difluoro-4-(4,4,5,5-tetramethyl-1,3,2-dioxaborolan-2-yl)benzaldehyde (66 mg, 0.24 mmol, Sigma-Aldrich), and potassium fluoride (24 mg, 0.4 mmol) in a tetrahydrofuran/water mixture (10:1, 10 mL) was purged with argon and tris(dibenzylideneacetone)palladium(0) (68 mg, 0.07 mmol) was added followed by tri-tert-butylphosphine (36 µL, 0.14 mmol). This mixture was heated at 80° C. for 4 hours. The solvent was removed under reduce pressure and the residue was purified by silica gel chromatography (gradient from 20-80% ethyl acetate in iso-hexanes) to afford the title compound 5a. $^1$H NMR (400 MHz, DMSO-$d_6$) δ 10.55 (s, 1H), 10.15 (s, 1H), 9.51 (s, 1H), 8.16 (d, J=8.0 Hz, 1H), 8.03 (d, J=7.0 Hz, 1H), 7.90 (d, J=6.9 Hz, 2H), 7.83 (d, J=8.8 Hz, 2H), 7.67-7.58 (m, 1H), 7.53 (d, J=8.8 Hz, 2H). LCMS (m/z) 387.1 [M+H], Tr=4.67 min (LCMS method 1).

Step 2: synthesis of (E)-4-((8-(4-(2-cyanovinyl)-2,6-difluorophenyl)quinazolin-2-yl)amino)benzonitrile (compound 5) (mixture E/Z=4/1)

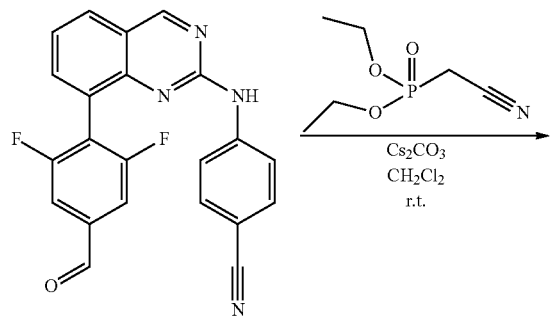

Compound 5

Cesium carbonate (1.5 g, 4.6 mmol) was added to a solution of compound 5a (70 mg, 0.18 mmol) and diethyl (cyanomethyl)phosphonate (32 μL, 0.2 mmol) in dry dichloromethane (25 mL) and the solvent was slowly removed under reduced pressure at 30° C. The resulting reaction mixture was allowed to stand overnight at room temperature. Dichloromethane was added to the residue and the solids were filtered off. The solvent was removed under reduced pressure and the residue was purified by HPLC (preparative column Phenomenex Gemini 10 micron C18, 250×21.2 mm, 10 mL/min, gradient from 10-100% acetonitrile in water) to afford the title compound 5 as a mixture of E/Z isomers 4/1. $^1$H NMR for the E isomer (400 MHz, DMSO-$d_6$) δ 10.54 (s, 1H), 9.49 (s, 1H), 8.16-8.12 (m, 1H), 8.0 (d, J=7.3 Hz, 1H), 7.87-7.83 (m, 3H), 7.73 (d, J=8.0 Hz, 2H), 7.63-7.58 (m, 1H), 7.56-7.52 (m, 2H), 6.81 (d, J=16.7 Hz, 1H). LCMS (m/z) 410.1 [M+H], Tr=4.76 min (LCMS method 1).

Example 6

(E)-4-((8-(4-(2-Cyanovinyl)-2,6-dimethylphenyl)-4-((cyclopropylmethyl)amino)quinazolin-2-yl)amino)benzonitrile—Compound 6

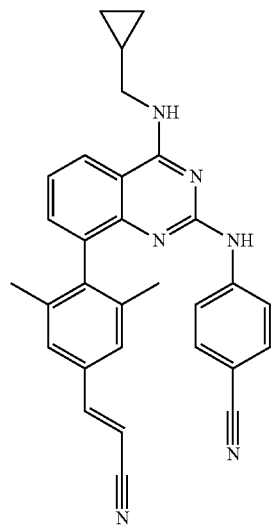 [SMILES: Cc1cc(/C=C/C#N)cc(C)c1-c1cccc2c(NCC3CC3)nc(Nc3ccc(C#N)cc3)nc12]

Step 1: Synthesis of 8-bromo-2-chloro-N-(cyclopropylmethyl)quinazolin-4-amine (Compound 6a)

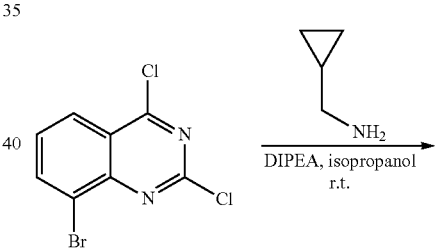

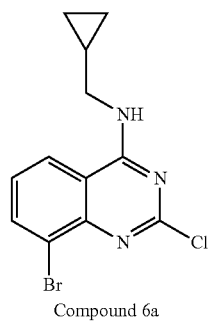

Compound 6a

Cyclopropylmethanamine (95 μL, 1.1 mmol) and N-ethyldiisopropylamine (0.35 mL, 2 mmol) were added to a solution of 8-bromo-2,4-dichloroquinazoline (0.278 mg, 1 mmol, Ark Pharm Inc., AK-28703) in isopropanol (5 mL). The reaction mixture was stirred at room temperature for 30 minutes. The solid product was filtered off and washed with water (2×5 mL) and pentane (3×5 mL) to give the title compound 6a. $^1$H NMR (400 MHz, DMSO-$d_6$) δ 9.03 (s, 1H), 8.30 (dd, J=8.3 Hz, J=1.3 Hz, 1H), 8.12 (dd, J=7.7 Hz, J=1.3 Hz, 1H), 7.44 (t, J=8.0 Hz, 1H), 3.41-3.35 (m, 2H), 1.23-1.11 (m, 1H), 0.52-0.45 (m, 2H), 0.34-0.28 (m, 2H). HRMS: (ESI+) calculated for $C_{12}H_{12}N_3BrCl$ [M+H] 311.9898. found 311.9898. LCMS (m/z) 312.0 [M+H], Tr 4.59 min (LCMS method 1).

Step 2: Synthesis of 4-((8-bromo-4-((cyclopropylmethyl)amino)quinazolin-2-yl)amino)benzonitrile hydrochloride (Compound 6b)

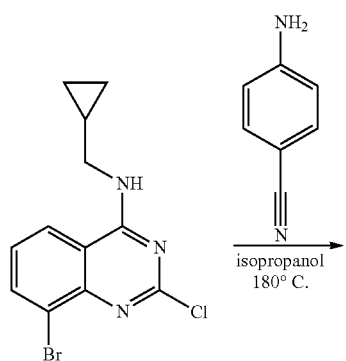

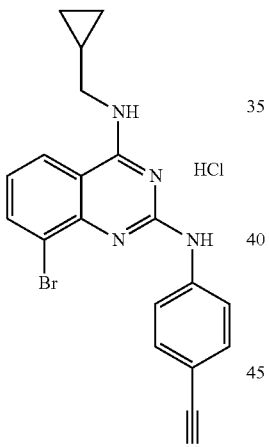

Compound 6b

A mixture of compound 6a (156 mg, 0.5 mmol) and 4-aminobenzonitrile (71 mg, 0.6 mmol, Sigma-Aldrich) in isopropanol (5 mL) was heated in microwave at 180° C. for 2 hours. The reaction mixture was cooled down to room temperature and the solid product was filtered off and washed twice with cold isopropanol and then three times with pentane to afford the compound 6b as the HCl salt. $^1$H NMR (400 MHz, DMSO-$d_6$) δ 8.39 (d, J=7.7 Hz, 1H), 8.15-7.99 (m, 3H), 7.81 (d, J=8.4 Hz, 2H), 7.33 (t, J=7.9 Hz, 1H), 3.53-3.45 (m, 2H), 1.30-1.17 (m, 1H), 0.54-0.48 (m, 2H), 0.37-0.32 (m, 2H). HRMS: (ESI+) calculated for $C_{19}H_{17}N_5Br$ [M+H] 394.0662. found 394.0661. LCMS (m/z) 394.0 [M+H], Tr 4.29 min (LCMS method 1).

Step 3: synthesis of (E)-4-((8-(4-(2-cyanovinyl)-2,6-dimethylphenyl)-4-((cyclopropylmethyl)amino)quinazolin-2-yl)amino)benzonitrile (compound 6)

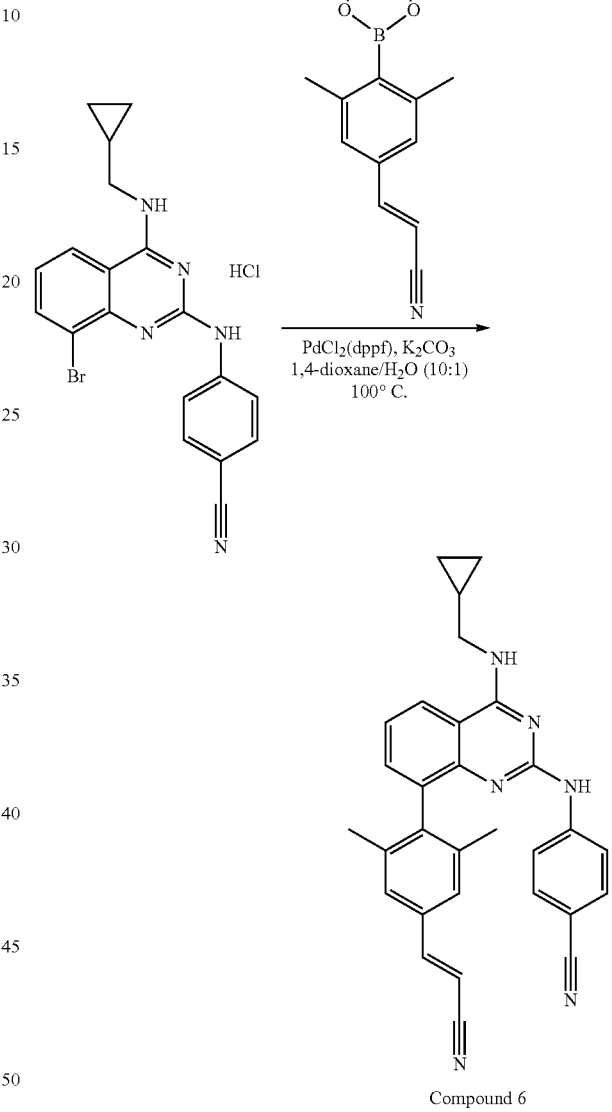

Compound 6

A mixture of compound 6b (65 mg, 0.15 mmol), compound 1c (64 mg, 0.23 mmol), [1,1'-bis(diphenylphosphino)ferrocene] dichloropalladium(II), complex with dichloromethane (37 mg, 0.05 mmol) and potassium carbonate (104 mg, 0.75 mmol) in the mixture of 1,4-dioxane and water (10:1, 5 mL) was purged with argon and heated at 100° C. for 1 hour. Solvents were removed under reduced pressure and the residue was purified by silica gel chromatography (gradient from 20-40% ethyl acetate in isohexanes) to afford the title compound 6. $^1$H NMR (400 MHz, DMSO-$d_6$) δ 9.49 (s, 1H), 8.39 (t, J=5.6 Hz, 1H), 8.24-8.13 (m, 2H), 7.74-7.69 (m, 2H), 7.51 (s, 2H), 7.46 (dd, J=7.2 Hz, J=1.4 Hz, 1H), 7.35 (t, J=8.2 Hz, 1H), 7.26 (d, J=8.9 Hz, 2H), 6.54 (d, J=16.7 Hz, 1H), 3.47-3.43 (m, 2H), 1.90 (s, 6H), 1.30-1.21 (m, 1H), 0.53-0.47 (m, 2H), 0.35-0.30 (m, 2H). HRMS: (ESI+) calculated for $C_{30}H_{27}N_6$ [M+H] 471.2292. found 471.2292. LCMS (m/z) 471.2 [M+H], Tr 4.05 min (LCMS method 1).

Example 7

(E)-4-((4-(Butylamino)-8-(4-(2-cyanovinyl)-2,6-dimethylphenyl)quinazolin-2-yl)amino)benzonitrile—Compound 7

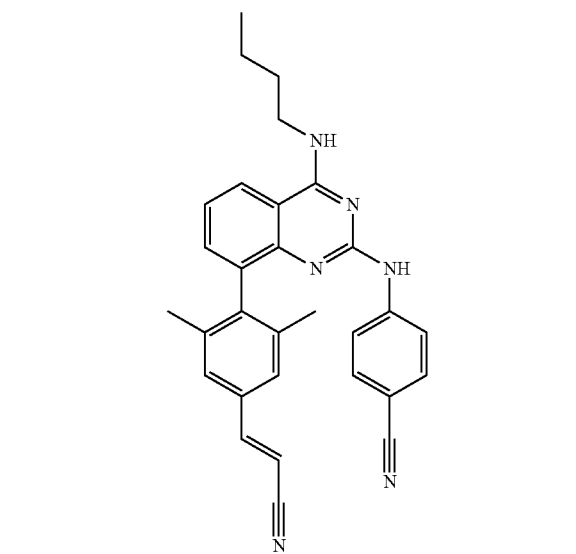 [SMILES: CCCCNc1nc(Nc2ccc(C#N)cc2)nc2c(-c3c(C)cc(/C=C/C#N)cc3C)cccc12]

Step 1: Synthesis of 8-bromo-N-butyl-2-chloroquinazolin-4-amine (Compound 7a)

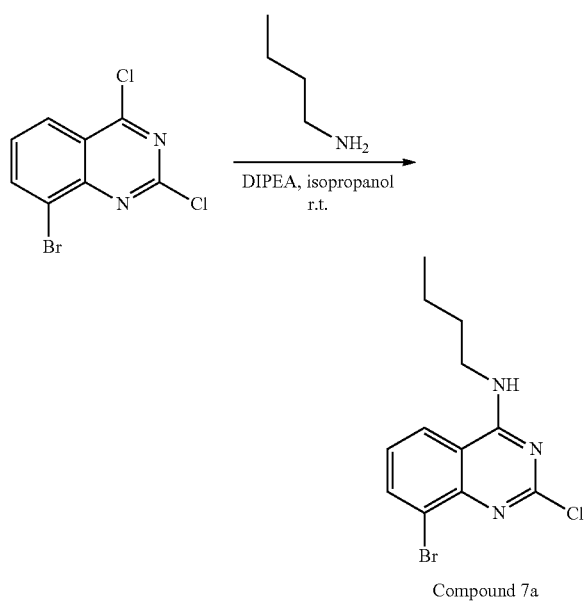

n-Butylamine (109 µL, 1.1 mmol) and N-ethyldiisopropylamine (0.35 mL, 2 mmol) were added to a solution of 8-bromo-2,4-dichloroquinazoline (278 mg, 1 mmol, Ark Pharm Inc., AK-28703) in isopropanol (5 mL). The reaction mixture was stirred at room temperature for 30 minutes. The solid product was filtered off and washed with water (2×5 mL) and pentane (3×5 mL) to give the title compound 7a. $^1$H NMR (400 MHz, DMSO-d$_6$) δ 8.87 (s, 1H), 8.27 (dd, J=8.3 Hz, J=1.2 Hz, 1H), 8.12 (dd, J=7.7 Hz, J=1.2 Hz, 1H), 7.43 (t, J=7.9 Hz, 1H), 3.55-3.48 (m, 2H), 1.66-1.57 (m, 2H), 1.41-1.31 (m, 2H), 0.92 (t, J=7.3 Hz, 3H). HRMS: (ESI+) calculated for $C_{12}H_{14}N_3BrCl$ [M+H] 314.0054, found 314.0055. LCMS (m/z) 314.0 [M+H], Tr 4.76 min (LCMS method 1).

Step 2: Synthesis of 4-((8-bromo-4-(butylamino) quinazolin-2-yl)amino)benzonitrile hydrochloride (Compound 7b)

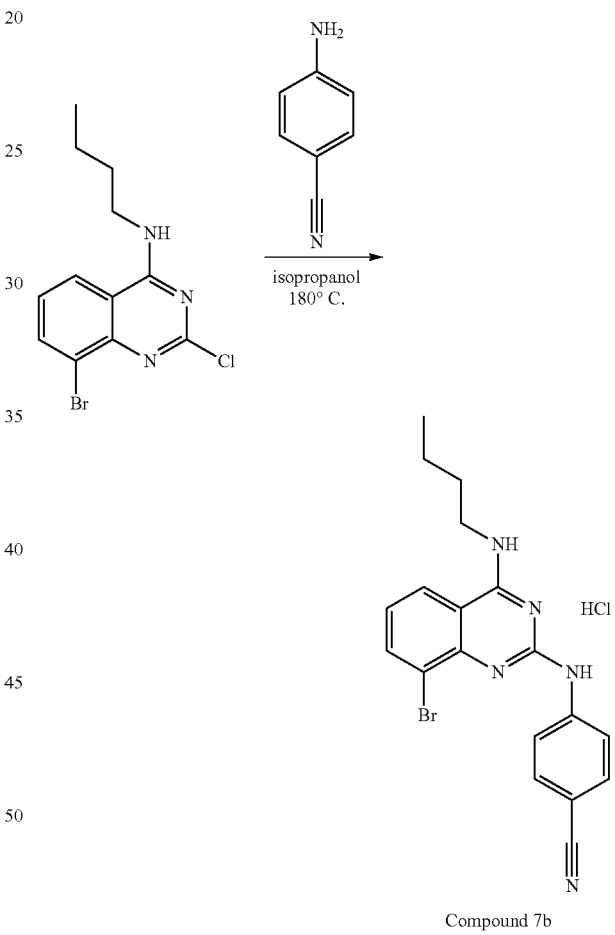

Compound 7b

A mixture of compound 7a (157 mg, 0.5 mmol) and 4-aminobenzonitrile (71 mg, 0.6 mmol, Sigma-Aldrich) in isopropanol (5 mL) was heated in microwave at 180° C. for 2 hours. The reaction mixture was cooled down to room temperature and the solid product was filtered off and washed twice with cold isopropanol and then three times with pentane to afford the compound 7b as the HCl salt. $^1$H NMR (400 MHz, DMSO-d$_6$) δ 8.32 (d, J=7.8 Hz, 1H), 8.21-7.79 (m, 3H), 7.79 (d, J=8.3 Hz, 2H), 7.29 (t, J=7.8 Hz, 1H), 3.65-3.63 (m, 2H), 1.74-1.59 (m, 2H), 1.43-1.33 (m, 2H), 0.92 (t, J=7.4 Hz, 3H). HRMS: (ESI+) calculated for $C_{19}H_{19}N_5Br$ [M+H] 396.0818. found 396.0816. LCMS (m/z) 396.1 [M+H], Tr 4.34 min (LCMS method 1).

Step 3: synthesis of (E)-4-((4-(butylamino)-8-(4-(2-cyanovinyl)-2,6-dimethylphenyl)quinazolin-2-yl)amino)benzonitrile (compound 7)

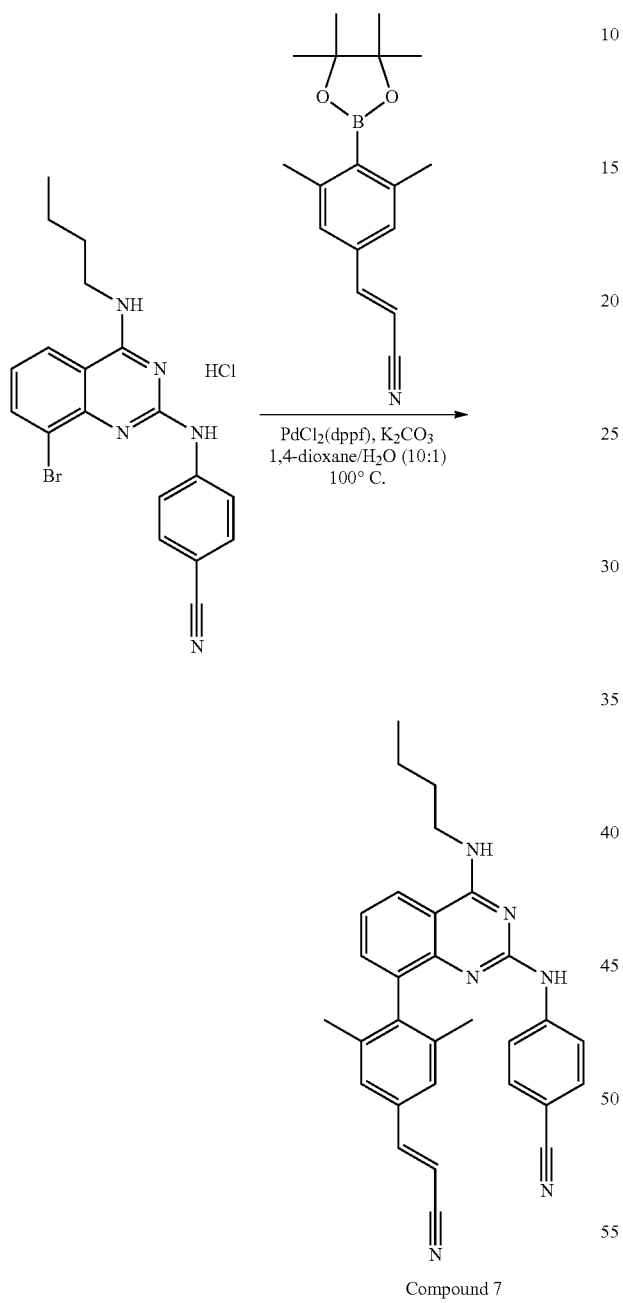

Compound 7

A mixture of compound 7b (65 mg, 0.15 mmol), compound 1c (64 mg, 0.23 mmol), [1,1'-bis(diphenylphosphino)ferrocene] dichloropalladium(II), complex with dichloromethane (37 mg, 0.05 mmol) and potassium carbonate (104 mg, 0.75 mmol) in the mixture of 1,4-dioxane and water (10:1, 5 mL) was purged with argon and heated at 100° C. for 1 hour. Solvents were removed under reduced pressure and the residue was purified by silica gel chromatography (gradient from 20-40% ethyl acetate in isohexanes) to afford the title compound 7. $^1$H NMR (400 MHz, DMSO-$d_6$) δ 9.45 (s, 1H), 8.25-8.16 (m, 2H), 7.78-7.69 (m, 3H), 7.51 (s, 2H), 7.46 (dd, J=7.1 Hz, J=1.3 Hz, 1H), 7.34 (t, J=8.2 Hz, 1H), 7.27 (d, J=8.9 Hz, 2H), 6.54 (d, J=16.7 Hz, 1H), 3.63-3.51 (m, 2H), 1.90 (s, 6H), 1.72-1.65 (m, 2H), 1.46-1.38 (m, 2H), 0.95 (t, J=7.4 Hz, 3H). MS-ESI$^+$ m/z (%): 473 (100, M+H$^+$), 495 (20, M+Na$^+$); HRMS: (ESI+) calculated for $C_3H_{29}N_6$ [M+H] 473.2448, found 473.2448. LCMS (m/z) 473.3 [M+H], Tr 4.14 min (LCMS method 1).

Example 8

(E)-4-((4-Amino-8-(4-(2-cyanovinyl)-2,6-difluorophenyl)quinazolin-2-yl)amino)benzonitrile—Compound 8 (mixture E/Z=3/2)

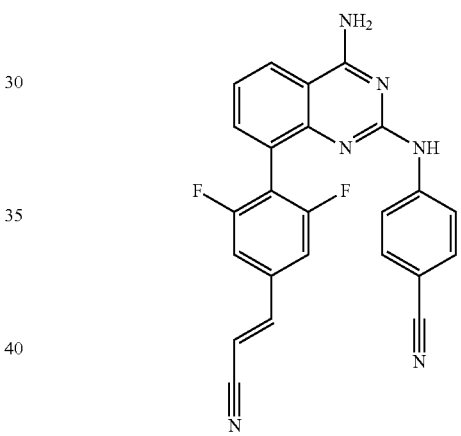

Step 1: Synthesis of 4-((4-amino-8-bromoquinazolin-2-yl)amino)benzonitrile (Compound 8a)

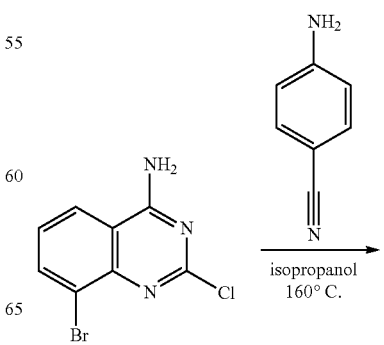

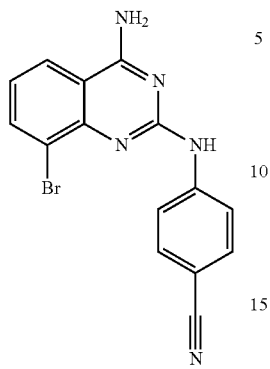

Compound 8a

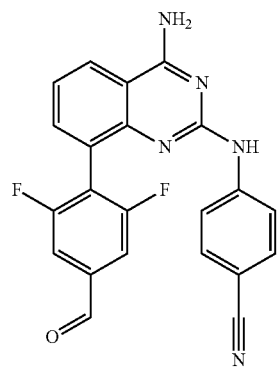

Compound 8b

A mixture of 8-bromo-2-chloroquinazolin-4-amine (259 mg, 1 mmol, Ark Pharm Inc, AK-28702) and 4-aminobenzonitrile (130 mg, 1.1 mmol, Sigma-Aldrich) in isopropanol (5 mL) was heated in microwave at 160° C. for 3 hours. The reaction mixture was cooled down to room temperature and the solid product was filtered off and washed with cold isopropanol and then with diethyl ether to afford the compound 2a. $^1$H NMR (400 MHz, DMSO-$d_6$) δ 9.74 (s, 1H), 8.35 (d, J=8.8 Hz, 2H), 8.16 (d, J=8.0 Hz, 1H), 8.01 (d, J=7.5 Hz, 1H), 7.71 (d, J=8.8 Hz, 2H), 7.16 (t, J=7.8 Hz, 1H). HRMS: (ESI+) calculated for $C_{15}H_{11}N_5Br$ [M+H] 340.0192, found 340.0192. LCMS (m/z) 340.0 [M+H], Tr=4.06 min (LCMS method 1).

Step 2: Synthesis of 4-((4-amino-8-(2,6-difluoro-4-formylphenyl)quinazolin-2-yl)amino)benzonitrile (Compound 8b)

A mixture of compound 8a (120 mg, 0.36 mmol), 3,5-difluoro-4-(4,4,5,5-tetramethyl-1,3,2-dioxaborolan-2-yl)benzaldehyde (285 mg, 1.06 mmol, Sigma-Aldrich), and potassium fluoride (102 mg, 1.76 mmol) in a tetrahydrofuran/water mixture (10:1, 30 mL) was purged with argon and tris(dibenzylideneacetone)palladium(0) (195 mg, 0.213 mmol) was added followed by tri-tert-butylphosphine (103 μL, 0.43 mmol). The mixture was heated at 80° C. for 4 hours. The solvent was removed under reduce pressure and the residue was purified by silica gel chromatography (gradient from 20-80% ethyl acetate in iso-hexanes) to afford the title compound 8b. $^1$H NMR (400 MHz, DMSO-$d_6$) δ 10.12 (s, 1H), 9.56 (s, 1H), 8.29 (dd, J=8.2 Hz, J=1.1 Hz, 2H), 7.87-7.73 (m, 6H), 7.44-7.34 (m, 3H). LCMS (m/z) 401.9 [M+H], Tr=4.28 min (LCMS method 1).

Step 3: synthesis of (E)-4-((4-amino-8-(4-(2-cyanovinyl)-2,6-difluorophenyl)quinazolin-2-yl)amino)benzonitrile (compound 8) (mixture E/Z=3/2)

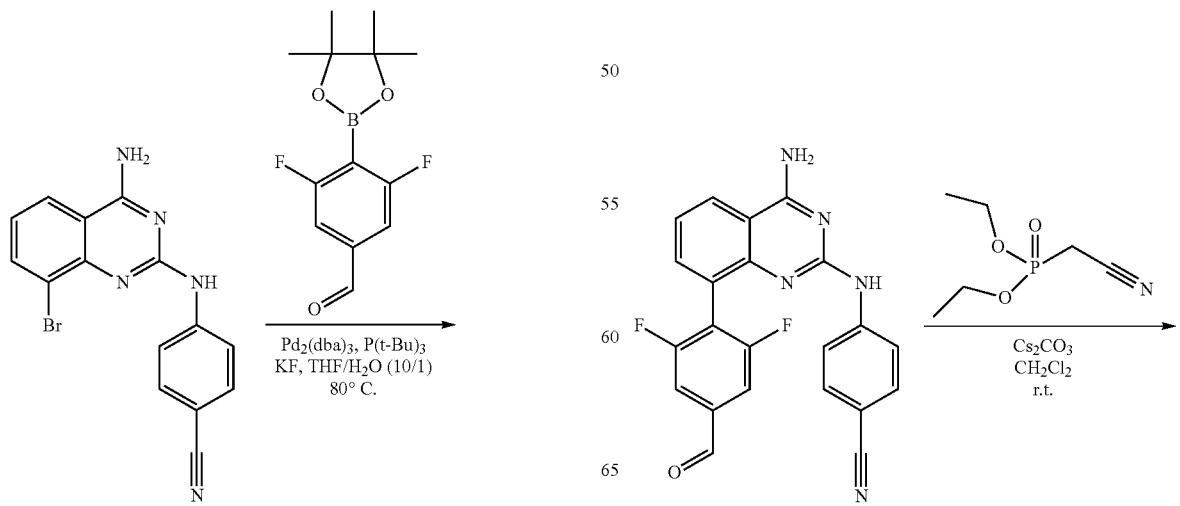

-continued

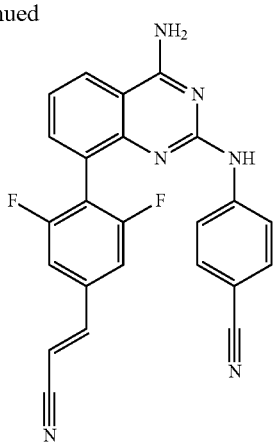

Compound 8

Cesium carbonate (2.5 g, 7.69 mmol) was added to a solution of compound 8b (74 mg, 0.18 mmol) and diethyl (cyanomethyl)phosphonate (30 µL, 0.18 mmol) in dry dichloromethane (25 mL) and the solvent was slowly removed under reduced pressure at 30° C. The resulting reaction mixture was allowed to stand overnight at room temperature. Dichloromethane was added to the residue and the solids were filtered off. The solvent was removed under reduced pressure and the residue was purified by HPLC (preparative column Phenomenex Gemini 10 micron C18, 250×21.2 mm, 10 mL/min, gradient from 10-100% acetonitrile in water) to afford the title compound 8 as a mixture of E/Z isomers 3/2. $^1$H NMR for the E isomer (400 MHz, DMSO-d$_6$) δ 9.54 (s, 1H), 8.29-8.24 (m, 2H), 7.84 (d, J=2.4 Hz, 1H), 7.82-7.78 (m, 2H), 7.72 (d, J=7.3, 2H), 7.66 (d, J=7.8 Hz, 2H), 7.43-7.39 (m, 2H), 7.38-7.33 (m, 1H), 6.77 (d, J=16.7 Hz, 1H). LCMS (m/z) 424.9 [M+H], Tr=3.46 min (LCMS method 1).

Example 9

(E)-5-((4-Amino-8-(4-(2-cyanovinyl)-2,6-dimethylphenyl)quinazolin-2-yl)amino)picolinonitrile—Compound 9

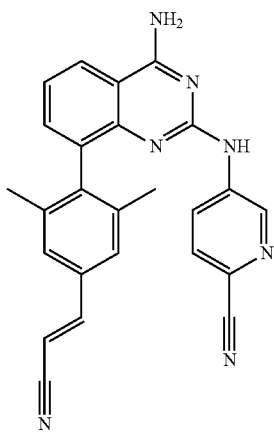 [SMILES: Cc1cc(/C=C/C#N)cc(C)c1-c1cccc2c(N)nc(Nc3ccc(C#N)nc3)nc12]

Step 1: Synthesis of 5-((4-amino-8-bromoquinazolin-2-yl)amino)picolinonitrile (compound 9a)

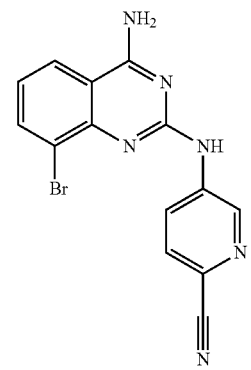

Compound 9a

A mixture of 8-bromo-2-chloroquinazolin-4-amine (500 mg, 1.9 mmol, Ark Pharm Inc, AK-28702) and 5-aminopicolinonitrile (253 mg, 2.1 mmol, Ark Pharm Inc, AK-26123) in isopropanol (10 mL) was heated under argon in microwave at 180° C. for 8 hours. The reaction mixture was cooled down to room temperature and the solid product was filtered off and washed with cold isopropanol and then with diethyl ether and hexane to afford the compound 9a. $^1$H NMR (400 MHz, DMSO-d$_6$) δ 9.98 (s, 1H), 9.35 (dd, J=2.6, 0.7 Hz, 1H), 8.85 (dd, J=8.7, 2.6 Hz, 1H), 8.17 (dd, J=8.2, 1.3 Hz, 1H), 8.03 (dd, J=7.6, 1.3 Hz, 1H), 7.95-7.91 (m, 2H), 7.23-7.10 (m, 2H). LCMS (m/z) 343.2 [M+H], Tr=2.31 min (LCMS method 2).

Step 2: synthesis of (E)-5-((4-amino-8-(4-(2-cyanovinyl)-2,6-dimethylphenyl)quinazolin-2-yl)amino)picolinonitrile (compound 9)

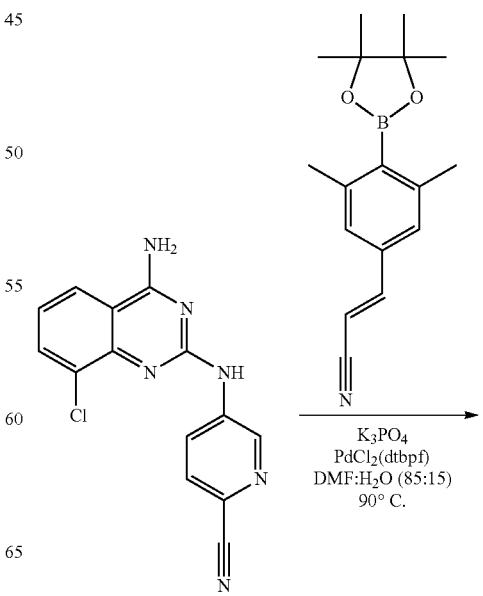

91
-continued

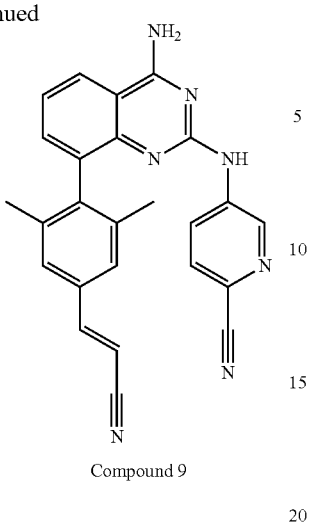

Compound 9

Compound 9a (150 mg, 0.44 mmol), compound 1c (498 mg, 1.76 mmol), potassium phosphate tribasic (560 mg, 2.64 mmol) and 1,1'-bis(di-tert-butylphosphino)ferrocene palladium dichloride (57 mg, 0.09 mmol) were dissolved in N,N-dimethylformamide:water mixture (85:15, 25 mL) under argon. The reaction was heated at 90° C. for 1 hour. The reaction mixture was cooled down to room temperature and diluted with water and ethyl acetate. The organic layer was separated. The water layer was washed with additional ethyl acetate. Combined organics were washed twice with brine and dried over magnesium sulfate. Solvents were removed under reduced pressure and the residue was purified by silica gel chromatography (gradient from 0-40% ethyl acetate and methanol (4/1) in iso-hexanes). Solvents were removed under reduced pressure and the solid residue was treated with the mixture of hexane/diethyl ether (5:1) in the sonic bath for 5 minutes, filtered off and washed with hexane to afford the title compound 9. $^1$H NMR (400 MHz, DMSO-$d_6$) δ 9.70 (s, 1H), 8.74 (d, J=2.5 Hz, 1H), 8.24-8.15 (m, 2H), 7.72 (d, J=16.7 Hz, 1H), 7.49 (d, J=7.6 Hz, 3H), 7.40-7.30 (m, 2H), 6.51 (d, J=16.7 Hz, 1H), 1.90 (s, 6H). LCMS (m/z) 418.3 [M+H], Tr=2.47 min (LCMS method 2).

Example 10

(E)-6-((4-Amino-8-(4-(2-cyanovinyl)-2,6-dimethylphenyl)quinazolin-2-yl)amino)nicotinonitrile—Compound 10

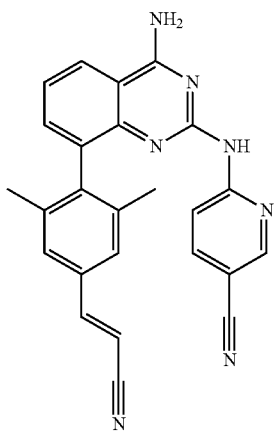 [SMILES: Cc1cc(/C=C/C#N)cc(C)c1-c1cccc2c(N)nc(Nc3ccc(C#N)cn3)nc12]

92

Synthesis of (E)-6-((4-amino-8-(4-(2-cyanovinyl)-2,6-dimethylphenyl)quinazolin-2-yl)amino)nicotinonitrile (compound 10)

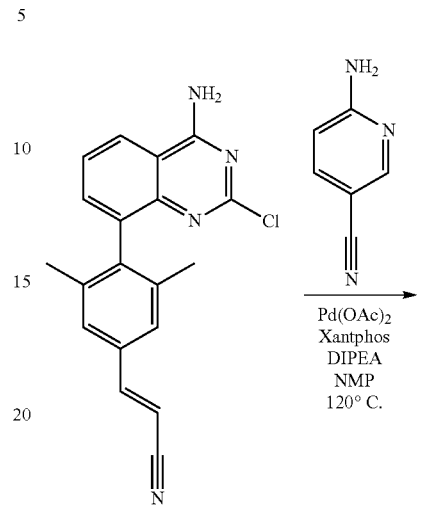

Compound 2a (820 mg, 2.45 mmol), 6-aminonicotinonitrile (875 mg, 7.35 mmol, Ark Pharm Inc, AK-32349), N,N-diisopropylethylamine (2.53 g, 19.6 mmol), (9,9-dimethyl-9H-xanthene-4,5-diyl)bis(diphenylphosphine) (142 mg, 0.25 mmol) and palladium (II) acetate (55 mg, 0.25 mmol) were combined under argon in N-methyl-2-pyrrolidone (40 mL). The reaction was heated at 120° C. in a sealed vessel for 4 hours. The reaction mixture was cooled down to room temperature and diluted with water and ethyl acetate. The organic layer was separated and washed twice with brine, dried over magnesium sulfate, 0.05 volume equivalent of hexane added and this mixture was filtered through a 2 cm layer of silica gel which was washed with additional ethyl acetate. Combined organics were concentrated down under reduced pressure. The crude residue was treated with diethyl ether/dichloromethane mixture (1:1) in the sonic bath for 5 minutes. The solid compound was filtered off and washed twice with diethyl ether and once with hexane to afford the title compound 10. $^1$H NMR (400 MHz, DMSO-$d_6$) δ 9.58 (s, 1H), 8.57 (dd, J=2.4, 0.8 Hz, 1H), 8.20 (dd, J=8.3, 1.4 Hz, 1H), 7.95 (dd, J=9.0, 0.8 Hz, 1H), 7.73 (d, J=16.7 Hz, 1H), 7.55-7.51 (m, 3H), 7.44-7.36 (m, 2H), 6.53 (d, J=16.7 Hz, 1H), 1.90 (s, 6H). LCMS (m/z) 418.3 [M+H], Tr=1.82 min (LCMS method 2).

Example 11

(E)-6-((4-Amino-8-(4-(2-cyanovinyl)-2,6-dimethylphenyl)quinazolin-2-yl)amino)pyridazine-3-carbonitrile—Compound 11

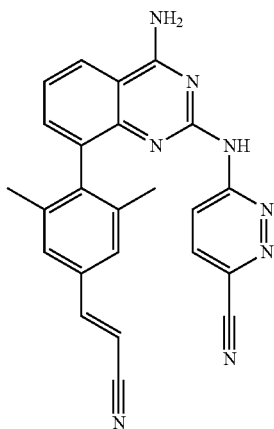 [SMILES: Cc1cc(/C=C/C#N)cc(C)c1-c1cccc2c(N)nc(Nc3ccc(C#N)nn3)nc12]

Synthesis of (E)-6-((4-amino-8-(4-(2-cyanovinyl)-2,6-dimethylphenyl)quinazolin-2-yl)amino)pyridazine-3-carbonitrile (compound 11)

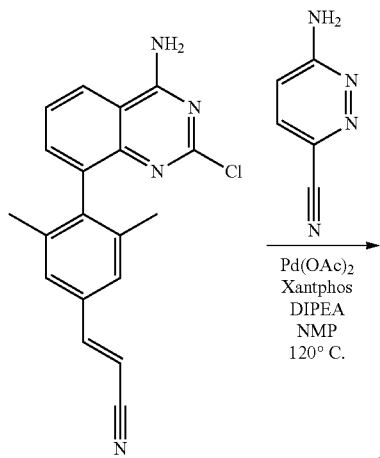

Compound 11

Compound 2a (20 mg, 0.06 mmol), 6-aminopyridazine-3-carbonitrile (22 mg, 0.18 mmol, Matrix Scientific, 112287), N,N-diisopropylethylamine (62 mg, 0.47 mmol), (9,9-dimethyl-9H-xanthene-4,5-diyl)bis(diphenylphosphine) (3 mg, 0.006 mmol) and palladium (II) acetate (1 mg, 0.006 mmol) were combined under argon in N-methyl-2-pyrrolidone (2 mL). The reaction was heated at 120° C. in a sealed vessel for 1 hour. The reaction mixture was cooled down to room temperature and purified by HPLC reverse phase chromatography (0-100% acetonitrile in water with 0.1% trifluoroacetic acid) to afford the TFA salt of compound 11. $^1$H NMR (400 MHz, DMSO-$d_6$) δ 8.35 (bs, 1H), 8.09 (bs, 1H), 7.78-7.39 (m, 6H), 6.54 (d, J=16.7 Hz, 1H), 1.93 (s, 6H). LCMS (m/z) 419.3 [M+H], Tr=2.03 min (LCMS method 2).

Example 12

(E)-5-((4-Amino-8-(4-(2-cyanovinyl)-2,6-dimethylphenyl)quinazolin-2-yl)amino)pyrazine-2-carbonitrile—Compound 12

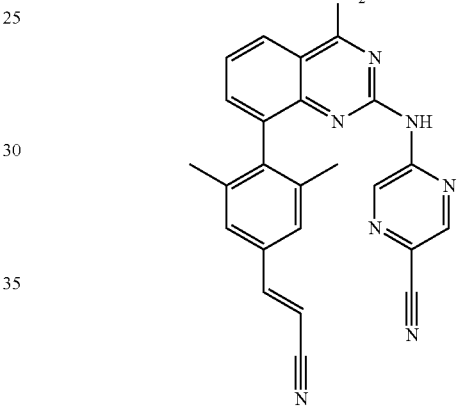

Synthesis of (E)-5-((4-amino-8-(4-(2-cyanovinyl)-2,6-dimethylphenyl)quinazolin-2-yl)amino)pyrazine-2-carbonitrile (compound 12)

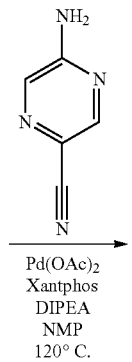

95

-continued

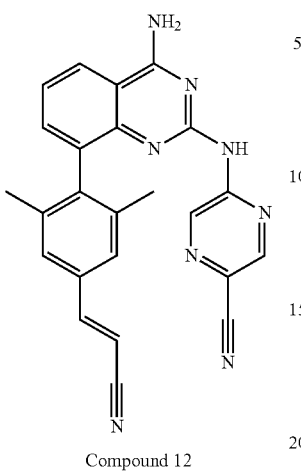

Compound 12

Compound 2a (20 mg, 0.06 mmol), 5-aminopyrazine-2-carbonitrile (22 mg, 0.18 mmol, Ark Pharm Inc, AK-21935), N,N-diisopropylethylamine (62 mg, 0.47 mmol), (9,9-dimethyl-9H-xanthene-4,5-diyl)bis(diphenylphosphine) (3 mg, 0.006 mmol) and palladium (II) acetate (1 mg, 0.006 mmol) were combined under argon in N-methyl-2-pyrrolidone (1 mL). The reaction was heated at 120° C. in a sealed vessel for 3 hours. The reaction mixture was cooled down to room temperature and purified by reverse phase chromatography (0-100% acetonitrile in water with 0.1% trifluoroacetic acid) to afford the TFA salt of compound 12. $^1$H NMR (400 MHz, DMSO-$d_6$) δ 8.98 (bs, 1H), 8.36 (bs, 1H), 7.85-7.28 (m, 6H), 6.59 (d, J=15.6 Hz, 1H), 1.94 (s, 6H). LCMS (m/z) 419.3 [M+H], Tr=1.89 min (LCMS method 2).

Example 13

(E)-6-((8-(4-(2-Cyanovinyl)-2,6-dimethylphenyl)quinazolin-2-yl)amino)nicotinonitrile—Compound 13

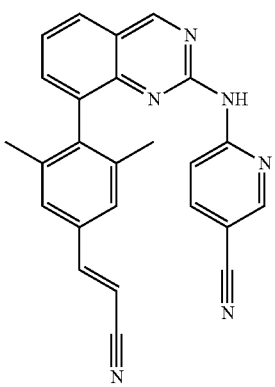 [SMILES: Cc1cc(/C=C/C#N)cc(C)c1-c1cccc2cnc(Nc3ccc(C#N)cn3)nc12]

96

Step 1: Synthesis of (E)-3-(4-(2-chloroquinazolin-8-yl)-3,5-dimethylphenyl)acrylonitrile (Compound 13a)

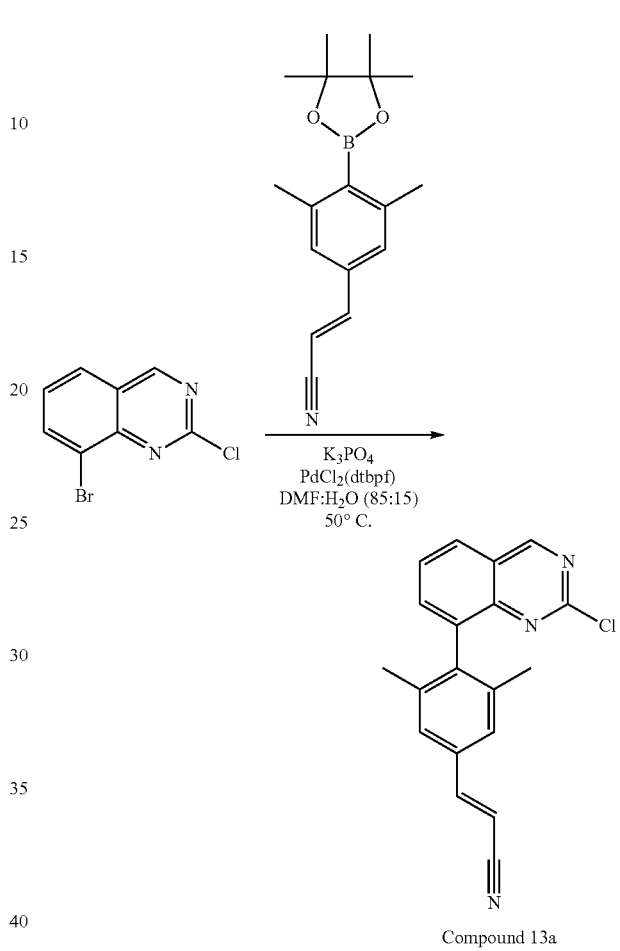

Compound 13a

A mixture of 8-bromo-2-chloroquinazoline (500 mg, 2.05 mmol, Ark Pharm Inc, AK-27609), compound 1c (776 mg, 2.67 mmol), potassium phosphate tribasic (633 mg, 3.08 mmol) and 1,1'-bis(di-tert-butylphosphino)ferrocene palladium dichloride (134 mg, 0.21 mmol) was dissolved in N,N-dimethylformamide:water mixture (85:15, 10 mL) under argon. The reaction was heated to 50° C. for 2 hours. The reaction mixture was cooled down to room temperature and diluted with water and ethyl acetate. The organic layer was separated and washed twice with brine, dried over magnesium sulfate, 0.5 volume equivalent of hexane added and this mixture was filtered through a 2 cm layer of silica gel which was washed with additional hexane/ethyl acetate mixture (1/1). Combined organics were concentrated down under reduced pressure and the residue was treated with diethyl ether in a sonic bath. The solid product was filtered off and washed twice with diethyl ether and once with hexane to afford the title compound 13a. $^1$H NMR (400 MHz, DMSO-$d_6$) δ 9.70 (s, 1H), 8.30 (dd, J=7.1, 2.5 Hz, 1H), 7.99-7.84 (m, 2H), 7.66 (d, J=16.7 Hz, 1H), 7.49 (s, 2H), 6.50 (d, J=16.7 Hz, 1H), 1.85 (s, 6H). LCMS (m/z) 320.1 [M+H], Tr=1.40 min (LCMS method 3).

Step 2: Synthesis of (E)-6-((4-amino-8-(4-(2-cyanovinyl)-2,6-dimethylphenyl)quinazolin-2-yl)amino)nicotinonitrile (compound 13)

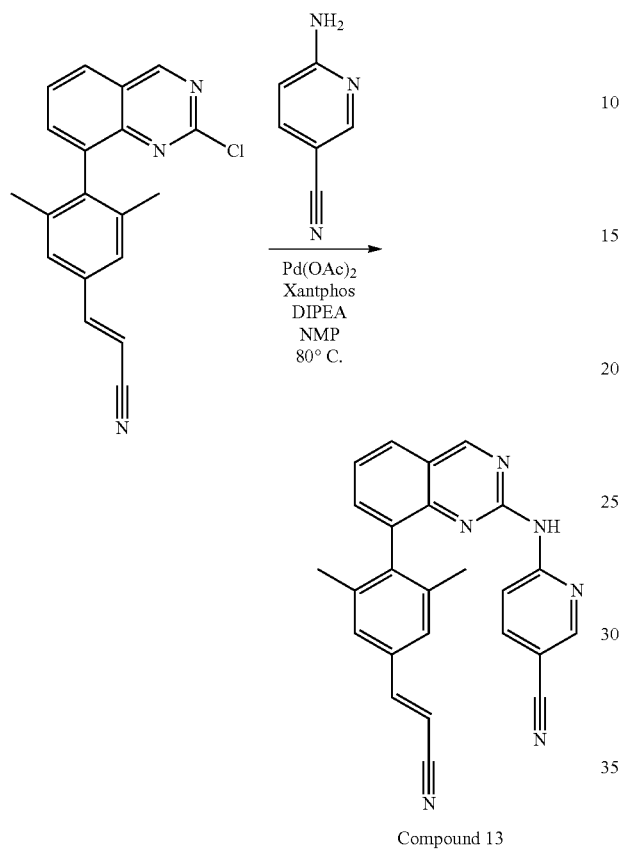

Compound 13

Compound 13a (508 mg, 1.60 mmol), 6-aminonicotinonitrile (567 mg, 4.77 mmol, Ark Pharm Inc, AK-32349), N,N-diisopropylethylamine (1.64 g, 12.71 mmol), (9,9-dimethyl-9H-xanthene-4,5-diyl)bis(diphenylphosphine) (93 mg, 0.16 mmol) and palladium (II) acetate (36 mg, 0.16 mmol) were combined under argon in N-methyl-2-pyrrolidone (10 mL). The reaction was heated at 80° C. in a sealed vessel for 30 minutes. The reaction mixture was cooled down to room temperature and diluted with water and ethyl acetate. The organic layer was separated and washed twice with brine, dried over magnesium sulfate, 0.5 volume equivalent of hexane added and this mixture was filtered through a 2 cm layer of silica gel which was washed with additional hexane/ethyl acetate mixture (1/1). Combined organics were concentrated down under reduced pressure. The crude residue was treated with diethyl ether in the sonic bath for 5 minutes. The solid compound was filtered off and washed twice with diethyl ether and once with hexane to afford the title compound 13. $^1$H NMR (400 MHz, DMSO-$d_6$) δ 10.85 (s, 1H), 9.52 (s, 1H), 8.66 (dd, J=2.3, 0.9 Hz, 1H), 8.10 (dd, J=8.0, 1.4 Hz, 1H), 7.92 (dd, J=8.9, 0.9 Hz, 1H), 7.85-7.70 (m, 2H), 7.65 (dd, J=8.1, 7.1 Hz, 1H), 7.57-7.48 (m, 3H), 6.56 (d, J=16.7 Hz, 1H), 1.89 (s, 6H). LCMS (m/z) 403.2 [M+H], Tr=1.48 min (LCMS method 3).

Example 14

(E)-6-((8-(4-(2-Cyanovinyl)-2,6-dimethylphenyl)-6-fluoroquinazolin-2-yl)amino)nicotinonitrile—Compound 14

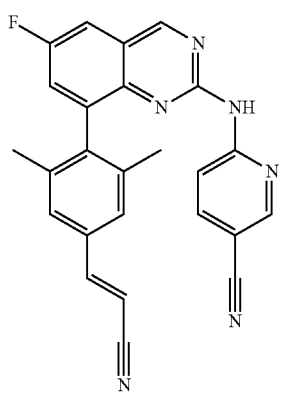 [SMILES: Cc1cc(/C=C/C#N)cc(C)c1-c1cc(F)cc2cnc(Nc3ccc(C#N)cn3)nc12]

Step 1: (E)-3-(4-(2-chloro-6-fluoroquinazolin-8-yl)-3,5-dimethylphenyl)acrylonitrile (Compound 14a)

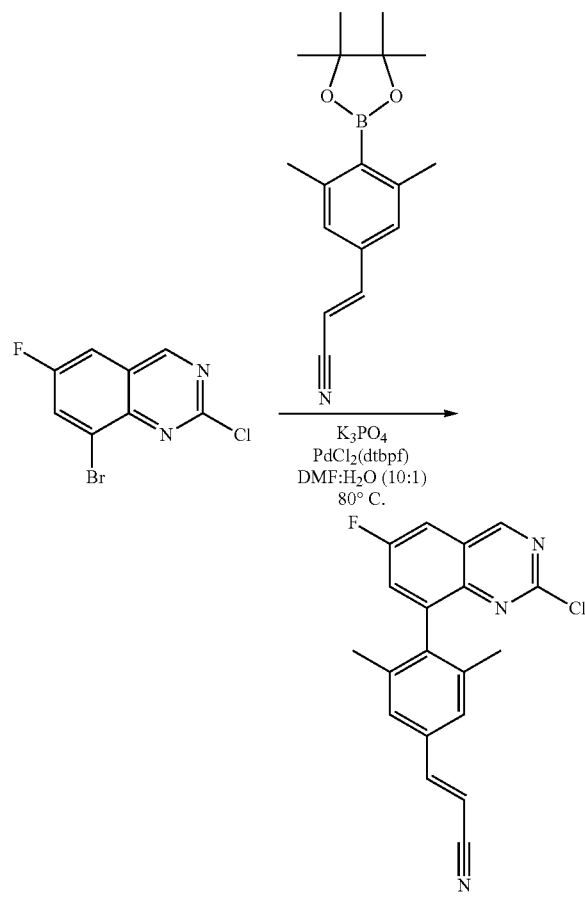

Compound 14a

A mixture of compound 1c (100 mg, 0.35 mmol), 8-bromo-2-chloro-6-fluoroquinazoline (100 mg, 0.38 mmol, Ark Pharm Inc, AK-93358), 1,1'-bis(di-tert-butylphosphino)ferrocene palladium dichloride (50 mg, 0.08 mmol) and potassium phosphate tribasic monohydrate (200 mg, 0.77 mmol) in N,N-dimethylformamide (3 mL) and water (0.3 mL) was heated under argon at 80° C. for 30 minutes. The reaction mixture was evaporated to dryness and the residue was purified by silica gel chromatography This was subjected to silica gel chromatography (gradient from 0-100% ethyl acetate in iso-hexanes) to afford compound 14a. LCMS (m/z) 337.9 [M+H], Tr=4.52 min (LCMS method 1).

Step 2: Synthesis of (E)-6-((8-(4-(2-cyanovinyl)-2,6-dimethylphenyl)-6-fluoroquinazolin-2-yl)amino)nicotinonitrile (compound 14)

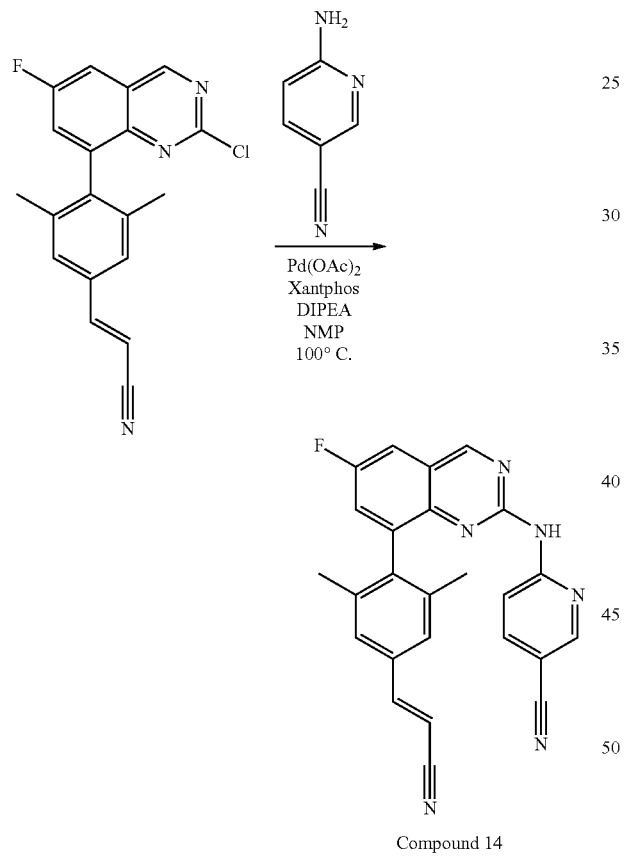

Compound 14

Compound 14aa (100 mg, 0.30 mmol), 6-aminonicotinonitrile (200 mg, 1.68 mmol, Ark Pharm Inc, AK-32349), N,N-diisopropylethylamine (0.5 mL, 2.86 mmol), (9,9-dimethyl-9H-xanthene-4,5-diyl)bis(diphenylphosphine) (180 mg, 0.31 mmol) and palladium (II) acetate (40 mg, 0.18 mmol) were combined under argon in N-methyl-2-pyrrolidone (3 mL). The reaction was heated at 100° C. in a sealed vessel for 1 hour. The reaction mixture was cooled down to room temperature and directly purified by silica gel chromatography (gradient from 60-100% ethyl acetate in iso-hexanes and then gradient from 0-20% methanol in ethyl acetate) to afford the title compound 14. $^1$H NMR (400 MHz, DMSO-d$_6$) δ 9.62 (s, 1H), 8.77 (dd, J=2.3, 0.8 Hz, 1H), 8.08-7.99 (m, 1H), 7.99-7.91 (m, 1H), 7.87 (d, J=16.7 Hz, 1H), 7.68 (s, 2H), 7.65-7.60 (m, 1H), 7.60-7.53 (m, 1H), 7.36 (d, J=8.2, Hz, 1H), 6.68 (d, J=16.7 Hz, 1H), 2.01 (s, 6H). LCMS (m/z) 420.9 [M+H], Tr=4.62 min (LCMS method 1).

Example 15

(E)-6-((4-Amino-8-(4-(2-cyanovinyl)-2,6-dimethylphenyl)quinazolin-2-yl)amino)-2,4-dimethylnicotinonitrile—Compound 15

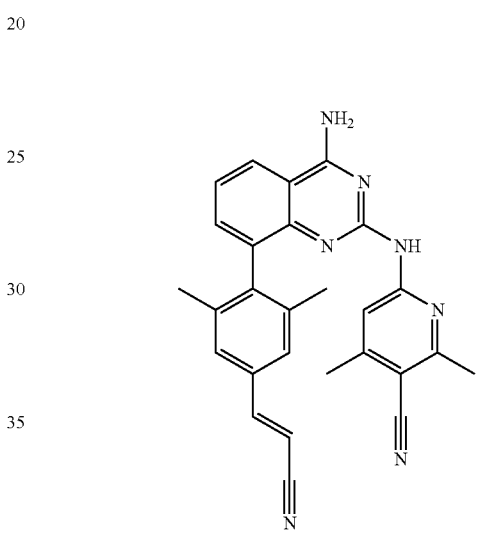

Synthesis of (E)-6-((4-amino-8-(4-(2-cyanovinyl)-2,6-dimethylphenyl)quinazolin-2-yl)amino)-2,4-dimethylnicotinonitrile (compound 15)

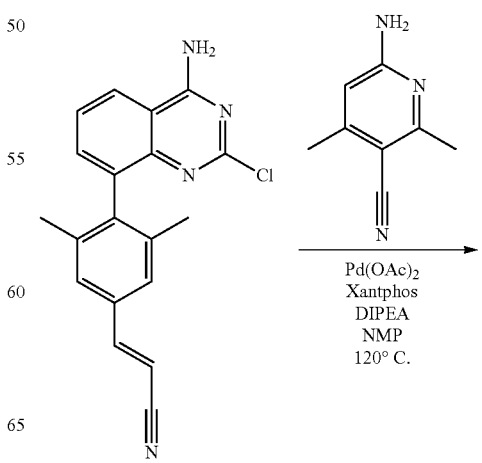

-continued

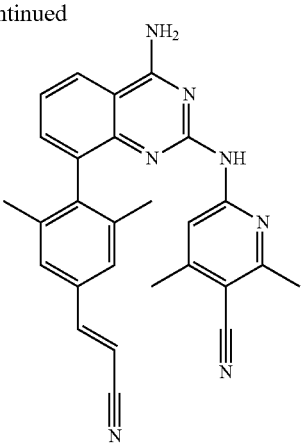

Compound 15

Compound 2a (20 mg, 0.06 mmol), 6-amino-2,4-dimethylnicotinonitrile (26 mg, 0.18 mmol, Key Organics Ltd, 1X-0933), N,N-diisopropylethylamine (622 mg, 0.48 mmol), (9,9-dimethyl-9H-xanthene-4,5-diyl)bis(diphenylphosphine) (4 mg, 0.006 mmol) and palladium (II) acetate (1 mg, 0.006 mmol) were combined under argon in N-methyl-2-pyrrolidone (1 mL). The reaction was heated at 120° C. in a sealed vessel for 4 hours. The reaction mixture was cooled down to room temperature and diluted with water and ethyl acetate. The organic layer was separated and washed twice with brine, dried over magnesium sulfate and this solution was filtered through a 2 cm layer of silica gel which was washed with additional ethyl acetate. Combined organics were concentrated down under reduced pressure. The crude residue was treated with diethyl ether in the sonic bath for 5 minutes. The solid compound was filtered off and washed twice with diethyl ether and once with hexane to afford the title compound 15. $^1$H NMR (400 MHz, DMSO-d$_6$) δ 9.56 (bs, 1H), 9.29 (bs, 1H), 8.44 (d, J=8.0 Hz, 1H), 7.99-7.47 (m, 5H), 7.41-7.10 (m, 1H), 6.55 (d, J=16.7 Hz, 1H), 2.41 (bs, 3H), 1.96 (s, 6H), 1.62 (bs, 3H). LCMS (m/z) 446.4 [M+H], Tr=1.19 min (LCMS method 3).

Example 16

(E)-6-((4-Amino-8-(4-(2-cyanovinyl)-2,6-dimethylphenyl)quinazolin-2-yl)amino)-2-methylnicotinonitrile—Compound 16

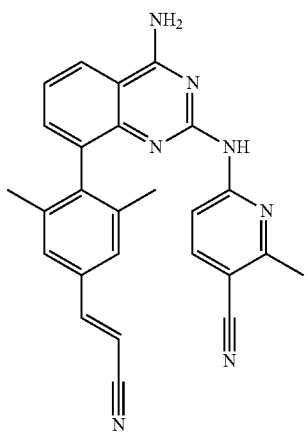

Synthesis of (E)-6-((4-amino-8-(4-(2-cyanovinyl)-2,6-dimethylphenyl)quinazolin-2-yl)amino)-2-methylnicotinonitrile (compound 16)

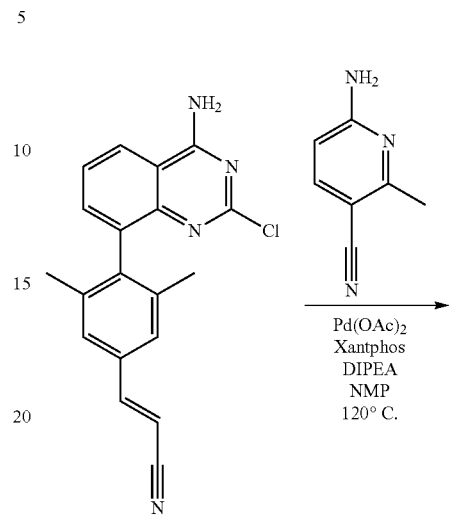

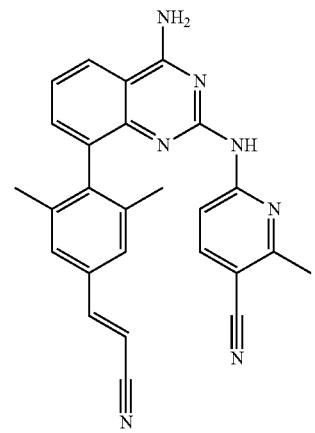

Compound 16

Compound 2a (20 mg, 0.06 mmol), 6-amino-2-methylnicotinonitrile (24 mg, 0.18 mmol, Ark Pharm Inc, AK-78835), N,N-diisopropylethylamine (622 mg, 0.48 mmol), (9,9-dimethyl-9H-xanthene-4,5-diyl)bis(diphenylphosphine) (4 mg, 0.006 mmol) and palladium (II) acetate (1 mg, 0.006 mmol) were combined under argon in N-methyl-2-pyrrolidone (1 mL). The reaction was heated at 120° C. in a sealed vessel for 4 hours. The reaction mixture was cooled down to room temperature and diluted with water and ethyl acetate. The organic layer was separated and washed twice with brine, dried over magnesium sulfate and this solution was filtered through a 2 cm layer of silica gel which was washed with additional ethyl acetate. Combined organics were concentrated down under reduced pressure. The crude residue was treated with diethyl ether in the sonic bath for 5 minutes. The solid compound was filtered off and washed twice with diethyl ether and once with hexane to afford the title compound 16. $^1$H NMR (400 MHz, DMSO-d$_6$) δ 10.92 (s, 1H), 9.55 (s, 1H), 9.10 (s, 1H), 8.46 (dd, J=8.3, 1.3 Hz, 1H), 8.19 (d, J=2.2 Hz, 1H), 7.89-7.73 (m, 3H), 7.69 (s, 2H), 7.32 (d, J=2.2 Hz, 1H), 6.68 (d, J=16.7 Hz, 1H), 2.37 (s, 3H), 1.95 (s, 6H). LCMS (m/z) 432.4 [M+H], Tr=1.15 min (LCMS method 3).

Example 17

(E)-6-((4-Amino-8-(4-(2-cyanovinyl)-2,6-dimethylphenyl)quinazolin-2-yl)amino)-5-methylnicotinonitrile—Compound 17

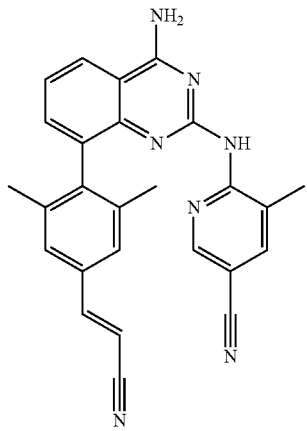

Synthesis of (E)-6-((4-amino-8-(4-(2-cyanovinyl)-2,6-dimethylphenyl)quinazolin-2-yl)amino)-5-methylnicotinonitrile (compound 17)

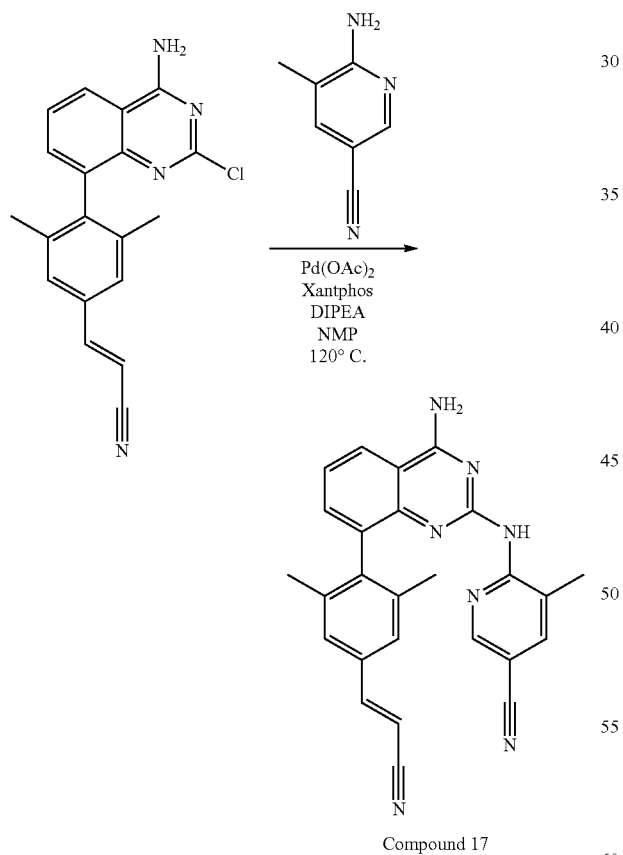

Compound 17

Compound 2a (20 mg, 0.06 mmol), 6-amino-5-methylnicotinonitrile (24 mg, 0.18 mmol, Ark Pharm Inc, AK-25043), N,N-diisopropylethylamine (622 mg, 0.48 mmol), (9,9-dimethyl-9H-xanthene-4,5-diyl)bis(diphenylphosphine) (4 mg, 0.006 mmol) and palladium (II) acetate (1 mg, 0.006 mmol) were combined under argon in N-methyl-2-pyrrolidone (1 mL). The reaction was heated at 120° C. in a scaled vessel for 4 hours. The reaction mixture was cooled down to room temperature and diluted with water and ethyl acetate. The organic layer was separated and washed twice with brine, dried over magnesium sulfate and this solution was filtered through a 2 cm layer of silica gel which was washed with additional ethyl acetate. Combined organics were concentrated down under reduced pressure. The crude residue was treated with diethyl ether in the sonic bath for 5 minutes. The solid compound was filtered off and washed twice with diethyl ether and once with hexane to afford the title compound 17. $^1$H NMR (400 MHz, DMSO-$d_6$) δ 10.92 (s, 1H), 9.55 (s, 1H), 9.10 (s, 1H), 8.46 (dd, J=8.3, 1.3 Hz, 1H), 8.25-8.13 (m, 1H), 7.91-7.72 (m, 3H), 7.69 (s, 2H), 7.35-7.29 (m, 1H), 6.68 (d, J=16.7 Hz, 1H), 2.37 (s, 3H), 1.95 (s, 6H). LCMS (m/z) 432.4 [M+H], Tr=1.19 min (LCMS method 3).

Example 18

(E)-6-((4-Amino-8-(4-(2-cyanovinyl)-2,6-dimethylphenyl)quinazolin-2-yl)amino)-4-methylnicotinonitrile—Compound 18

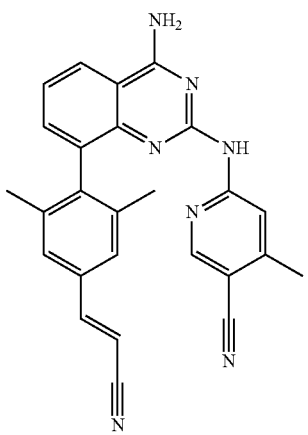

Synthesis of (E)-6-((4-amino-8-(4-(2-cyanovinyl)-2,6-dimethylphenyl)quinazolin-2-yl)amino)-4-methylnicotinonitrile (compound 18)

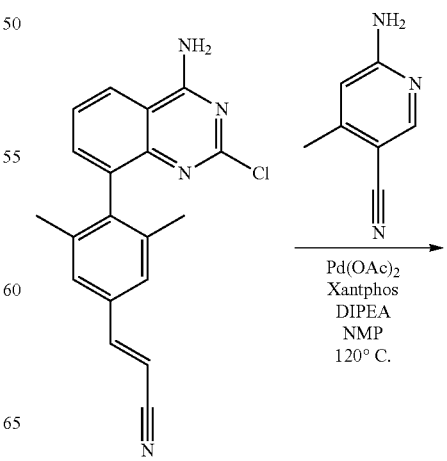

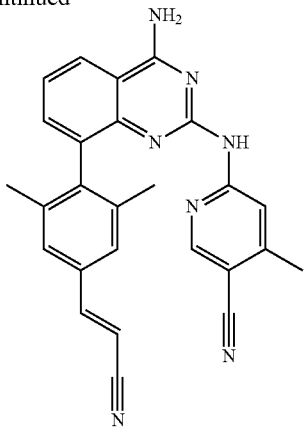

Compound 18

Compound 2a (20 mg, 0.06 mmol), 6-amino-4-methylnicotinonitrile (24 mg, 0.18 mmol, Ark Pharm Inc, AK-80125), N,N-diisopropylethylamine (622 mg, 0.48 mmol), (9,9-dimethyl-9H-xanthene-4,5-diyl)bis(diphenylphosphine) (4 mg, 0.006 mmol) and palladium (II) acetate (1 mg, 0.006 mmol) were combined under argon in N-methyl-2-pyrrolidone (1 mL). The reaction was heated at 120° C. in a sealed vessel for 4 hours. The reaction mixture was cooled down to room temperature and diluted with water and ethyl acetate. The organic layer was separated and washed twice with brine, dried over magnesium sulfate and this solution was filtered through a 2 cm layer of silica gel which was washed with additional ethyl acetate. Combined organics were concentrated down under reduced pressure. The crude residue was treated with diethyl ether in the sonic bath for 5 minutes. The solid compound was filtered off and washed twice with diethyl ether and once with hexane to afford the title compound 18. $^1$H NMR (400 MHz, DMSO-$d_6$) δ 11.97 (bs, 1H), 9.55 (bs, 1H), 9.32 (bs, 1H), 8.48-8.37 (m, 1H), 7.90-7.62 (m, 5H), 7.52-7.43 (m, 1H), 7.32-7.23 (m, 1H), 6.69 (d, J=16.7 Hz, 1H), 2.45 (s, 3H), 1.96 (s, 6H). LCMS (m/z) 432.3 [M+H], Tr=1.25 min (LCMS method 3).

Example 19

(E)-4-((4-Amino-6-chloro-8-(4-(2-cyanovinyl)-2,6-dimethylphenyl)quinazolin-2-yl)amino)benzonitrile—Compound 19

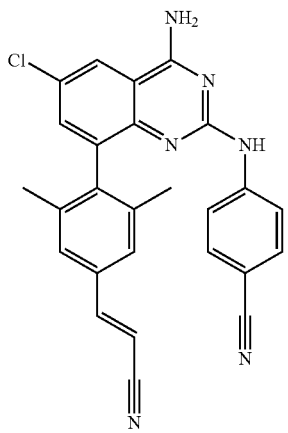 [SMILES: Cc1cc(/C=C/C#N)cc(C)c1-c1cc(Cl)cc2c(N)nc(Nc3ccc(C#N)cc3)nc12]

Step 1: Synthesis of 2-amino-3-bromo-5-chlorobenzoic acid (Compound 19a)

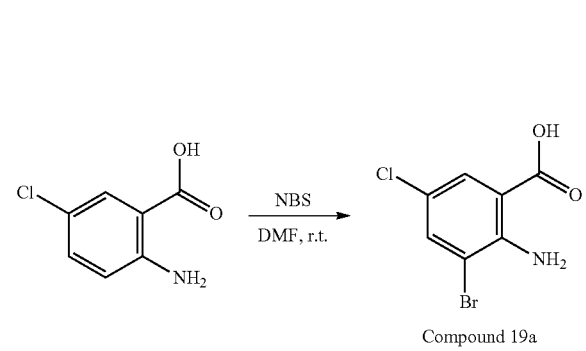

Compound 19a

A mixture of 2-amino-5-chlorobenzoic acid (5 g, 29 mmol, Ark Pharm Inc, AK-26989) and N-bromosuccinimide (5.4 g, 30 mmol) in N,N-dimethylformamide (100 mL) was stirred at room temperature for 14 hours. The reaction mixture was poured into water (400 mL) and product was extracted with diethylether (400 mL). The organic phase was washed with brine (200 mL), dried over sodium sulfate, filtered and concentrated down under reduced pressure to afford the title compound 19a. LCMS (m/z) 250.0 [M+H], Tr=4.05 min (LCMS method 1).

Step 2: Synthesis of 8-bromo-6-chloroquinazoline-2,4(1H,3H)-dione (compound 19b)

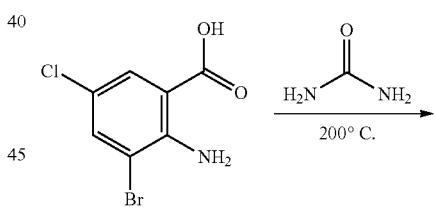

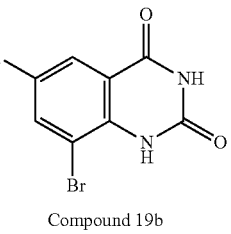

Compound 19b

A mixture of compound 19a (5.3 g, 21 mmol) and urea (30 g, 500 mmol) was heated at 200° C. for 3 hours. The reaction mixture was cooled down, diluted with methanol (100 mL) and the product was filtered off. The solid was washed with water (50 mL) and methanol (50 mL) to afford the title compound 19b. LCMS (m/z) 275.0 [M+H], Tr=3.32 min (LCMS method 1).

Step 3: Synthesis of 8-bromo-2,6-dichloroquinazolin-4-amine (compound 19c)

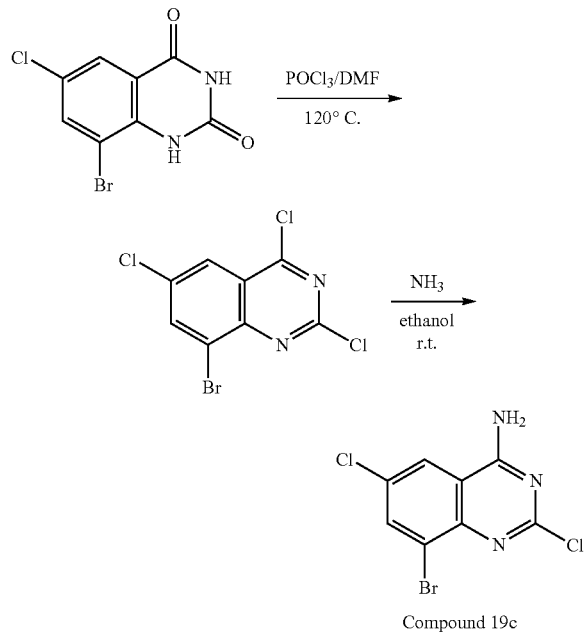

Compound 19c

A mixture of compound 19b (5.3 g, 21 mmol), phosphorus (V) oxychloride (15 mL) and N,N-dimethylformamide (3 drops) was heated at 120° C. for 14 hours. The reaction mixture was cooled down, poured into water (200 mL) and the product was filtered off. The solid was dried in vacuo for 2 hours, suspended in saturated ethanolic solution of ammonia (50 mL) and stirred at room temperature for 14 hours. The solid product was filtered off to afford the title compound 19c. $^1$H NMR (400 MHz, DMSO-d$_6$) δ 8.65 (s, 2H), 8.47 (d, J=2.2 Hz, 1H), 8.25 (d, J=2.2 Hz, 1H). LCMS (m/z) 291.9 [M+H], Tr=3.86 min (LCMS method 1).

Step 4: synthesis of (E)-3-(4-(4-amino-2,6-dichloroquinazolin-8-yl)-3,5-dimethylphenyl)acrylonitrile (compound 19d)

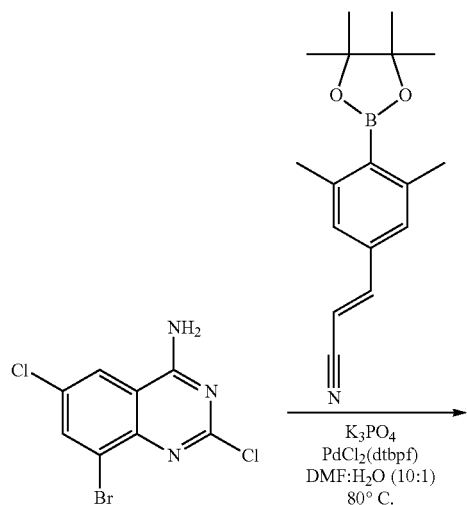

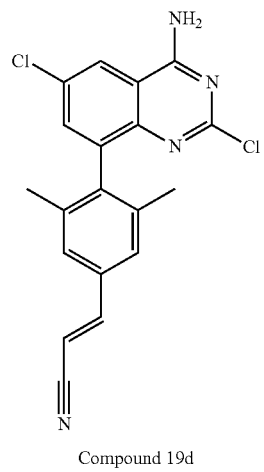

Compound 19d

A mixture of compound 19c (146 mg, 0.5 mmol), compound 1c (170 mg, 0.6 mmol), potassium phosphate tribasic monohydrate (230 mg, 1 mmol) and [1,1'-bis(diphenylphosphino)ferrocene] dichloropalladium(II), complex with dichloromethane (65 mg, 0.1 mmol) was dissolved in a mixture of N,N-dimethylformamide and water (10:1, 5.5 mL) under argon and this mixture was stirred at 80° C. for 30 minutes. The product was isolated by silica gel chromatography (gradient from 80-100% ethyl acetate in isohexanes) to afford the title compound 19d. LCMS (m/z) 369.0 [M+H], Tr=4.30 (LCMS method 1).

Step 5: synthesis of (E)-4-((4-amino-6-chloro-8-(4-(2-cyanovinyl)-2,6-dimethylphenyl)quinazolin-2-yl)amino)benzonitrile (compound 19)

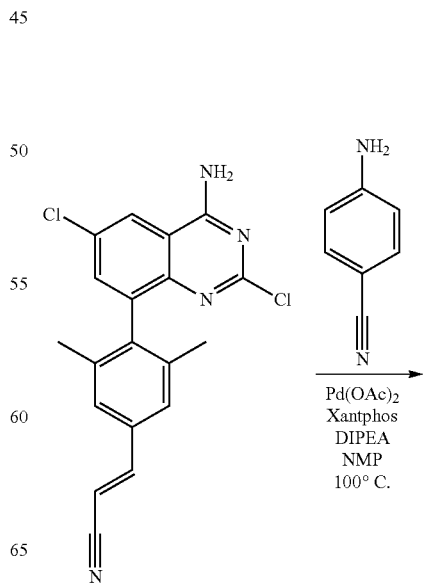

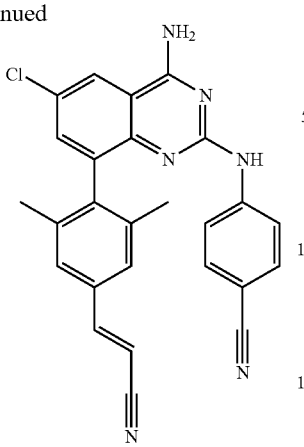

Compound 19

A mixture of compound 19d (85 mg, 0.23 mmol), 4-aminobenzonitrile (33 mg, 0.28 mmol, Sigma-Aldrich), palladium(II) acetate (10 mg, 0.046 mmol) and (9,9-dimethyl-9H-xanthene-4,5-diyl)bis(diphenylphosphine) (27 mg, 0.046 mmol) was dissolved in N-methyl-2-pyrrolidone (2 mL) under argon. N,N-Diisopropylethylamine (174 µL, 1 mmol) was then added via syringe and the reaction mixture was stirred at 100° C. for 1 hour. The product was isolated by silica gel flash chromatography (gradient from 40-60% ethyl acetate in iso-hexanes) and then repurified by reverse phase flash chromatography (5.5 g C-18 RediSep pre-packed column, gradient 5-100%, acetonitrile in water) to afford the title compound 19. $^1$H NMR (400 MHz, DMSO-d$_6$) δ 9.55 (s, 1H), 8.34 (d, J=2.3 Hz, 1H), 7.74 (d, J=16.7 Hz, 1H), 7.66 (d, J=8.9 Hz, 2H), 7.55 (d, J=2.3 Hz, 1H), 7.52 (s, 2H), 7.40-7.35 (m, 2H), 7.26 (d, J=8.9 Hz, 2H), 6.55 (d, J=16.7 Hz, 1H), 1.93 (s, 6H). LCMS (m/z) 451.2 [M+H], Tr=4.25 min (LCMS method 1).

Example 20

(E)-6-((4-Amino-8-(4-(2-cyanovinyl)-2,6-dimethylphenyl)-6-fluoroquinazolin-2-yl)amino)nicotinonitrile—Compound 20

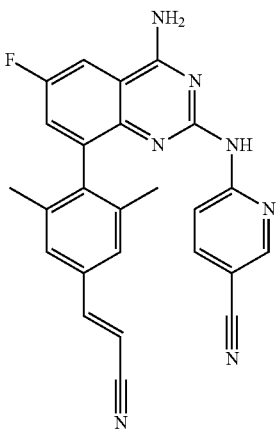 [SMILES: Cc1cc(/C=C/C#N)cc(C)c1-c1cc(F)cc2c(N)nc(Nc3ccc(C#N)cn3)nc12]

Step 1: Synthesis of 2-amino-3-bromo-5-fluorobenzoic acid (Compound 20a)

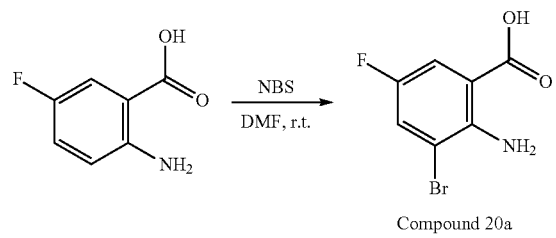

Compound 20a

A mixture of 2-amino-5-fluorobenzoic acid (10 g, 65 mmol, Ark Pharm Inc, AK-35193) and N-bromosuccinimide (12 g, 67 mmol) in N,N-dimethylformamide (100 mL) was stirred at room temperature for 14 hours. The reaction mixture was poured into water (500 mL), the solid product was filtered off and washed with water to afford the title compound 20a. LCMS (m/z) 233.7 [M+H], Tr=3.75 min (LCMS method 1).

Step 2: Synthesis of 8-bromo-6-fluoroquinazoline-2,4(1H,3H)-dione (compound 20b)

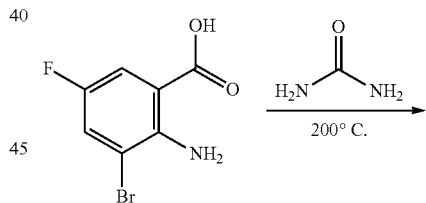

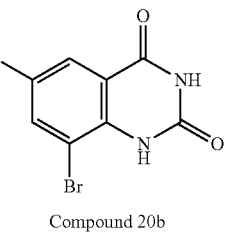

Compound 20b

A mixture of compound 20a (12 g, 51 mmol) and urea (20 g, 333 mmol) was heated at 200° C. for 3 hours. The reaction mixture was cooled down and diluted with water (100 mL). The solid product was filtered off and washed with methanol (50 mL) to afford the title compound 20b. LCMS (m/z) 259.0 [M+H], Tr=3.23 min (LCMS method 1).

Step 3: Synthesis of 8-bromo-2-chloro-6-fluoroquinazolin-4-amine (compound 20c)

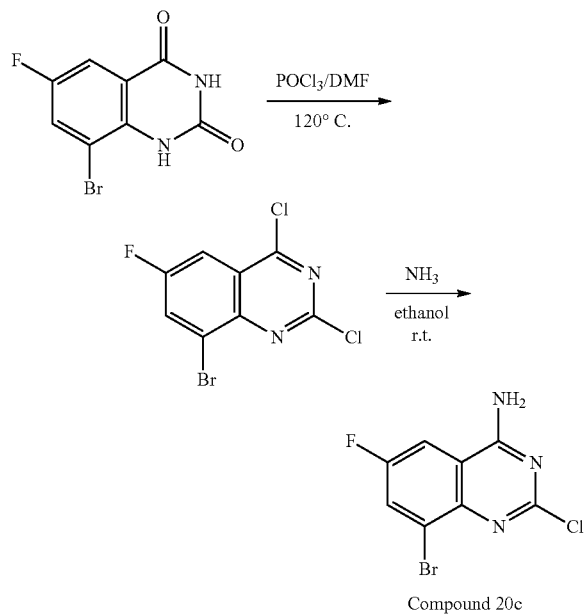

Compound 20c

A mixture of compound 20b (3 g, 20 mmol), phosphorus (V) oxychloride (20 mL) and N,N-dimethylformamide (3 drops) was heated at 120° C. for 14 hours. The reaction mixture was cooled down, poured into ice water mixture (200 mL) and the solid product was filtered off. The solid was dried in vacuo for 2 hours, suspended in saturated ethanolic solution of ammonia (100 mL) and stirred at room temperature for 14 hours. The reaction mixture was evaporated to dryness and the solid residue was suspended in water. The solid product was filtered off to afford the title compound 20c. $^1$H NMR (400 MHz, DMSO-$d_6$) δ 8.59 (s, 1H), 8.46 (s, 1H), 8.19 (dd, J=8.3, 2.7 Hz, 1H), 8.13 (dd, J=9.2, 2.7 Hz, 1H). LCMS (m/z) 275.7 [M+H], Tr=3.74 min (LCMS method 1).

Step 4: synthesis of (E)-3-(4-(4-amino-2-chloro-6-fluoroquinazolin-8-yl)-3,5-dimethylphenyl)acrylonitrile (compound 20d)

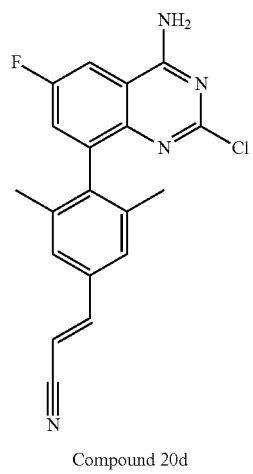

Compound 20d

A mixture of compound 20c (276 mg, 1 mmol), compound 1c (340 mg, 1.2 mmol), potassium phosphate tribasic monohydrate (460 mg, 2 mmol) and [1,1'-bis(diphenylphosphino)ferrocene] dichloropalladium(II), complex with dichloromethane (65 mg, 0.1 mmol) was dissolved in a mixture of N,N-dimethylformamide and water (10:1, 11 mL) under argon and this mixture was stirred at 80° C. for 30 minutes. The product was isolated by silica gel chromatography (gradient from 80-100% ethyl acetate in isohexanes) to afford the title compound 20d. LCMS (m/z) 352.9 [M+H], Tr=4.12 min (LCMS method 1).

Step 5: synthesis of (E)-6-((4-amino-8-(4-(2-cyanovinyl)-2,6-dimethylphenyl)-6-fluoroquinazolin-2-yl)amino)nicotinonitrile (compound 20)

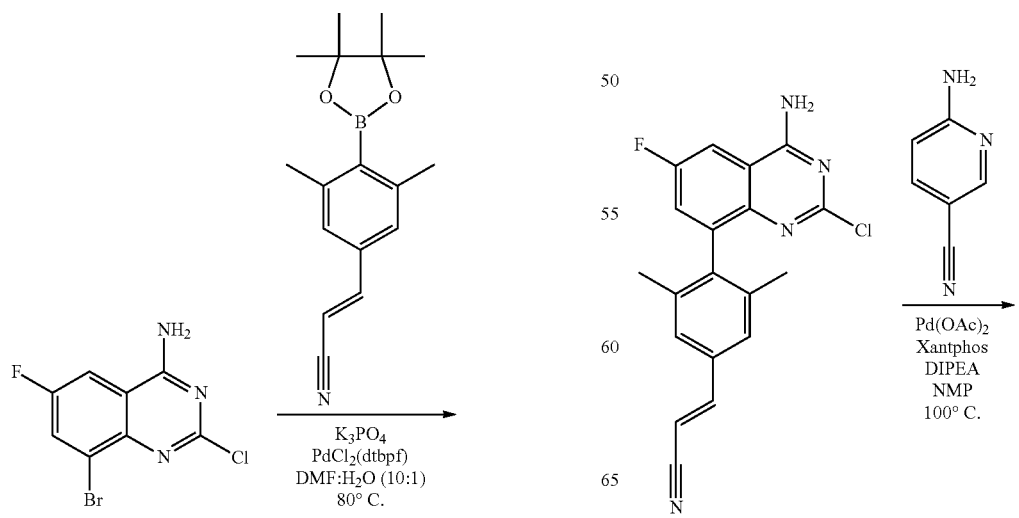

Step 1: Synthesis of 2-amino-3-bromo-5-methylbenzoic acid (Compound 21a)

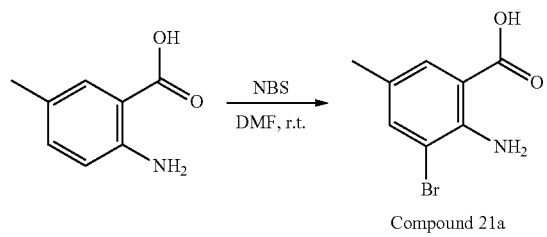

Compound 21a

A mixture of 2-amino-5-methylbenzoic acid (10 g, 66 mmol, Ark Pharm, Inc AK-34555) and N-bromosuccinimide (12 g, 67 mmol) in N,N-dimethylformamide (100 mL) was stirred at room temperature for 14 hours. The reaction mixture was poured into water (500 mL) and the solid product was filtered off and washed with water to afford the title compound 21a. LCMS (m/z) 229.80 [M+H], Tr=3.87 min (LCMS method 1).

Step 2: synthesis of 8-bromo-6-methylquinazoline-2,4(1H,3H)-dione (compound 21b)

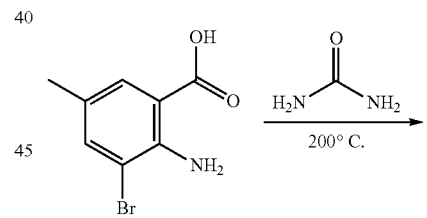

Compound 21b

A mixture of compound 21a (5 g, 22 mmol) and urea (30 g, 500 mmol) was heated at 200° C. for 3 hours. The reaction mixture was cooled down, and diluted with water (100 mL). The solid product was filtered off and washed with methanol (50 mL) and water (50 mL) to afford the title compound 21b. LCMS (m/z) 254.7 [M+H], Tr=3.19 min (LCMS method 1).

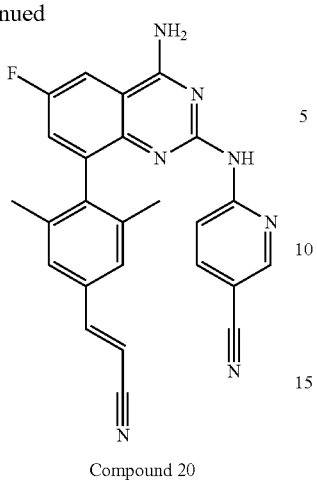

Compound 20

A mixture of compound 20d (176 mg, 0.5 mmol), 6-aminonicotinonitrile (178 mg, 1.5 mmol, Ark Pharm Inc, AK-32349), palladium(II) acetate (22 mg, 0.1 mmol) and (9,9-dimethyl-9H-xanthene-4,5-diyl)bis(diphenylphosphine) (58 mg, 0.1 mmol) was dissolved in N-methyl-2-pyrrolidone (5 mL) under argon. N,N-Diisopropylethylamine (348 µL, 2 mmol) was then added via syringe and the reaction mixture was stirred at 100° C. for 1 hour. The product was isolated by silica gel chromatography (gradient from 40-100% ethyl acetate in iso-hexanes) and then repurified by reverse phase flash chromatography (5.5 g C-18 RediSep prepacked column, gradient 5-100%, acetonitrile in water with 0.1% TFA) to afford the title compound 20 as the TFA salt. $^1$H NMR (400 MHz, DMSO-$d_6$) δ 9.56 (bs, 1H), 9.46 (bs, 1H), 8.40-8.20 (m, 2H), 8.02-7.84 (m, 1H), 7.82 (d, J=16.6 Hz, 1H), 7.69 (s, 2H), 7.51 (bs, 1H), 7.42 (bs, 1H), 6.69 (d, J=16.6 Hz, 1H), 1.98 (s, 6H). LCMS (m/z) 435.8 [M+H], Tr=3.45 min (LCMS method 1).

Example 21

(E)-6-((4-Amino-8-(4-(2-cyanovinyl)-2,6-dimethylphenyl)-6-methylquinazolin-2-yl)amino)nicotinonitrile—Compound 21

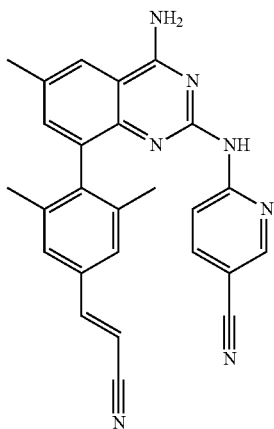 [SMILES: Cc1cc(-c2c(C)cc(/C=C/C#N)cc2C)c2nc(Nc3ccc(C#N)cn3)nc(N)c2c1]

Step 3: synthesis of 8-bromo-2-chloro-6-methylquinazolin-4-amine (compound 21c)

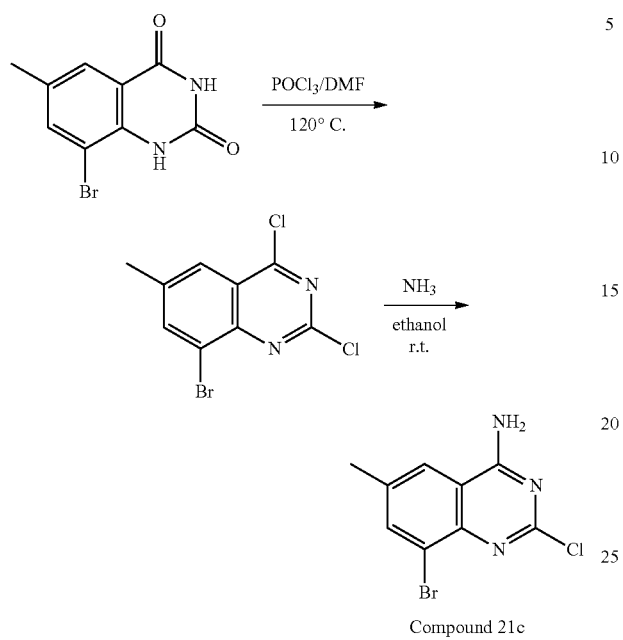

A mixture of compound 21b (5 g, 20 mmol), phosphorus (V) oxychloride (15 mL) and N,N-dimethylformamide (3 drops) was heated at 120° C. for 14 hours. The reaction mixture was cooled down, poured into ice water mixture (200 mL) and the solid product was filtered off. The solid was dried in vacuo for 2 hours, suspended in saturated ethanolic solution of ammonia (100 mL) and stirred at room temperature for 14 hours. The solid product was filtered off to afford the title compound 21c. $^1$H NMR (400 MHz, DMSO-$d_6$) δ 8.41 (s, 2H), 8.06 (d, J=1.7 Hz, 1H), 8.01 (d, J=1.7 Hz, 1H), 2.42 (s, 3H). LCMS (m/z) 271.8 [M+H], Tr=3.65 min (LCMS method 1).

Step 4: synthesis of (E)-3-(4-(4-amino-2-chloro-6-methylquinazolin-8-yl)-3,5-dimethylphenyl)acrylonitrile (compound 21d)

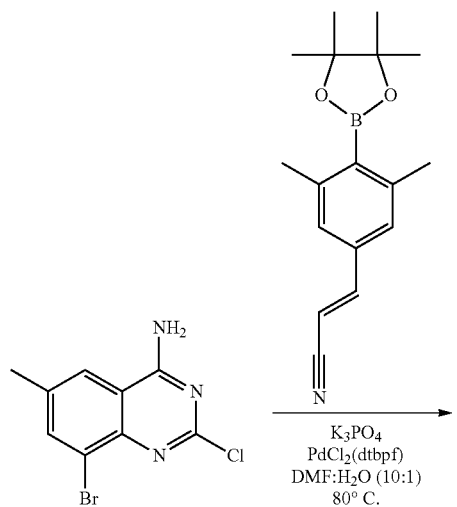

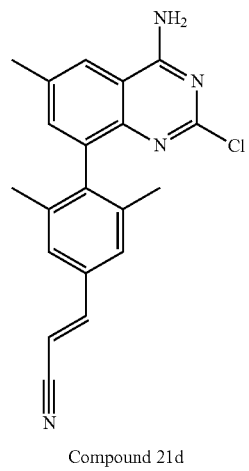

Compound 21d

A mixture of compound 21c (273 mg, 1 mmol), compound 1c (340 mg, 1.2 mmol), potassium phosphate tribasic monohydrate (460 mg, 2 mmol) and [1,1'-bis(diphenylphosphino)ferrocene] dichloropalladium(II), complex with dichloromethane (65 mg, 0.1 mmol) was dissolved in a mixture of N,N-dimethylformamide and water (10:1, 5.5 mL) under argon and this reaction mixture was stirred at 80° C. for 30 minutes. The product was isolated by silica gel chromatography (gradient from 40-100% ethyl acetate in iso-hexanes) to afford the title compound 21d. LCMS (m/z) 348.9 [M+H], Tr=4.17 min (LCMS method 1).

Step 5: synthesis of (E)-6-((4-amino-8-(4-(2-cyanovinyl)-2,6-dimethylphenyl)-6-methylquinazolin-2-yl)amino)nicotinonitrile (compound 21)

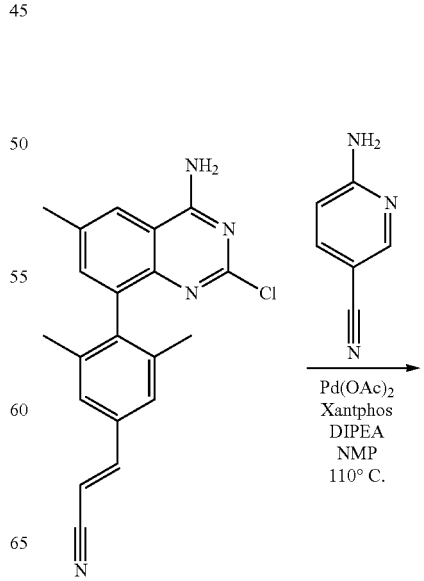

Step 1: Synthesis of 2-amino-3-bromo-5-nitrobenzoic acid (Compound 22a)

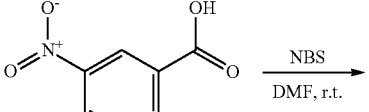

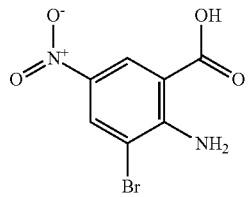

Compound 22a

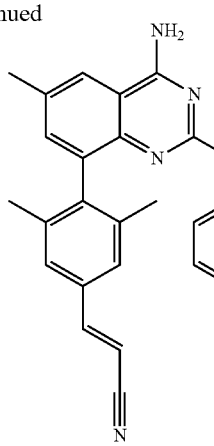

Compound 21

A mixture of compound 21d (175 mg, 0.5 mmol), 6-aminonicotinonitrile (298 mg, 2.5 mmol, Ark Pharm Inc, AK-32349), palladium(II) acetate (23 mg, 0.1 mmol) and (9,9-dimethyl-9H-xanthene-4,5-diyl)bis(diphenylphosphine) (58 mg, 0.1 mmol) was dissolved in N-methyl-2-pyrrolidone (5 mL) under argon. N,N-Diisopropylethylamine (435 µL, 2.5 mmol) was then added via syringe and the reaction mixture was stirred at 110° C. for 6 hours. The product was isolated by silica gel chromatography (gradient from 40-100% ethyl acetate in iso-hexanes) and then repurified by reverse phase flash chromatography (5.5 g C-18 RediSep prepacked column, gradient 5-100%, acetonitrile in water with 0.1% TFA) to afford the title compound 21 as the TFA salt. $^1$H NMR (400 MHz, DMSO-$d_6$) δ 9.51 (s, 1H), 9.31 (s, 1H), 8.33-8.24 (m, 2H), 7.82 (d, J=16.7 Hz, 1H), 7.77-7.66 (m, 3H), 7.58-7.50 (m, 1H), 7.45-7.36 (m, 1H), 6.69 (d, J=16.7 Hz, 1H), 2.54 (s, 3H), 1.96 (s, 6H). LCMS (m/z) 432.0 [M+H], Tr=3.56 min (LCMS method 1).

A mixture of 2-amino-5-nitrobenzoic acid (5 g, 27 mmol, Sigma-Aldrich) and N-bromosuccinimide (6 g, 34 mmol) in N,N-dimethylformamide (100 mL) was stirred at room temperature for 14 hours. The reaction mixture was poured into water (500 mL) and the solid product was filtered off and washed with water to afford the title compound 22a. LCMS (m/z) 261.03 [M+H], Tr=3.70 min (LCMS method 1).

Step 2: Synthesis of 8-bromo-6-nitroquinazoline-2,4(1H,3H)-dione (compound 22b)

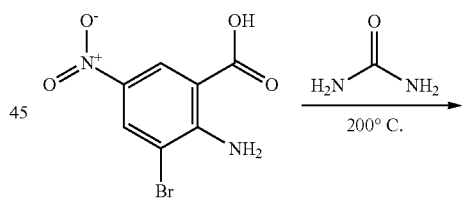

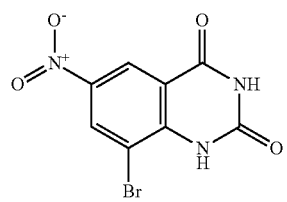

Compound 22b

Example 22

(E)-6-((4-Amino-8-(4-(2-cyanovinyl)-2,6-dimethylphenyl)-6-nitroquinazolin-2-yl)amino)nicotinonitrile—Compound 22

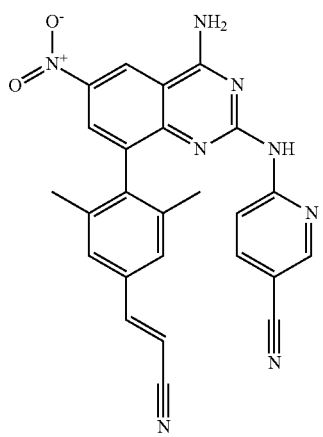 [SMILES: Cc1cc(/C=C/C#N)cc(C)c1-c1cc([N+](=O)[O-])cc2c(N)nc(Nc3ccc(C#N)cn3)nc12]

A mixture of compound 22a (5 g, 22 mmol) and urea (20 g, 333 mmol) was heated at 200° C. for 3 hours. The reaction mixture was cooled down, and diluted with water (100 mL). The solid product was filtered off and washed with methanol (50 mL) and water (50 mL) to afford the title compound 22b. LCMS (m/z) 286.2 [M+H], Tr=3.21 min (LCMS method 1).

Step 3: Synthesis of 8-bromo-2-chloro-6-nitroquinazolin-4-amine (compound 22c)

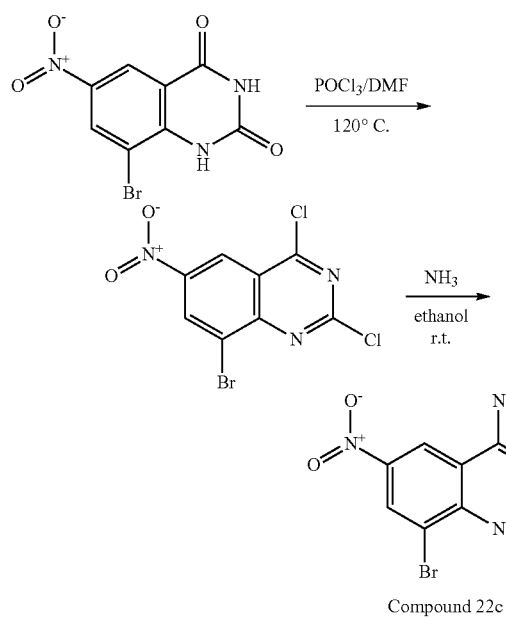

A mixture of compound 22b (5 g, 17 mmol), phosphorus (V) oxychloride (15 mL) and N,N-dimethylformamide (4 drops) was heated at 120° C. for 14 hours. The reaction mixture was cooled down, poured into ice water mixture (200 mL) and the solid product was filtered off. The solid was dried in vacuo for 2 hours, suspended in saturated ethanolic solution of ammonia (100 mL) and stirred at room temperature for 14 hours. The reaction mixture was concentrated down under reduced pressure and water was added. The solid product was filtered off to afford the title compound 22c. $^1$H NMR (400 MHz, DMSO-$d_6$) δ 9.34 (d, J=2.4 Hz, 1H), 8.79 (d, J=2.4 Hz, 1H). LCMS (m/z) 303.0 [M+H], Tr=3.97 min (LCMS method 1).

Step 4: synthesis of (E)-3-(4-(4-amino-2-chloro-6-nitroquinazolin-8-yl)-3,5-dimethylphenyl)acrylonitrile (compound 22d)

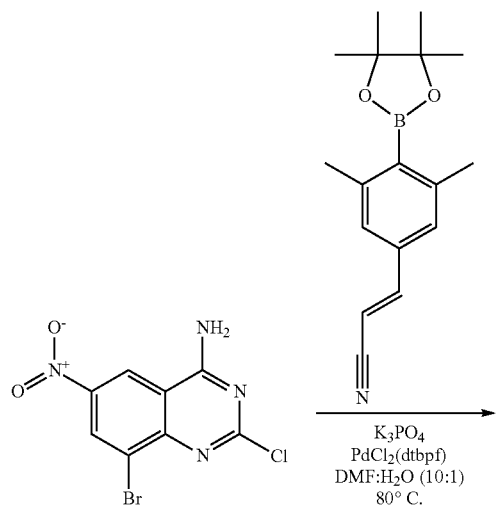

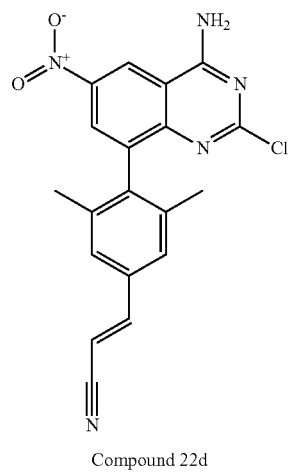

Compound 22d

A mixture of compound 22c (152 mg, 0.5 mmol), compound 1c (170 mg, 0.6 mmol), potassium phosphate tribasic monohydrate (230 mg, 1 mmol) and [1,1'-bis(diphenylphosphino)ferrocene] dichloropalladium(II), complex with dichloromethane (33 mg, 0.05 mmol) was dissolved in a mixture of N,N-dimethylformamide and water (10:1, 5.5 mL) under argon and this reaction mixture was stirred at 80° C. for 7 hours. The product was isolated by silica gel chromatography (gradient from 40-100% ethyl acetate in iso-hexanes) to afford the title compound 22d. LCMS (m/z) 379.9 [M+H], Tr=4.40 min (LCMS method 1).

Step 5: synthesis of (E)-6-((4-amino-8-(4-(2-cyanovinyl)-2,6-dimethylphenyl)-6-nitroquinazolin-2-yl)amino)nicotinonitrile (compound 22)

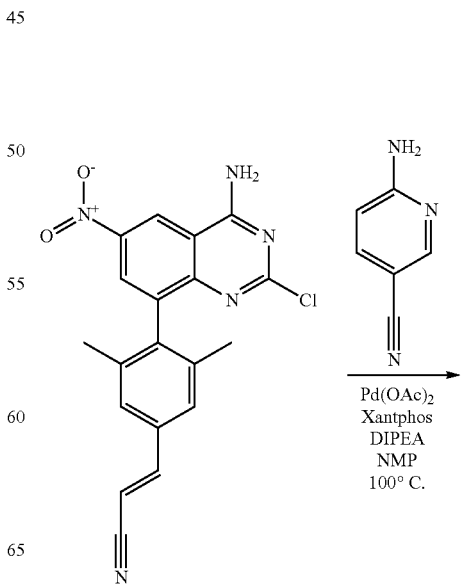

-continued

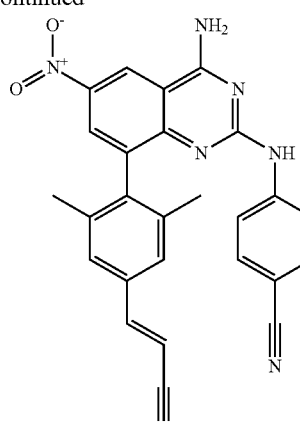

Compound 22

A mixture of compound 22d (110 mg, 0.29 mmol), 6-aminonicotinonitrile (171 mg, 1.45 mmol, Ark Pharm Inc, AK-32349), palladium(II) acetate (13 mg, 0.06 mmol) and (9,9-dimethyl-9H-xanthene-4,5-diyl)bis(diphenylphosphine) (34 mg, 0.06 mmol) was dissolved in N-methyl-2-pyrrolidone (5 mL) under argon. N,N-Diisopropylethylamine (514 µL, 2.95 mmol) was then added via syringe and the reaction mixture was stirred at 100° C. for 1 hour. The product was isolated by silica gel chromatography (gradient from 40-100% ethyl acetate in iso-hexanes) and then repurified by reverse phase flash chromatography (5.5 g C-18 RediSep prepacked column, gradient 5-100%, acetonitrile in water with 0.1% TFA) to afford the title compound 22 as the TFA salt. $^1$H NMR (400 MHz, DMSO-$d_6$) δ 9.43 (bs, 2H), 7.80 (d, J=16.7 Hz, 1H), 7.77-7.50 (m, 7H), 7.48 (bs, 1H), 6.53 (d, J=16.7 Hz, 1H), 1.97 (s, 6H). LCMS (m/z) 463.0 [M+H], Tr=3.98 min (LCMS method 1).

Example 23

(E)-6-((4,6-Diamino-8-(4-(2-cyanovinyl)-2,6-dimethylphenyl)quinazolin-2-yl)amino)nicotinonitrile—Compound 23

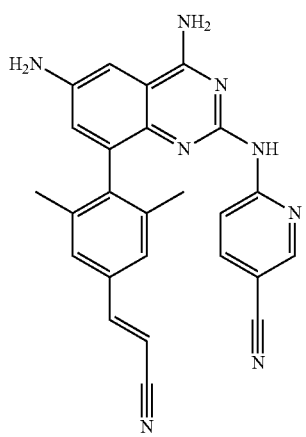 [SMILES: Cc1cc(/C=C/C#N)cc(C)c1-c1cc(N)cc2c(N)nc(Nc3ccc(C#N)cn3)nc12]

Synthesis of (E)-6-((4,6-diamino-8-(4-(2-cyanovinyl)-2,6-dimethylphenyl)quinazolin-2-yl)amino) nicotinonitrile (compound 23)

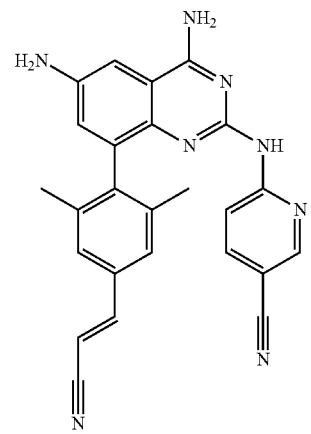

Compound 23

Compound 22 (20 mg, 0.043 mmol) was dissolved in the methanol-acetic acid mixture (10:1, 2 mL), iron dust (20 mg, 0.358 mmol) was added in one portion and the reaction mixture was stirred at room temperature for 24 hours. The product was isolated by silica gel chromatography (gradient from 10-30% methanol in ethyl acetate) and then repurified by reverse phase flash chromatography (5.5 g C-18 RediSep prepacked column, gradient 5-100%, acetonitrile in water with 0.1% TFA) to afford the title compound 23 as the TFA salt. $^1$H NMR (400 MHz, DMSO-$d_6$) δ 9.22 (s, 1H), 9.04 (s, 1H), 8.26-8.21 (m, 1H), 7.82 (d, J=16.6 Hz, 1H), 7.83-7.74 (m, 1H), 7.68 (s, 2H), 7.51 (s, 1H), 7.38-7.32 (m, 1H), 7.11 (s, 1H), 6.69 (d, J=16.6 Hz, 1H), 1.98 (s, 6H). LCMS (m/z) 433.1 [M+H], Tr=3.68 min (LCMS method 1).

Example 24

(E)-6-((4-Amino-8-(4-(2-cyanovinyl)-2,6-dimethyl-phenyl)-6-methoxyquinazolin-2-yl)amino)nicotino-nitrile—Compound 24

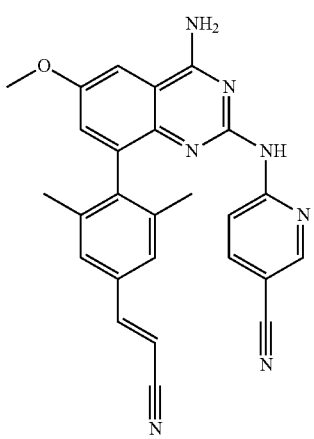 [SMILES: COc1cc(-c2c(C)cc(/C=C/C#N)cc2C)c2nc(Nc3ccc(C#N)cn3)nc(N)c2c1]

Step 1: Synthesis of 2-amino-3-bromo-5-methoxybenzoic acid (Compound 24a)

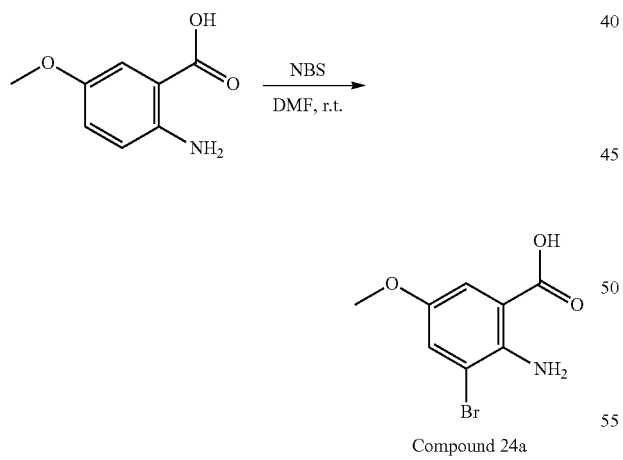

Compound 24a

A mixture of 2-amino-5-methoxybenzoic acid (3.95 g, 23.6 mmol, Sigma-Aldrich) and N-bromosuccinimide (4.2 g, 23.6 mmol) in N,N-dimethylformamide (80 mL) was stirred at room temperature for 14 hours. The reaction mixture was poured into water (400 mL) and the solid product was filtered off and washed with water to afford the title compound 24a. LCMS (m/z) 245.8 [M+H], Tr=4.06 min (LCMS method 1).

Step 2: synthesis of 8-bromo-6-methoxyquinazoline-2,4(1H,3H)-dione (compound 24b)

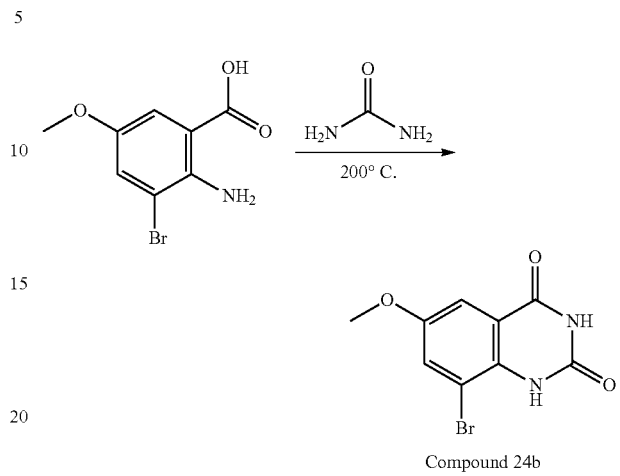

Compound 24b

A mixture of compound 24a (2.19 g, 8.9 mmol) and urea (12 g, 200 mmol) was heated at 200° C. for 3 hours. The reaction mixture was cooled down, and diluted with water (100 mL). The solid product was filtered off and washed with water (50 mL) to afford the title compound 24b.

Step 3: synthesis of 8-bromo-2-chloro-6-methoxyquinazolin-4-amine (compound 24c)

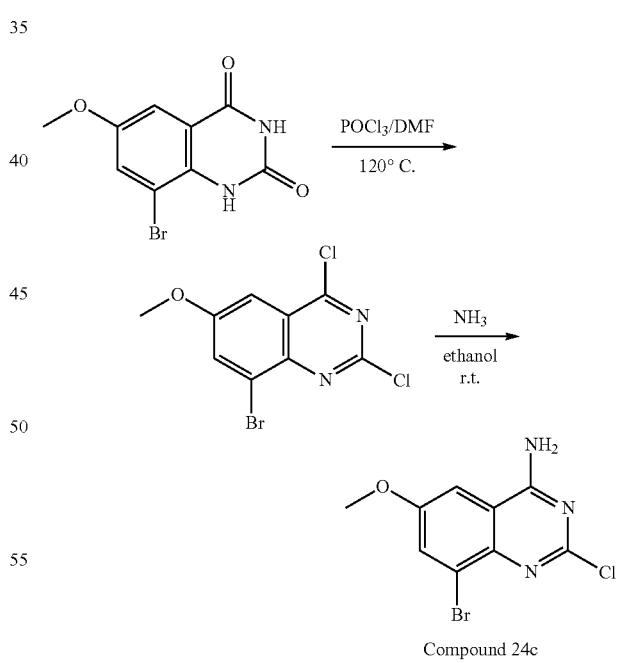

Compound 24c

A mixture of compound 24b (2.45 g, 9 mmol), phosphorus (V) oxychloride (10 mL) and N,N-dimethylformamide (5 drops) was heated at 120° C. for 14 hours. The reaction mixture was cooled down, poured into ice water mixture (200 mL) and the solid product was filtered off. The solid was dried in vacuo for 2 hours, suspended in saturated ethanolic solution of ammonia (100 mL) and stirred at room temperature for 14 hours. The reaction mixture was concentrated down under reduced pressure and water (20 mL) was added. The solid product was filtered off to afford the title compound 24c. LCMS (m/z) 287.7 [M+H]. Tr=4.33 min (LCMS method 1).

Step 4: synthesis of (E)-3-(4-(4-amino-2-chloro-6-methoxyquinazolin-8-yl)-3,5-dimethylphenyl)acrylonitrile (compound 24d)

Step 5: synthesis of (E)-6-((4-amino-8-(4-(2-cyanovinyl)-2,6-dimethylphenyl)-6-methoxyquinazolin-2-yl)amino)nicotinonitrile (compound 24)

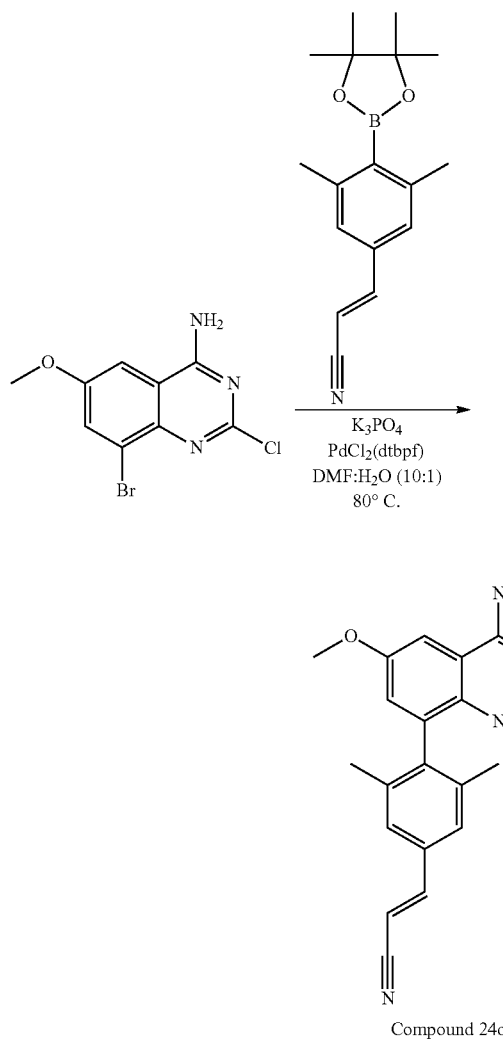

Compound 24d

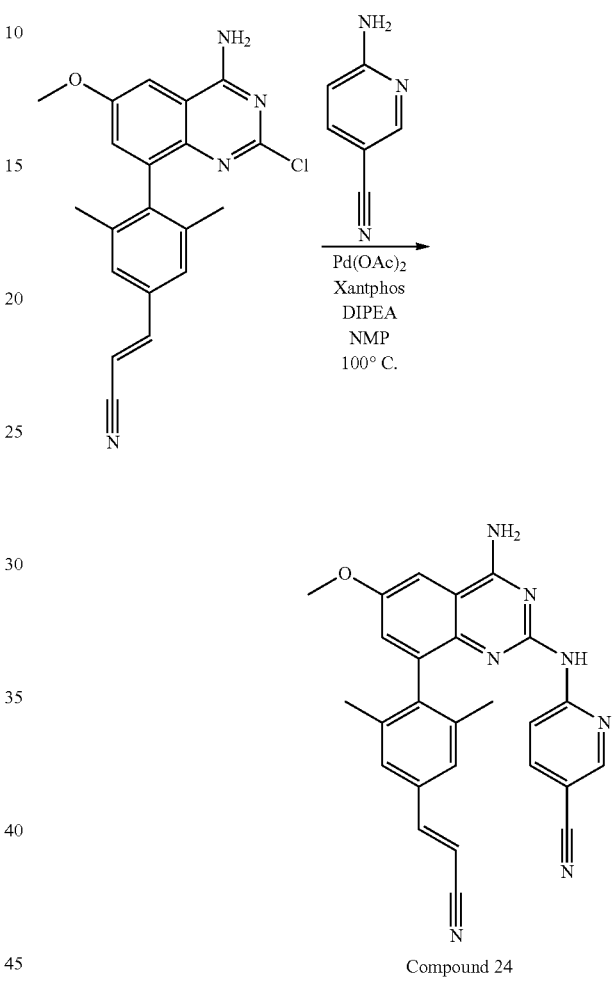

Compound 24

A mixture of compound 24c (30 mg, 0.1 mmol), compound 1c (34 mg, 0.12 mmol), potassium phosphate tribasic monohydrate (46 mg, 0.2 mmol) and [1,1'-bis(diphenylphosphino)ferrocene] dichloropalladium(II), complex with dichloromethane (13 mg, 0.02 mmol) was dissolved in a mixture of N,N-dimethylformamide and water (10:1, 2 mL) under argon and this reaction mixture was stirred at 80° C. for 30 minutes. The product was isolated by silica gel chromatography (gradient from 50-100% ethyl acetate in iso-hexanes) to afford the title compound 24d. LCMS (m/z) 364.9 [M+H], Tr=4.65 min (LCMS method 1).

A mixture of compound 24d (15 mg, 0.041 mmol), 6-aminonicotinonitrile (24 mg, 0.21 mmol, Ark Pharm Inc, AK-32349), palladium(II) acetate (4 mg, 0.016 mmol) and (9,9-dimethyl-9H-xanthene-4,5-diyl)bis(diphenylphosphine) (10 mg, 0.016 mmol) was dissolved in N-methyl-2-pyrrolidone (1 mL) under argon. N,N-Diisopropylethylamine (37 µL, 0.21 mmol) was then added via syringe and the reaction mixture was stirred at 100° C. for 2 hours. The product was isolated by silica gel chromatography (gradient from 60-100% ethyl acetate in iso-hexanes) and then repurified by reverse phase flash chromatography (5.5 g C-18 RediSep prepacked column, gradient 5-100%, acetonitrile in water with 0.1% TFA) to afford the title compound 24 as the TFA salt. $^1$H NMR (400 MHz, DMSO-$d_6$) δ 13.52 (bs, 1H), 11.99 (bs, 1H), 9.46 (bs, 1H), 9.26 (bs, 1H), 8.28 (s, 1H), 7.97 (s, 1H), 7.83 (d, J=16.7 Hz, 1H), 7.70 (s, 2H), 7.62-7.48 (m, 2H), 7.42-7.36 (m, 1H), 6.69 (d, J=16.7 Hz, 1H), 3.95 (s, 3H), 1.98 (s, 6H). LCMS (m/z) 448.0 [M+H], Tr=3.95 min (LCMS method 1).

Example 25

(E)-4-((4-Amino-6-bromo-8-(4-(2-cyanovinyl)-2,6-dimethylphenyl)quinazolin-2-yl)amino)benzonitrile—Compound 25

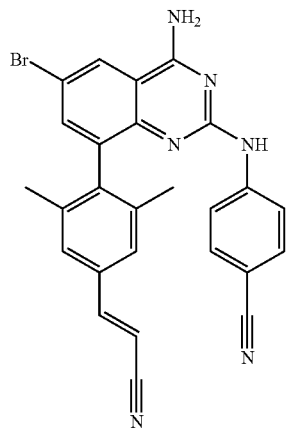

Step 1: Synthesis of 2-amino-5-bromo-3-iodobenzoic acid (Compound 25a)

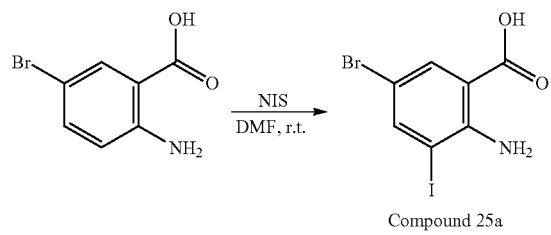

Compound 25a

A mixture of 2-amino-5-bromobenzoic acid (1 g, 4.6 mmol, Sigma-Aldrich) and N-iodosuccinimide (1.9 g, 8.4 mmol) in N,N-dimethylformamide (30 mL) was stirred at room temperature for 48 hours. The reaction mixture was poured into water (100 mL). The solid product was filtered off and washed with water to afford the title compound 25a. LCMS (m/z) 341.9 [M+H], Tr=4.53 min (LCMS method 1).

Step 2: Synthesis of 6-bromo-8-iodoquinazoline-2,4(1H,3H)-dione (compound 25b)

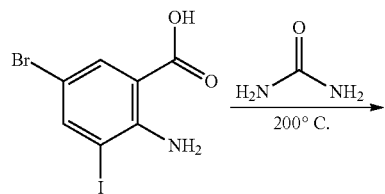

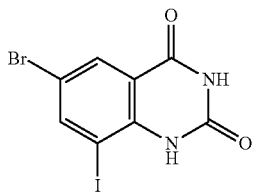

Compound 25b

A mixture of compound 25a (1.2 g, 3.5 mmol) and urea (10 g, 166 mmol) was heated at 200° C. for 3 hours. The reaction mixture was cooled down, and diluted with water (100 mL). The solid product was filtered off and washed with methanol (50 mL) and water (50 mL) to afford the title compound 25b.

Step 3: Synthesis of 6-bromo-2-chloro-8-iodoquinazolin-4-amine (compound 25c)

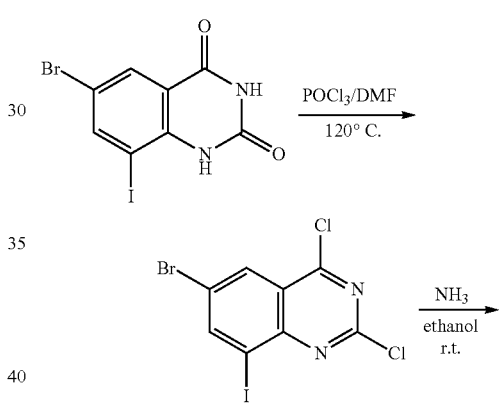

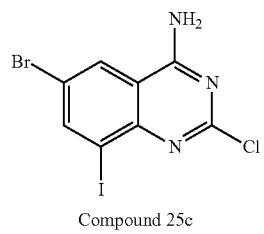

Compound 25c

A mixture of compound 25b (5.33 g, 14.5 mmol), phosphorus(V) oxychloride (30 mL) and N,N-dimethylformamide (3 drops) was heated at 120° C. for 14 hours. The reaction mixture was cooled down, poured into ice water mixture (0.200 mL) and the solid product was filtered off. The solid was dried in vacuo for 2 hours, suspended in saturated ethanolic solution of ammonia (100 mL) and stirred at room temperature for 14 hours. The reaction mixture was concentrated down under reduced pressure and subjected to silica gel column chromatography (gradient from 10-50% ethyl acetate in iso-hexanes) to afford the title compound 25c. $^1$H NMR (400 MHz, DMSO-d$_6$) δ 7.97 (d, J=2.4 Hz, 1H), 7.86 (d, J=2.4 Hz, 1H), 6.78 (bs, 2H). LCMS (m/z) 383.9 [M+H], Tr=5.98 min (LCMS method 1).

Step 4: synthesis of (E)-3-(4-(4-amino-6-bromo-2-chloroquinazolin-8-yl)-3,5-dimethylphenyl)acrylonitrile (compound 25d)

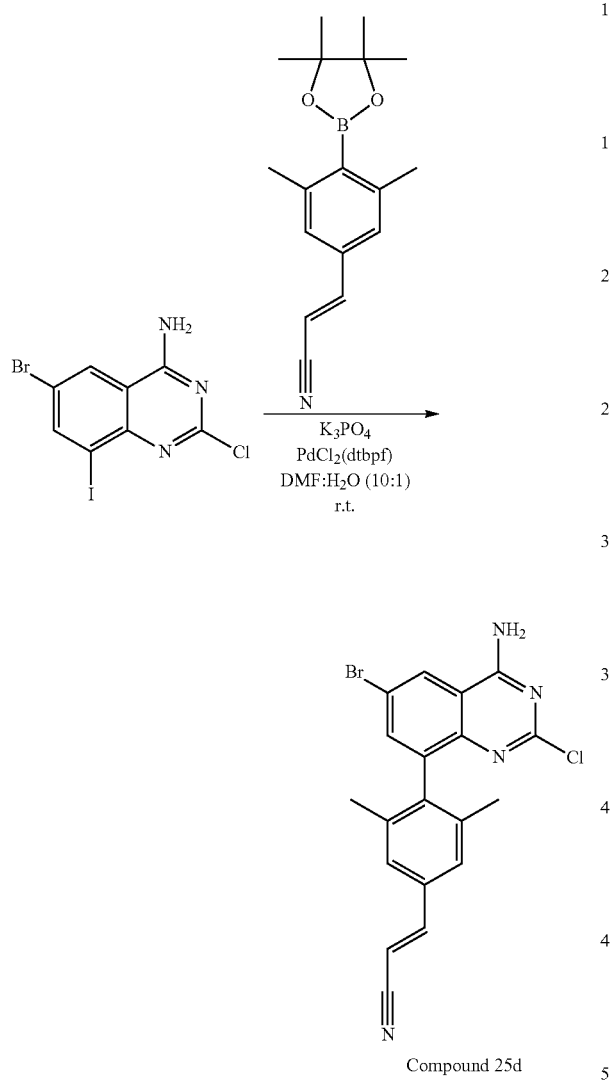

Compound 25d

A mixture of compound 25c (120 mg, 0.31 mmol), compound 1c (106 mg, 0.37 mmol), potassium phosphate tribasic monohydrate (143 mg, 0.62 mmol) and [1,1'-bis(diphenylphosphino)ferrocene] dichloropalladium(II), complex with dichloromethane (40 mg, 0.062 mmol) was dissolved in a mixture of N,N-dimethylformamide and water (10:1, 3 mL) under argon and this reaction mixture was stirred at room temperature for 24 hours. The reaction was quenched by addition of saturated ammonium chloride and the product was isolated by silica gel chromatography (gradient from 30-60% ethyl acetate in iso-hexanes) to afford the title compound 25d. LCMS (m/z) 412.8 [M+H], Tr=4.62 min (LCMS method 1).

Step 5: synthesis of (E)-4-((4-amino-6-bromo-8-(4-(2-cyanovinyl)-2,6-dimethylphenyl)quinazolin-2-yl)amino)benzonitrile (compound 25)

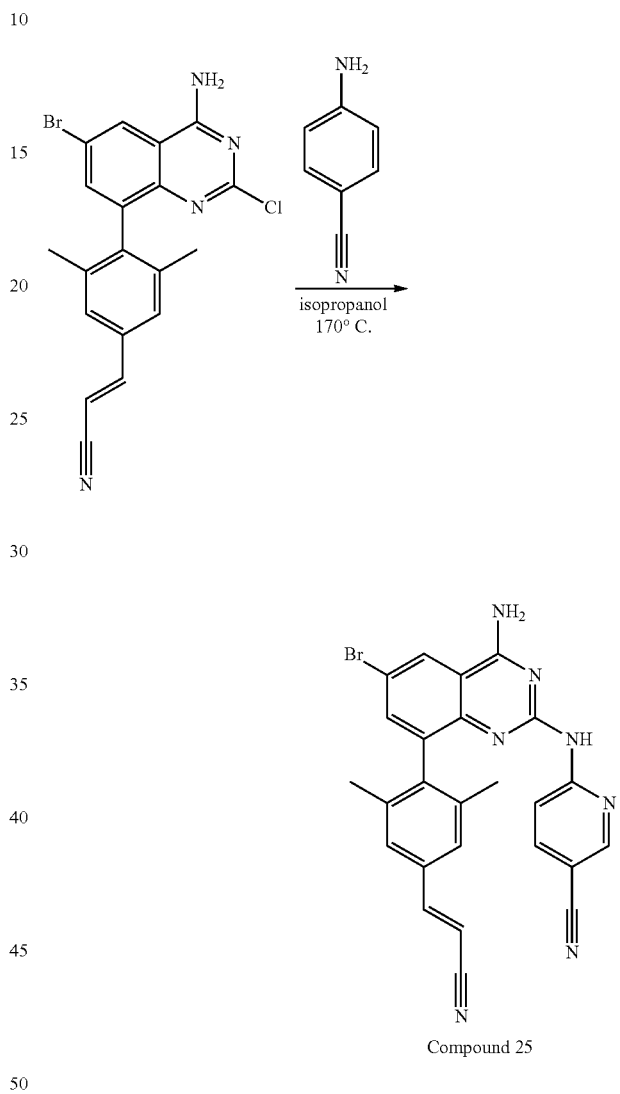

Compound 25

A mixture of compound 25d (55 mg, 0.13 mmol) and 4-aminobenzonitrile (20 mg, 0.17 mmol, Sigma-Aldrich) in isopropanol (2 mL) was heated under microwave conditions at 170° C. for 30 minutes. The reaction mixture was concentrated down under reduced pressure and purified by silica gel column chromatography (gradient from 0-100% ethyl acetate in iso-hexanes) to afford the title compound 25. $^1$H NMR (400 MHz, DMSO-d$_6$) δ 9.57 (s, 1H), 8.47 (d, J=2.2 Hz, 1H), 7.75 (d, J=16.7 Hz, 1H), 7.68-7.63 (m, 3H), 7.52 (s, 2H), 7.32-7.21 (m, 2H), 6.56 (d, J=16.7 Hz, 1H), 1.92 (s, 6H). LCMS (m/z) 495.1 [M+H], Tr=4.58 min (LCMS method 1).

Example 26

(E)-5-((4-Amino-8-(4-(2-cyanovinyl)-2,6-dimethyl-phenyl)-6-fluoroquinazolin-2-yl)amino)pyrazine-2-carbonitrile—Compound 26

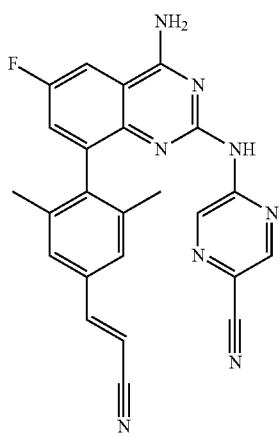 [SMILES: Cc1cc(/C=C/C#N)cc(C)c1-c1cc(F)cc2c(N)nc(Nc3cnc(C#N)cn3)nc12]

Synthesis of (E)-5-((4-amino-8-(4-(2-cyanovinyl)-2,6-dimethylphenyl)-6-fluoroquinazolin-2-yl)amino)pyrazine-2-carbonitrile (compound 26)

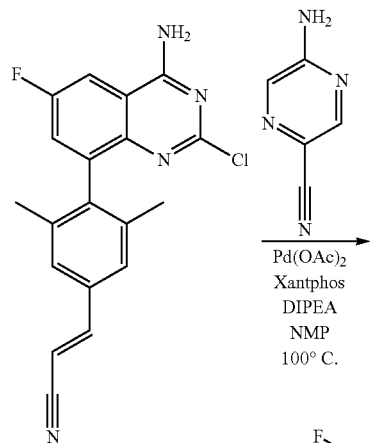

Compound 26

Compound 20d (92 mg, 0.21 mmol), 5-aminopyrazine-2-carbonitrile (60 mg, 0.50 mmol, Ark Pharm Inc, AK-21935), N,N-diisopropylethylamine (174 µL, 1.0 mmol), (9,9-dimethyl-9H-xanthene-4,5-diyl)bis(diphenyl-phosphine) (24 mg, 0.042 mmol) and palladium (II) acetate (9 mg, 0.042 mmol) were combined under argon in N-methyl-2-pyrrolidone (2 mL). The reaction was heated at 100° C. in a sealed vessel for 7 hours. The reaction mixture was cooled down to room temperature, purified by silica gel chromatography (gradient from 50-100% ethyl acetate in iso-hexanes) and then re-purified by reverse phase chromatography (5-100% acetonitrile in water with 0.1% trifluoroacetic acid) to afford the TFA salt of compound 26. $^1$H NMR (400 MHz, DMSO-d$_6$) δ 9.10 (s, 1H), 8.20 (s, 1H), 7.74 (d, J=16.7 Hz, 1H), 7.77-7.60 (m, 2H), 7.57 (s, 2H), 6.56 (d, J=16.7 Hz, 1H), 1.94 (s, 6H). LCMS (m/z) 436.9 [M+H], Tr=3.59 min (LCMS method 1).

Example 27

(E)-6-((4-Amino-8-(4-(2-cyanovinyl)-2,6-dimethyl-phenyl)-6-fluoroquinazolin-2-yl)amino)pyridazine-3-carbonitrile—Compound 27

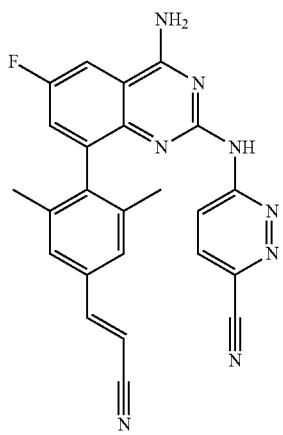 [SMILES: Cc1cc(/C=C/C#N)cc(C)c1-c1cc(F)cc2c(N)nc(Nc3ccc(C#N)nn3)nc12]

Synthesis of (E)-6-((4-amino-8-(4-(2-cyanovinyl)-2,6-dimethylphenyl)-6-fluoroquinazolin-2-yl)amino)pyridazine-3-carbonitrile (compound 27)

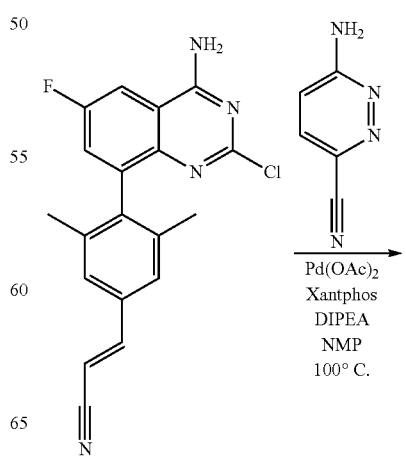

133
-continued

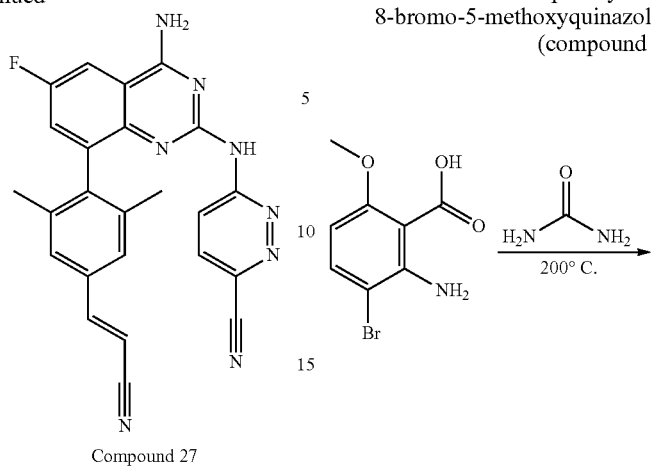
Compound 27

Compound 20d (92 mg, 0.21 mmol), 6-aminopyridazine-3-carbonitrile (60 mg, 0.50 mmol, Matrix Scientific, 112287), N,N-diisopropylethylamine (174 µL, 1.0 mmol), (9,9-dimethyl-9H-xanthene-4,5-diyl)bis(diphenylphosphine) (24 mg, 0.042 mmol) and palladium (II) acetate (9 mg, 0.042 mmol) were combined under argon in N-methyl-2-pyrrolidone (2 mL). The reaction was heated at 100° C. in a sealed vessel for 7 hours. The reaction mixture was cooled down to room temperature, purified by silica gel chromatography (gradient from 50-100% ethyl acetate in isohexanes) and then re-purified by reverse phase chromatography (5-100% acetonitrile in water with 0.1% trifluoroacetic acid) to afford the TFA salt of compound 27. $^1$H NMR (400 MHz, DMSO-$d_6$) δ 8.18 (bs, 1H), 8.06 (bs, 1H), 7.73 (d, J=16.7 Hz, 1H), 7.71-7.58 (m, 2H), 7.54 (s, 2H), 6.55 (d, J=16.7 Hz, 1H), 1.93 (s, 6H). LCMS (m/z) 436.9 [M+H], Tr=3.73 min (LCMS method 1).

Example 28

(E)-4-((4-Amino-8-(4-(2-cyanovinyl)-2,6-dimethylphenyl)-5-methoxyquinazolin-2-yl)amino)benzonitrile—Compound 28

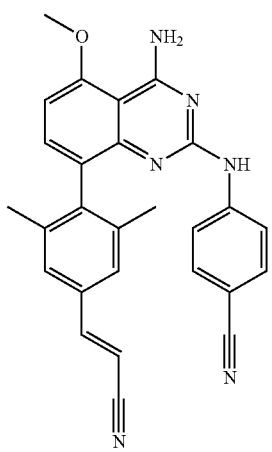 [SMILES: COc1ccc(-c2c(C)cc(/C=C/C#N)cc2C)c2nc(Nc3ccc(C#N)cc3)nc(N)c12]

134

Step 1: synthesis of 8-bromo-5-methoxyquinazoline-2,4(1H,3H)-dione (compound 28a)

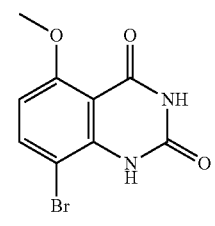

Compound 28a

A mixture of 2-amino-3-bromo-6-methoxybenzoic acid (2 g, 8.1 mmol, Ark Pharm Inc, AK137474) and urea (12 g, 200 mmol) was heated at 200° C. for 2 hours. The reaction mixture was cooled down, and diluted with water (100 mL). The solid product was filtered off and washed with water (50 mL) to afford the title compound 28a.

Step 2: synthesis 8-bromo-2-chloro-5-methoxyquinazolin-4-amine (compound 28b)

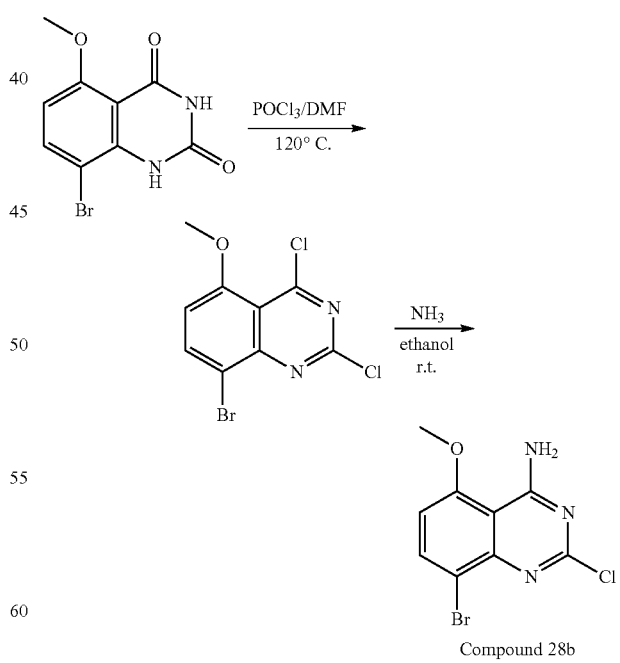

Compound 28b

A mixture of compound 28a (4.67 g, 17 mmol), phosphorus(V) oxychloride (20 mL) and N,N-dimethylformamide (3 drops) was heated at 120° C. for 14 hours. The reaction mixture was cooled down, poured into ice water mixture (200 mL) and the solid product was filtered off. The solid was dried in vacuo for 2 hours, suspended in saturated ethanolic solution of ammonia (100 mL) and stirred at room temperature for 14 hours. The reaction mixture was concentrated down under reduced pressure and the solid residue was subjected to extraction with acetone. The acetone solution was concentrated down under reduced pressure to afford the title compound 28b. $^1$H NMR (400 MHz, DMSO-$d_6$) δ 8.66 (s, 1H), 8.26 (s, 1H), 8.02 (d, J=8.7 Hz, 1H), 6.95 (d, J=8.7 Hz, 1H), 3.98 (s, 3H). LCMS (m/z) 288.1 [M+H], Tr=3.74 min (LCMS method 1).

Step 3: synthesis of (E)-3-(4-(4-amino-2-chloro-5-methoxyquinazolin-8-yl)-3,5-dimethylphenyl)acrylonitrile (compound 28c)

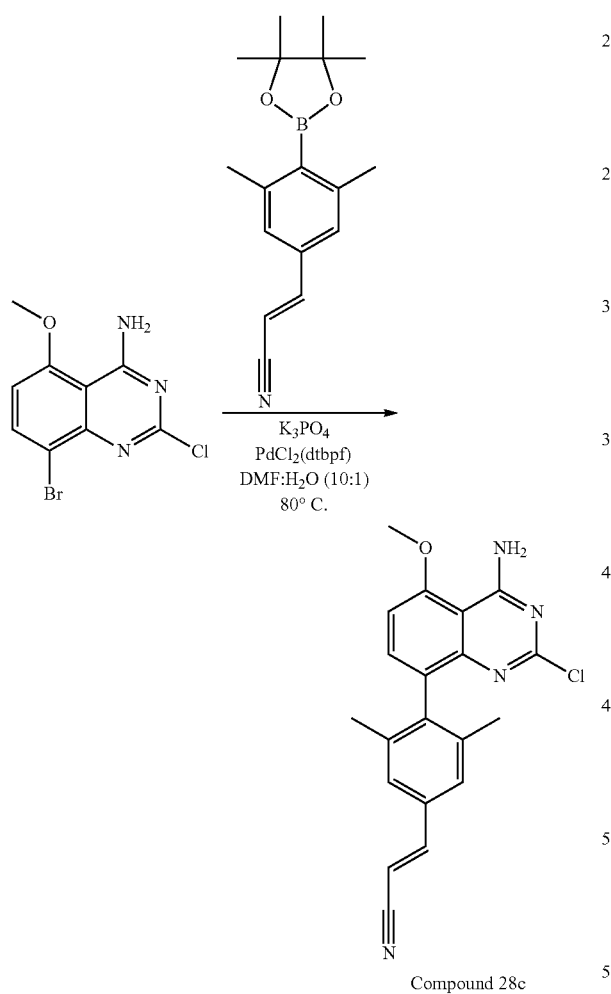

A mixture of compound 28b (100 mg, 0.35 mmol), compound 1c (118 mg, 0.42 mmol), potassium phosphate tribasic monohydrate (159 mg, 0.69 mmol) and [1,1'-bis(diphenylphosphino)ferrocene] dichloropalladium(II), complex with dichloromethane (23 mg, 0.035 mmol) was dissolved in a mixture of N,N-dimethylformamide and water (10:1, 5 mL) under argon and this reaction mixture was stirred at 80° C. for 30 minutes. The product was isolated by silica gel chromatography (gradient from 60-100% ethyl acetate in iso-hexanes) to afford the title compound 28c. LCMS (m/z) 364.9 [M+H], Tr=4.38 min (LCMS method 1).

Step 4: synthesis of (E)-4-((4-amino-8-(4-(2-cyanovinyl)-2,6-dimethylphenyl)-5-methoxyquinazolin-2-yl)amino)benzonitrile (compound 28)

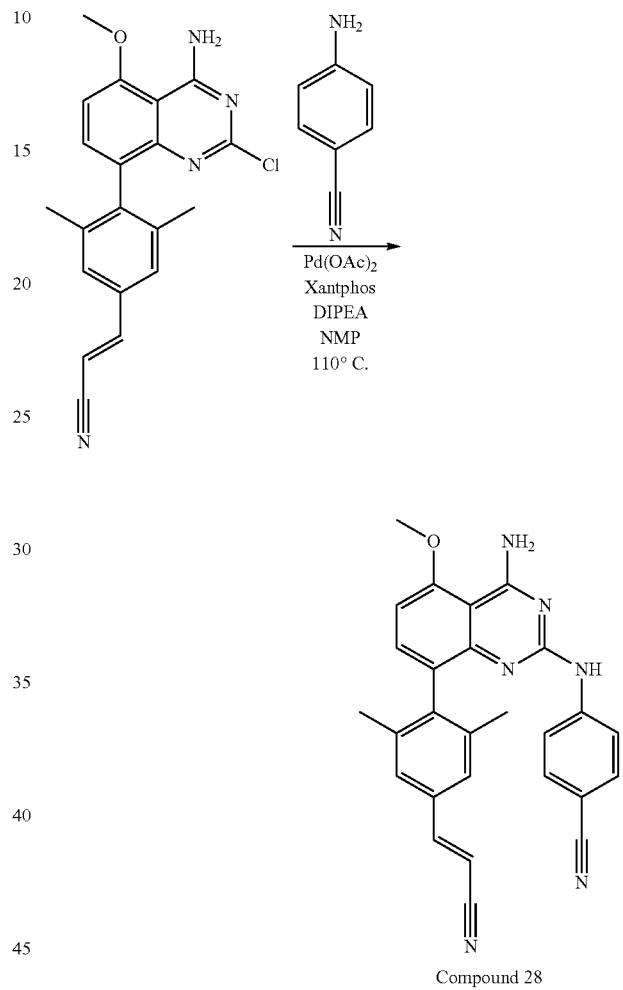

A mixture of compound 28c (37 mg, 0.1 mmol), 4-aminobenzonitrile (60 mg, 0.5 mmol, Sigma-Aldrich), palladium (II) acetate (4 mg, 0.02 mmol) and (9,9-dimethyl-9H-xanthene-4,5-diyl)bis(diphenylphosphine) (12 mg, 0.02 mmol) was dissolved in N-methyl-2-pyrrolidone (2 mL) under argon. N,N-Diisopropylethylamine (87 µL, 0.5 mmol) was then added via syringe and the reaction mixture was stirred at 110° C. for 6 hours. The product was isolated by silica gel chromatography (gradient from 50-100% ethyl acetate in iso-hexanes) and then repurified by reverse phase flash chromatography (5.5 g C-18 RediSep prepacked column, gradient 5-100%, acetonitrile in water with 0.1% TFA) to afford the title compound 28 as the TFA salt. $^1$H NMR (400 MHz, DMSO-$d_6$) δ 7.90-7.65 (m, 3H), 7.71 (d, J=16.7 Hz, 1H), 7.58-7.45 (m, 4H), 7.07 (s, 1H), 6.55 (d, J=16.7 Hz, 1H), 4.07 (s, 3H), 1.95 (s, 6H). LCMS (m/z) 447.0 [M+H], Tr=3.85 min (LCMS method 1).

Example 29

(E)-6-((4-Amino-8-(4-(2-cyanovinyl)-2,6-dimethylphenyl)-5-methoxyquinazolin-2-yl)amino)nicotinonitrile—Compound 29

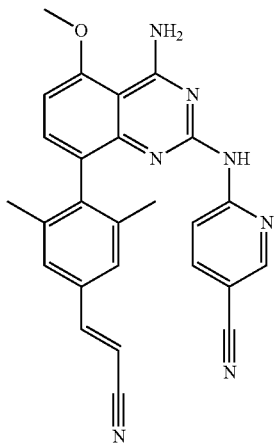 [SMILES: COc1ccc(-c2c(C)cc(/C=C/C#N)cc2C)c2nc(Nc3ccc(C#N)cn3)nc(N)c12]

Synthesis of (E)-6-((4-amino-8-(4-(2-cyanovinyl)-2,6-dimethylphenyl)-5-methoxyquinazolin-2-yl)amino)nicotinonitrile (compound 29)

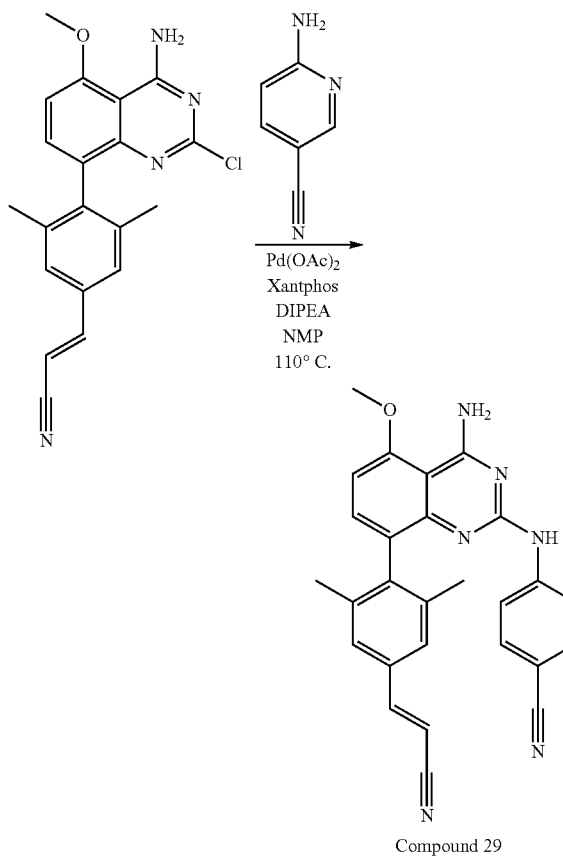

Compound 28 (37 mg, 0.1 mmol), 6-aminonicotinonitrile (60 mg, 0.5 mmol, Ark Pharm Inc, AK-32349), N,N-diisopropylethylamine (87 µL, 0.5 mmol), (9,9-dimethyl-9H-xanthene-4,5-diyl)bis(diphenylphosphine) (12 mg, 0.02 mmol) and palladium (II) acetate (4 mg, 0.02 mmol) were combined under argon in N-methyl-2-pyrrolidone (2 mL). The reaction was heated at 110° C. in a sealed vessel for 6 hours. The reaction mixture was cooled down to room temperature, purified by silica gel chromatography (gradient from 50-100% ethyl acetate in iso-hexanes) and then re-purified by reverse phase chromatography (5-100% acetonitrile in water with 0.1% trifluoroacetic acid) to afford the TFA salt of compound 29. $^1$H NMR (400 MHz, DMSO-$d_6$) δ 13.31 (bs, 1H), 11.92 (bs, 1H), 9.49 (s, 1H), 9.09 (s, 1H), 8.27 (d, J=8.4 Hz, 1H), 7.82 (d, J=16.7 Hz, 1H), 7.77 (d, J=9.2 Hz, 1H), 7.68 (s, 2H), 7.55-7.40 (m, 2H), 7.30 (d, J=8.4 Hz, 1H), 6.69 (d, J=16.7 Hz, 1H), 4.13 (s, 3H), 1.97 (s, 6H). LCMS (m/z) 448.0 [M+H], Tr=3.60 min (LCMS method 1).

Example 30

(E)-4-((8-(4-(2-Cyanovinyl)-2,6-dimethylphenyl)-4-(methylamino)quinazolin-2-yl)amino)benzonitrile—Compound 30

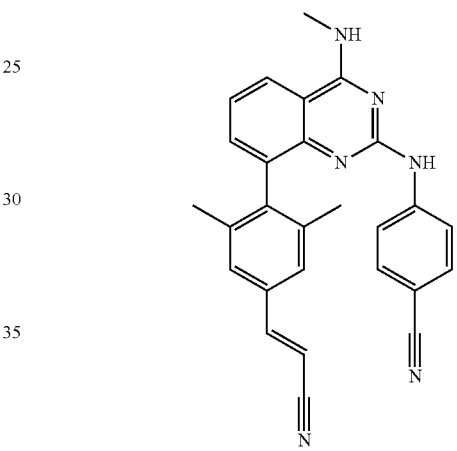

Step 1: Synthesis of 8-bromo-2-chloro-N-methylquinazolin-4-amine (compound 30a)

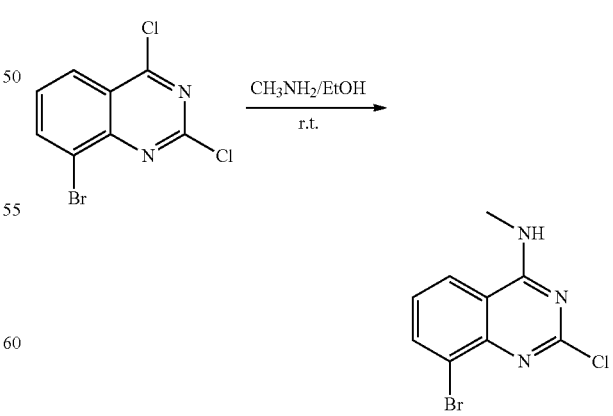

8-Bromo-2,4-dichloroquinazoline (556 mg, 2 mmol, Ark Pharm Inc., AK-28703) was dissolved in 6 mL of 20% solution of methylamine in ethanol and the reaction was stirred at room temperature for 15 minutes. Volatiles were removed under reduced pressure and the solid residue was suspended in water. The solid product was filtered off and washed with water (3×5 mL) and pentane (3×5 mL) to give the title compound 30a. $^1$H NMR (400 MHz, DMSO-$d_6$) δ 8.96 (d, J=4.7 Hz, 1H), 8.19 (dd, J=8.3 Hz, J=1.2 Hz, 1H), 8.11 (dd, J=7.7 Hz, J=1.2 Hz, 1H), 7.42 (t, J=7.9 Hz, 1H), 3.00 (d, J=4.3 Hz, 3H). HRMS: (ESI+) calculated for $C_9H_8N_3BrCl$ [M+H] 271.9585, found 271.9585. LCMS (m/z) 272.0 [M+H], Tr 3.80 min (LCMS method 1).

Step 2: Synthesis of (E)-3-(4-(2-chloro-4-(methylamino)quinazolin-8-yl)-3,5-dimethylphenyl)acrylonitrile (compound 30b)

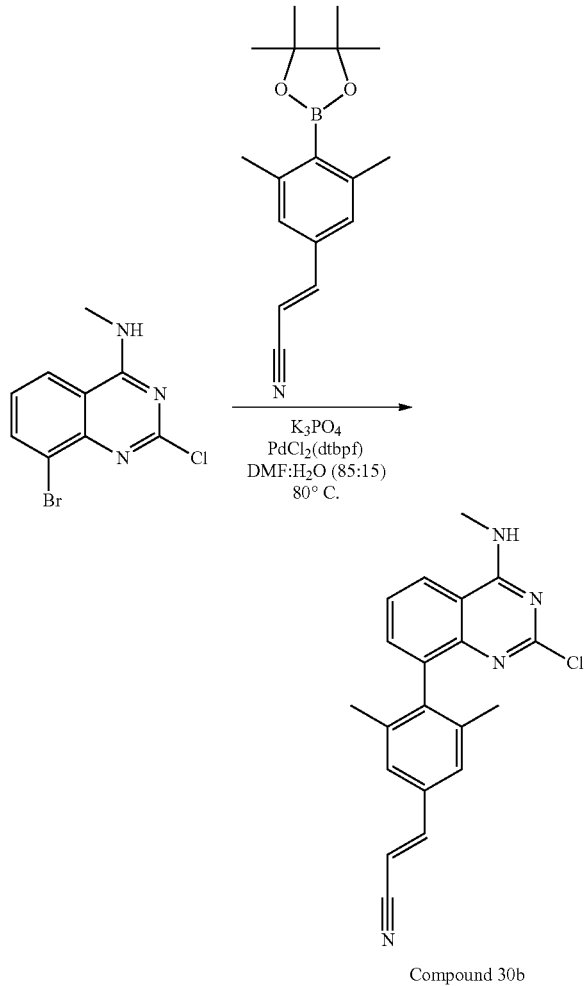

Compound 30b

A mixture of compound 30a (110 mg, 0.4 mmol), compound 1c (147 mg, 0.52 mmol), potassium phosphate tribasic monohydrate (138 mg, 0.6 mmol) and [1,1'-bis(diphenylphosphino)ferrocene] dichloropalladium(II), complex with dichloromethane (26 mg, 0.04 mmol) was dissolved in a mixture of N,N-dimethylformamide and water (85:15, 5 mL) under argon and this reaction mixture was stirred at 80° C. for 20 minutes. The reaction mixture was concentrated down under reduced pressure and the product was isolated by silica gel chromatography (gradient from 50-80% ethyl acetate in iso-hexanes) to afford the title compound 30b. $^1$H NMR (400 MHz, DMSO-$d_6$) δ 8.88 (d, J=4.4 Hz, 1H), 8.25 (dd, J=8.2 Hz, J=1.5 Hz, 1H), 7.67-7.58 (m, 2H), 7.53 (dd, J=7.2 Hz, J=1.5 Hz, 1H), 7.43 (s, 2H), 6.46 (d, J=16.7 Hz, 1H), 3.01 (d, J=4.4 Hz, 3H), 1.85 (s, 6H). HRMS: (ESI+) calculated for $C_{20}H_8N_4Cl$ [M+H] 349.1215, found 349.1216. LCMS (m/z) 349.1 [M+H], Tr 4.51 min (LCMS method 1).

Step 3: synthesis of (E)-4-((8-(4-(2-cyanovinyl)-2,6-dimethylphenyl)-4-(methylamino)quinazolin-2-yl)amino)benzonitrile (compound 30)

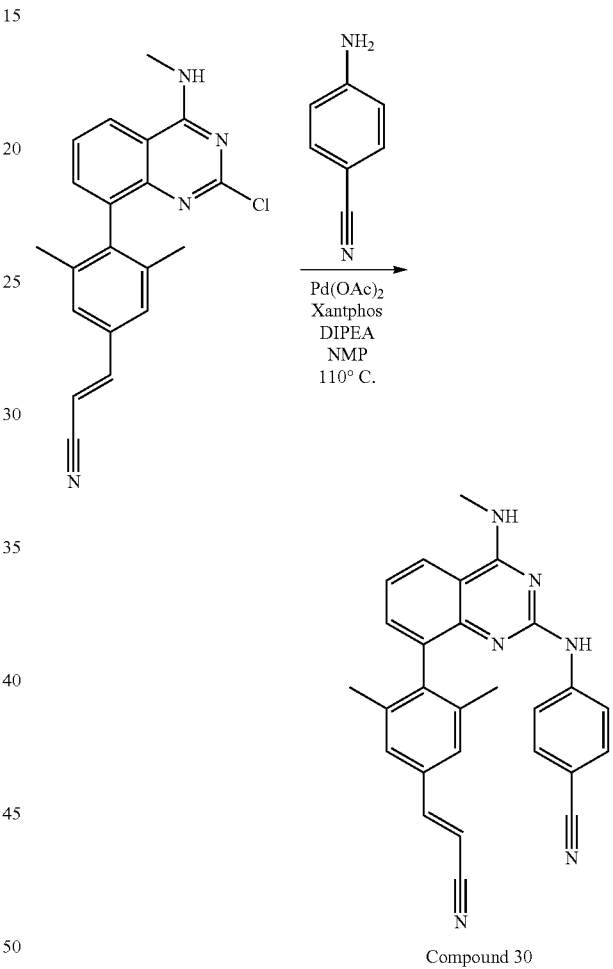

Compound 30

A mixture of compound 30b (52 mg, 0.15 mmol), 4-aminobenzonitrile (90 mg, 0.75 mmol, Sigma-Aldrich), palladium(II) acetate (20 mg, 0.064 mmol) and (9,9-dimethyl-9H-xanthene-4,5-diyl)bis(diphenylphosphine) (40 mg, 0.064 mmol) was dissolved in N-methyl-2-pyrrolidone (3 mL) under argon. N,N-Diisopropylethylamine (150 μL, 0.85 mmol) was then added via syringe and the reaction mixture was stirred at 110° C. for 3 hours. The reaction mixture was concentrated down under reduced pressure and the product was isolated by silica gel chromatography (gradient from 80-100% ethyl acetate in iso-hexanes) and then repurified by reverse phase flash chromatography (5.5 g C-18 RediSep prepacked column, gradient 0-100%, acetonitrile in water) to afford the title compound 30. $^1$H NMR (400 MHz, DMSO-$d_6$) δ 9.54 (s, 1H), 8.31 (d, J=4.3 Hz, 1H), 8.11 (d, J=8.4 Hz, 1H), 7.77-7.70 (m, 3H), 7.51 (s, 2H), 7.46 (d, J=7.5 Hz, 1H), 7.35 (t, J=7.7 Hz, 1H), 7.27 (d, J=8.8 Hz, 2H), 6.54 (d, J=16.7 Hz, 1H), 3.06 (d, J=4.3 Hz, 3H), 1.90 (s, 6H). HRMS: (ESI+) calculated for $C_{27}H_{23}N_6$ [M+H] 431.1979, found 431.1977. LCMS (m/z) 431.2 [M+H], Tr 3.67 min (LCMS method 1).

Example 31

(E)-6-((8-(4-(2-Cyanovinyl)-2,6-dimethylphenyl)-4-(methylamino)quinazolin-2-yl)amino)nicotinonitrile—Compound 31

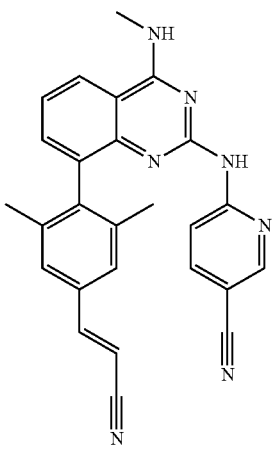 [SMILES: CNc1nc(Nc2ccc(C#N)cn2)nc2c(-c3c(C)cc(/C=C/C#N)cc3C)cccc12]

Synthesis of (E)-6-((8-(4-(2-cyanovinyl)-2,6-dimethylphenyl)-4-(methylamino)quinazolin-2-yl)amino)nicotinonitrile (compound 31)

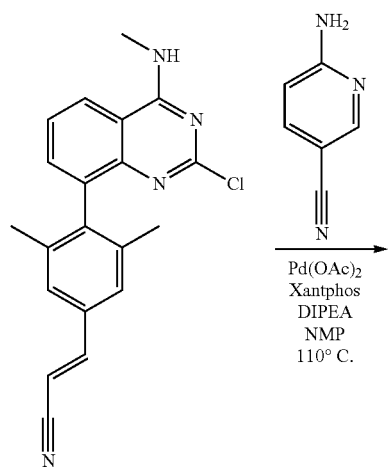

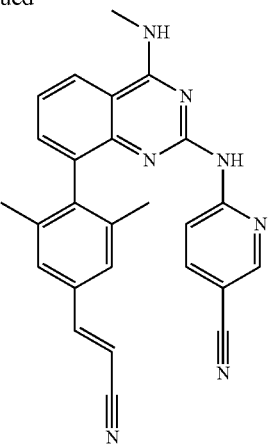

Compound 31

A mixture of compound 30b (52 mg, 0.15 mmol), 6-aminonicotinonitrile (90 mg, 0.75 mmol, Ark Pharm Inc, AK-32349), palladium(II) acetate (20 mg, 0.064 mmol) and (9,9-dimethyl-9H-xanthene-4,5-diyl)bis(diphenylphosphine) (40 mg, 0.064 mmol) was dissolved in N-methyl-2-pyrrolidone (3 mL) under argon. N,N-Diisopropylethylamine (150 µL, 0.85 mmol) was then added via syringe and the reaction mixture was stirred at 110° C. for 4 hours. The reaction mixture was concentrated down under reduced pressure and the product was isolated by silica gel chromatography (gradient from 80-100% ethyl acetate in isohexanes) and then repurified by reverse phase flash chromatography (5.5 g C-18 RediSep prepacked column, gradient 0-100%, acetonitrile in water with 0.1% trifluoroacetic acid) to afford the TFA salt of the title compound 31. $^1$H NMR (400 MHz, DMSO-$d_6$) δ 13.53 (s, 1H), 12.28 (s, 1H), 10.13 (s, 1H), 8.41 (d, J=8.4 Hz, 1H), 8.29 (d, J=8.8 Hz. 1H), 7.88-7.80 (m, 2H), 7.80-7.72 (m, 1H), 7.71 (s, 2H), 7.59-7.49 (m, 1H), 7.46-7.41 (m, 1H), 6.70 (d, J=16.7 Hz, 1H), 3.21 (d, J=4.4 Hz, 3H), 1.96 (s, 6H). HRMS: (ESI+) calculated for $C_{26}H_{22}N_7$ [M+H] 432.1931, found 432.1929. LCMS (m/z) 432.2 [M+H], Tr 3.53 min (LCMS method 1).

Example 32

(E)-4-((4-Amino-8-(4-(2-cyanovinyl)-2,6-dimethoxyphenyl)quinazolin-2-yl)amino)benzonitrile—Compound 32

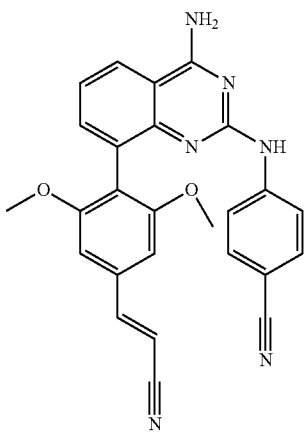 [SMILES: COc1cc(/C=C/C#N)cc(OC)c1-c1cccc2c(N)nc(Nc3ccc(C#N)cc3)nc12]

Step 1: Synthesis of 4-((4-amino-8-(trimethylstannyl)quinazolin-2-yl)amino)benzonitrile (compound 32a)

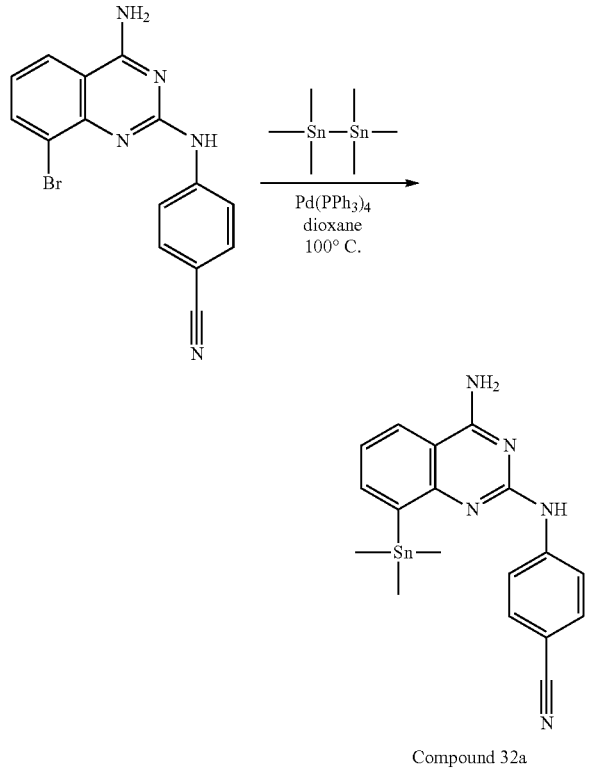

Compound 32a

To a mixture of 8a (1000 mg, 2.94 mmol) and tetrakis(triphenylphosphine)palladium(0) (200 mg, 0.17 mmol) in dry dioxane (5 mL) was added hexamethylditin (1 mL, 4.82 mmol) under argon. The reaction mixture was heated to 100° C. for 14 hours under argon, then cooled down to room temperature and directly purified by silica gel chromatography (gradient from 25-50% ethyl acetate in iso-hexanes) to afford the title compound 32a. $^1$H NMR (400 MHz, DMSO-$d_6$) δ 9.42 (s, 1H), 8.08-8.18 (m, 3H), 7.73 (d, J=9.9 Hz, 1H), 7.64 (d, J=8.9 Hz, 2H), 7.51 (bs, 2H), 7.20-7.28 (m, 1H), 0.36 (s, 9H). LCMS (m/z) 424.0 [M−H], Tr=4.84 min (LCMS method 1).

Step 2: Synthesis of (E)-3-(4-bromo-3,5-dimethoxyphenyl)acrylonitrile (compound 32b)

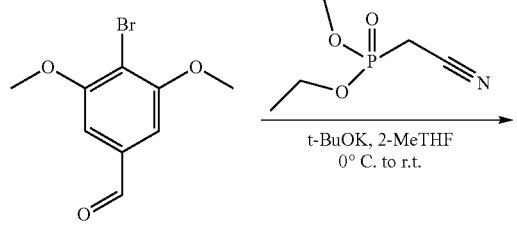

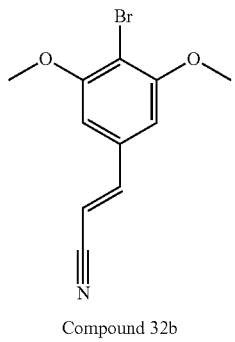

Compound 32b

To a solution of 4-bromo-3,5-dimethoxybenzaldehyde (24.5 g, 100 mmol, Ark Pharm Inc., AK-34641) and diethylcyanomethyl phosphonate (18.6 g, 105 mmol) in anhydrous 2-methyltetrahydrofuran (400 mL) was slowly added potassium t-butoxide (12.3 g, 110 mmol) at 0° C. under argon. The reaction mixture was vigorously stirred at 0° C. for 1 hour and then at room temperature for 3 hours. The reaction mixture was diluted with ethyl acetate and washed twice with water and once with brine. The organic layer was dried over MgSO$_4$ and, filtered through a 3 cm layer of silica gel which was washed with additional ethyl acetate. The combined organics were concentrated down under reduced pressure and the solid residue was treated in sonic bath with hexane/diethyl ether mixture (1/3) for 3 minutes. The solid product was filtered off and washed with hexane to afford the title compound 32b. $^1$H NMR (400 MHz, DMSO-$d_6$) δ 7.61 (d, J=16.7 Hz, 1H), 7.06 (s, 2H), 6.65 (d, J=16.7 Hz, 1H), 3.87 (s, 6H). LCMS (m/z) no MS signal, Tr 2.50 min (LCMS method 2).

Step 3: synthesis of (E)-4-((4-amino-8-(4-(2-cyanovinyl)-2,6-dimethoxyphenyl)quinazolin-2-yl)amino)benzonitrile (compound 32)

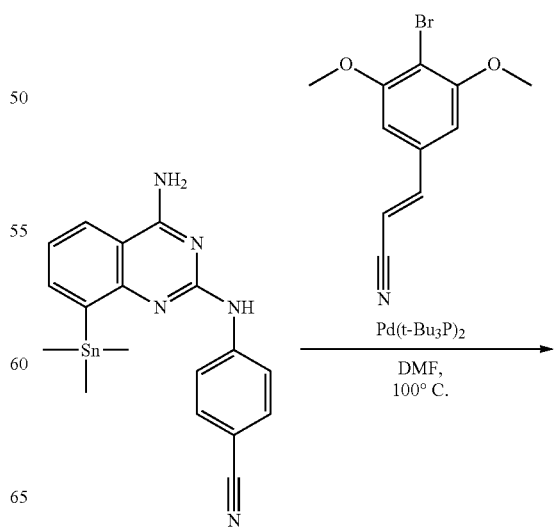

145

-continued

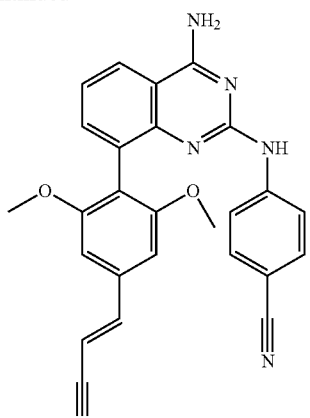

Compound 32

A mixture of compound 32a (20 mg, 0.047 mmol), compound 32b (20 mg, 0.075 mmol) and bis(tri-tert-butylphosphine)palladium(0) (20 mg, 0.039 mmol) in N,N-dimethylformamide (2 mL) was heated under argon at 100° C. for 2 hours. The reaction mixture was concentrated down under reduced pressure, purified by silica gel chromatography (gradient from 50-100% ethyl acetate in iso-hexanes) and then repurified by reverse phase flash chromatography (5.5 g C-18 RediSep prepacked column, gradient 0-100%, acetonitrile in water with 0.1% TFA) to afford the TFA salt of the title compound 32. $^1$H NMR (400 MHz, DMSO-$d_6$) δ 10.53 (bs, 1H), 9.72-9.53 (m, 2H), 7.88-7.83 (m, 2H), 7.77 (d, J=16.7 Hz, 1H), 7.71 (d, J=7.8 Hz, 2H), 7.58 (bs, 1H), 7.54 (bs, 1H), 7.41-7.34 (m, 1H), 7.16 (s, 2H), 6.76 (d, J=16.7 Hz, 1H), 3.72 (s, 6H). LCMS (m/z) 449.0 [M+H], Tr=3.48 min (LCMS method 1).

Example 33

(E)-4-((8-(4-(2-Cyanovinyl)-2,6-dimethoxyphenyl)quinazolin-2-yl)amino)benzonitrile—Compound 33

146

Step 1: Synthesis of 4-((8-(trimethylstannyl)quinazolin-2-yl)amino)benzonitrile (compound 33a)

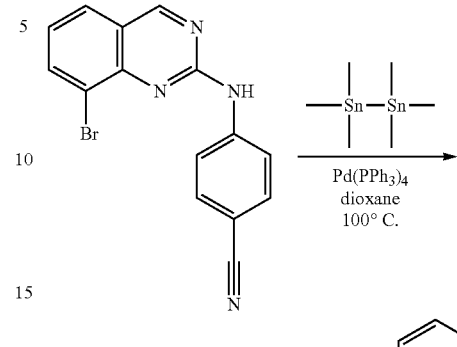

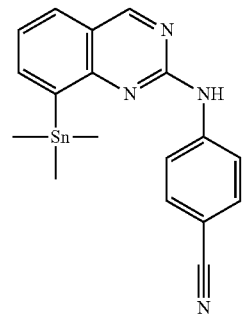

Compound 33a

To a mixture of 1a (1000 mg, 3.07 mmol) and tetrakis(triphenylphosphine)palladium(0) (200 mg, 0.17 mmol) in dry dioxane (5 mL) was added hexamethylditin (1 mL, 4.82 mmol) under argon. The reaction mixture was heated to 110° C. for 4 hours under argon, then cooled down to room temperature and directly purified by silica gel chromatography (gradient from 0-30% ethyl acetate in iso-hexanes) to afford the title compound 33a. $^1$H NMR (400 MHz, DMSO-$d_6$) δ 10.53 (s, 1H), 9.47 (s, 1H), 8.34 (d, J=8.8 Hz, 1H), 8.31-8.24 (m, 2H), 8.09-8.02 (m, 1H), 7.90-7.85 (m, 2H), 7.60-7.51 (m, 1H), 0.05 (s, 9H). LCMS (m/z) 409.0 [M+H], Tr=5.54 min (LCMS method 1).

Step 2: synthesis of (E)-4-((8-(4-(2-cyanovinyl)-2,6-dimethoxyphenyl)quinazolin-2-yl)amino)benzonitrile (compound 33)

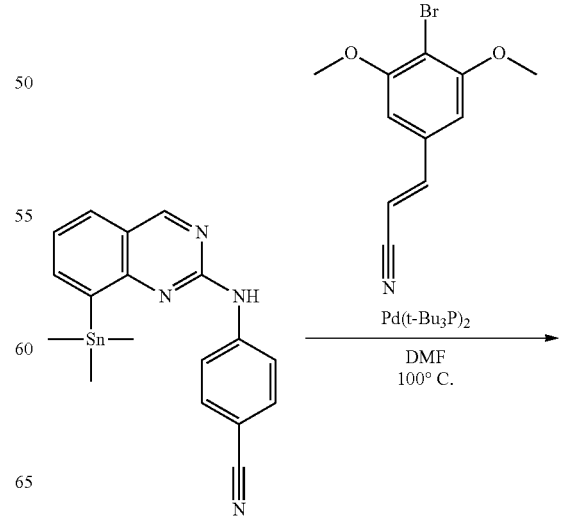

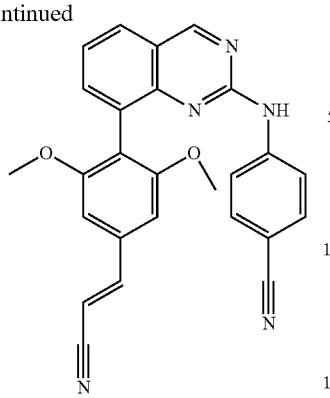

Compound 33

A mixture of compound 33a (20 mg, 0.048 mmol), compound 32b (20 mg, 0.075 mmol) and bis(tri-tert-butylphosphine)palladium(0) (20 mg, 0.039 mmol) in N,N-dimethylformamide (2 mL) was heated under argon at 100° C. for 2 hours. The reaction mixture was concentrated down under reduced pressure, purified by silica gel chromatography (gradient from 0-50% ethyl acetate in iso-hexanes) and then repurified by reverse phase flash chromatography (5.5 g C-18 RediSep prepacked column, gradient 0-100%, acetonitrile in water with 0.1% TFA) to afford the TFA salt of the title compound 33. $^1$H NMR (400 MHz, DMSO-$d_6$) δ 10.38 (s, 1H), 9.40 (s, 1H), 7.96 (dd, J=8.1, 1.4 Hz, 1H), 7.78-7.85 (m, 3H), 7.71 (dd, J=7.2, 1.4 Hz, 1H), 7.44-7.54 (m, 3H), 7.21 (s, 2H), 6.77 (d, J=16.7 Hz, 1H), 3.62 (s, 6H). LCMS (m/z) 433.98 [M+H], Tr=4.39 min (LCMS method 1).

Example 34

(E)-6-((8-(4-(2-Cyanovinyl)-2,6-dimethylphenyl)-4-oxo-3,4-dihydroquinazolin-2-yl)amino)nicotinonitrile—Compound 34

Step 1: Synthesis of 8-bromo-2-chloroquinazolin-4(3H)-one (Compound 34a)

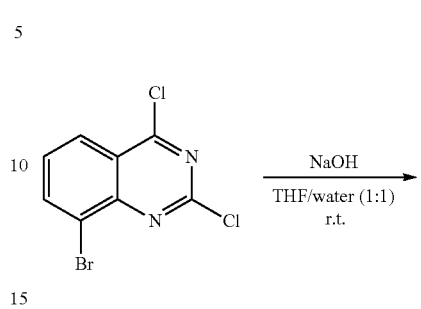

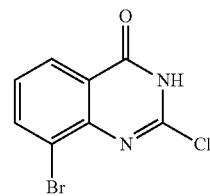

Compound 34a

Aqueous sodium hydroxide (30 mL, 0.2 M, 6 mmol) was added into a solution of 8-bromo-2,4-dichloroquinazoline (556 mg, 2 mmol, Ark Pharm Inc., AK-28703) in tetrahydrofuran (30 mL). The reaction mixture was stirred at room temperature for 0.5 hour. Then the reaction mixture was acidified with glacial acetic acid to pH=5 and concentrated down under reduced pressure. Water was added and the solid product was filtered off and washed with water (3×20 ml) to afford the title compound 34a. $^1$H NMR (400 MHz, DMSO-$d_6$) δ 13.51 (s, 1H), 8.15 (d, J=7.8 Hz, 1H), 8.09 (d, J=7.8 Hz, 1H), 7.42-7.51 (m, 1H). HRMS: (ESI+) calculated for $C_8H_4ON_2BrClNa$ [M+Na] 280.9088. found 280.9089. LCMS (m/z) 259.0 [M+H], Tr 3.58 min (LCMS method 1).

Step 2: Synthesis of (E)-3-(4-(2-chloro-4-oxo-3,4-dihydroquinazolin-8-yl)-3,5-dimethylphenyl)acrylonitrile (compound 34b)

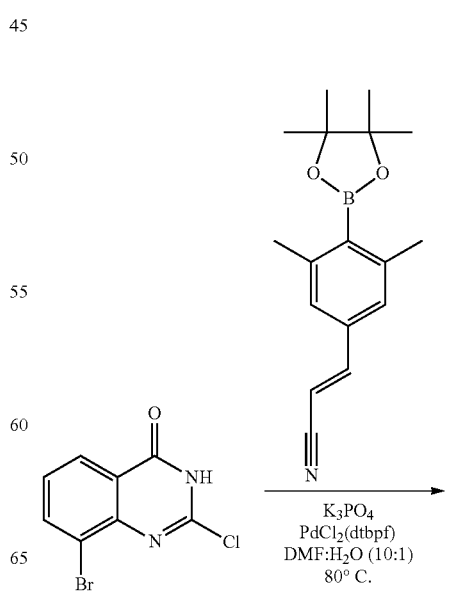

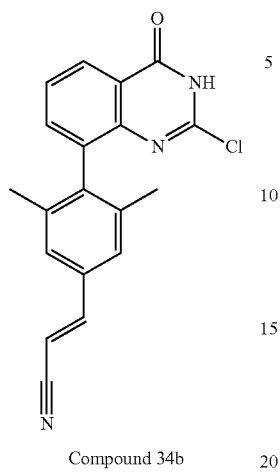

Compound 34b

A mixture of compound 34a (74 mg, 0.28 mmol), compound 1c (120 mg, 0.42 mmol), potassium phosphate tribasic monohydrate (200 mg, 0.87 mmol) and [1,1'-bis(diphenylphosphino)ferrocene] dichloropalladium(II), complex with dichloromethane (30 mg, 0.05 mmol) was dissolved in a mixture of N,N-dimethylformamide and water (10:1, 3.3 mL) under argon and this mixture was stirred at 80° C. for 2 hours. The product was isolated by silica gel chromatography (gradient from 0-100% ethyl acetate in iso-hexanes) to afford the title compound 34b. $^1$H NMR (400 MHz, DMSO-$d_6$) δ 13.30 (bs, 1H), 8.16 (dd, J=7.7, 1.8 Hz, 1H), 7.67-7.51 (m, 3H), 7.43 (s, 2H), 6.46 (d, J=16.7 Hz, 1H), 1.88 (s, 6H). LCMS (m/z) 336.1 [M+H], Tr=4.24 (LCMS method 1).

Step 3: synthesis of (E)-6-((8-(4-(2-cyanovinyl)-2,6-dimethylphenyl)-4-oxo-3,4-dihydroquinazolin-2-yl)amino)nicotinonitrile (compound 34)

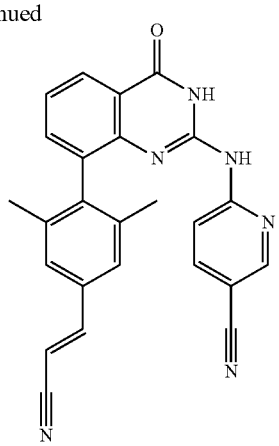

Compound 34

A mixture of compound 34b (80 mg, 0.24 mmol), 6-aminonicotinonitrile (200 mg, 1.68 mmol, Ark Pharm Inc, AK-32349), palladium(II) acetate (20 mg, 0.09 mmol) and (9,9-dimethyl-9H-xanthene-4,5-diyl)bis(diphenylphosphine) (100 mg, 0.17 mmol) was dissolved in N-methyl-2-pyrrolidone (3 mL) under argon. N,N-Diisopropylethylamine (1 mL, 5.7 mmol) was then added via syringe and the reaction mixture was stirred at 100° C. for 1 hour. The product was isolated by silica gel flash chromatography (gradient from 0-100% ethyl acetate in iso-hexanes) and then repurified by reverse phase flash chromatography (5.5 g C-18 RediSep pre-packed column, gradient 0-100% acetonitrile in water with 0.1% trifluoroacetic acid) to afford the TFA salt of compound 34. $^1$H NMR (400 MHz, DMSO-$d_6$) δ 12.16 (bs, 1H), 10.26 (bs, 1H), 8.74 (bs, 1H), 8.10 (dd, J=7.8, 1.6 Hz, 1H), 7.94-7.81 (m, 1H), 7.69 (d, J=16.7 Hz, 1H), 7.59-7.36 (m, 5H), 6.51 (d, J=16.7 Hz, 1H), 1.94 (s, 6H). LCMS (m/z) 418.9 [M+H], Tr=4.11 min (LCMS method 1).

Example 35

(E)-4-((4-Amino-8-(4-(2-cyanovinyl)-2,6-diethylphenyl)quinazolin-2-yl)amino)benzonitrile—Compound 35

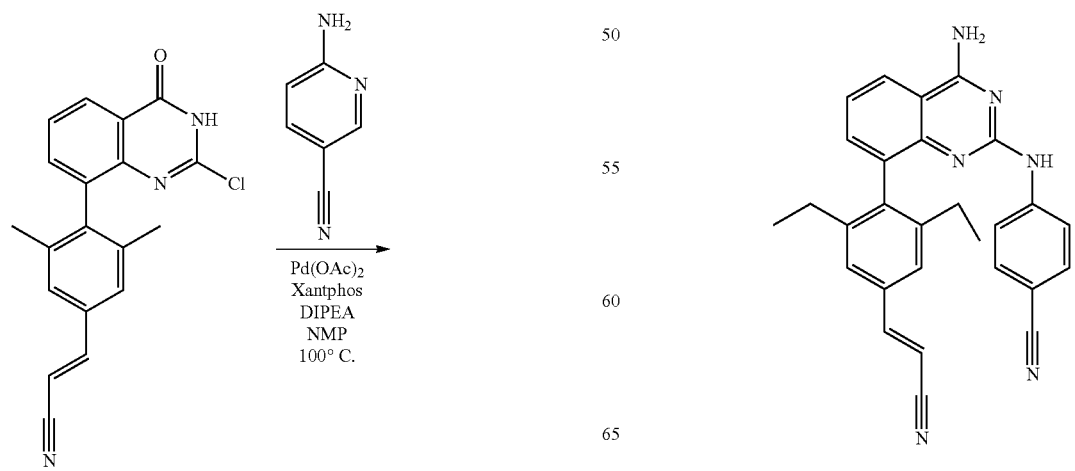

Step 1: synthesis of (E)-3-(4-bromo-3,5-diethylphenyl)acrylonitrile (compound 35a)

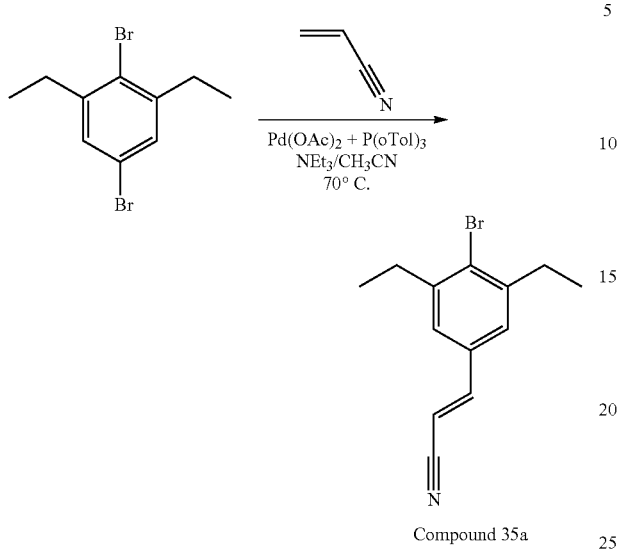

Compound 35a

To a solution of 2,5-dibromo-1,3-diethylbenzene (2920 mg, 10 mmol, Oakwood Products, Inc.—034265) in anhydrous acetonitrile (25 mL) was added palladium(II) acetate (224 mg, 1 mmol), acrylonitrile (1060 mg, 20 mmol), tri(o-tolyl)phosphine (913 mg, 3 mmol) and triethylamine (4 mL, 30 mmol) then the mixture was purged with argon and heated at 70° C. for 3 hours. The reaction mixture was filtered through Celite and the filter pad was washed with tetrahydrofuran (10 mL). The filtrate was evaporated then re-dissolved with ethyl acetate (50 mL). The solution was washed with water (50 mL). The water layer was back extracted with ethyl acetate (50 mL). The combined organics were washed with brine (30 mL), dried over sodium sulfate, filtered and concentrated under reduced pressure to give a crude residue. This was subjected to silica gel chromatography (gradient from 0-20% ethyl acetate in iso-hexanes) to afford the title compound 35a. $^1$H NMR (400 MHz, CDCl$_3$) δ 7.31 (d, J=16.6 Hz, 1H), 7.12 (s, 2H), 5.86 (d, J=16.6 Hz, 1H), 2.79 (q, J=7.5 Hz, 4H), 1.22 (t, J=7.5 Hz, 6H). LCMS (m/z) no MS signal. Tr=3.07 min (LCMS method 2).

Step 2: synthesis of (E)-3-(3,5-diethyl-4-(4,4,5,5-tetramethyl-1,3,2-dioxaborolan-2-yl)phenyl)acrylonitrile (compound 35b)

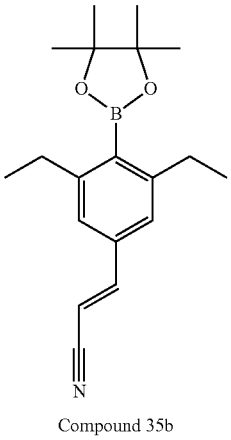

Compound 35b

A mixture of compound 35a (300 mg, 1.14 mmol), 4,4,4',4',5,5,5',5'-octamethyl-2,2'-bi(1,3,2-dioxaborolane) (432 mg, 1.70 mmol), potassium carbonate (471 mg, 3.4 mmol), palladium(II) acetate (13 mg, 0.06 mmol) and dicyclohexyl(2',6'-dimethoxy-[1,1'-biphenyl]-2-yl)phosphine (SPhos, 58 mg, 0.14 mmol) in dry N,N-dimethylformamide (20 mL) was purged with argon and heated at 100° C. for 2 hour. The reaction mixture was filtered through Celite and the filter pad was washed with tetrahydrofuran (10 mL). The filtrate was evaporated then re-dissolved with ethyl acetate (50 mL). The solution was washed with water (50 mL). The water layer was back extracted with ethyl acetate (50 mL). The combined organics were washed with brine (30 mL), dried over sodium sulfate, filtered and concentrated under reduced pressure to give a crude residue which was purified by silica gel chromatography (gradient from 0-15% ethyl acetate in iso-hexanes) to afford compound 35b. $^1$H NMR (400 MHz, CDCl$_3$) 7.33 (d, J=16.6 Hz, 1H), 7.04 (s, 2H), 5.85 (d, J=16.6 Hz, 1H), 2.67 (q, J=7.6 Hz, 4H), 1.38 (s, 12H), 1.20 (t, J=7.6 Hz, 6H). LCMS (m/z) no MS signal, Tr=3.07 min (LCMS method 2).

Step 3: Synthesis of (E)-3-(4-(4-amino-2-chloroquinazolin-8-yl)-3,5-diethylphenyl)acrylonitrile (Compound 35c)

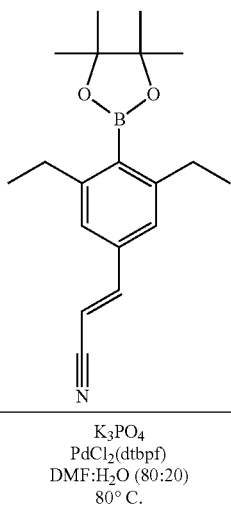

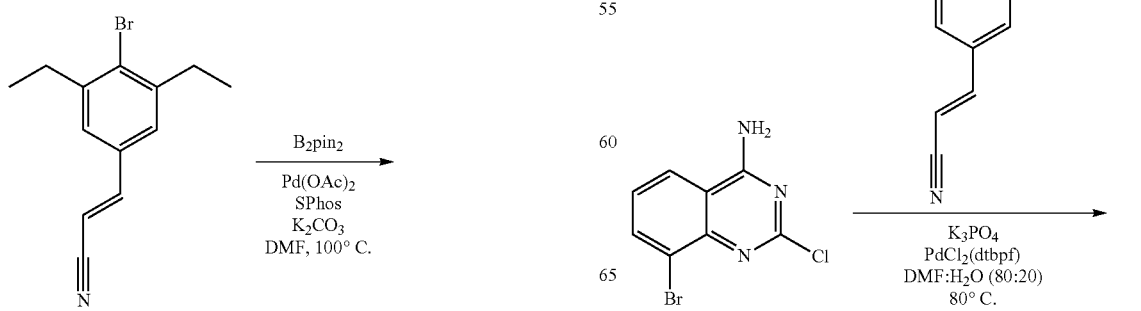

-continued

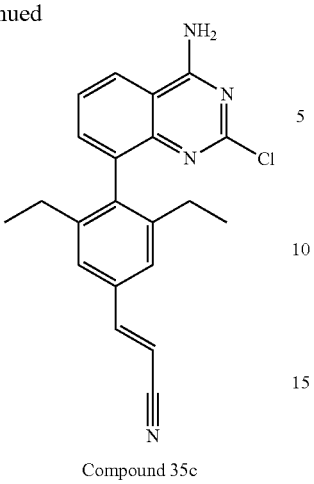

Compound 35c

A mixture of 8-bromo-2-chloroquinazolin-4-amine (90 mg, 0.35 mmol, Ark Pharm Inc, AK-28702), compound 35b (130 mg, 0.42 mmol), potassium phosphate tribasic (96 mg, 0.45 mmol) and 1,1'-bis(di-tert-butylphosphino)ferrocene palladium dichloride (23 mg, 0.04 mmol) was dissolved in N,N-dimethylformamide:water mixture (80:20, 5 mL) under argon. The reaction was heated at 80° C. for 60 minutes. The reaction mixture was cooled down to room temperature and diluted with water and ethyl acetate. The organic layer was separated and washed twice with brine, dried over magnesium sulfate, 1 volume equivalent of hexane added and this mixture was filtered through a 2 cm layer of silica gel which was washed with additional ethyl acetate. Combined organics were concentrated down under reduced pressure and the residue was treated with hexane in a sonic bath. The solid product was filtered off and washed twice with hexane to afford the title compound 35c. $^1$H NMR (400 MHz, DMSO-$d_6$) δ 8.39 (bs, 2H), 8.29 (dd, J=7.2, 2.5 Hz, 1H), 7.67 (d, J=16.7 Hz, 1H), 7.61-7.54 (m, 2H), 7.46 (s, 2H), 6.52 (d, J=16.7 Hz, 1H), 2.22-2.01 (m, 4H), 0.91 (t, J=7.5 Hz, 6H). LCMS (m/z) 363.3 [M+H], Tr=2.68 min (LCMS method 2).

Step 4: synthesis of (E)-4-((4-amino-8-(4-(2-cyanovinyl)-2,6-diethylphenyl)quinazolin-2-yl)amino)benzonitrile (compound 35)

-continued

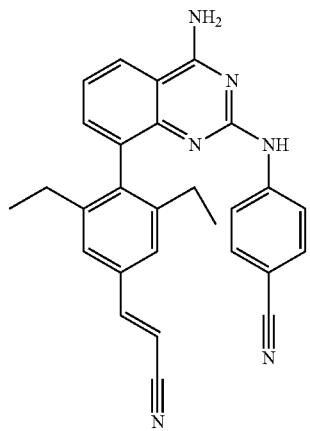 [SMILES: CCc1cc(/C=C/C#N)cc(CC)c1-c1cccc2c(N)nc(Nc3ccc(C#N)cc3)nc12]

Compound 35

A mixture of compound 35c (40 mg, 0.11 mmol), 4-cyanoaniline (18 mg, 0.154 mmol, Sigma-Aldrich) and hydrogen chloride solution in 1,4-dioxane (4M, 3 μL, 0.011 mmol) in dry N-methyl-2-pyrrolidone (1 mL) was heated under argon at 120° C. for 12 hours. The reaction mixture was cooled down to room temperature and purified directly by HPLC reverse phase chromatography (gradient 0-100% acetonitrile in water with 0.1% trifluoroacetic acid) to afford the TFA salt of compound 35. $^1$H NMR (400 MHz, DMSO-$d_6$) δ 10.57-9.84 (m, 1H), 9.82-8.84 (m, 2H), 8.27 (bs, 1H), 7.86-7.22 (m, 7H), 6.62 (d, J=16.8 Hz, 1H), 2.40-1.98 (m, 4H), 0.94 (t, J=7.2 Hz, 6H). LCMS (m/z) 445.4 [M+H], Tr=2.59 min (LCMS method 2).

Example 36

(E)-6-((4-Amino-8-(4-(2-cyanovinyl)-2,6-diethylphenyl)quinazolin-2-yl)amino)nicotinonitrile—Compound 36

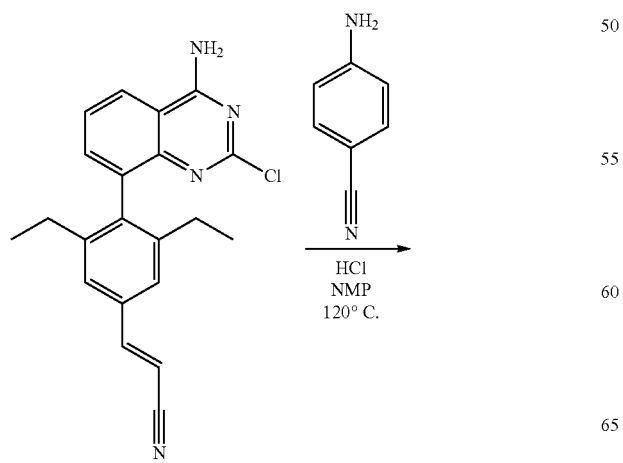

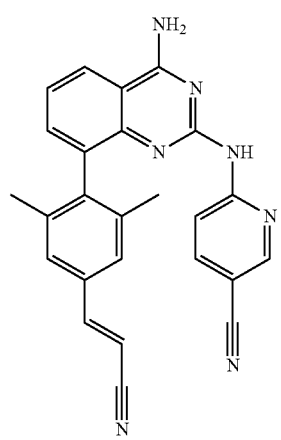 [SMILES: Cc1cc(/C=C/C#N)cc(C)c1-c1cccc2c(N)nc(Nc3ccc(C#N)cn3)nc12]

155

Synthesis of (E)-6-((4-amino-8-(4-(2-cyanovinyl)-2,6-diethylphenyl)quinazolin-2-yl)amino)nicotinonitrile (compound 36)

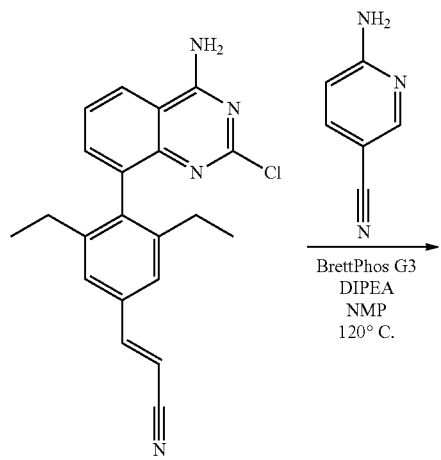

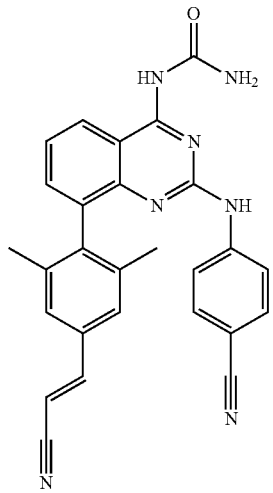

Compound 36

Compound 35c (40 mg, 0.11 mmol), 6-aminonicotinonitrile (53 mg, 0.44 mmol, Ark Pharm Inc, AK-32349), N,N-diisopropylethylamine (28 mg, 0.22 mmol) and [(2-dicyclohexylphosphino-3,6-dimethoxy-2',4',6'-triisopropyl-1,1'-biphenyl)-2-(2'-amino-1,1'-biphenyl)]palladium(II) methanesulfonate (9 mg, 0.011 mmol) were combined under argon in N-methyl-2-pyrrolidone (1 mL). The reaction was heated at 120° C. in a sealed vessel for 4 hours. The reaction mixture was cooled down to room temperature and purified directly by HPLC reverse phase chromatography (gradient 0-100% acetonitrile in water with 0.1% trifluoroacetic acid) to afford the TFA salt of compound 36. $^1$H NMR (400 MHz, DMSO-$d_6$) δ 13.54 (bs, 1H), 12.09 (bs, 1H), 9.62 (bs, 1H), 9.38 (bs, 1H), 8.46 (d, J=8.2 Hz, 1H), 8.37-8.15 (m, 1H), 7.94-7.83 (m, 2H), 7.80-7.66 (m, 3H), 7.56-7.27 (m, 2H), 6.76 (d, J=16.7 Hz, 1H), 2.40-2.01 (m, 4H), 0.94 (t, J=7.5 Hz, 6H). LCMS (m/z) 446.4 [M+H], Tr=1.98 min (LCMS method 2).

156

Example 37

(E)-1-(2-((4-Cyanophenyl)amino)-8-(4-(2-cyanovinyl)-2,6-dimethylphenyl)quinazolin-4-yl)urea—Compound 37

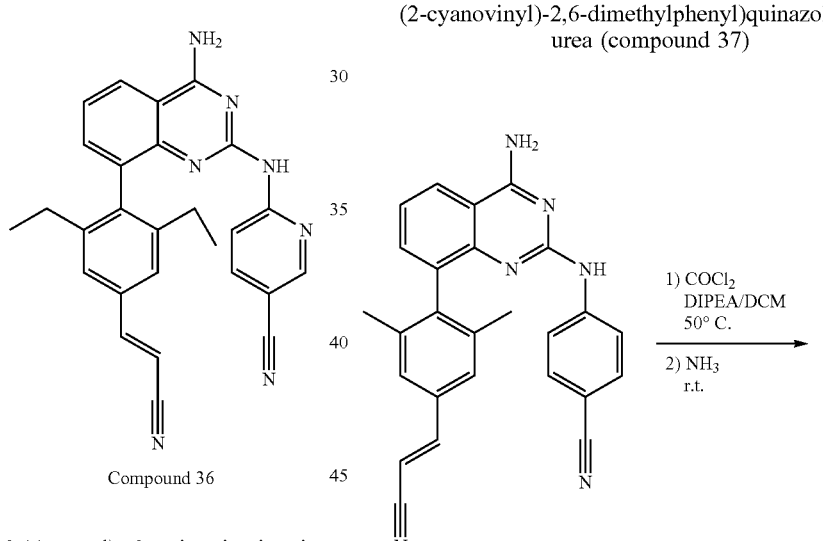

Synthesis of (E)-1-(2-((4-cyanophenyl)amino)-8-(4-(2-cyanovinyl)-2,6-dimethylphenyl)quinazolin-4-yl)urea (compound 37)

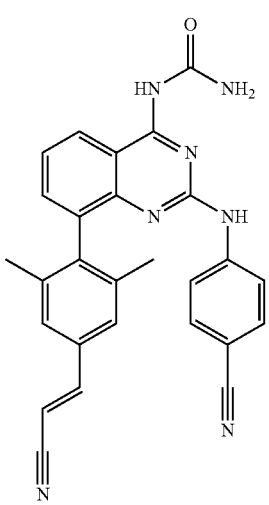 [SMILES: Cc1cc(/C=C/C#N)cc(C)c1-c1cccc2c(NC(N)=O)nc(Nc3ccc(C#N)cc3)nc12]

Compound 37

Compound 2 (42 mg, 0.10 mmol) was suspended in dry dichloromethane (2 mL), and N,N-diisopropylethylamine (0.1 mL, 0.57 mmol) was added to the suspension followed by dropwise addition of phosgene (0.5 mL, 20% solution in toluene). The mixture was stirred at 50° C. for 1 hour. Another portion of N,N-diisopropylethylamine (0.1 mL, 0.57 mmol) and phosgene (0.2 mL, 20% solution in toluene) was added to the reaction mixture and this mixture was stirred at 50° C. for another 1 hour. The mixture was cooled down to room temperature and saturated aqueous ammonia (1 mL) was added. Volatiles were removed under reduced pressure and the crude residue was purified by HPLC using gradient from 50-100% acetonitrile in water (HPLC preparative column Phenomenex Gemini 10u, C18, 250×21.2 mm, 10 mL/min) to afford the title compound 37. $^1$H NMR (400 MHz, DMSO-$d_6$) δ 9.35 (bs, 1H), 8.26-8.07 (m, 1H), 7.78-7.65 (m, 3H), 7.62-7.45 (m, 3H), 7.44-7.30 (m, 3H), 7.29-7.16 (m, 3H), 6.43 (d, J=16.7 Hz, 1H), 1.81 (s, 6H). LCMS (m/z) 460.3 [M+H], Tr=3.98 min (LCMS method 1).

Example 38

(E)-4-((4-Amino-8-(4-(1-cyanoprop-1-en-2-yl)-2,6-dimethylphenyl)quinazolin-2-yl)amino)benzonitrile—Compound 38

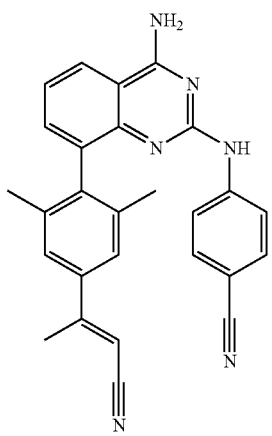 [SMILES: C/C(=C\C#N)c1cc(C)c(-c2cccc3c(N)nc(Nc4ccc(C#N)cc4)nc23)c(C)c1]

Step 1: Synthesis of 4-bromo-3,5-dimethylbenzoic acid (Compound 38a)

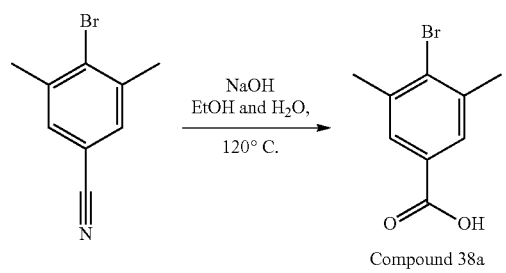

4-Bromo-3,5-dimethylbenzonitrile (630 mg, 3 mmol, Ark Pharm Inc, AK-44760) was dissolved in ethanol (1 mL), and 8M sodium hydroxide solution (5 mL) was added and this reaction mixture was stirred in a sealed vessel at 120° C. for 12 hours. The reaction mixture was diluted with water (100 mL) and washed with diethylether (2×50 mL), aqueous layer was acidified with concentrated hydrochloric acid (to pH=3) and extracted with diethylether (2×100 mL). Combined organic layers were dried over sodium sulfate and concentrated down under reduced pressure to afford the title compound 38a. $^1$H NMR (600 MHz, DMSO-$d_6$) δ 7.72 (s, 2H), 2.41 (s, 6H).

Step 2: synthesis of 1-(4-bromo-3,5-dimethylphenyl)ethanone (compound 38b)

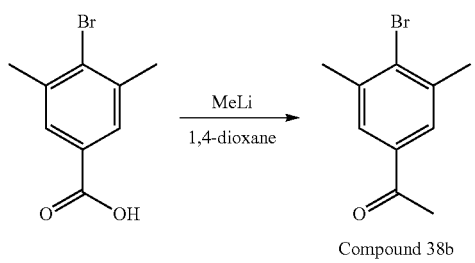

Compound 38a (100 mg, 0.44 mmol) was suspended in dry 1,4-dioxane (5 mL) and methyllithium (0.8 mL, 1.6 M solution in diethyl ether) was added dropwise under argon. The mixture was stirred at room temperature for 1 hour. The reaction was quenched by addition of methanol (10 mL) and concentrated down under reduced pressure. The solid residue was extracted with ethyl acetate (3×10 mL). Combined organic solutions were concentrated down under reduced pressure to afford the title compound 38b. LCMS (m/z) 227.0 [M+H], Tr=4.65 min (LCMS method 1).

Step 3: synthesis of (E)-3-(4-bromo-3,5-dimethylphenyl)but-2-enenitrile and (Z)-3-(4-bromo-3,5-dimethylphenyl)but-2-enenitrile (compound 38c and compound 38d)

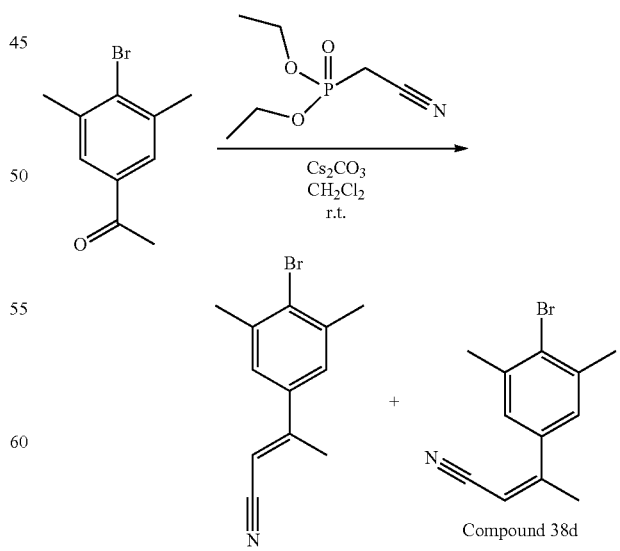

Compound 38b (95 mg, 0.42 mmol) and diethyl (cyanomethyl)phosphonate (70 µL, 0.40 mmol) were dissolved in dry dichloromethane (5 mL). Cesium carbonate (1 g, 3.07 mmol) was added and the solution was slowly concentrated down under reduced pressure at 30° C. The resulting solid was allowed to stand at room temperature for 4 hours. Dichloromethane was added to the residue and the solids were filtered off. The solvent was removed under reduced pressure and the crude product was purified by silica gel chromatography using gradient from 0-10% ethyl acetate in iso-hexanes to afford the title compound 38c LCMS (m/z) 250.0 [M+H], Tr=5.01 min (LCMS method 1); and the title compound 38d LCMS (m/z) 250.0 [M+H], Tr=4.48 min (LCMS method 1).

Step 4: synthesis of (E)-4-((4-amino-8-(4-(1-cyanoprop-1-en-2-yl)-2,6-dimethylphenyl)quinazolin-2-yl)amino)benzonitrile (compound 38)

phosphine)palladium(0) (20 mg, 0.039 mmol) in N,N-dimethylformamide (2 mL) was heated under argon at 100° C. for 14 hours. The reaction mixture was concentrated down under reduced pressure, purified by silica gel chromatography (gradient from 50-100% ethyl acetate in iso-hexanes) and then re-purified on HPLC (preparative column Phenomenex Gemini 10 micron C18, 250×21.2 mm, 10 mL/min, gradient from 10-100% acetonitrile in water) to afford the title compound 38. $^1$H NMR (600 MHz, DMSO-$d_6$) δ 8.23 (bs, 1H), 7.83-7.72 (m, 2H), 7.60-7.29 (m, 7H), 6.17 (q, J=1.0 Hz, 1H), 2.52-2.51 (m, 3H), 1.96 (s, 6H). LCMS (m/z) 430.9 [M+H], Tr=3.83 min (LCMS method 1).

Example 39

(Z)-4-((4-Amino-8-(4-(1-cyanoprop-1-en-2-yl)-2,6-dimethylphenyl)quinazolin-2-yl)amino)benzonitrile—Compound 39

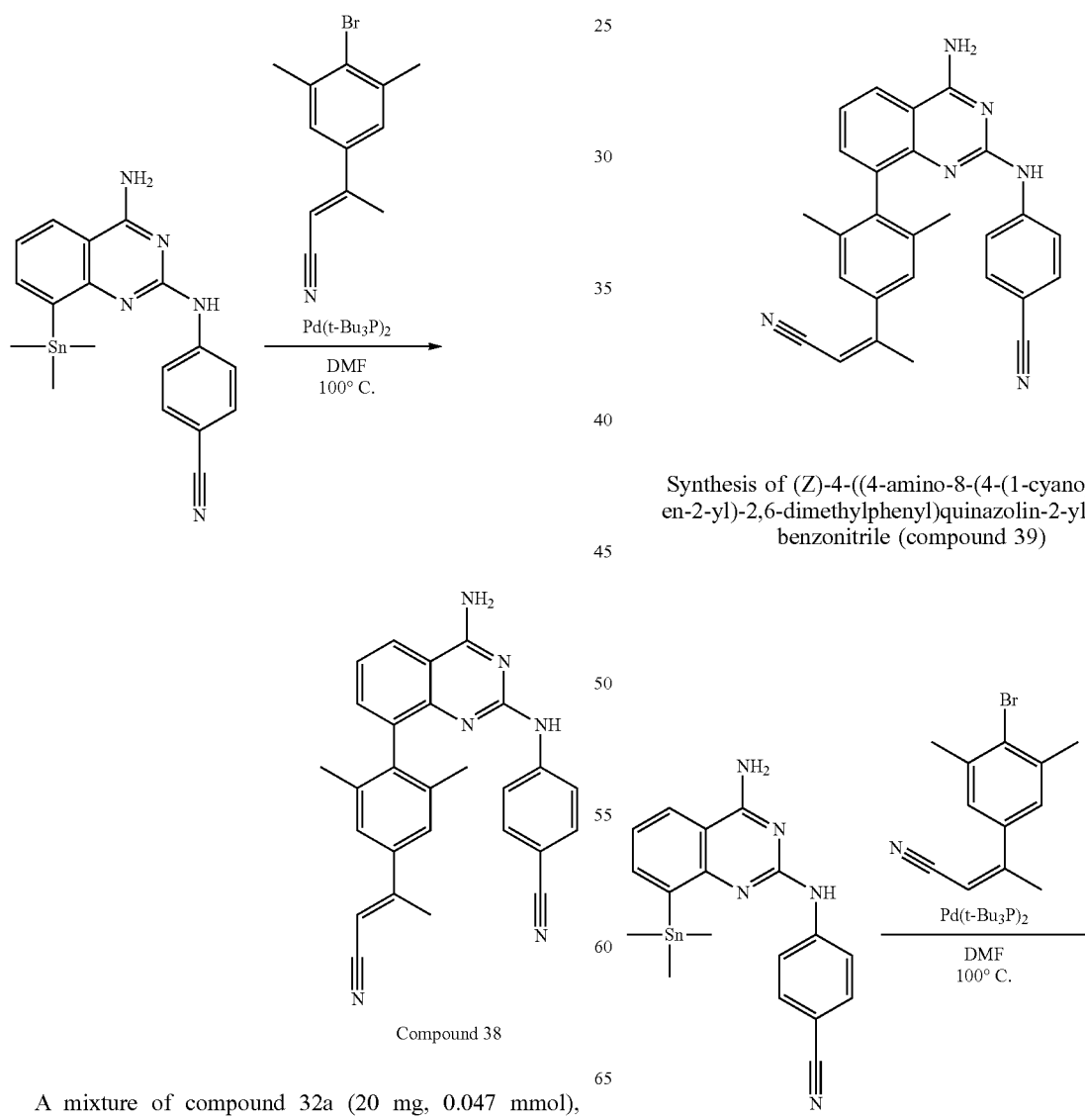

Synthesis of (Z)-4-((4-amino-8-(4-(1-cyanoprop-1-en-2-yl)-2,6-dimethylphenyl)quinazolin-2-yl)amino)benzonitrile (compound 39)

A mixture of compound 32a (20 mg, 0.047 mmol), compound 38c (20 mg, 0.080 mmol) and bis(tri-tert-butyl- -continued

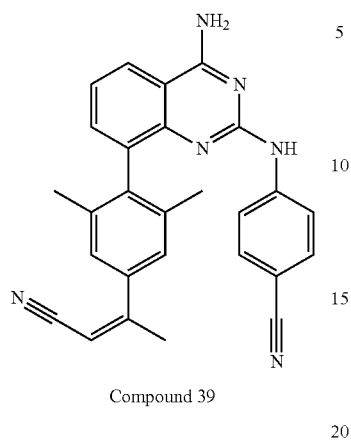

Compound 39

A mixture of compound 32a (20 mg, 0.047 mmol), compound 38d (18 mg, 0.072 mmol) and bis(tri-tert-butylphosphine)palladium(0) (20 mg, 0.039 mmol) in N,N-dimethylformamide (2 mL) was heated under argon at 100° C. for 14 hours. The reaction mixture was concentrated down under reduced pressure, purified by silica gel chromatography (gradient from 50-100% ethyl acetate in iso-hexanes) and then re-purified on HPLC (preparative column Phenomenex Gemini 10 micron C18, 250×21.2 mm, 10 mL/min. gradient from 10-100% acetonitrile in water) to afford the title compound 38. $^1$H NMR (600 MHz, DMSO-$d_6$) δ 8.22 (bs, 1H), 7.84-7.71 (m, 4H), 7.62-7.29 (m, 5H), 5.89-5.79 (m, 1H), 2.36 (d, J=1.5 Hz, 3H), 1.97 (s, 6H). LCMS (m/z) 430.9 [M+H], Tr=3.76 min (LCMS method 1).

Example 40

4-((4-Amino-8-(4-(2-cyanoprop-1-en-1-yl)-2,6-dimethylphenyl)quinazolin-2-yl)amino)benzonitrile—Compound 40 (mixture E/Z=1/1)

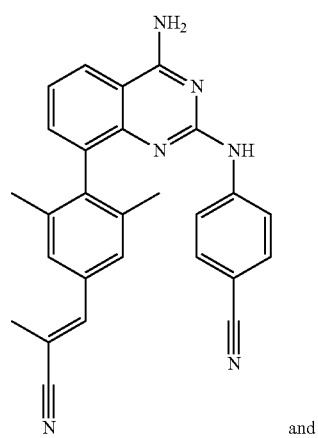

and

-continued

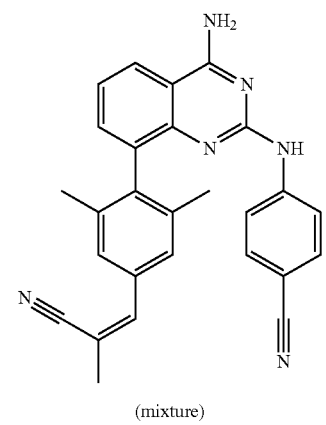

(mixture)

Step 1: Synthesis of
4-bromo-3,5-dimethylbenzaldehyde (Compound 40a)

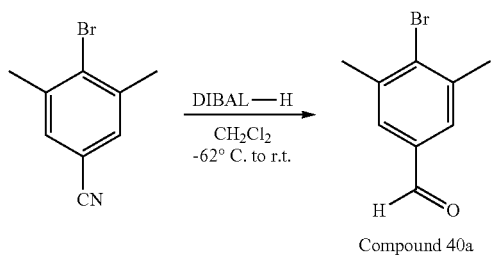

Compound 40a

A mixture of 4-bromo-3,5-dimethylbenzonitrile (2 g, 9.57 mmol, Ark Pharm Inc, AK-44760) in dichloromethane (25 mL) was cooled to −62° C. A solution of diisobutylaluminium hydride (1M in dichloromethane, 11 mL) was added dropwise and the reaction was left to reach room temperature during 2 hours. After that, 5% aqueous solution of hydrochloric acid (0.10 mL) was added and the reaction mixture was heated to reflux for 30 minutes. Then, the reaction mixture was diluted with dichloromethane, washed with brine. The organic layer was dried over calcium chloride. The solvent was removed under reduced pressure and the crude product was subjected to silica gel chromatography (gradient from 0-10% ethyl acetate in iso-hexanes) to afford the title compound 40a. $^1$H NMR (400 MHz, CDCl$_3$) δ 9.93 (s, 1H), 7.57 (s, 2H), 2.50 (s, 6H). HRMS: (TOF CI+) calculated for C$_9$H$_{10}$BrO [M+H] 212.9915, found 212.9913. LCMS (m/z) 213.0 [M+H], Tr=4.59 min (LCMS method 1).

Step 2: synthesis of 3-(4-bromo-3,5-dimethylphenyl)-2-methylacrylonitrile (compound 40b) mixture E/Z=1/1

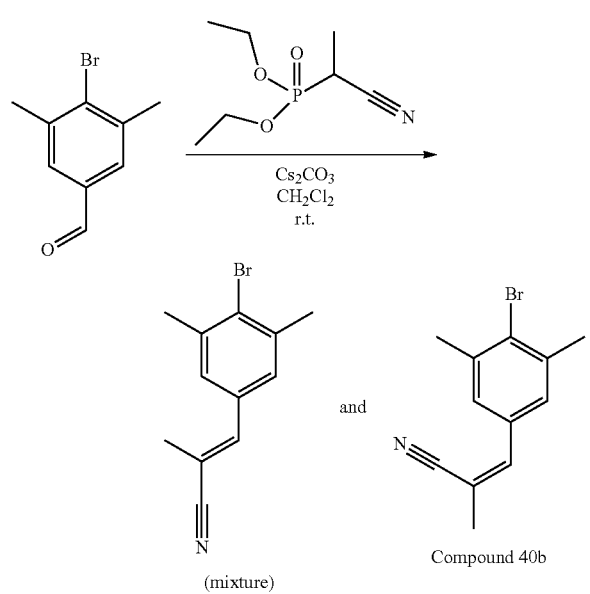

Compound 40a (100 mg, 0.47 mmol) and diethyl (1-cyanoethyl)phosphonate (70 μL, 0.40 mmol) were dissolved in dry dichloromethane (5 mL). Cesium carbonate (1 g, 3.07 mmol) was added and the solution was slowly concentrated down under reduced pressure at 30° C. The resulting solid was allowed to stand at room temperature for 4 hours. Dichloromethane was added to the residue and the solids were filtered off. The solvent was removed under reduced pressure and the crude product was purified by silica gel chromatography using gradient from 0-10% ethyl acetate in iso-hexanes to afford the title compound 40b as a 1:1 mixture of E/Z isomers. LCMS (m/z) 250.0 [M+H], Tr=5.07 and 5.10 min (LCMS method 1).

Step 4: synthesis of 4-((4-amino-8-(4-(2-cyanoprop-1-en-1-yl)-2,6-dimethylphenyl)quinazolin-2-yl)amino)benzonitrile (compound 40) mixture E/Z=1/1

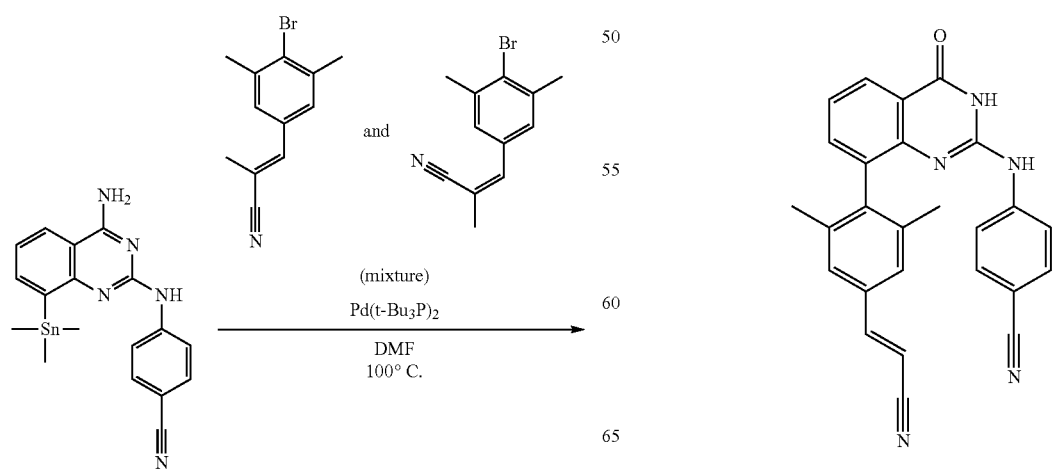

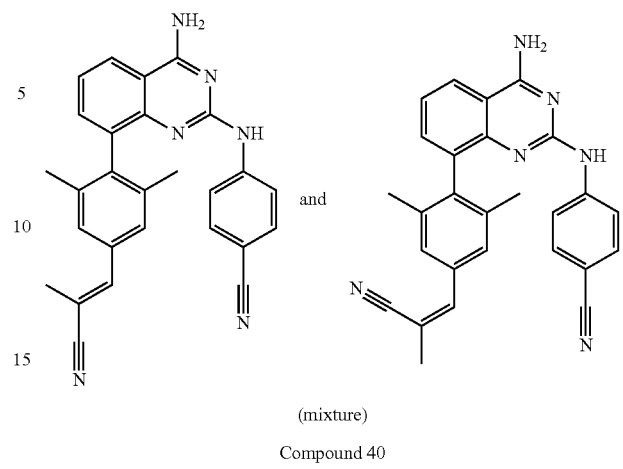

(mixture)
Compound 40

A mixture of compound 32a (20 mg, 0.047 mmol), compound 40b (20 mg, 0.080 mmol) and bis(tri-tert-butylphosphine)palladium(0) (20 mg, 0.039 mmol) in N,N-dimethylformamide (2 mL) was heated under argon at 100° C. for 8 hours. The reaction mixture was concentrated down under reduced pressure, purified by silica gel chromatography (gradient from 50-100% ethyl acetate in iso-hexanes) and then re-purified on HPLC (preparative column Phenomenex Gemini 10 micron C18, 250×21.2 mm, 10 mL/min, gradient from 10-100% acetonitrile in water) to afford the title compound 40 as a 1:1 mixture of E/Z isomers. $^1$H NMR (600 MHz, DMSO-$d_6$) δ 8.26 (s, 1H), 7.82-7.74 (m, 2H), 7.64-7.23 (m, 7H), 2.23-2.19 (m, 3H), 1.96 (s, 6H). LCMS (m/z) 430.8 [M+H], Tr=3.86 min (LCMS method 1).

Example 41

(E)-4-((8-(4-(2-Cyanovinyl)-2,6-dimethylphenyl)-4-oxo-3,4-dihydroquinazolin-2-yl)amino)benzonitrile—Compound 41

Step 1: Synthesis of 4-((8-bromo-4-oxo-3,4-dihydroquinazolin-2-yl)amino)benzonitrile (Compound 41a)

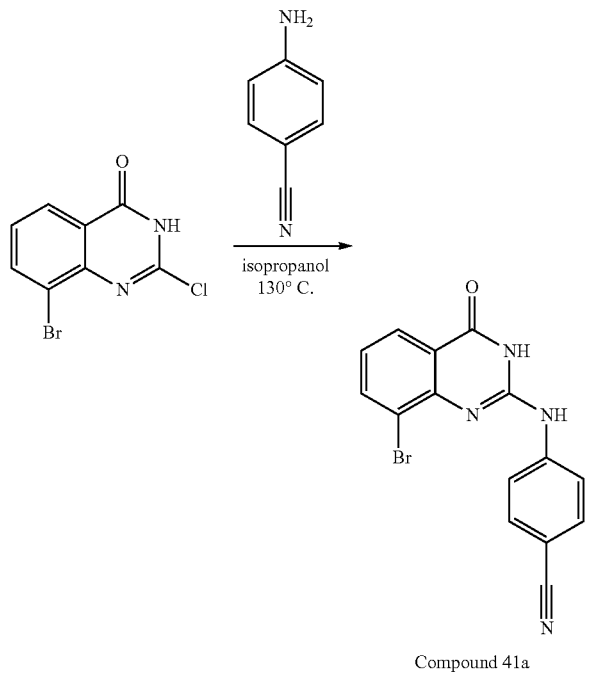

Compound 41a

A mixture of compound 34a (260 mg, 1 mmol) and 4-aminobenzonitrile (130 mg, 1.1 mmol, Sigma-Aldrich) in isopropanol (5 mL) was heated in microwave at 130° C. for 30 minutes. The reaction mixture was cooled down to room temperature and diethyl ether (10 mL) was added. The solid product was filtered off and washed with diethyl ether (3×20 mL) to afford the title compound 41a. $^1$H NMR (400 MHz, DMSO-$d_6$) δ 11.13 (bs, 1H), 9.41 (bs, 1H), 8.11 (d, J=8.8 Hz, 2H), 8.04-7.96 (m, 2H), 7.80 (d, J=8.8 Hz, 2H), 7.19 (t, J=7.8 Hz, 1H). HRMS: (ESI+) calculated for $C_{15}H_{10}ON_4Br$ [M+H] 341.0033, found 341.0033. LCMS (m/z) 341.1 [M+H], Tr 4.52 min (LCMS method 1).

Step 2: synthesis of (E)-4-((8-(4-(2-cyanovinyl)-2,6-dimethylphenyl)-4-oxo-3,4-dihydroquinazolin-2-yl)amino)benzonitrile (compound 41)

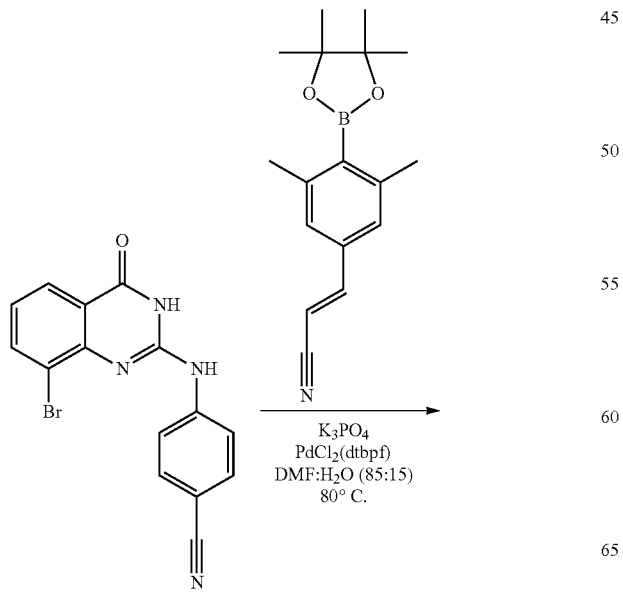

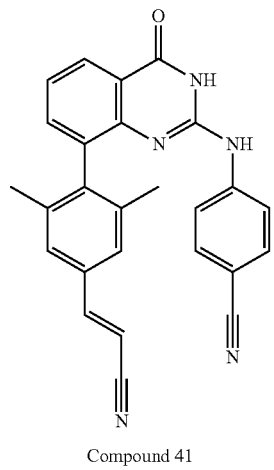

Compound 41

A mixture of compound 41a (68 mg, 0.2 mmol), compound 1c (85 mg, 0.3 mmol), potassium phosphate tribasic (92 mg, 0.4 mmol) and 1,1'-bis(di-tert-butylphosphino)ferrocene palladium dichloride (26 mg, 0.04 mmol) was dissolved in N,N-dimethylformamide:water mixture (85:15, 40 mL) under argon. The reaction was heated to 80° C. for 3 hours. The reaction mixture was concentrated down under reduced pressure and the residue was purified by silica gel chromatography (gradient from 50-80% ethyl acetate in iso-hexanes) and then repurified by HPLC reverse phase chromatography (gradient 5-100% acetonitrile in water with 0.1% trifluoroacetic acid) to afford the TFA salt of compound 41, $^1$H NMR (400 MHz, DMSO-$d_6$) δ 10.96 (bs, 1H), 9.15 (bs, 1H), 8.05 (dd, J=7.9, 1.6 Hz, 1H), 7.75 (d, J=16.7 Hz, 1H), 7.57 (dd, J=7.3 mmol), 1.6 Hz, 1H), 7.53 (s, 2H), 7.48-7.29 (m, 6H), 6.56 (d, J=16.7 Hz, 1H), 1.93 (s, 6H). LCMS (m/z) 418.3 [M+H], Tr=2.72 min (LCMS method 2).

Example 42

Alternative synthesis of (E)-3-(4-bromo-3,5-dimethylphenyl)acrylonitrile—Compound 1b

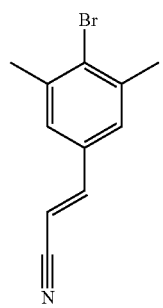

Alternative synthesis of (E)-3-(4-bromo-3,5-dimethylphenyl)acrylonitrile (compound 1b)

Step 1: synthesis of 3-bromo-2-((triphenylphosphoranylidene)amino)benzonitrile (compound 43a)

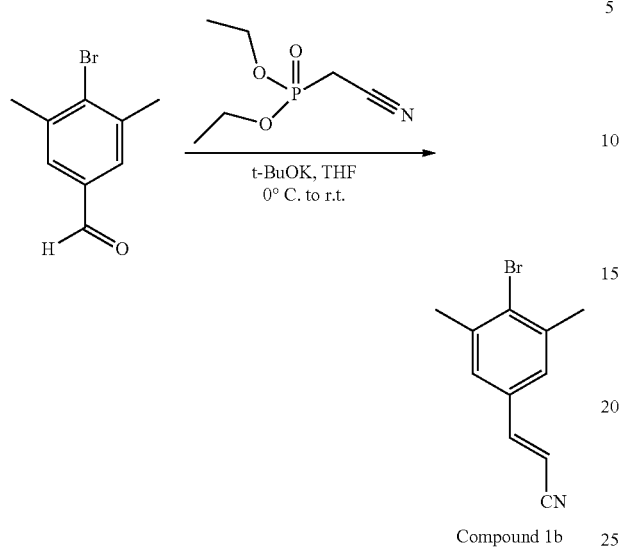

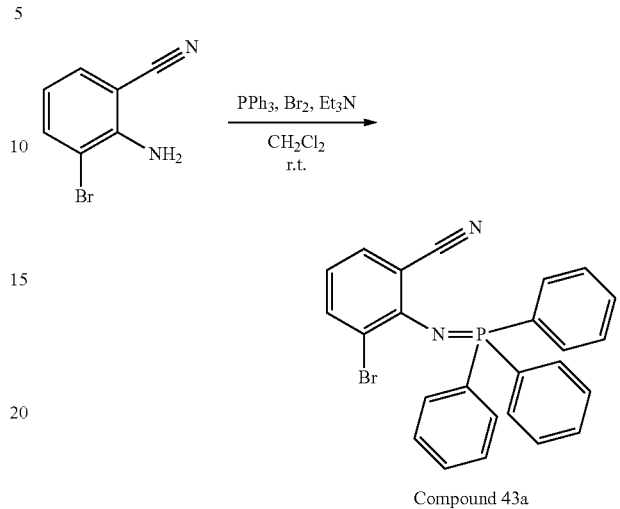

Compound 1b

Compound 43a

To a solution of diethyl cyanomethylphosphonate (266 mg, 1.5 mmol) in tetrahydrofuran (10 mL) was added potassium t-butoxide (168 mg, 1.5 mmol) at 0° C. with stirring for 30 minutes. After that, compound 40a (212 mg, 1 mmol) in tetrahydrofuran (10 mL) was added dropwise into the reaction mixture at room temperature and the reaction mixture was stirred at room temperature overnight. The reaction mixture was quenched with water. Ethyl acetate was added and the organic layer was washed with brine, dried over anhydrous calcium chloride and concentrated down under reduced pressure. The residue was purified by silica gel column chromatography (gradient from 0-20% ethyl acetate in iso-hexanes) to afford the title compound 1b. $^1$H NMR (400 MHz, CDCl$_3$) δ 7.25 (d, J=16.6 Hz, 1H), 7.12 (s, 2H), 5.84 (d, J=16.6 Hz, 1H), 2.42 (s, 6H). LCMS (m/z) no MS signal, Tr=2.78 min (LCMS method 2).

A solution of triphenylphosphine (10.65 g, 40.6 mmol) in dichlormomethane (200 mL) was treated slowly with bromine (6.49 g, 40.6 mmol) at 0° C. for 5 minutes. Then triethylamine (8.22 g, 81.2 mmol) was added followed by addition of 2-amino-3-bromobenzonitrile (4.00 g, 20.3 mmol, Abblis, AB1000095). Then, the ice bath was removed and the reaction mixture was stirred at room temperature for 8 hours. The reaction mixture was poured onto water and extracted two times with dichloromethane. The combined organics were washed with brine and dried over magnesium sulfate. Solvent was removed under reduced pressure and the residue was subjected to silica gel chromatography (gradient from 0-30% ethyl acetate in iso-hexanes) to afford the title compound 43a. $^1$H NMR (400 MHz, DMSO-d$_6$) δ 7.80-7.70 (m, 6H), 7.66 (dt, J=7.9, 1.4 Hz, 1H), 7.64-7.58 (m, 3H), 7.57-7.47 (m, 6H), 7.40 (dt, J=7.7, 1.5 Hz, 1H), 6.64 (td, J=7.8, 1.5 Hz, 1H). LCMS (m/z) 457.1 [M+H], Tr=2.99 min (LCMS method 2).

Example 43

Alternative synthesis of 4-((4-amino-8-bromoquinazolin-2-yl)amino)benzonitrile—Compound 8a Step 2: alternative synthesis 4-((4-amino-8-bromoquinazolin-2-yl)amino)benzonitrile (Compound 8a)

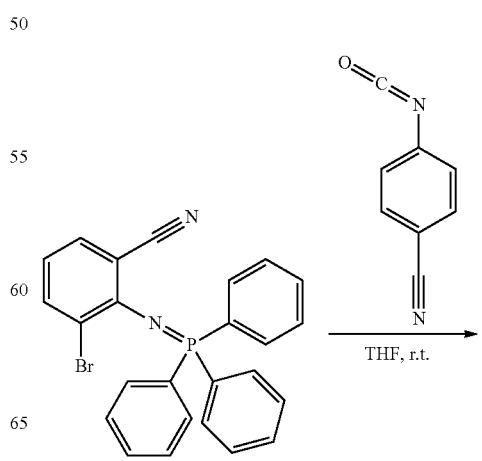

-continued

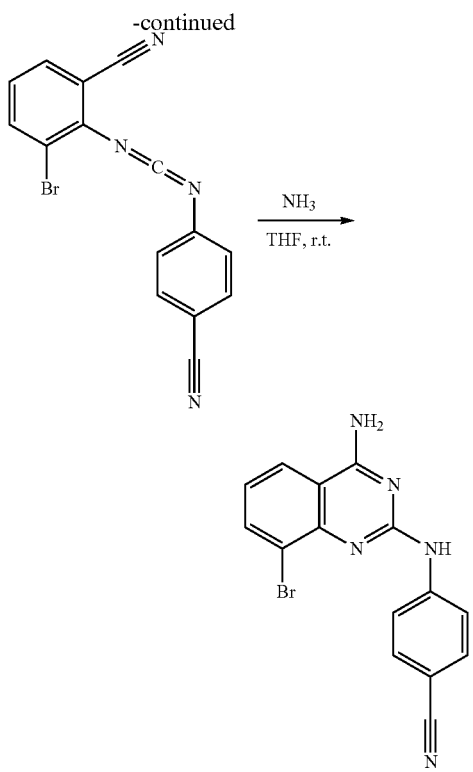

Compound 8a

To a solution of compound 43a (500 mg, 1.09 mmol) in 2-methyltetrahydrofuran (10 mL) was added 4-isocyanatobenzonitrile (173 mg, 1.20 mmol, Sigma-Aldrich) at 0° C. and the reaction mixture was stirred at 0° C. for 30 minutes. 2M ammonia in isopropanol (3.3 mL, 6.6 mmol) was added and the reaction mixture was heated to reflux for 3 hours then concentrated down under reduced pressure. The residue was purified by silica gel chromatography (gradient from 0-40% ethyl acetate in iso-hexanes) to afford the title compound 8a. $^1$H NMR (400 MHz, DMSO-$d_6$) δ 9.74 (s, 1H), 8.35 (d, J=8.8 Hz, 2H), 8.16 (d, J=8.0 Hz, 1H), 8.01 (d, J=7.5 Hz, 1H), 7.71 (d, J=8.8 Hz, 2H), 7.16 (t, J=7.8 Hz, 1H). LCMS (m/z) 340.0 [M+H], Tr=4.06 min (LCMS method 1).

Biological Examples

Example A

High Throughput Screening of Anti-HIV-1 RT (Reverse Transcriptase)

Compounds were screened in a miniaturized, high throughput cytopathic effect assay for activity against HIV-1 HBX2 (wild type) and HIV-1 reverse transcriptase mutants K103N and Y181C. In Tables 1 and 2 below. "w.t." refers to results of the tested compounds run with the wildtype 1 and "w.t, assay 2" refers results of the tested compounds run with the wildtype on the same day as the testing of the compounds with the mutants. Thus, "w.t, assay 2" was run under the same conditions as the testing of the compounds with the mutants and provides a direct comparison with the results from the testing with the mutants.

Ten-point serial dilutions of compounds with half-log step size were generated in DMSO, AZT (5 μM) was used as the positive control and DMSO as the negative control. The Echo acoustic dispenser was used to deliver 200 nL of serially diluted compound into sterile 384 well tissue culture assay plates. Two million MT-4 cells were incubated with each of the 3 viruses at MOI of 0.0005 in separate 1 mL infection tubes for 1 hour at 37° C. The cells were diluted in cell culture medium (RPMI+10% FBS) to 50.000 cells/mL. The infected cells were added to 384 well assay plates containing serially dilute compounds. Assay plates were incubated for 5 days in a humidified incubator set at 37° C., and 5% $CO_2$. To measure the cytopathic effect of HIV, 40 μL Cell TiterGlo was added to each well and the resulting luminescence signal is read with the Envision plate reader (Perkin Elmer). Data were normalized to positive and negative controls in each plate and expressed as % CPE Protection. $EC_{50}$ values were defined as the compound concentration that caused a 50% decrease in luminescence signal, and were calculated by non-linear regression using Pipeline Pilot software by applying a four parameter fit equation (Accelrys, San Diego, Calif.). Results are disclosed in Table 1.

TABLE 1

| Compound ID | MT4 $EC_{50}$ (nM) against w.t. | MT4 $EC_{50}$ (nM) against | | | FC against mutant | |
|---|---|---|---|---|---|---|
| | w.t. | assay 2* | K103N | Y181C | K103N | Y181C |
| 1 | 3.0 | 6.2 | 8.8 | 17.8 | 1.4 | 2.9 |
| 2 | 3.7 | 3.6 | 4.0 | 10.9 | 1.1 | 3.0 |
| 3 | NA | 12.9 | 12.0 | 50.2 | 0.9 | 3.9 |
| 4 | 9.2 | 9.8 | 19.1 | 47.0 | 2.0 | 4.8 |
| 5 | 1.3 | 1.5 | 2.5 | 12.0 | 1.7 | 8.2 |
| 6 | 99.3 | 82.6 | 81.1 | 469.5 | 1.0 | 5.7 |
| 7 | 122.2 | 116.8 | 130.5 | >500 | 1.1 | >4.3 |
| 8 | 2.7 | 2.8 | 3.7 | 21.7 | 1.3 | 7.8 |
| 9 | 3.4 | 3.2 | 3.5 | 10.8 | 1.1 | 3.4 |
| 10 | 2.8 | 3.0 | 2.9 | 29.3 | 1.0 | 9.8 |
| 11 | 4.7 | 4.2 | 5.2 | 126.4 | 1.2 | 29.8 |
| 12 | 1.8 | 1.8 | 1.7 | 12.5 | 0.9 | 6.9 |
| 13 | 3.2 | 4.3 | 5.9 | 27.4 | 1.4 | 6.4 |
| 14 | 8.1 | 12.7 | 15.1 | 121.9 | 1.2 | 9.6 |
| 15 | 22.6 | 33.2 | 72.2 | 179.5 | 2.2 | 5.4 |
| 16 | 6.3 | 7.5 | 12.5 | 42.6 | 1.7 | 5.7 |
| 17 | 229.1 | 189.9 | 150.8 | >500 | 0.8 | >2.6 |
| 18 | 21.9 | 13.1 | 12.1 | 112.3 | 0.9 | 8.6 |
| 19 | 27.5 | 29.0 | 30.3 | 79.7 | 1.0 | 2.7 |
| 20 | 7.0 | 6.6 | 7.1 | 69.9 | 1.1 | 10.5 |
| 21 | 10.1 | 10.6 | 10.8 | 187.0 | 1.0 | 17.6 |
| 22 | 69.3 | 87.5 | 101.4 | >500 | 1.2 | >5.7 |
| 23 | 8.7 | NA | NA | NA | NA | NA |
| 24 | 27.8 | 27.8 | 32.5 | 478.5 | 1.2 | 17.2 |
| 25 | 39.1 | 28.3 | 44.1 | 159.8 | 1.6 | 5.6 |
| 26 | 2.7 | 2.0 | 2.4 | 27.2 | 1.2 | 13.5 |
| 27 | 6.3 | 3.8 | 5.3 | 399.7 | 1.4 | 105.9 |
| 28 | 11.4 | 9.1 | 14.3 | 57.2 | 1.6 | 6.3 |
| 29 | 22.1 | 18.6 | 33.4 | >500 | 1.8 | >26.9 |
| 30 | 15.9 | 13.0 | 17.0 | 55.6 | 1.3 | 4.3 |
| 31 | 10.5 | 8.6 | 17.6 | 432.5 | 2.1 | 50.5 |
| 32 | 1.9 | 1.3 | 1.5 | 10.5 | 1.2 | 8.3 |
| 33 | 2.1 | 1.5 | 3.2 | 12.3 | 2.1 | 7.9 |
| 34 | 2.4 | 3.0 | 3.2 | 11.3 | 1.0 | 3.7 |
| 35 | 12.8 | 16.8 | 16.9 | 38.6 | 1.0 | 2.3 |
| 36 | 7.7 | 10.5 | 10.1 | 87.3 | 1.0 | 8.3 |
| 37 | 4.7 | 6.8 | 7.8 | 22.1 | 1.2 | 3.3 |
| 38 | 6.0 | 7.9 | 7.0 | 18.6 | 0.9 | 2.4 |
| 39 | 5.9 | 8.9 | 12.1 | 27.2 | 1.4 | 3.0 |
| 40 (mixture of isomers) | 6.8 | 9.9 | 16.3 | 36.1 | 1.7 | 3.7 |
| 41 | 6.3 | 9.5 | 15.7 | 32.8 | 1.6 | 3.4 |

*w.t. assay 2 were run on the same day as the assays with K103N and Y181C mutants.

The high-throughput screening was also run for nevirapine ("NPV"), rilpivirine ("RPV"), and efavirenz ("EFV"). Nevirapine was obtained from Toronto Research Chemicals, Inc. (Toronto, Canada; Catalogue #N391275). Rilpivirine was obtained from Key Organics Ltd. (Camelford, Cornwall, United Kingdom; Catalogue #KE-0036). Efavirenz was obtained from Toronto Research Chemicals, Inc. (Toronto, Canada; Catalogue #E425000). The results are shown below in Table 2.

TABLE 2

| Compound | MT4 $EC_{50}$ (nM) against w.t. | MT4 $EC_{50}$ (nM) against | | | FC against mutant | |
|---|---|---|---|---|---|---|
| | assay 2* | K103N | Y181C | K103N | Y181C |
| Nevirapine ("NVP") | 65.0 | ND | ND | ND | ND | ND |
| Rilpivirine ("RPV") | 0.9 | 1.3 | 1.5 | 3.8 | 1.2 | 3.1 |
| Efavirenz ("EFV") | 1.3 | 1.6 | 46.4 | 3.8 | 28.9 | 2.3 |

*w.t. assay 2 were run on the same day as the assays with K103N and Y181C mutants.
ND: not determined It is understood that $EC_{50}$ may be evaluated by techniques known in the art. In one embodiment, the compounds exhibit an $EC_{50}$ of less than about 3000 nM in the wild-type or any of the HIV RT mutants, as measured by the method disclosed in the "high throughput screening of anti-HIV mutants K103N and Y181C" assay section discussed above. In one embodiment, the compounds exhibit an $EC_{50}$ of less than about 1000 nM, 500 nM, 400 nM, 300 nM, 250 nM, 200 nM, 100 nM, 50 nM, 25 nM, 10 nM, 5 nM, or 1 nM in the wild-type or any of the HIV RT mutants (e.g., K103N, Y181C).

Example B

Resistance Profile Against HIV-1 RT (Reverse Transcriptase) Mutants

Compounds were tested for antiviral activity against a panel of NNRTI resistant viruses. A panel of 8 clonal site-directed mutant viruses representing the major resistance development pathways against rilpivirine ("RPV"), efavirenz ("EFV"), and nevirapine ("NVP"), containing both single and double mutations within HIV-1 reverse transcriptase was employed. Further details and background can be found in Janssen et al. J. Med. Chem, 2005, 48, 1901-1909; Das et al., Proc. Nat. Acad. Sci., 2008, vol., 105, no. 5, 1466-1471; and Kuroda et al., Nature Chemistry, 2013, DOI: 10.1038/NCHEM.1559. Retention of full antiviral potency against the K103N mutation relative to the wild type virus was considered especially desirable as this mutation is present in a minor subset of treatment-naïve patients (1.4%). HIV-1 recombinant strains encoding reverse transcriptase mutations K103N, Y181C, Y188L, G190A, K103N/Y181C, L100I/Y181C, E138K or E138K/M184V were constructed by site-directed mutagenesis. Wild-type and mutant viruses were prepared by transfecting infectious proviral HXB2-based cDNA clones into MT-2 cells and harvesting the cell supernatants. MT-2 cells were infected with wild-type and mutant HIV-1 strains at a multiplicity of infection (MOI) of 0.005 by gentle mixing for 3 hours at 37° C. and then added at a density of 16,667 cells per well in 50 µL complete RPMI cell culture media (containing 10% fetal bovine serum (FBS) and 10% penicillin-streptomycin) to 96-well plates containing 50 µL of a 3-fold serial dilution of test compounds in RPMI medium. After 5 days of incubation at 37° C. in a humidified incubator in the presence of 5% $CO_2$, 100 µL of Cell Titer-Glo™ Reagent (Promega Biosciences, Inc., Madison, Wis.) was added to each well and the relative light units (RLU) measured on an Envision plate reader. The virus-induced cytopathic effect was determined as a percentage of the RLU measurements from samples with fully suppressed virus replication after subtracting the signal from untreated (DMSO) controls. The $EC_{50}$ value was defined as the compound concentration inducing a 50% decrease in virus replication. Data analysis for the antiviral activity observed in MT-2 cells was performed using XL-Fit™ software (IDBS, Guildford, Surrey, UK) to calculate $EC_{50}$ from an 8-point dose-response curve using the following equation:

$$y = M - \frac{(M-H) \times EC_{50}^n}{(EC_{50}^n + x^n)}$$

where y=virus inhibition, x=drug concentration, M=maximum inhibition, H=minimum inhibition and n=Hill coefficient. $EC_{50}$ values (mean±standard deviation) were calculated from at least three independent experiments performed in triplicate. The level of resistance was calculated as a ratio of the mean $EC_{50}$ for each mutant/WT virus. Results are disclosed in FIG. 1 and in Tables 3 and 4 below.

TABLE 3

| | Biology resistance panel-low throughput fold change (FC) | | | | | | |
|---|---|---|---|---|---|---|---|
| Compound | K103N | Y181C | L100I/ Y181C | K103N/ Y181C | Y188L | G190A | E138K/ M184V |
| 1 | 1.3 | 5.7 | 6.9 | 14.8 | 15.2 | 0.6 | ND |
| 2 | 0.9 | 4.0 | 1.6 | 4.1 | 10.0 | 1.6 | 5.0 |
| 3 | 1.0 | 3.4 | 1.0 | 3.4 | 13.7 | ND | ND |
| 4 | 1.4 | 4.9 | 5.4 | 12.8 | 16.9 | ND | ND |
| 5 | 1.6 | 15.4 | 18.9 | 208.0 | 174.0 | ND | ND |
| 9 | 1.0 | 5.7 | 4.0 | 14.7 | 11.4 | ND | ND |
| 10 | 0.9 | 11.9 | 3.8 | 19.9 | 53.6 | ND | ND |
| 11 | 2.1 | 154.0 | 85.0 | 157.0 | 161.0 | ND | ND |
| 34 | 1.4 | 3.4 | 1.7 | 12.4 | 18.7 | ND | 4.2 |

ND: not determined

The resistance profile against HIV-1 RT mutants was also run for nevirapine ("NPV"), rilpivirine ("RPV"), and efavirenz ("EFV"). Nevirapine was obtained from Toronto Research Chemicals, Inc. (Toronto, Canada; Catalogue #N391275). Rilpivirine was obtained from Key Organics Ltd. (Camelford, Cornwall, United Kingdom; Catalogue

KE-0036). Efavirenz was obtained from Toronto Research Chemicals, Inc. (Toronto, Canada; Catalogue #E425000). The results are shown below in Table 4.

Next, 1 μM cisapride (positive control) was added. Finally, washout with External Solution was performed until the recovery current reached steady state.

TABLE 4

| | Biology resistance panel-low throughput fold change (FC) | | | | | | |
|---|---|---|---|---|---|---|---|
| Compound | K103N | Y181C | L100I/ Y181C | K103N/ Y181C | Y188L | G190A | E138K/ M184V |
| Nevirapine ("NVP") | 87.0 | >229 | >229 | ND | >229 | 183.0 | ND |
| Rilpivirine ("RPV") | 1.0 | 4.6 | 18.1 | 7.7 | 22.8 | 0.8 | 3.0 |
| Efavirenz ("EFV") | 48.1 | 3.6 | >200 | 83.5 | 132.5 | 14.8 | ND |

ND: not determined

Example C hERG assay

Cells:

AVIVA's CHO cell line, which stably expresses hERG channels, was used for the study. Cells were cultured in DMEM/F12 containing 10% FBS, 1% penicillin/streptomycin and 500 μg/ml G418. Before testing, cells were harvested using Accumax (Innovative Cell Technologies).

Solutions:

For electrophysiological recordings, the following solutions were used:

External Solution: 2 mM $CaCl_2$; 2 mM $MgCl_2$; 4 mM KCl; 150 mM NaCl; 10 mM Glucose; 10 mM HEPES; 305-315 mOsm; pH 7.4 (adjusted with 5M NaOH.)

Internal Solution: 140 mM KCl; 10 mM $MgCl_2$; 6 mM EGTA; 5 mM HEPES-Na; 5 mM ATP-Mg; 295-305 mOsm; pH 7.25 (adjusted with 1M KOH).

Electrophysiology:

Whole cell recordings were performed using PX 7000A (Axon Instruments) with AVIVA's SealChip™ technology. Cells were voltage clamped at a holding potential of −80 mV. The hERG current was then activated by a depolarizing step to −50 mV for 300 ms. This first step at −50 mV was used as a baseline for measuring peak amplitude of the tail current. Next, a voltage step to +20 mV was applied for 5 s to activate the channels. Finally, a step back to −50 mV for 5 s removed activation and the deactivating tail current was recorded.

Test Article Handling and Dilutions:

All test articles were prepared from 10 mM DMSO stock solutions. Solutions were mixed by sonication for 20 min, followed by vigorous vortexing. Prior to testing, compounds were diluted to test concentrations in glass vials using External Solution. Dilutions were prepared no longer than 20 min prior to use.

Electrophysiology Procedures

After achieving whole cell configuration, cells were monitored for 90 s to assess stability and then washed with External Solution for 66 s. The voltage protocol was then applied to the cells every 12 s throughout the procedure. Only stable cells with recording parameters above threshold were allowed to enter the drug addition procedure.

External solution containing 0.1% DMSO (vehicle) was applied to the cells to establish a baseline. After allowing the current to stabilize for 3 to 10 min, test articles were applied. Test article solutions were added to cells in 4 separate additions. Cells were kept in test solution until effect of the test article reached steady state, to a maximum of 12 min.

Data Analysis

Data analysis was performed using DataXpress (Axon Instruments), Clampfit (Axon Instruments) and Origin (OriginLab Corporation) software. Results are disclosed in Table 5. The greater than values in Table 5 indicate the maximum achievable concentration in the assay (e.g., coupounds achieving their solubility limit).

TABLE 5

| Compound No. | hERG (μM) |
|---|---|
| 2 | >1 |
| 9 | >3 |
| 10 | >3 |
| 11 | >3 |
| 12 | >3 |
| 13 | 1.3 |
| 34 | >3 |

The hERG assay was also run for rilpivirine ("RPV"). The result was 0.5 μM.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

The Examples disclosed herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure.

What is claimed is:

1. A compound of formula:

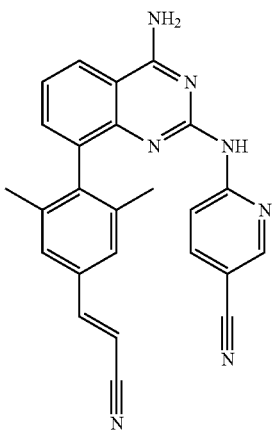 [SMILES: Cc1cc(/C=C/C#N)cc(C)c1-c1cccc2c(N)nc(Nc3ccc(C#N)cn3)nc12]

or a tautomer or a pharmaceutically acceptable salt thereof.

2. A pharmaceutical composition comprising a compound of claim 1, or a tautomer or a pharmaceutically acceptable salt thereof, and a pharmaceutically acceptable carrier.

3. The pharmaceutical composition of claim 2, further comprising one, two, three, or four additional therapeutic agents.

4. The pharmaceutical composition of claim 3, wherein the therapeutic agent is independently selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

* * * * *